(12) United States Patent
Moore et al.

(10) Patent No.: US 8,347,088 B2
(45) Date of Patent: Jan. 1, 2013

(54) SECURITY SYSTEMS AND METHODS FOR USE WITH STRUCTURED AND UNSTRUCTURED DATA

(75) Inventors: James F. Moore, Lincoln, MA (US); Bela A. Labovitch, Newton, MA (US)

(73) Assignee: Newsilike Media Group, Inc, Lincoln, MA (US)

( * ) Notice: Subject to any disclaimer, the term of this patent is extended or adjusted under 35 U.S.C. 154(b) by 941 days.

(21) Appl. No.: 11/346,586

(22) Filed: Feb. 1, 2006

(65) Prior Publication Data

US 2007/0061266 A1 Mar. 15, 2007

Related U.S. Application Data

(63) Continuation-in-part of application No. 11/223,826, filed on Sep. 10, 2005.

(60) Provisional application No. 60/649,311, filed on Feb. 1, 2005, provisional application No. 60/649,312, filed on Feb. 1, 2005, provisional application No. 60/649,504, filed on Feb. 2, 2005, provisional application No. 60/649,502, filed on Feb. 2, 2005, provisional application No. 60/657,840, filed on Mar. 1, 2005, provisional application No. 60/594,298, filed on Mar. 26, 2005, provisional application No. 60/594,416, filed on Apr. 6, 2005, provisional application No. 60/669,666, filed on Apr. 8, 2005, provisional application No. 60/594,456, filed on Apr. 10, 2005, provisional application No. 60/594,478, filed on Apr. 12, 2005, provisional application No. 60/673,661, filed on Apr. 20, 2005, provisional application No. 60/680,879, filed on May 13, 2005, provisional application No. 60/684,092, filed on May 23, 2005, provisional application No. 60/685,904, filed on May 31, 2005, provisional application No. 60/686,630, filed on Jun. 2, 2005, provisional application No. 60/688,826, filed on Jun. 9, 2005, provisional application No. 60/694,080, filed on Jun.

(Continued)

(51) Int. Cl.
*H04L 29/06* (2006.01)
*G06F 17/30* (2006.01)
(52) U.S. Cl. ............................... 713/166; 726/2; 726/27
(58) Field of Classification Search ........ 707/9; 705/51; 726/2, 27; 713/166
See application file for complete search history.

(56) References Cited

U.S. PATENT DOCUMENTS 5,664,109 A   9/1997   Johnson et al.
(Continued)

FOREIGN PATENT DOCUMENTS

DD   226868   9/1984
(Continued)

OTHER PUBLICATIONS

Schneier, "Applied Cryptography: Protocols, Algorithms, and Source Code in C", 1996, John Wiley & Sons, Inc., Second Edition, pp. 584-587.*

(Continued)

*Primary Examiner* — Michael Simitoski
(74) *Attorney, Agent, or Firm* — GTC Law Group LLP & Affiliates

(57) ABSTRACT

Disclosed herein are systems and methods including hardware, software and electronic service components and systems to provide large-scale, reliable, and secure foundations for distributed databases and content management systems combining unstructured and structured data, and allowing post-input reorganization to achieve a high degree of flexibility.

21 Claims, 38 Drawing Sheets

Related U.S. Application Data 24, 2005, provisional application No. 60/695,029, filed on Jun. 28, 2005, provisional application No. 60/699,631, filed on Jul. 15, 2005, provisional application No. 60/700,122, filed on Jul. 18, 2005, provisional application No. 60/702,467, filed on Jul. 26, 2005, provisional application No. 60/703,688, filed on Jul. 29, 2005, provisional application No. 60/703,535, filed on Jul. 29, 2005, provisional application No. 60/703,544, filed on Jul. 29, 2005, provisional application No. 60/709,683, filed on Aug. 19, 2005, provisional application No. 60/719,073, filed on Sep. 21, 2005, provisional application No. 60/719,283, filed on Sep. 21, 2005, provisional application No. 60/719,284, filed on Sep. 21, 2005, provisional application No. 60/720,250, filed on Sep. 22, 2005, provisional application No. 60/721,803, filed on Sep. 28, 2005, provisional application No. 60/722,021, filed on Sep. 29, 2005, provisional application No. 60/724,956, filed on Oct. 7, 2005, provisional application No. 60/725,166, filed on Oct. 7, 2005, provisional application No. 60/726,542, filed on Oct. 14, 2005, provisional application No. 60/726,731, filed on Oct. 14, 2005, provisional application No. 60/726,727, filed on Oct. 14, 2005, provisional application No. 60/734,187, filed on Nov. 6, 2005, provisional application No. 60/734,156, filed on Nov. 6, 2005, provisional application No. 60/735,712, filed on Nov. 11, 2005, provisional application No. 60/741,770, filed on Dec. 1, 2005, provisional application No. 60/741,958, filed on Dec. 2, 2005, provisional application No. 60/742,975, filed on Dec. 6, 2005, provisional application No. 60/749,757, filed on Dec. 13, 2005, provisional application No. 60/750,291, filed on Dec. 14, 2005, provisional application No. 60/751,254, filed on Dec. 15, 2005, provisional application No. 60/751,249, filed on Dec. 16, 2005, provisional application No. 60/753,959, filed on Dec. 23, 2005, provisional application No. 60/756,774, filed on Jan. 6, 2006, provisional application No. 60/759,483, filed on Jan. 16, 2006.

(56) References Cited

U.S. PATENT DOCUMENTS

| | | | |
|---|---|---|---|
| 5,758,095 | A | 5/1998 | Albaum et al. |
| 5,784,635 | A | 7/1998 | Mccallum |
| 5,845,255 | A | 12/1998 | Mayaud |
| 5,930,764 | A | 7/1999 | Melchione et al. |
| 5,931,946 | A | 8/1999 | Terada et al. |
| 5,933,136 | A | 8/1999 | Brown |
| 6,022,315 | A | 2/2000 | Iliff |
| 6,070,189 | A | 5/2000 | Bender et al. |
| 6,131,085 | A | 10/2000 | Rossides |
| 6,199,082 | B1 | 3/2001 | Ferrel et al. |
| 6,233,618 | B1 | 5/2001 | Shannon |
| 6,253,210 | B1 | 6/2001 | Smith et al. |
| 6,311,194 | B1 | 10/2001 | Sheth et al. |
| 6,442,333 | B1 | 8/2002 | Izawa |
| 6,551,243 | B2 | 4/2003 | Bocionek et al. |
| 6,598,161 | B1 * | 7/2003 | Kluttz et al. ............... 713/166 |
| 6,678,764 | B2 | 1/2004 | Parvulescu et al. |
| 6,693,947 | B1 | 2/2004 | Schroeder |
| 6,734,886 | B1 * | 5/2004 | Hagan et al. ............... 715/853 |
| 6,904,461 | B1 | 6/2005 | Randhava et al. |
| 6,931,532 | B1 | 8/2005 | Davis et al. |
| 6,954,532 | B1 * | 10/2005 | Handley et al. ............... 380/54 |
| 6,993,522 | B2 | 1/2006 | Chen et al. |
| 7,010,681 | B1 * | 3/2006 | Fletcher et al. ............... 713/154 |
| 7,058,710 | B2 | 6/2006 | McCall et al. |
| 7,072,934 | B2 | 7/2006 | Helgeson et al. |
| 7,117,504 | B2 | 10/2006 | Smith et al. |
| 7,127,328 | B2 | 10/2006 | Ransom |
| 7,142,691 | B2 | 11/2006 | Levy |
| 7,146,415 | B1 | 12/2006 | Doi et al. |
| 7,149,813 | B2 | 12/2006 | Flanagin et al. |
| 7,188,144 | B2 | 3/2007 | Fuisz |
| 7,269,664 | B2 | 9/2007 | Hütsch et al. |
| 7,296,077 | B2 | 11/2007 | Harmon et al. |
| 7,308,477 | B1 * | 12/2007 | Gress et al. ............... 709/206 |
| 7,406,427 | B1 | 7/2008 | Guyan et al. |
| 7,412,534 | B2 | 8/2008 | Tsang et al. |
| 7,421,155 | B2 | 9/2008 | King |
| 7,451,147 | B1 | 11/2008 | Kao et al. |
| 7,472,349 | B1 | 12/2008 | Srivastava et al. |
| 7,519,591 | B2 | 4/2009 | Landi et al. |
| 7,565,410 | B2 | 7/2009 | Stickler |
| 7,584,208 | B2 | 9/2009 | Spivack et al. |
| 7,904,367 | B2 | 3/2011 | Chung et al. |
| 7,949,666 | B2 | 5/2011 | Wolff et al. |
| 7,953,725 | B2 | 5/2011 | Burris et al. |
| 8,010,282 | B2 | 8/2011 | Barry et al. |
| 8,140,482 | B2 | 3/2012 | Moore |
| 8,200,700 | B2 | 6/2012 | Moore et al. |
| 8,200,775 | B2 | 6/2012 | Moore |
| 2001/0016851 | A1 | 8/2001 | Gramsamer et al. |
| 2001/0051881 | A1 | 12/2001 | Filler |
| 2001/0052933 | A1 | 12/2001 | Nybo et al. |
| 2001/0056359 | A1 | 12/2001 | Abreu |
| 2002/0010616 | A1 | 1/2002 | Itzhaki |
| 2002/0010764 | A1 | 1/2002 | Spicer |
| 2002/0029157 | A1 | 3/2002 | Marchosky |
| 2002/0032742 | A1 | 3/2002 | Anderson |
| 2002/0038316 | A1 | 3/2002 | Onyon et al. |
| 2002/0049613 | A1 | 4/2002 | Schmieding |
| 2002/0059049 | A1 | 5/2002 | Bradbury et al. |
| 2002/0059399 | A1 | 5/2002 | Learmonth |
| 2002/0091734 | A1 * | 7/2002 | Redlich et al. ............... 707/511 |
| 2002/0138467 | A1 | 9/2002 | Jacobson et al. |
| 2002/0143742 | A1 | 10/2002 | Nonomura et al. |
| 2002/0143819 | A1 | 10/2002 | Han et al. |
| 2002/0152210 | A1 | 10/2002 | Johnson et al. |
| 2002/0152318 | A1 | 10/2002 | Menon et al. |
| 2002/0154178 | A1 | 10/2002 | Barnett et al. |
| 2002/0188522 | A1 | 12/2002 | McCall et al. |
| 2003/0046434 | A1 | 3/2003 | Flanagin et al. |
| 2003/0050801 | A1 | 3/2003 | Ries et al. |
| 2003/0055818 | A1 | 3/2003 | Faybishenko et al. |
| 2003/0055825 | A1 | 3/2003 | Chen et al. |
| 2003/0061404 | A1 | 3/2003 | Atwal et al. |
| 2003/0069751 | A1 | 4/2003 | Lichtenstein et al. |
| 2003/0074352 | A1 | 4/2003 | Raboczi et al. |
| 2003/0088544 | A1 | 5/2003 | Kan et al. |
| 2003/0126120 | A1 | 7/2003 | Faybishenko et al. |
| 2003/0217047 | A1 | 11/2003 | Marchisio |
| 2003/0225718 | A1 * | 12/2003 | Shmulevich et al. ............... 706/46 |
| 2003/0229692 | A1 | 12/2003 | Vo |
| 2004/0002966 | A1 | 1/2004 | Perkowski |
| 2004/0034550 | A1 | 2/2004 | Menschik et al. |
| 2004/0054675 | A1 | 3/2004 | Li |
| 2004/0054722 | A1 | 3/2004 | DeFloor et al. |
| 2004/0064428 | A1 | 4/2004 | Larkin et al. |
| 2004/0073661 | A1 | 4/2004 | Eibach et al. |
| 2004/0078231 | A1 | 4/2004 | Wilkes et al. |
| 2004/0078236 | A1 | 4/2004 | Stoodley et al. |
| 2004/0093412 | A1 | 5/2004 | Chen et al. |
| 2004/0133580 | A1 | 7/2004 | Liu et al. |
| 2004/0139317 | A1 * | 7/2004 | Fronberg ............... 713/164 |
| 2004/0139327 | A1 * | 7/2004 | Brown et al. ............... 713/176 |
| 2004/0143623 | A1 | 7/2004 | Fukui et al. |
| 2004/0172423 | A1 | 9/2004 | Kaasten et al. |
| 2004/0181679 | A1 * | 9/2004 | Dettinger et al. ............... 713/193 |
| 2004/0207659 | A1 | 10/2004 | Goodman et al. |
| 2004/0221226 | A1 | 11/2004 | Lin et al. |
| 2004/0224674 | A1 | 11/2004 | O'Farrell et al. |
| 2004/0230674 | A1 | 11/2004 | Pourheidari et al. |
| 2004/0254816 | A1 | 12/2004 | Myers |

| | | |
|---|---|---|
| 2004/0260767 A1 | 12/2004 | Kedem et al. |
| 2004/0267610 A1 | 12/2004 | Gossett et al. |
| 2005/0027567 A1 | 2/2005 | Taha |
| 2005/0027871 A1 | 2/2005 | Bradley et al. |
| 2005/0038717 A1* | 2/2005 | McQueen et al. ............... 705/27 |
| 2005/0055308 A1 | 3/2005 | Meyer et al. |
| 2005/0108057 A1 | 5/2005 | Cohen et al. |
| 2005/0120300 A1 | 6/2005 | Schwager et al. |
| 2005/0132048 A1 | 6/2005 | Kogan et al. |
| 2005/0165615 A1* | 7/2005 | Minar ............................... 705/1 |
| 2005/0198021 A1 | 9/2005 | Wilcox et al. |
| 2005/0216315 A1 | 9/2005 | Andersson |
| 2005/0234740 A1 | 10/2005 | Krishnan et al. |
| 2005/0262340 A1* | 11/2005 | Rabb ............................ 713/165 |
| 2005/0267973 A1 | 12/2005 | Carlson et al. |
| 2005/0289468 A1 | 12/2005 | Kahn et al. |
| 2006/0004691 A1 | 1/2006 | Sifry |
| 2006/0010251 A1 | 1/2006 | Mrsic-Flogel et al. |
| 2006/0053156 A1 | 3/2006 | Kaushansky et al. |
| 2006/0059208 A1 | 3/2006 | Chen et al. |
| 2006/0064320 A1 | 3/2006 | Postrel |
| 2006/0064326 A1 | 3/2006 | Tucker |
| 2006/0073812 A1 | 4/2006 | Punaganti et al. |
| 2006/0074980 A1 | 4/2006 | Sarkar |
| 2006/0075426 A1 | 4/2006 | Koch et al. |
| 2006/0080166 A1 | 4/2006 | Takahashi |
| 2006/0085412 A1 | 4/2006 | Johnson et al. |
| 2006/0085788 A1 | 4/2006 | Amir et al. |
| 2006/0095507 A1 | 5/2006 | Watson |
| 2006/0095628 A1 | 5/2006 | Ludwig et al. |
| 2006/0101035 A1 | 5/2006 | Mustakallio et al. |
| 2006/0106655 A1 | 5/2006 | Lettovsky et al. |
| 2006/0106748 A1 | 5/2006 | Chafle et al. |
| 2006/0111938 A1 | 5/2006 | Vitiello |
| 2006/0112076 A1* | 5/2006 | Burris et al. ..................... 707/3 |
| 2006/0136259 A1 | 6/2006 | Weiner et al. |
| 2006/0149591 A1* | 7/2006 | Hanf et al. ....................... 705/2 |
| 2006/0155698 A1* | 7/2006 | Vayssiere ......................... 707/6 |
| 2006/0167860 A1 | 7/2006 | Eliashberg et al. |
| 2006/0173985 A1 | 8/2006 | Moore |
| 2006/0178910 A1 | 8/2006 | Eisenberger et al. |
| 2006/0178918 A1 | 8/2006 | Mikurak |
| 2006/0184617 A1 | 8/2006 | Nicholas et al. |
| 2006/0188327 A1 | 8/2006 | Moon |
| 2006/0200380 A1 | 9/2006 | Ho et al. |
| 2006/0200478 A1 | 9/2006 | Pasztor et al. |
| 2006/0221076 A1 | 10/2006 | Takahashi et al. |
| 2006/0229911 A1 | 10/2006 | Gropper et al. |
| 2006/0230011 A1 | 10/2006 | Tuttle et al. |
| 2006/0230021 A1 | 10/2006 | Diab et al. |
| 2006/0230221 A1 | 10/2006 | Hsu et al. |
| 2006/0247961 A1 | 11/2006 | Klemow |
| 2006/0265489 A1 | 11/2006 | Moore |
| 2006/0265508 A1 | 11/2006 | Angel et al. |
| 2006/0288011 A1 | 12/2006 | Gandhi et al. |
| 2006/0288329 A1 | 12/2006 | Gandhi et al. |
| 2007/0011665 A1 | 1/2007 | Gandhi et al. |
| 2007/0011710 A1 | 1/2007 | Chiu |
| 2007/0027710 A1 | 2/2007 | Mohr |
| 2007/0038712 A1 | 2/2007 | Affronti et al. |
| 2007/0050446 A1 | 3/2007 | Moore |
| 2007/0061266 A1 | 3/2007 | Moore |
| 2007/0061393 A1 | 3/2007 | Moore et al. |
| 2007/0061487 A1 | 3/2007 | Moore et al. |
| 2007/0073934 A1* | 3/2007 | Rogers ............................ 710/59 |
| 2007/0079237 A1 | 4/2007 | Abrams et al. |
| 2007/0081550 A1 | 4/2007 | Moore |
| 2007/0088807 A1 | 4/2007 | Moore |
| 2007/0094156 A1 | 4/2007 | Isaacs |
| 2007/0094350 A1 | 4/2007 | Moore |
| 2007/0094365 A1 | 4/2007 | Nussey et al. |
| 2007/0094389 A1 | 4/2007 | Nussey et al. |
| 2007/0100959 A1 | 5/2007 | Eichstaedt et al. |
| 2007/0106536 A1 | 5/2007 | Moore |
| 2007/0106537 A1 | 5/2007 | Moore |
| 2007/0106649 A1 | 5/2007 | Moore |
| 2007/0106650 A1 | 5/2007 | Moore |
| 2007/0106750 A1 | 5/2007 | Moore |
| 2007/0106751 A1 | 5/2007 | Moore |
| 2007/0106752 A1 | 5/2007 | Moore |
| 2007/0106753 A1 | 5/2007 | Moore |
| 2007/0106754 A1 | 5/2007 | Moore |
| 2007/0116036 A1 | 5/2007 | Moore |
| 2007/0116037 A1 | 5/2007 | Moore |
| 2007/0130457 A1 | 6/2007 | Kamat et al. |
| 2007/0139182 A1 | 6/2007 | O'Connor et al. |
| 2007/0143215 A1 | 6/2007 | Willems |
| 2007/0150482 A1 | 6/2007 | Taylor et al. |
| 2007/0156809 A1 | 7/2007 | Dickinson et al. |
| 2007/0168461 A1 | 7/2007 | Moore |
| 2007/0207782 A1 | 9/2007 | Tran |
| 2007/0220016 A1 | 9/2007 | Estrada et al. |
| 2007/0225047 A1 | 9/2007 | Bakos |
| 2007/0245020 A1 | 10/2007 | Ott, IV |
| 2008/0005086 A1 | 1/2008 | Moore |
| 2008/0040151 A1 | 2/2008 | Moore |
| 2008/0046369 A1 | 2/2008 | Wood |
| 2008/0046437 A1 | 2/2008 | Wood |
| 2008/0046471 A1 | 2/2008 | Moore et al. |
| 2008/0052162 A1 | 2/2008 | Wood |
| 2008/0052343 A1 | 2/2008 | Wood |
| 2008/0126178 A1 | 5/2008 | Moore |
| 2008/0126476 A1 | 5/2008 | Nicholas et al. |
| 2008/0141126 A1 | 6/2008 | Johnson et al. |
| 2008/0195483 A1 | 8/2008 | Moore |
| 2008/0244091 A1 | 10/2008 | Moore et al. |
| 2009/0172773 A1 | 7/2009 | Moore |

FOREIGN PATENT DOCUMENTS

| | | |
|---|---|---|
| DE | 4434369 A1 | 3/1996 |
| EP | 0504774 A2 | 9/1992 |
| GB | 901723 | 7/1962 |
| JP | 06347169 A | 12/1994 |
| JP | 09145249 A | 6/1997 |
| WO | WO-8304161 A1 | 12/1983 |
| WO | WO-03077558 A2 | 9/2003 |
| WO | WO-2004001574 | 2/2004 |
| WO | WO-2006083958 A2 | 8/2006 |
| WO | WO-2007130865 A2 | 11/2007 |
| WO | WO-2007137145 A2 | 11/2007 |
| WO | WO-2008036464 A2 | 3/2008 |

OTHER PUBLICATIONS

Kifer et al., "Database Systems: An Application-Oriented Approach", 2005, Addison-Wesley, Second Edition, pp. 1151-1152.*

Hammond, Tony et al. "The Role of RSS in Science Publishing: Syndication and Annotation on the Web", 2004.*

Lewin, James. "An introduction to RSS news feeds Using open formats for content syndication", Nov. 2000.*

Wood, Charlie "Introducing Spanning Feed Builder for AppExchange", http://www.spanningpartners.com/2006/07/introducing_spa.html, (Jul. 2, 2006).

Wood, Charlie "Blog of Subscribe Your Calendar to Your Salesforce.com Events", http://globelogger.com/item.php?id=660, (May 12, 2006).

Wood, Charlie "Subscribe Your Calendar to Your Salesforce.com Events", http://www.spanningpartners.com/2006/05/subscribe_your_.html, (May 12, 2006).

Wood, Charlie "RSS-Enabled AppExchange Applications", http://www.spanningpartners.com/2006/05/spanning_partne_1.html, (May 30, 2006).

Wood, Charlie "Latest Spanning Salesforce Release", http://www.spanningpartners.com/2006/04/latest_spanning.html, (Apr. 5, 2006).

Wood, Charlie "New Spanning Salesforce Feeds and Features", http://globelogger.com/item.php?id=606, (Mar. 14, 2006).

Wood, Charlie "On Creating Real Business Value with RSS", http://www.spanningpartners.com/2006/02/on_creating_rea.html, (Feb. 23, 2006).

Wood, Charlie "Spanning Salesforce 2.0 is Live", http://globelogger.com/item.php?id=466, (Aug. 28, 2005).

Wood, Charlie "Introducing Spanning Salesforce 2.0", http://www.spanningpartners.com/2005/08/introducing_spa.html, (Aug. 28, 2005).

Wood, Charlie "Adoption Using RSS to Track Sales Leads", http://globelogger.com/item.php?id=285, (Jan. 28, 2005).
Wood, Charlie "Adoption Salesforce.com via RSS", http://globelogger.com/item.php?id=294, (Feb. 6, 2005).
Wood, Charlie "Spanning Salesforce Goes Public", http://globelogger.com/item.php?id=285, (Jul. 17, 2005).
Krill, Paul "Microsoft to demo CRM-RSS", http://weblog.infoworld.com/techwatch/archives/003933.html, (Sep. 7, 2005).
USPTO, ""U.S. Appl. No. 11/615,030 Non Final Office Action mailed Jan. 23, 2008"", (Jan. 23, 2008),all.
Gawlick, Dieter et al., "Using the Oracle Database as a Declarative RSS Hub", *International Conference on Management of Data*, Proceedings of the 2006 ACM SIGMOD international conference on Management of data,(2006),722.
USPTO, "U.S. Appl. No. 11/458,092, Non-Final Office Action mailed Jun. 9, 2008", OARN,23 pgs.
Appnel, T. "RSS: The Web Services We Already Have", (Jan. 22, 2003).
Maurer, L. "U.S. Appl. No. 09/584,318 (Appendix)".
"Customer", *Roget's II The New Thesaurus*. Boston: Houghton Mifflin. Credo Reference. [online][retrieved on Jul. 10, 2011], 2003.
"Serve", *Chambers 21st Century Dictionary*. London: Chambers Harrap. Credo Reference [online][retrieved on Jul. 10, 2011], 2001.
"Service", *Chambers 21st Century Dictionary*. London: Chambers Harrap. Credo Reference. [online][retrieved on Jul. 10, 2011], 2001.
"Definition Metadata", Webster's New World Computer Dictionary, 2003.
"Definition: Dicom introduction", http://www.cabiatl.com/micro/dicom/index.html, 10 pages.
"Digital Imaging and Communications (DICOM) part 10", PS Mar. 10, 2004, National Electronics Manufactures Association, Rosslyn, Virgina, 2004, 33 pages.
"Drugs and Herbs", http://web.archive.org/web/20051101101459/http://www.webmd.com/drugs/index-drugs.aspx (accessed online Jul. 11, 2011), 45 pages.
"OPML 1.0 Specification", http://www.opml.org/spec, 2000, (accessed online Jul. 5, 2011), 6 pages.
"RDF Primer", W3C Recommendation, http://www.w3.org/TR/rdf-syntax/ , 2004, (accessed online Jul. 5, 2011), 73 pages.
"UDDI Version 2.04 API Specification", UDDI Committee Specification, http://www.uddi.org/pubs/ProgrammersAPI-V2.04-Published_20020719.htm, Jul. 19, 2002, (Accessed online Jul. 5, 2011), pp. 1-66.
"Urchin RSS Aggregator", http://urchin.sourceforge.net/index.html, version 0.92, 2004, (accessed online Jun. 2, 2009), pp. 1-5.
Refsnes Data, "W3Schools Online Web Tutorials", 2002, pp. 3-5.
FEMA, "FEMA: Federal Disaster Declarations RSS", FEMA.gov, http://web.archive.org/web/20050413031904/http://fema.gov/news . . . (accessed online Dec. 29, 2010), 1 page.
FEMA, "FEMA: News Releases", feed://web.archive.org/web/20050403173625/www.fema.gov/news/recentnews_rss.fema, (access online Jul. 5, 2011), Apr. 3, 2005, 2 pages.
FEMA, "RSS," http://www.fema.gov/help/rss.shtm, Apr. 16, 2005, 2 pages.
Lund, Ben, "Using Urchin, Notes for Webmasters", Urchin version 0.8, 2003, 8 pages.
Marshall, James, "HTTP Made Really Easy", A Practical Guide to Writing Clients and Servers, http:www.jmarshall.com/easy/http/, (accessed online Jul. 12, 2011), 1997, 21 pages.
Nakano, Yusuke, et al., "A proposal of RSS WebCrawler model of product information", Active Media Technology, Proceedings of the 2005 International Conference on Active Media Technology, pp. 147-151 (2005).
International Application Serial No. PCT/US06/27794, International Preliminary Report on Patentability, 7 pages.
International Application Serial No. PCT/US06/27794, International Search Report, 5 pages.
International Application Serial No. PCT/US06/27794, Written Opinion of the International Searching Authority, 6 pages.
International Application Serial No. PCT/US07/069195, International Preliminary Report on Patentability, 6 pages.
International Application Serial No. PCT/US07/069195, International Search Report, PCT/US07/069195, 4 pages.
International Application Serial No. PCT/US07/069195, Written Opinion of the International Searching Authority, 5 pages.
International Application Serial No. PCT/US07/67643, International Preliminary Report on Patentability, 6 pages.
International Application Serial No. PCT/US07/67643, International Search Report, PCT/US07/67643, 2 pages.
International Application Serial No. PCT/US07/67643, Written Opinion of the International Searching Authority, 5 pages.
International Application Serial No. PCT/US07/74475, International Preliminary Report on Patentability, 4 pages.
International Application Serial No. PCT/US07/74475 International Search Report, 3 pages.
International Application Serial No. PCT/US07/74475, Written Opinion of the International Searching Authority, 3 pages.
International Application Serial No. PCT/US2006/003544, International Preliminary Report on Patentability mailed Sep. 17, 2008, 7 pages.
International Application Serial No. PCT/US2006/003544, International Search Report mailed Sep. 17, 2008, 4 pages.
International Application Serial No. PCT/US2006/003544, Written Opinion mailed Sep. 17, 2008, 6 pages.
International Application Serial No. PCT/US2006/034944, International Preliminary Report on Patentability mailed Mar. 11, 2008, 8 pages.
International Application Serial No. PCT/US2006/034944, Written Opinion mailed Mar. 9, 2008, 7 pages.
International Application Serial No. PCT/US2006/034944, International Search Report mailed Mar. 19, 2007, 7 pages.
Pilgrim, Mark, "How to consume RSS safely", http://diveintomark.org/archives/2003/06/12/how_to_consume_rss_safely, 2003, (accessed Jul. 5, 2011), 28 pages.
Ponnekanti, Shankar R. and Armando Fox, "SWORD: A Developer Toolkit for Web Service Composition," http://www2002.org/CDROM/alternate/786/ , 2002, (accessed online Jul. 5, 2011), pp. 1-22.
Roszkowski, Michael, et al., "A Distributed Architecture for Resource Discovery Using Metadata," D-Lib Magazine, pp. 1-11 (Jun. 1998).
Stal, Michael, "Web Services: Beyond Component Based Computing Seeking a Better Solution to the Application Integration Problem," Communications of the ACM, vol. 45, No. 10, pp. 71-76 (Oct. 2002).
Winer, Dave, "OPML About Page", http://ww.opml.org/about , (accessed online Jul. 5, 2011), 2 pages, (Nov. 7, 2000).

* cited by examiner

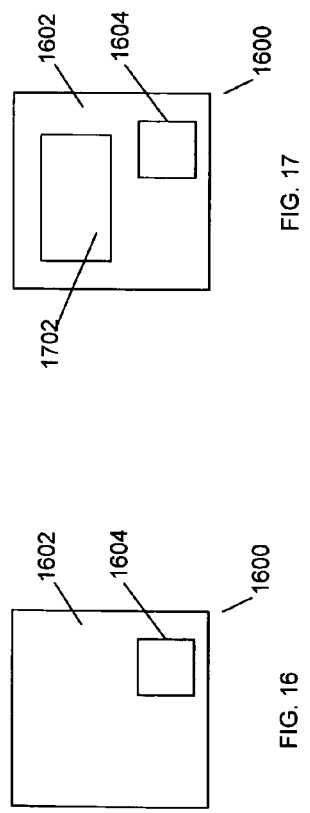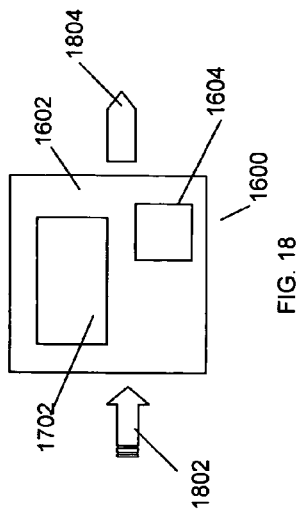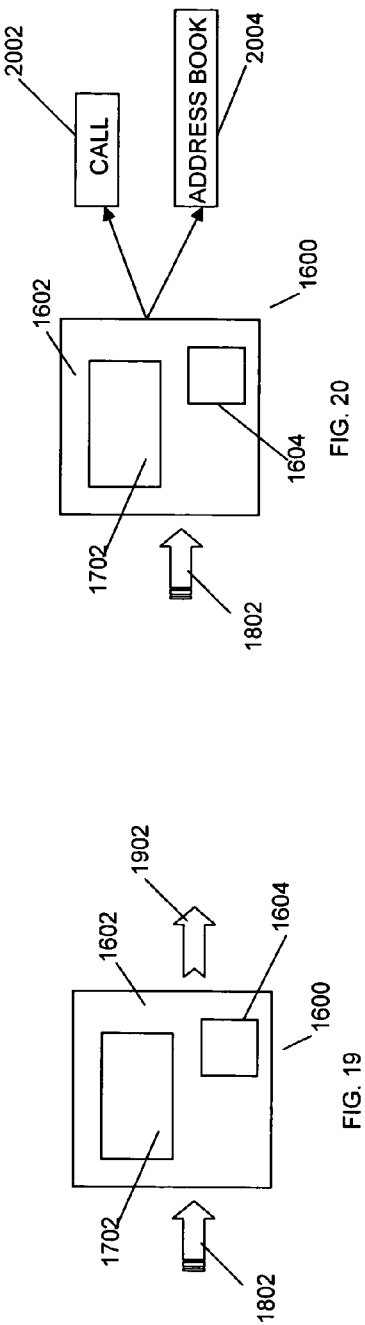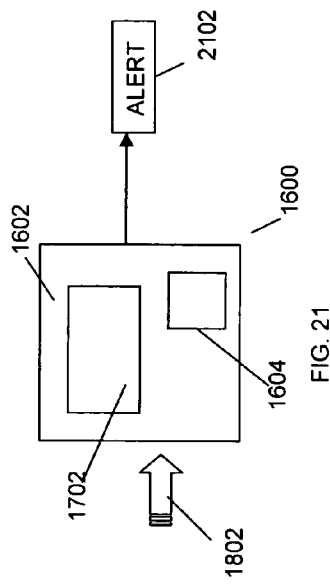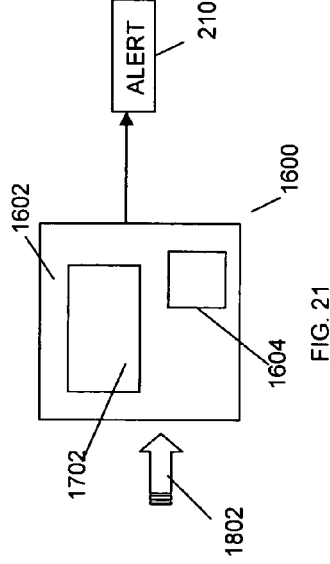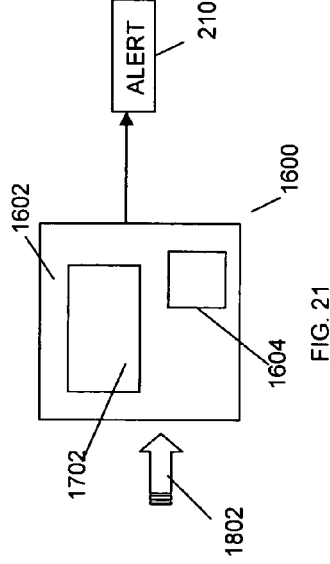

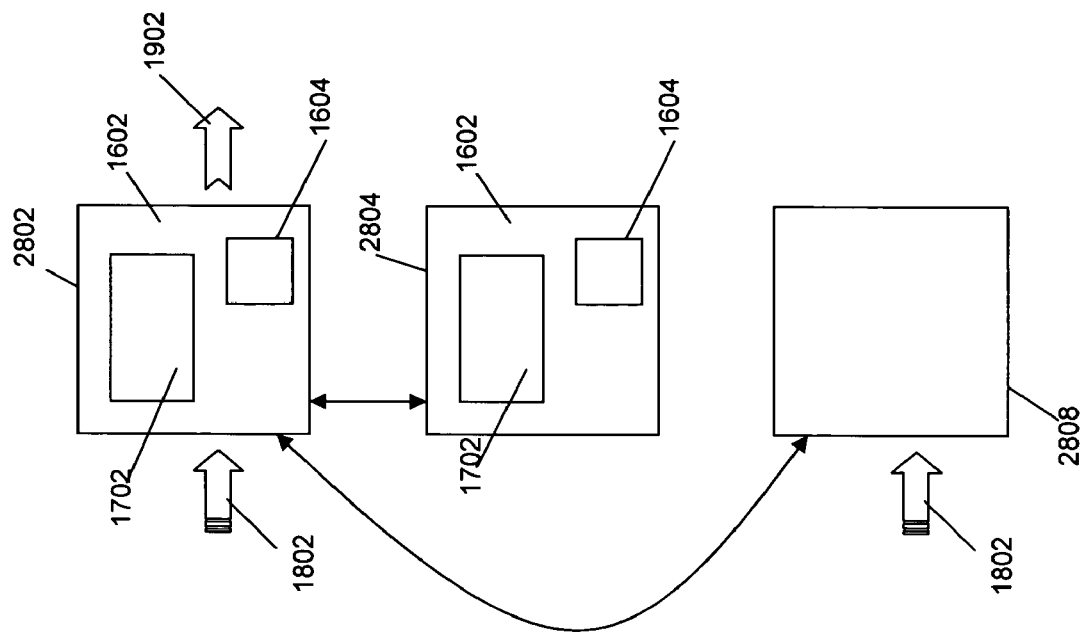
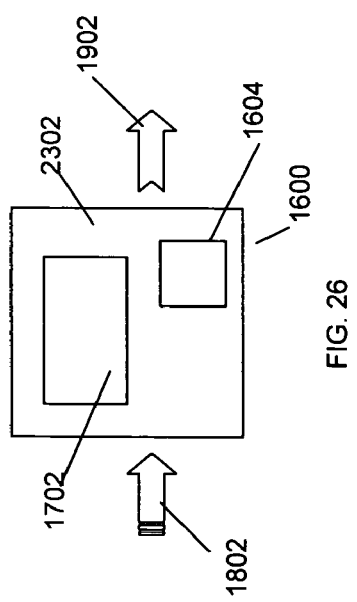
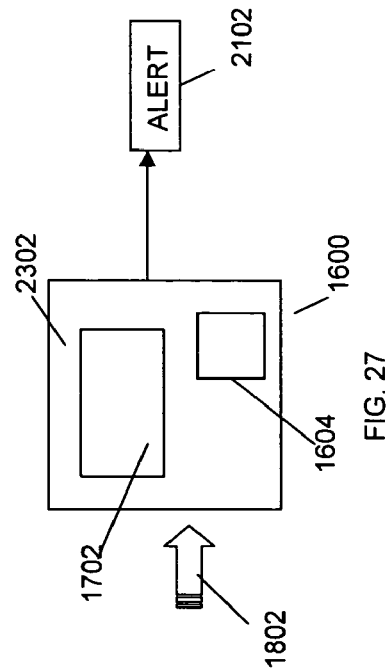

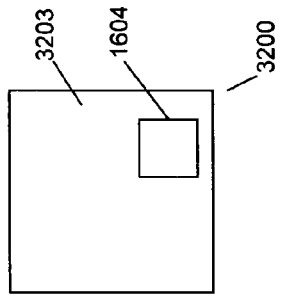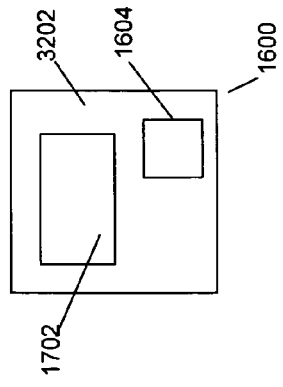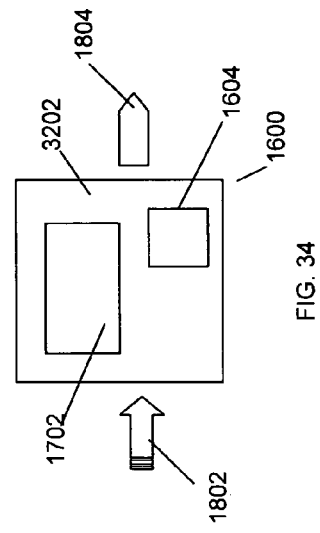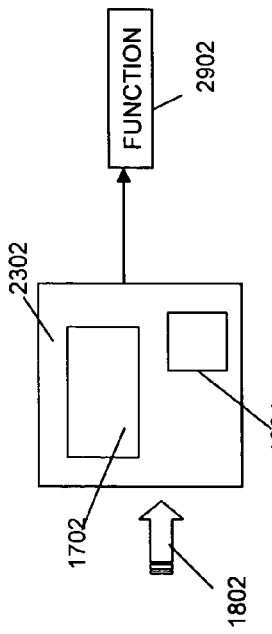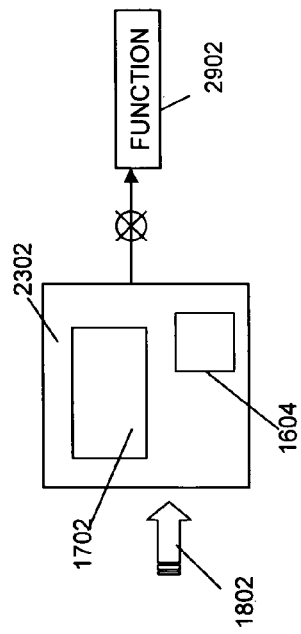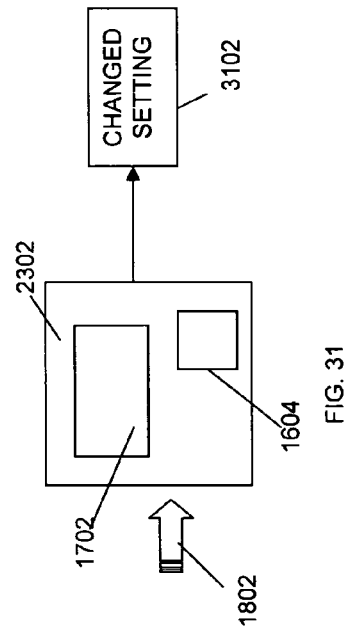

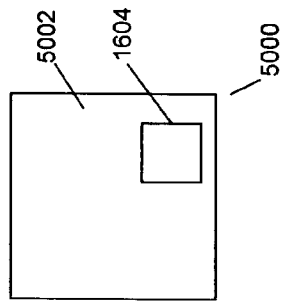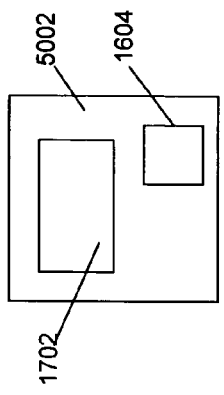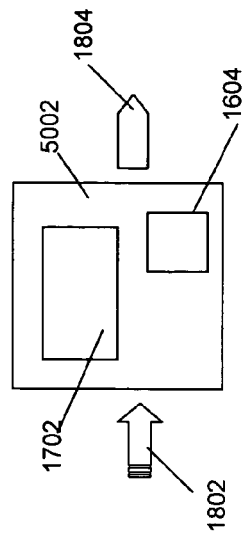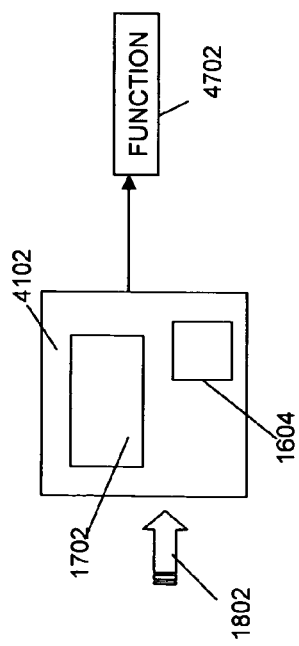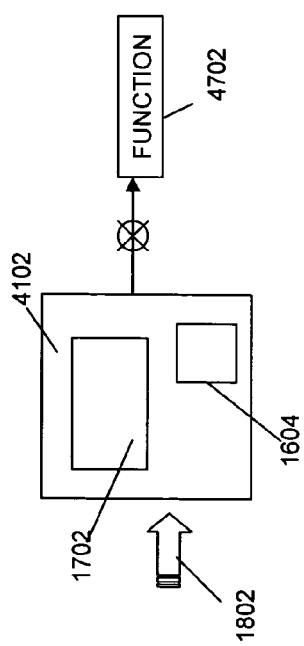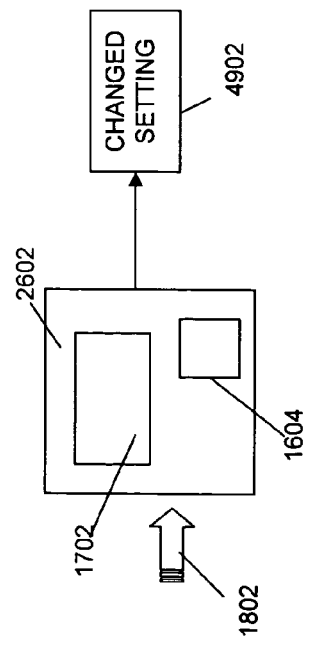

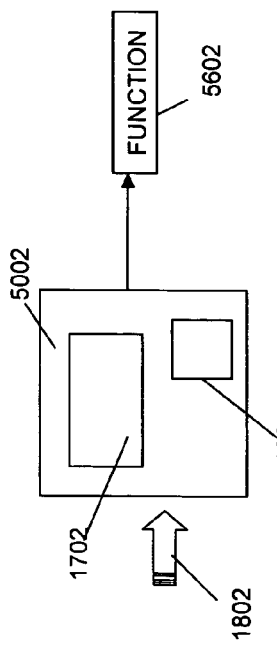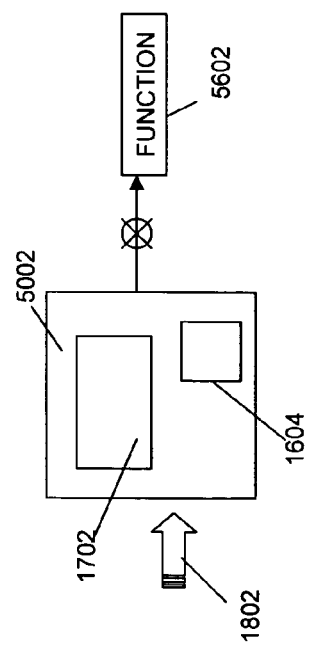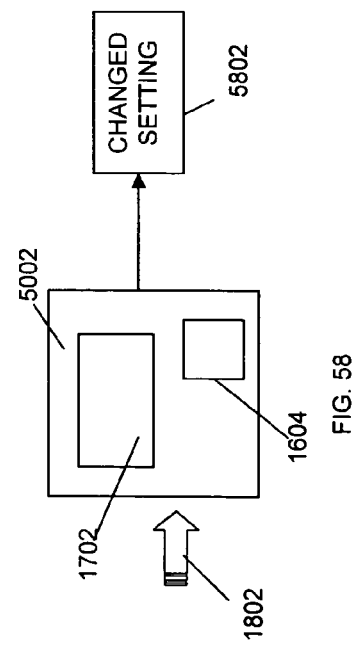

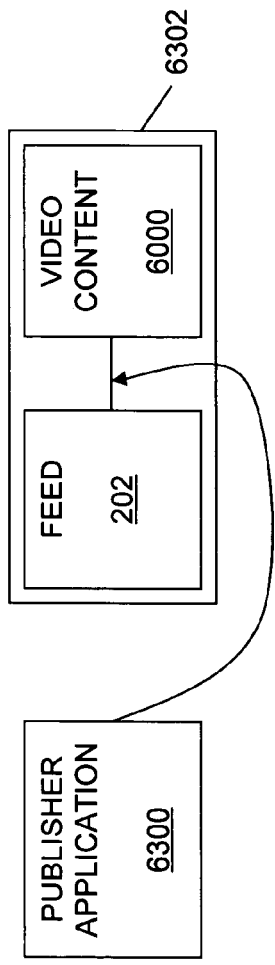
Fig. 63
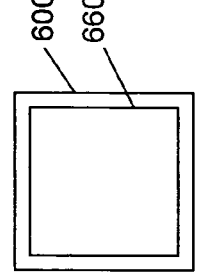
Fig. 66
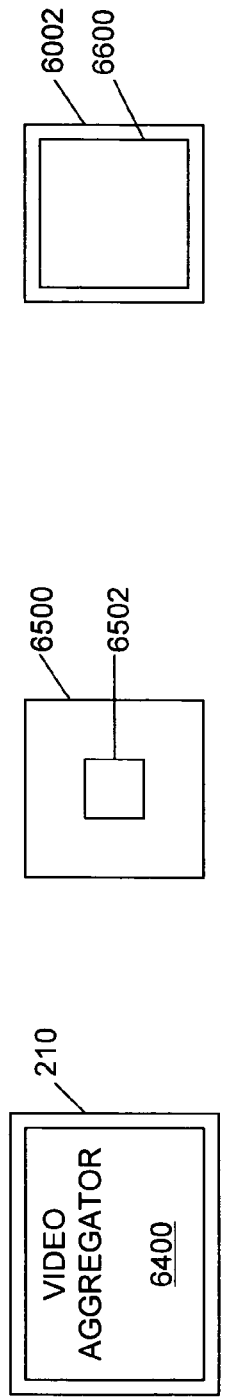
Fig. 64
Fig. 65
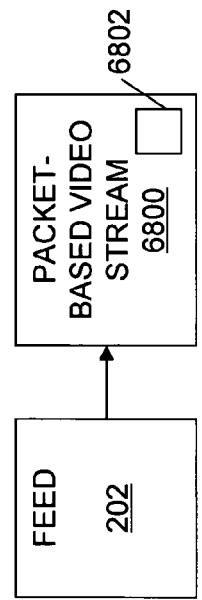
Fig. 68
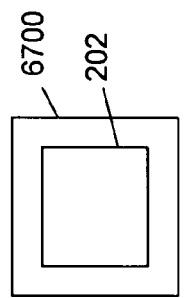
Fig. 67

```
<opml version="1.0>
  <head>
    <title>sample.xml</title>
    <dateCreated>Thu, 16 Dec 2005 03:22:45 GMT</dateCreated>
    <dateModified>Fri, 17 Dec 2005 09:44:15 GMT</dateModified>
    <ownerName>Snargle Kierkegaard</ownerName>
  </head>
  <body>
    <outline title="news">
      <outline text="BREAKING NEWS: Floridian lands world's largest tuna" type="rss" xmlUrl="http://www.foxnews.com/tuna.xml" />
    </outline>
  </body>
</opml>
```

Patient ID = 143943, Lateral view
----
hematologic lab test result = HDL 45 mg/dl
hematologic lab test result = LDL 135 mg/dl
X-ray = ftp://images.local/3245.tif
contact information: John Doe, 1 Main Street, Anytown, MA 00000
health insurance: Blue Cross/Blue Shield, member #123456
SSN: 012-34-567

```
<opml version="1.0">
  <head>
    <title>aggregation of databases, hierarchical lab-test-first view</title>
    <dateCreated>Mon, 05 Dec 2005 10:40:00 GMT</dateCreated>
  </head>
  <body>
    <outline title="hematologic lab test results">
      <outline title="LDL < 100">
        <outline text="Patient #43523">
          <outline title="X-ray images">
            <outline text="ftp://images.local/43245.tif"/>
            <outline text="ftp://images.local/34959.tif"/>
          </outline>
          <outline title="health insurance information">
            <outline text="Blue Cross/Blue Shield #594864"/>
          </outline>
        </outline>
        <outline text="Patient #54343">
          <outline title="X-ray images">
            <outline text="ftp://images.local/54748.tif"/>
          </outline>
          <outline title="health insurance information">
            <outline text="Medicare A #574822"/>
            <outline text="Medicare Supplement #3849234"/>
          </outline>
        </outline>
      </outline>
      <outline title="LDL 100 to 189">
        ...
      </outline>
      <outline title="LDL > 189">
        ...
      </outline>
    </outline>
  </body>
</opml>
```

Fig. 83

SECURITY SYSTEMS AND METHODS FOR USE WITH STRUCTURED AND UNSTRUCTURED DATA

CROSS-REFERENCE TO RELATED APPLICATIONS

This application is a continuation-in-part of U.S. patent application Ser. No. 11/223,826, filed on Sep. 10, 2005, and entitled ENHANCED SYNDICATION.

This application also claims the benefit of the following commonly owned U.S. Provisional Applications, each of which is hereby incorporated by reference in its entirety:

Ser. No. 60/649,311, filed on Feb. 1, 2005, and entitled DATA STREAM MANAGEMENT.

Ser. No. 60/649,312, filed on Feb. 1, 2005, and entitled DATA STREAM MANAGEMENT SOFTWARE.

Ser. No. 60/649,504, filed on Feb. 2, 2005, and entitled RSS MEDIA PROCESSING SYSTEMS.

Ser. No. 60/649,502, filed on Feb. 2, 2005, and entitled SEMANTIC PROCESSING.

Ser. No. 60/657,840, filed on Mar. 1, 2005, and entitled USER INTERFACES AND WORKFLOWS FOR USE WITH DATA STREAM MANAGEMENT SYSTEMS.

Ser. No. 60/594,298, filed on Mar. 26, 2005, and entitled USES OF METADATA IN A STRUCTURED DATA FEED ENVIRONMENT.

Ser. No. 60/594,416, filed on Apr. 6, 2005, and entitled DATA STREAM MANAGEMENT.

Ser. No. 60/669,666, filed on Apr. 8, 2005, and entitled DATA STREAM MANAGEMENT.

Ser. No. 60/594,456, filed on Apr. 10, 2005, and entitled FUNCTIONAL SEARCH OUTLINES.

Ser. No. 60/594,478, filed on Apr. 12, 2005, and entitled DATA STREAM MANAGEMENT.

Ser. No. 60/673,661, filed on Apr. 20, 2005, and entitled DATA STREAM MANAGEMENT.

Ser. No. 60/680,879, filed on May 13, 2005, and entitled DATA STREAM SECURITY SYSTEMS.

Ser. No. 60/684,092, filed on May 23, 2005, and entitled FUNCTIONAL SEARCH OUTLINES.

Ser. No. 60/685,904, filed on May 31, 2005, and entitled WIRELESS DELIVERY OF RSS CONTENT.

Ser. No. 60/686,630, filed on Jun. 2, 2005, and entitled DATA STREAM ADVERTISING.

Ser. No. 60/688,826, filed on Jun. 9, 2005, and entitled USES OF OUTLINES AND STRUCTURED DATA.

Ser. No. 60/694,080, filed on Jun. 24, 2005, and entitled USES OF LISTS, OUTLINES AND STRUCTURED DATA.

Ser. No. 60/695,029, filed on Jun. 28, 2005, and entitled EVALUATION OF DATA FEED CONTENT.

Ser. No. 60/699,631, filed on Jul. 15, 2005, and entitled OPML SEARCH ENGINES AND SUPERSERVICES.

Ser. No. 60/700,122, filed on Jul. 18, 2005, and entitled WEB SUPERSERVICES.

Ser. No. 60/702,467, filed on Jul. 26, 2005, and entitled VERTICAL MARKETS AND FEATURES FOR ENHANCED WEB SYSTEMS.

Ser. No. 60/703,688, filed on Jul. 29, 2005, and entitled OPML SYSTEMS.

Ser. No. 60/703,535, filed on Jul. 29, 2005, and entitled OPML CONVERTER.

Ser. No. 60/703,544, filed on Jul. 29, 2005, and entitled OPML SEARCH ENGINE.

Ser. No. 60/709,683, filed on Aug. 19, 2005, and entitled USER INTERFACES FOR OPML SEARCH ENGINES.

Ser. No. 60/719,073, filed on Sep. 21, 2005, and entitled WEB SUPERSERVICES.

Ser. No. 60/719,283, filed on Sep. 21, 2005, and entitled HEALTH CARE INFORMATION MANAGEMENT.

Ser. No. 60/719,284, filed on Sep. 21, 2005, and entitled OPML ROUTERS.

Ser. No. 60/720,250, filed on Sep. 22, 2005, and entitled BEHAVIORAL METADATA IN SYNDICATION AND STRUCTURED DATA ENVIRONMENTS.

Ser. No. 60/721,803, filed on Sep. 28, 2005, and entitled WEB SUPERSERVICES.

Ser. No. 60/722,021, filed on Sep. 29, 2005, and entitled INFORMATION POOLS.

Ser. No. 60/724,956, filed on Oct. 7, 2005, and entitled HEATH CARE INFORMATION MANAGEMENT.

Ser. No. 60/725,166, filed on Oct. 7, 2005, and entitled COMPUTER PROGRAMS FOR SEARCH, MANAGEMENT, AND USE OF OUTLINES.

Ser. No. 60/726,542, filed on Oct. 14, 2005, and entitled RSS ENABLED DEVICES.

Ser. No. 60/726,731, filed on Oct. 14, 2005, and entitled SEMICONDUCTER-BASED SYNCIDATION AND OUTLINING.

Ser. No. 60/726,727, filed on Oct. 14, 2005, and entitled SYNDICATION FILTERS.

Ser. No. 60/734,187, filed on Nov. 6, 2005, and entitled OPML SYSTEMS.

Ser. No. 60/734,156, filed on Nov. 6, 2005, and entitled NOTIFICATION SERVICES FOR USE WITH OUTLINING AND SYNDICATION.

Ser. No. 60/735,712, filed on Nov. 11, 2005, and entitled OPML PROCESSING MODULES AND SYSTEMS.

Ser. No. 60/741,770, filed on Dec. 1, 2005, and entitled NAVIGATION AND MANIPULATION OF DISTRIBUTED CONTENT.

Ser. No. 60/741,958, filed on Dec. 2, 2005, and entitled DATABASES USING OPML-BASED CONTENT POOLS AND SYNDICATED CONTENT.

Ser. No. 60/742,975, filed on Dec. 6, 2005, and entitled SYNDICATED DATA IN MEDICAL DECISION MAKING.

Ser. No. 60/749,757, filed on Dec. 13, 2005, and entitled AN ENTERPRISE PLATFORM FOR ENHANCED SYNDICATION.

Ser. No. 60/750,291, filed on Dec. 14, 2005, and entitled CREATING AND MANAGING VIEWS OF SYNDICATED INFORMATION.

Ser. No. 60/751,254, filed on Dec. 15, 2005, and entitled SYNDICATED TELECOMMUNICATION SERVICES.

Ser. No. 60/751,249, filed on Dec. 16, 2005, and entitled USE OF SYNDICATED DATA WITHIN INSTITUTIONAL HEALTHCARE PRACTICES.

Ser. No. 60/753,959, filed on Dec. 23, 2005, and entitled METHODS AND SYSTEMS FOR CREATING AND MANAGING VIEWS OF SYNDICATED INFORMATION VIA A COMMUNICATIONS NETWORK.

Ser. No. 60/756,774, filed on Jan. 6, 2006, and entitled COMPOSITE SERVICE VISUALIZATION TOOLS.

Ser. No. 60/759,483, filed on Jan. 16, 2006, and entitled USE OF SYNDICATED DATA WITHIN HEALTHCARE PROVIDER AND GROUP PRACTICES.

BACKGROUND

1. Field of Invention

The invention relates to hardware, software and electronic service components and systems to provide large-scale, reliable, and secure foundations for distributed databases and content management systems, combining unstructured and structured data, and allowing post-input reorganization to achieve a high degree of flexibility.

2. Description of Related Art

One can envision highly distributed databases capable of managing simultaneous participation by billions of users, and highly distributed content management systems coordinating the contributions of billions, routinely integrating the contributions of both people and machines, and spanning multiple organizations, firms, and the globe itself. One can imagine flexible systems, where data is input in unstructured as well as structured forms, and subsequent users can access and present the data in flexible, evolving forms not anticipated at the point of data entry. Massively parallel processing—envisioned as occurring inside one machine or cluster of machines—was once the premier challenge facing the database and content management community. The new challenge, in our view, is massively parallel, and flexible, participation of billions.

In order to accomplish this, the world will need a new "business ecosystem." Advances in information technology often show three related themes that may be thought of as analogous to the biological processes of expansion of and species succession in natural ecosystems. First, non-expert end-users will be empowered to solve problems. Second, technology platforms will be created that modularize technology contributions into niches. The niche contributions interrelate with each other through standard protocols and interfaces that are made "open" to technologists and the general public, so that tens, hundreds, and sometimes millions of innovators can contribute to the resulting business ecosystem, each according to his or her choice, creativity and competence. In turn new niches will be established, opened-up, and will bring in further new contributors and contributions.

As the business ecosystem expands, some specific technological components will become critical enablers to the continuing advance of the whole. Issues of flexibility, scale, reliability, and security will become vital to the community. These vital components, for example microprocessors, storage controllers, and network devices in the personal computer ecosystem, will require systematic application of research and development, capital investment, and coordination with industry partners in order that the whole ecosystem can progress. If the world is to make real the vision of the flexible participation of billions, there are a number of core components and systems that have not been invented, and will need to be invented.

The flexible participation of billions has been presaged by blogging—that is, the act of individuals creating Web sites and adding to them more or less daily. By dramatically increasing production and sharing of Web-based content, the blogging movement now produces a virtual river of content—available continuously and with global circulation. Just as word processing empowered millions to create their own documents, blogging software has made it relatively easy for millions to produce their own Web sites and keep them continually updated. By the promotion of a simple underlying standard for sharing text and other media, blogging has popularized the "syndication" or passing on of content borrowed from others—extending the reach of any given blogger and further increasing the total quantity of information in circulation.

A number of companies have emerged as niche players targeting various aspects of large-scale distributed databases, content management, and group participation. For example, some companies such as FeedDemon, NewsGator, myYahoo (Yahoo), and Bloglines have focused on client-side aggregation and presentation. Companies such as Technorati, Google, and Feedster have focused on the complementary services of searching for data feeds of interest. Other companies have focused on technologies for providing syndicated data streams such as SixApart, Drupal, TypePad, Flickr, Picasa (Google), and Blogger (Google). Other companies have positioned themselves as content providers, including new companies such as Engadget, Weblogs Inc., Topix.net, and MySpace, as well as established media companies such as the New York Times and BBC. Of course, various generic Internet technologies are also relevant to the rapidly growing weblog data flow, such as BitTorrent or Akamai's EdgePlatform.

While offering significant advancement in terms of experiences such as sharing news, music, videos and other items, as well as enabling players of games to interact with each other individually and in groups, the value chain is weak, fragmented, and closed to interoperability among contributors in many areas. The value chain will benefit from both improved contributions in specific functions or niches, as well as a more comprehensive overall vision of a possible "flexible participations of billions" ecosystem, additional niches (layers and modules) of functionality, recast functionality among modules, rationalization of protocols and interfaces among modules, and custom combinations of functions that establish end-to-end solutions for specific purposes. For example, available services are weak in presentation, search, signal, and network routing. Aggregators that centralize content use display formats that are widely criticized, despite a general agreement among users that they improve over conventional search engine displays. Storage of most blog content is in proprietary, isolated data sets controlled by blog service operators, and the data cannot be easily restructured or even moved from one provider to another. In their current form, services fail to provide enterprise-class features such as security, privacy, data integrity, and quality of service.

There remains a vital need for components and services that explicitly address the challenge of enabling the "flexible participation of billions" and that are capable of levels of scale, reliability, security and flexibility as yet unrealized and perhaps unimagined. There is a need for a new global business ecosystem, within which innovation by millions of people will be embraced, in order to meet the challenge. In order to stimulate the formation and rapid evolution of such a business ecosystem, there will have to be systematic development of general purpose software, systems and protocols specifically engineered to enable the flexible participation of billions.

SUMMARY OF THE INVENTION

Disclosed herein are systems and methods including hardware, software and electronic service components and systems to provide large-scale, reliable, and secure foundations for distributed databases and content management systems combining unstructured and structured data, and allowing post-input reorganization to achieve a high degree of flexibility.

A method and system disclosed herein may include providing a record including a first data item and a second data item, the first data item including personal data and the second data item including non-personal data; transmitting the first data item to a secure data pool; and transmitting the second data item to an unsecure data pool.

In embodiments, the first data item may include one or more of a name, birth date, social security number, bank account, and/or password. The second data item may include medical data. The secure data pool may provide conditional access to content. The conditional access may include password-based access, role-based access, conditional read access, or conditional write access.

In embodiments, the record may include one or more of a medical record, a financial record, a psychological record, or a tax record. The unsecure data pool may be available for public use. The unsecure data pool may be available for use within an enterprise.

In embodiments, the first data may be syndicated data. The syndicated data may be structured. The structure may be enabled by OPML. The syndicated data may be published by a device. The syndicated data may be accessed by a user interface configured to display the information on a device.

In embodiments, the storing a relationship may be between the first data item and the second item in an OPML document. The transmitting of the OPML document may be to the unsecure data pool. The transmitting of the OPML document may be to the secure data pool.

A method and system disclosed herein may include providing a record including a first data item and a second data item; storing the first data item in a first pool.

Storing the second data item in a second pool; expressing a relationship between the first data item and the second data item in a file external to the first pool and the second pool.

In embodiments, the access to the first pool may be controlled by a security layer. The content in the first pool may include syndicated content with message-level encryption. The content in the first pool may include syndicated content with tag-level encryption. The content in the first pool may include syndicated content with channel-level encryption. The security layer may employ an Active Directory service. The file may be encrypted. The file may include a password for accessing at least one of the first item and the second item.

In embodiments, the first data item may include a syndicated message. The syndicated message may include an RSS message or an OPML file. The syndicated message may be published by a device or may be accessed by a user interface configured to display the information on a device.

In embodiments, the file may be an OPML file. The file may include an outline processing markup language. The file may be an XML file. The elements of the record including the first data item and the second data item may be uniquely identified. The method and system may further include spidering the first pool and the second pool to index data items associated with the record. The first pool and second pool may be physically separated. The first pool and second pool may be remote from one another.

A method and system disclosed herein may include providing encoded syndicated information; and associating a decoder with a collection facility, wherein the decoder is adapted to automatically decode the encoded syndicated information.

In embodiments, the collection facility may be adapted to search for encoded data. The encoded data may contain at least one searchable attribute. The at least one searchable attribute may be unsecure. The at least one searchable attribute may require decoding.

In embodiments, the encoded syndication information may comprise healthcare information. In embodiments, the encoded syndicated information may include tag-level security, message-level security, or channel-level security. In embodiments, the syndicated information may be provided in at least one pool. In embodiments, the syndicated information may be structured. The structure maybe enabled by OPML. The syndicated information may be published by a device.

The syndicated information may be accessed by a user interface configured to display the information on a device.

A method and system disclosed herein may include collecting syndicated information through a secure data stream.

A method and system disclosed herein may include providing a device-based facility for subscribing to syndicated information; and providing a local security facility associated with the device that permits a user of the device to access the syndicated information.

In embodiments, the method and system may further comprising providing a second security facility for allowing access to the syndicated information. The syndicated information may be in an RSS format. The syndicated information may be in an OPML format.

In embodiments, the device may be a medical device, a medical instrument, a handheld medical device, a cell phone, or a PDA.

In embodiments, the device may be associated with an operating room. The device may be configured to display an electronic medical record. The device may be configured to run a health care software application. The device may be associated with a hospital environment. The device may be used to examine a health condition. The device may be used to measure an environmental condition of a healthcare environment.

In embodiments, the syndicated information may reside in at least one pool. The syndicated information may be structured. The structure may be enabled by OPML. The syndicated information may be published by a device. The syndicated information may be accessed by a user interface configured to display the information on a device.

A method and system disclosed herein may include providing a device-based facility for publishing syndicated information; and providing a local security facility associated with the device that permits a user of the device to publish the syndicated information.

In embodiments, the method and system may further comprising providing a second security facility for allowing a subscriber to access the syndicated information under conditions specified by the user of the device.

In embodiments, the syndicated information may be in an RSS format. The syndicated information may be in an OPML format.

In embodiments, the device may be a medical device, a medical instrument, a handheld medical device, a cell phone, or a PDA.

In embodiments, the device may be associated with an operating room. The device may be configured to display an electronic medical record. The device may be configured to run a health care software application. The device may be associated with a hospital environment. The device may be used to examine a health condition. The device may be used to measure an environmental condition of a healthcare environment.

In embodiments, the syndicated information may reside in at least one pool. The syndicated information may be structured. The structure may be enabled by OPML. The syndicated information may be published by a device. The syndicated information may be accessed by a user interface configured to display the information on a device.

A method and system disclosed herein may include receiving syndicated data; displaying the syndicated data; and destroying the syndicated data after display.

In embodiments, the method and system may further comprise certifying the destruction of the syndicated data.

In embodiments, the method and system may further comprise certifying the destruction of the syndicated to an authority.

In embodiments, the syndicated data may be received from at least one pool. The syndicated data may be structured. The structure may be enabled by OPML. The syndicated information may be published by a device.

In embodiments, the syndicated information may be accessed by a user interface configured to display the information on a device.

A method and system disclosed herein may include providing a set of pools of data configured to be syndicated for use by one or more subscription facilities; and optimizing the location of the pools on a network to facilitate rapid access by frequent subscribers.

In embodiments, the pools may be pools of health care data. The pools may be configured with redundancy in order to maintain accessibility in the event of damage to one of the pools. The pools may be configured to allow rapid access to portions of a medical record that may be stored in separate pools. Requests for information in the pools may be routed according to the configuration of a network.

In embodiments, there may be a plurality of redundant pools. The record request may span one or more pools. The record request may be routed to pools according to network parameters, where the network parameters may be geographic proximity, congestion, latency or, routing efficiency. The record request may assemble a single item from a plurality of redundant pools.

In embodiments, the syndication configuration may involve structuring the data. The structure may be enabled by OPML.

A security method and system disclosed herein may include providing a plurality of pools of information suitable for syndication; and associating with one or more of the pools a security facility that is based on the domain of the pool.

In embodiments, the domain may consist of the entity that publishes the pool. The domain may consist of an area of authorization with respect to the information in the pool. The domain may consist of a network domain. The domain may consist of the type of data in the pool. The type of data may be a type determined in relation to compliance with a regulation. The regulation may be a privacy regulation.

A method and system disclosed herein may include providing a user interface for aggregating syndicated health care data, wherein the user interface may allow a user to search, filter and cluster health care data from a plurality of syndicated information sources.

A method and system disclosed herein may include providing an engine for aggregating syndicated health care data, wherein the engine may support a user interface that may allow a user to search, filter and cluster health care data from a plurality of syndicated information sources.

A method and system disclosed herein may include providing a data facility for healthcare information, wherein the data facility may provide a structure for subscribing to syndicated healthcare data, wherein a user may modify the structure through which the user accesses the syndicated health care data.

In embodiments, the structure may be enabled by OPML. The data may be stored in pools. A security facility may be associated with the structure, so that only a permitted user may modify the structure. The security facility may be associated with the data, so that only a permitted user may access the health care data.

A method and system disclosed herein may include storing syndicated data in a first data pool; replicating the syndicated data; and storing the replicated syndicated data in a second data pool.

In embodiments, the first data pool may be associated with a first server. The second data pool may be associated with a second server.

In embodiments, write access may be coordinated between the first data pool and the second data pool. The method and system may further comprise providing a transaction lock for active content to prohibit concurrent access by more than one user.

In embodiments, the recover dead link may be from a redundant/alternative location.

In embodiments, the syndicated data may be structured. The structure may be enabled by OPML. The syndicated data may be published by a device. The syndicated data may be accessed by a user interface configured to display the information on a device.

A method and system disclosed herein may allow a user anonymous access to health care data by including disposing the health care data in a secure pool; generating a secure key that may allow a user access to the secure pool; providing the user the key; and certifying the destruction of the record that the user may have access to the key.

In embodiments, the key may allow time-based user access.

In embodiments, the health care data may be in a syndicated data structured. The structure may be enabled by OPML. The syndicated data may be published by a device. The syndicated data may be accessed by a user interface configured to display the information on a device.

A method and system disclosed herein of publishing authenticated health care data may include disposing health care data into a plurality of pools, the health care data being disposed by authenticated sources; and syndicating the data, wherein the syndicated data may be associated with an authentication certificate that certifies that the data may have been published by an authenticated pool.

In embodiments, the method and system may further comprise aggregating authenticated data from multiple pools.

In embodiments, the syndicated data may be structured. The structure may be enabled by OPML. The syndicated data may be published by a device. The syndicated data may be accessed by a user interface configured to display the information on a device.

A method and system disclosed herein of anonymous publication may include storing data into a plurality of data storage facilities; authenticating the identity of the entity storing the data; de-identifying the data; and syndicating the data.

In embodiments, the method and system may further comprise providing a certification of the authenticity of the data without revealing the identity of the publisher.

In embodiments, the data storage facilities may be pools. The identity of the entity storing the data may be recovered upon satisfaction of certain conditions. The conditions may be legal conditions.

A method and system disclosed herein may include receiving a request for a data feed from a requester; processing the request to provide responsive content; and publishing the responsive content as the data feed.

In embodiments, the processing may include determining an identity of the requester. The processing may include determining an access privilege of the requester. The processing may include accessing non-syndicated data. The non-syndicated data may be a relational database, a file, or a secure data facility. The processing may include accessing one or more pools.

Each aspect of the foregoing may be embodied in one or more of a client-side application, a server-side application, one or more semiconductor devices, a computer program product embodied in a computer readable medium, a web service, a services-oriented architecture service, an applet, or an application, either alone or in combination. Further, each of the foregoing systems may also, or instead, be embodied in a method, or in a computer program product embodied in a computer readable medium, that, when executing on one or more computers, performs the steps of such a method.

The terms "feed", "data feed", "data stream" and the like, as well as the S-definition described further below, as used herein, are intended to refer interchangeably to syndicated data feeds and/or descriptions of such feeds. While RSS is one popular example of a syndicated data feed, any other source of news or other items may be used with the systems described herein, such as the outlining markup language, OPML; these terms should be given the broadest possible meaning unless a narrow sense is explicitly provided or clear from the context. Similarly, terms such as "item", "news item", "post", "message" and the like, as well as the S-messages described further below, are intended to refer to items within a data feed and may contain text and/or binary data encoding any digital media, including still or moving images, audio, application-specific file formats, and so on. These "attachments" or "enclosures" may encapsulate non-syndicated content from any source, or having any format, for association with a syndicated medium such as a feed.

The term "syndication" is intended to refer to publication, republication, or other distribution of feeds, data feeds, or data streams, as described above, or any other content, using any suitable technology, including RSS and any extensions or modifications thereto, such as the enhanced syndication functions and features described below, as well as any other publish-subscribe or similar technology that may be suitably adapted to the methods and systems described herein. "Syndicated" is intended to describe content in syndication.

BRIEF DESCRIPTION OF THE FIGURES

The foregoing and other objects and advantages of the invention will be appreciated more fully from the following further description thereof, with reference to the accompanying drawings, wherein:

FIG. 8 shows a user interface for a syndication system.

FIG. 9 shows a user interface for a syndication system.

FIG. 16 depicts a syndication-enabled telecommunications device.

FIG. 17 depicts a syndication-enabled telecommunications device with a display.

FIG. 18 depicts a syndication-enabled telecommunications device receiving an RSS feed.

FIG. 19 depicts a syndication-enabled telecommunications device transmitting an RSS feed.

FIG. 20 depicts a syndication-enabled telecommunications device extracting certain information from an RSS feed.

FIG. 21 depicts a syndication-enabled telecommunications device generating an alert.

FIG. 26 depicts a syndication-enabled home appliance transmitting an RSS feed.

FIG. 27 depicts a syndication-enabled home appliance generating an alert.

FIG. 28 depicts a syndication-enabled home appliance communicating with one or more other devices.

FIG. 29 depicts a syndication-enabled home appliance performing a function based on the data contained in the RSS feed.

FIG. 30 depicts a syndication-enabled home appliance ceasing performance of a function based on the data contained in the RSS feed.

FIG. 31 depicts a syndication-enabled home appliance adjusting at least one setting in response to an RSS feed.

FIG. 32 depicts a syndication-enabled entertainment device.

FIG. 33 depicts a syndication-enabled entertainment device with a display.

FIG. 34 depicts a syndication-enabled entertainment device receiving an RSS feed.

FIG. 47 depicts a syndication-enabled mobile electronic device performing a function based on the data contained in the RSS feed.

FIG. 48 depicts a syndication-enabled mobile electronic device ceasing performance of a function based on the data contained in the RSS feed.

FIG. 49 depicts a syndication-enabled mobile electronic device adjusting at least one setting in response to an RSS feed.

FIG. 50 depicts a syndication-enabled computing device.

FIG. 51 depicts a syndication-enabled computing device with a display.

FIG. 52 depicts a syndication-enabled computing device receiving an RSS feed.

FIG. 56 depicts a syndication-enabled computing device performing a function based on the data contained in the RSS feed.

FIG. 57 depicts a syndication-enabled computing device ceasing performance of a function based on the data contained in the RSS feed.

FIG. 58 depicts a syndication-enabled computing device adjusting at least one setting in response to an RSS feed.

FIG. 63 depicts a publisher application and Feed-Video content.

FIG. 64 depicts a video aggregator.

FIG. 65 depicts a remote control for a video device.

FIG. 66 depicts an on-screen interactive menu.

FIG. 67 depicts a video stream.

FIG. 68 depicts a feed as it is converted into a packet-based video stream.

FIG. 81 depicts an OPML file.

FIG. 82 depicts the contents of a flat file representing a lateral view.

FIG. 83 depicts an OPML file representing a hierarchical view.

DETAILED DESCRIPTION

Various embodiments of the present invention are described below, including certain embodiments relating particularly to RSS feeds and other syndicated data streams. It should be appreciated, however, that the present invention is not limited to any particular protocol for data feeds and that the various embodiments discussed explicitly herein are primarily for purposes of illustration. Thus, the term syndication generally, and references to RSS specifically, should be understood to include, for example, RDF, RSS v 0.90, 0.91, 0.9x, 1.0, and 2.0, variously attributable to Netscape, UserLand Software, and other individuals and organizations, as well as Atom from the AtomEnabled Alliance, and any other similar formats, as well as non-conventional syndication formats that can be adapted for syndication, such as OPML. Still more generally, while RSS technology is described, and RSS terminology is used extensively throughout, it will be appreciated that the various concepts discussed herein may be usefully employed in a variety of other contexts. For example, various privacy and identity techniques described herein could be usefully combined with HTML Web content rather than RSS-based XML data. Similarly, some of the branding and advertising techniques described herein may be usefully combined with list servers, bulletin boards, or other Internet news sources. Thus, it will be understood that the embodiments described herein are provided by way of example only and are not intended to limit the scope of the inventive concepts disclosed herein.

Figure 1:
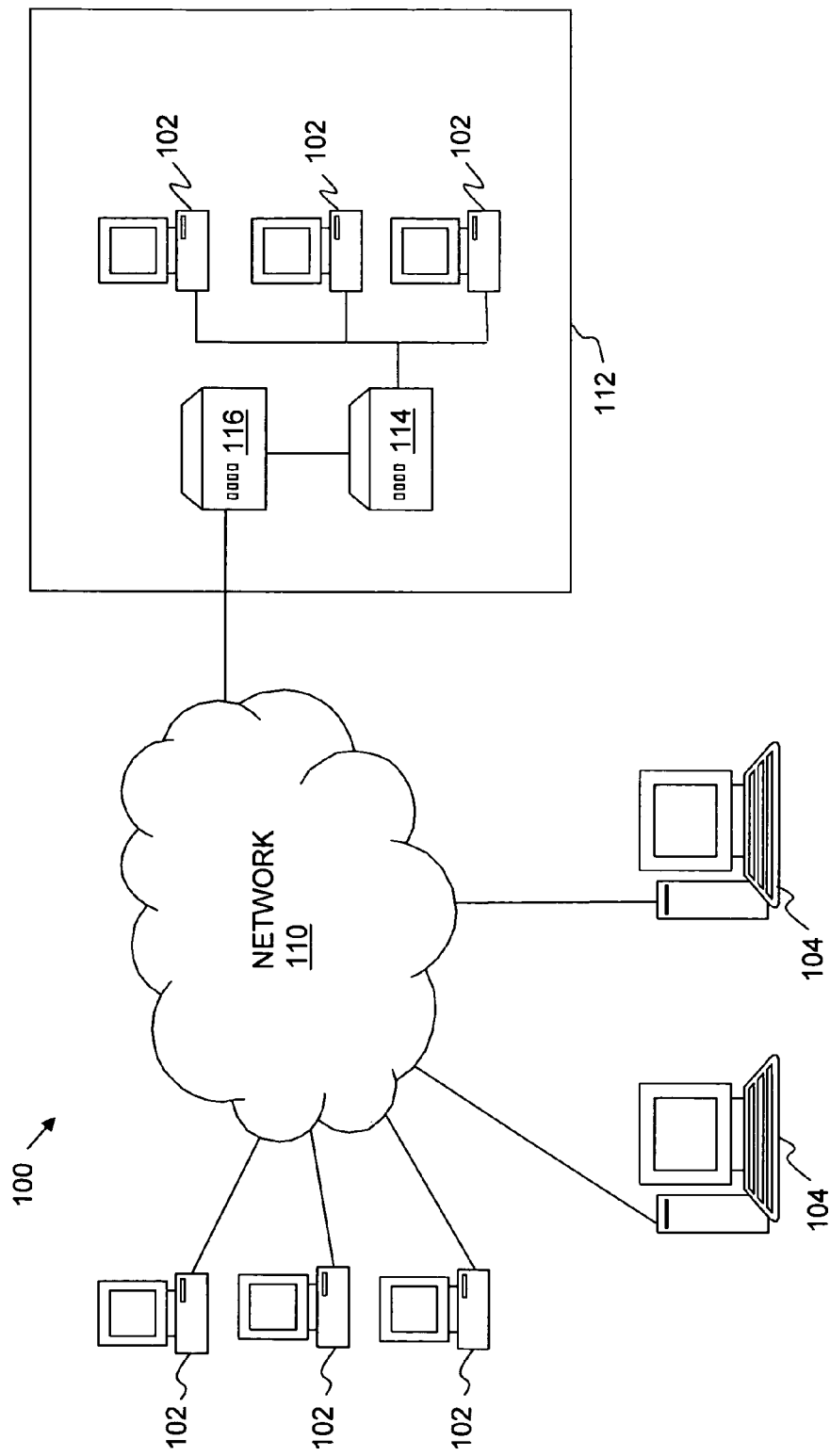
FIG. 1 shows a network that may be used with the systems described herein.

FIG. 1 shows a network for providing a syndicated data stream such as an RSS stream. Short for Really Simple Syndication, RDF (Resource Description Framework) Site Summary or Rich Site Summary, RSS is an XML format for syndicating Web content. A Web site operator who wants to allow other sites to publish some of the Web site's content may create an RSS document and register the document with an RSS publisher. The published or "syndicated" content can then be presented on a different site, or through an aggregator or other system, directly at a client device. Syndicated content may include such data as news feeds, events listings, news stories, headlines, project updates, and excerpts from discussion forums or even corporate information. While RSS content often includes text, other data may also be syndicated, typically in binary form, such as images, audio, and so forth. The systems described herein may use all such forms of data feed. In one embodiment, the XML/RSS feed itself may be converted to binary in order to conserve communications bandwidth. This may employ, for example, Microsoft's DINE specification for binary information or any other suitable binary format.

As shown in FIG. 1, a network 100 may include a plurality of clients 102 and servers 104 connected via an internetwork 110. Any number of clients 102 and servers 104 may participate in such a system 100. The system may further include one or more local area networks ("LAN") 112 interconnecting clients 102 through a hub 114 (in, for example, a peer network such as a wired or wireless Ethernet network) or a local area network server 114 (in, for example, a client-server network). The LAN 112 may be connected to the internetwork 110 through a gateway 116, which provides security to the LAN 112 and ensures operating compatibility between the LAN 112 and the internetwork 110. Any data network may be used as the internetwork 110 and the LAN 112.

In one aspect of the systems described herein, a device within the internetwork 110 such as a router or, on an enterprise level, a gateway or other network edge or switching device, may cache popular data feeds to reduce redundant traffic through the internetwork 110. In other network enhancements, clients 102 may be enlisted to coordinate sharing of data feeds using techniques such as those employed in a BitTorrent peer-to-peer network. In the systems described herein, these and other techniques generally may be employed to improve performance of an RSS or other data feed network.

In one embodiment, the internetwork 110 is the Internet, and the World Wide Web provides a system for interconnecting clients 102 and servers 104 in a communicating relationship through the Internet 110. The internetwork 110 may also, or instead, include a cable network, and at least one of the clients 102 may be a set-top box, cable-ready game console, or the like. The internetwork 110 may include other networks, such as satellite networks, the Public Switched Telephone Network, WiFi networks, WiMax networks, cellular networks, and any other public, private, or dedicated networks that might be used to interconnect devices for transfer of data.

An exemplary client 102 may include a processor, a memory (e.g. RAM), a bus which couples the processor and the memory, a mass storage device (e.g. a magnetic hard disk or an optical storage disk) coupled to the processor and the memory through an I/O controller, and a network interface coupled to the processor and the memory, such as a modem, digital subscriber line ("DSL") card, cable modem, network interface card, wireless network card, or other interface device capable of wired, fiber optic, or wireless data communications. One example of such a client 102 is a personal computer equipped with an operating system such as Microsoft Windows XP, UNIX, or Linux, along with software support for Internet communication protocols. The personal computer may also include a browser program, such as Microsoft Internet Explorer, Netscape Navigator, or FireFox, to provide a user interface for access to the internetwork 110. Although the personal computer is a typical client 102, the client 102 may also be a workstation, mobile computer, Web phone, VOIP device, television set-top box, interactive kiosk, personal digital assistant, wireless electronic mail device, or other device capable of communicating over the Internet. As used herein, the term "client" is intended to refer to any of the above-described clients 102 or other client devices, and the term "browser" is intended to refer to any of the above browser programs or other software or firmware providing a user interface for navigating an internetwork 110 such as the Internet.

An exemplary server 104 includes a processor, a memory (e.g. RAM), a bus which couples the processor and the memory, a mass storage device (e.g. a magnetic or optical disk) coupled to the processor and the memory through an I/O controller, and a network interface coupled to the processor and the memory. Servers may be clustered together to handle more client traffic and may include separate servers for different functions such as a database server, an application server, and a Web presentation server. Such servers may further include one or more mass storage devices such as a disk farm or a redundant array of independent disk ("RAID") system for additional storage and data integrity. Read-only devices, such as compact disk drives and digital versatile disk drives, may also be connected to the servers. Suitable servers and mass storage devices are manufactured by, for example, Compaq, IBM, and Sun Microsystems. Generally, a server 104 may operate as a source of content and provide any associated back-end processing, while a client 102 is a consumer of content provided by the server 104. However, it should be appreciated that many of the devices described above may be configured to respond to remote requests, thus operating as a server, and the devices described as servers 104 may operate as clients of remote data sources. In contemporary peer-to-peer networks and environments such as RSS environments, the distinction between clients and servers blurs. Accordingly, as used herein, the term "server" as used herein is generally intended to refer to any of the above-described servers 104, or any other device that may be used to provide content such as RSS feeds in a networked environment.

In one aspect, a client 102 or server 104 as described herein may provide OPML-specific functionality or, more generally, functionality to support a system using outlining grammar or markup language with processing, storage, search, routing, and the like.

For example, the network 100 may include an OPML or RSS router. While the following discussion details routing of OPML content, it will be understood that the system described may also, or instead, be employed for RSS or any other outlined or syndicated content. The network 100 may include a plurality of clients 102 that are OPML users and a number of servers 104 that are OPML sources connected via an internetwork 110. Any number of clients 102 and servers 104 may participate in such a network 100. A device within the internetwork 110 such as a router or, on an enterprise level, a gateway or other network edge or switching device, may cache popular data feeds to reduce redundant traffic through the internetwork 110. In other network enhancements, clients 102 may be enlisted to coordinate sharing of data feeds using techniques such as those employed in a BitTorrent peer-to-peer network. In the systems described herein, these and other techniques generally may be employed to improve performance of an OPML data network.

A router generally may be understood as a computer networking device that forwards data packets across an internetwork through a process known as routing. A router may act as a junction between two networks, transferring data packets between them and validating that information is sent to the correct location. Routing most typically is associated with Internet Protocol (IP); however, specialized routers exist for routing particular types of data, such as ADSL routers for asynchronously routing signals across digital subscriber lines. An OPML router may route data across an internetwork, such as the Internet, which may include data in OPML format. In particular, the OPML router may be configured to route data in response to or in correspondence with the structure or the content of an OPML document; that is, various species of OPML router may be provided that correspond to user-developed outline structures in OPML. For example, a financial services OPML outline may correspond to a financial services OPML router that is configured to route financial services data packets among constituent networks of one or more financial services institutions.

An OPML router may use a configuration table, also known as a routing table, to determine the appropriate route for sending a packet, including an OPML data packet. The configuration table may include information on which connections lead to particular groups of addresses, connection priorities, and rules for handling routine and special types of network traffic. In embodiments, the configuration table is dynamically configurable in correspondence to the incoming structure of an OPML data packet; that is, an OPML structure may be provided that includes routing instructions that are automatically executed by the OPML router. In other embodiments, a configuration table is configured to route particular portions of an OPML-structured document to particular addresses. In embodiments an OPML router includes rules that can be triggered by OPML content, such as rules for prioritizing nodes, rules for routing OPML content to particular locations, and the like. The rules may be triggered by the structure of an OPML document, the title, or one or more content items within the OPML document.

In the process of transferring data between networks, an OPML router may perform translations of various protocols between the two networks, including, for example, translating data from one data format to another, such as taking RSS input data and outputting data in another format. In embodiments the OPML router may also protect networks from one another by preventing the traffic on one from unnecessarily spilling over to the other, or it may perform a security function by using rules that limit the access that computers from outside the network may have to computers inside the network. The security rules may be triggered by the content of the OPML document, the structure of an OPML document, or other features, such as the author, title, or the like. For example, an OPML router may include an authentication facility that requires an OPML document to contain a password, a particular structure, an embedded code, or the like in order to be routed to a particular place. Such a security feature can protect networks from each other and can be used to enable features such as version control.

OPML routers may be deployed in various network contexts and locations. An OPML edge router may connect OPML clients to the Internet. An OPML core router may serve solely to transmit OPML and other data among other routers. Data traveling over the Internet, whether in the form of a Web page, a downloaded file or an e-mail message, travels over a packet-switching network. In this system, the data in a message or file is broken up into packages approximately 1,500 bytes long. Each of these packages has a "wrapper" that includes information on the sender's address, the receiver's address, the package's place in the entire message, and how the receiving computer can be sure that the package arrived intact. Each data package, called a packet, is then sent off to its destination via the best available route. In embodiments, the OPML router determines the best available route taking into account the structure of the OPML document, including the need to maintain associations among packets. A selected route may be taken by all packets in the message or only a single packet in a message. By packaging data in this manner, a network can continuously balance the data load on its equipment. For example, if one component of a network is overloaded or malfunctioning, data packets may be routed for processing on other network equipment that has a lighter data load and/or is properly working. An OPML router may also route OPML content according to semantic structure. For example, an OPML router configured to handle medical records may route X-Rays to an expert in reading X-Rays while routing insurance information to another department of a hospital.

Routers may reconfigure the paths that data packets take because they look at the information surrounding the data packet and can communicate with each other about line conditions within the network, such as delays in receiving and sending data and the overall traffic load on a network. An OPML router may communicate with other OPML routers to determine, for example, whether the entire structure of an OPML document was preserved or whether recipients of a particular component in fact received the routed component. Again, the OPML document itself may include a structure for routing it. A router may also locate preferential sources for OPML content using caching and other techniques. Thus, for example, where an OPML document includes content from an external reference, the external reference may be a better source for that portion of the OPML document based upon an analysis of, e.g., network congestion, geographic proximity, and the like.

An OPML router may use a subnet mask to determine the proper routing for a data packet. The subnet mask may employ a model similar to IP addressing. This tells the OPML router that all messages in which the sender and receiver have an address sharing the first three groups of numbers are on the same network and shouldn't be sent out to another network. For example, if a computer at address 15.57.31.40 sends a request to the computer at 15.57.31.52, the router will match the first three groups in the IP addresses (15.57.31) and keep the packet on the local network. OPML routers may be programmed to understand the most common network protocols. This programming may include information regarding the format of addresses, the format of OPML documents, the number of bytes in the basic package of data sent out over the network, and the method which insures all the packages reach their destination and get reassembled, including into the structure of an OPML document, if desired.

There are two major routing algorithms in common use: global routing algorithms and decentralized routing algorithms. In decentralized routing algorithms, each router has information about the routers to which it is directly connected but does not know about every router in the network. These algorithms are also known as DV (distance vector) algorithms. In global routing algorithms, every router has complete information about all other routers in the network and the traffic status of the network. These algorithms are also known as LS (link state) algorithms. In LS algorithms, every router identifies the routers that are physically connected to them and obtains their IP addresses. When a router starts working, it first sends a "HELLO" packet over the network. Each router that receives this packet replies with a message that contains its IP address. All routers in the network measure the delay time (or any other important parameters of the network, such as average traffic) for its neighboring routers within the network. In order to do this, the routers send echo packets over the network. Every router that receives these packets replies with an echo reply packet. By dividing round trip time by two, routers can compute the delay time. This delay time includes both transmission and processing times (i.e., the time it takes the packets to reach the destination and the time it takes the receiver to process them and reply). Because of this inter-router communication, each OPML router within the network knows the structure and status of the network and can use this information to select the best route between two nodes of a network.

The selection of the best available route between two nodes on a network may be done using an algorithm, such as the Dijkstra shortest path algorithm. In this algorithm, an OPML router, based on information that has been collected from other OPML routers, builds a graph of the network. This graph shows the location of OPML routers in the network and their links to each other. Every link is labeled with a number called the weight or cost. This number is a function of delay time, average traffic, and sometimes simply the number of disparate links between nodes. For example, if there are two links between a node and a destination, the OPML router chooses the link with the lowest weight.

Closely related to the function of OPML routers, OPML switches may provide another network component that improves data transmission speed in a network. OPML switches may allow different nodes (a network connection point, typically a computer) of a network to communicate directly with one another in a smooth and efficient manner. Switches that provide a separate connection for each node in a company's internal network are called LAN switches. Essentially, a LAN switch creates a series of instant networks that contain only the two devices communicating with each other at that particular moment. An OPML switch may be configured to route data based on the OPML structure of that data.

In one embodiment, an OPML router may be a one-armed router used to route packets in a virtual LAN environment. In the case of a one-armed router, the multiple attachments to different networks are all over the same physical link. OPML routers may also function as an Internet gateway (e.g., for small networks in homes and offices), such as where an Internet connection is an always-on broadband connection like cable modem or DSL.

The network 100 may also, or instead, include an OPML server, as described in greater detail below. OPML, which may, for example, be encapsulated within an RSS data feed, may contain one or more RSS channel identifiers or items, or may be a separate document, has the general format shown in the OPML specification hosted at www.opml.org/spec, the entire contents of which is incorporated herein by reference. The structure generally includes OPML delimiters, general authorship and creation data, formatting/viewing data (if any), and a series of outline entries according to a knowledge structure devised by the author.

An OPML server may be provided for manipulating OPML content. The OPML server may provide services and content to clients 102 using, for example, a Web interface, an API, an XML processing interface, an RSS feed, an OPML renderer, and the like.

The OPML server may, for example, provide a search engine service to visitors. Output from the OPML server may be an OPML file, an HTML file, or any other file suitable for rendering to a client device or subsequent processing. The file may, for example, have a name that explicitly contains the search query from which it was created in order to facilitate redistribution, modification, recreation, synchronization, updating, and storage of the OPML file. A user may also manipulate the file, such as by adding or removing outline elements representing individual search results, or by reprioritizing or otherwise reorganizing the results, and the user may optionally store the revised search as a new OPML file. Thus in one aspect the OPML server may create new, original OPML content based upon user queries submitted thereto. In a sense, this function is analogous to the function of aggregators in an RSS syndication system, where new content may be dynamically created from a variety of different sources and republished in a structured form.

The OPML server may, more generally, provide a front-end for an OPML database that stores OPML content. The OPML database may store OMPL data in a number of forms, such as by casting the OPML structure into a corresponding relational database where each OPML file is encapsulated as one or more records. The OPML database may also store links to external OPML content or may traverse OPML content through any number of layers and store data, files, and the like externally referenced in OPML documents. Thus, for example, where an OPML file references an external OPML file, the external OPML file may be retrieved by the database and parsed and stored. The external OPML file may, in turn, reference other external OPML files that may be similarly processed to construct, within the database, an entire OPML tree. The OMPL database may also, or instead, store OPML files as simple text or in any number of formats optimized for searching (such as a number of well-known techniques used by large scale search engines Google, AltaVista, and the like), or for OPML processing, or for any other purpose(s). The OPML database may provide coherency for formation of an OPML network among an array of clients 102 and servers 104, where content within the network 100 is structured according to user-created OPML outlines.

The OPML server may provide a number of functions or services related to OPML content. For example, the OPML server may permit a user to publish OPML content, either at a hosted site or locally from a user's computer. The OPML server may provide a ping service for monitoring updates of OPML content. The OPML server may provide a validation service to validate content according to the OPML specification. The OPML server may provide a search service or function which may permit searching against a database of OPML content, or it may provide user-configurable spidering capabilities to search for OPML content across a wide area network. The OPML server may provide an interface for browsing (or more generally, navigating) and/or reading OPML content. The OPML server may provide tools for creating, editing, and/or managing OPML content.

The OPML server may provide a number of complementary functions or services to support OPML-based transactions, content management, and the like. In one aspect, a renderer or converter may be provided to convert between a structured format such as OPML and a presentation format such as PowerPoint and display the respective forms. While the converter may be used with OPML and PowerPoint, it should be understood that the converter may be usefully employed with a variety of other structured, hierarchical, or outlined formats and a variety of presentation formats or programs. For example, the presentation format may include Portable Document Format, Flash Animation, electronic books, a variety of Open Source alternatives to PowerPoint (e.g., OpenOffice.org's Presenter, KDE's KPresenter, HTML Slidy, and so forth), whether or not they are PowerPoint compatible. The structured format may include OPML, an MS Word outline, simple text, or any other structured content, as well as files associated with leaf nodes thereof, such as audio, visual, moving picture, text, spreadsheet, chart, table, graphic, or any other format, any of which may be rendered in association with the structured format and/or converted between a structured format and a presentation format It will also be understood that the converter may be deployed on a client device for local manipulation, processing, and/or republication of content.

The OPML database may, for example, operate through the OPML server to generate, monitor, and/or control spiders that locate OPML content. A spider may, upon identification of a valid OPML file, retrieve the file and process it into the database. A spider may also process an OPML file to identify external references, systematically traversing an entire OPML tree. A spider may be coordinated using known techniques to identify redundant references within a hierarchy. A spider may also differentiate processing according to, e.g., structure, content, location, file types, metadata, and the like. The user interface described below may also include one or more tools for configuring spiders, including a front end for generating initial queries, displaying results, and tagging results with any suitable metadata.

By way of example, and not of limitation, medical records may be stored as OPML files, either within the database or in a distributed fashion among numerous locations across the OPML network. Thus, for example, assorted X-Ray data may be maintained in one location, MRI data in another location, patient biographical data in another location, and clinical notes in another location. These data may be entirely decoupled from individual patients (thus offering a degree of security/privacy) and optionally may include references to other content, such as directories of other types of data, directories of readers or interpretive metadata for understanding or viewing records, and the like. Separately, OPML files may be created to provide structure to the distributed data. For example, a CT Scan OPML master record may index the locations of all CT Scan records, which may be useful, for example, for studies or research relating to aggregated CT Scan data. This type of horizontal structure may be captured in one or more OPML records which may themselves be hierarchical. Thus, for example, one OPML file may identify participating hospitals by external reference to OPML records for those hospitals. Each hospital may provide a top-level OPML file that identifies OPML records that are available, which may in turn identify all CT Scan records maintained at that hospital. The CT Scan master record may traverse the individual hospital OPML records to provide a flattened list of CT Scan records available in the system. As another example, an OPML file may identify medical data for a particular patient. This OPML file may traverse records of any number of different hospitals or other medical institutions, or it may directly identify particular records where, for example, concerns about confidentiality cause institutions to strip any personally identifying data from records. For certain applications, it may be desirable to have a central registry of data so that records such as patient data are not inadvertently lost due to, for example, data migration within a particular hospital.

Thus in one embodiment there is generally disclosed herein a pull-based data management system in which atomic units of data are passively maintained at any number of network-accessible locations, while structure is imposed on the data through atomic units of relationship that may be arbitrarily defined through OPML or other grammars. The source data may be selectively pulled and organized according to user-defined OPML definitions. The OPML server and OPML database may enable such a system by providing a repository for organization and search of source data in the OPML network. Traversing OPML trees to fully scope an outline composed of a number of nested OPML outlines may be performed by a client 102 or may be performed by the OPML server, either upon request from a client 102 for a particular outline or continually in a manner that insures integrity of external reference links.

In another aspect, there is disclosed herein a link maintenance system for use in an OPML network. In general, a link maintenance system may function to insure integrity of external references contained within OPML files. Broken links, which may result for example from deletion or migration of source content, may be identified and addressed in a number of ways. For example, a search can be performed using the OPML server and OPML database for all OPML files including a reference to the missing target. Additionally, the OPML server and/or OPML database may include a registry of content sources including an e-mail contact manager/administrator of outside sources. Notification of the broken link including a reference to the content may be sent to all owners of content. Optionally, the OPML server may automatically modify content to delete or replace the reference, assuming the OPML server has authorization to access such content. The OPML server may contact the owner of the missing content. The message to the owner may include a request to provide an alternative link which may be forwarded to owners of all content that references the missing content. If the referenced subject matter has been fully indexed by the OPML server and/or OPML database, the content may itself be reconstructed and a replacement link to the location of the reconstructed content provided. Various combinations of reconstruction and notification, such as those above, may be applied to maintain the integrity of links in OPML source files indexed in the database. In various embodiments the links may be continuously verified and updated, or the links may be updated only when an OPML document with a broken link is requested by a client 102 and processed or traversed by the client 102 or the OPML server in response.

The OPML server may provide a client-accessible user interface to view items in a data stream or OMPL outline. The user interface may be presented, for example, through a Web page viewed using a Web browser or through an outliner or outline viewer specifically adapted to display OPML content. In general, an RSS or OPML file may be converted to HTML for display at a Web browser of a client 102. For example, the source file on a server 104 may be converted to HTML using a Server-Side Include ("SSI") to bring the content into a template by iterating through the XML/RSS internal structure. The resulting HTML may be viewed at a client 102 or posted to a different server 104 along with other items. The output may also, or instead, be provided in OPML form for viewing through an OPML renderer. Thus, feeds and items may be generally mixed, shared, forwarded, and the like in a variety of formats.

Again it is noted that specific references to OPML and RSS above are not intended to be limiting and more generally should be understood as references to any outlining, syndication, or other grammar suitable for use with the systems described herein.

Focusing now on the internetwork 110, one embodiment is the Internet. The structure of the Internet 110 is well known to those of ordinary skill in the art and includes a network backbone with networks branching from the backbone. These branches, in turn, have networks branching from them and so on. The backbone and branches are connected by routers, bridges, switches, and other switching elements that operate to direct data through the internetwork 110. For a more detailed description of the structure and operation of the Internet 110, one may refer to "The Internet Complete Reference," by Harley Hahn and Rick Stout, published by McGraw-Hill, 1994. However, one may practice the present invention on a wide variety of communication networks. For example, the internetwork 110 can include interactive television networks, telephone networks, wireless voice or data transmission systems, two-way cable systems, customized computer networks, Asynchronous Transfer Mode networks, and so on. Clients 102 may access the internetwork 110 through an Internet Service Provider ("ISP", not shown) or through a dedicated DSL service, ISDN leased lines, t1 lines, OC3 lines, digital satellite service, cable modem service, or any other connection, or through an ISP providing same.

In its present deployment as the Internet, the internetwork 110 includes a worldwide computer network that communicates using the well-defined Transmission Control Protocol ("TCP") and Internet Protocol ("IP") to provide transport and network services. Computer systems that are directly connected to the Internet 110 each have a unique IP address. The IP address consists of four one-byte numbers (although a planned expansion to sixteen bytes is underway with IPv6). To simplify Internet addressing, the Domain Name System ("DNS") was created. The DNS allows users to access Internet resources with a simpler alphanumeric naming system. A DNS name consists of a series of alphanumeric names separated by periods. When a domain name is used, the computer accesses a DNS server to obtain the explicit four-byte IP address. It will be appreciated that other internetworks 110 may be used with the invention. For example, the internetwork 110 may be a wide-area network, a local area network, a campus area network, or corporate area network. The internetwork 110 may be any other network used to communicate data, such as a cable broadcast network.

To further define the resources on the Internet 110, the Uniform Resource Locator system was created. A Uniform Resource Locator ("URL") is a descriptor that specifically defines a protocol for an Internet resource along with its location. URLs have the following format:
protocol://domain.address/path-name
    in which the domain address and path-name provide a location for a resource, and the protocol defines the type of protocol used to access the resource. It will be appreciated that, in the context of this paragraph only, the term "resource" is used in the conventional sense of RFC 1738 to refer to a document, image, or the like available on the Web. Web documents are identified by the protocol "http" which indicates that the hypertext transfer protocol should be used to access the document. Other common protocols include "ftp" (file transmission protocol), "mailto" (send electronic mail), "file" (local file), and "telnet." The domain address defines the domain name address of the computer on which the resource is located. Finally, the path-name defines a directory path within the file system of the server that identifies the resource. As used herein, the term "IP address" is intended to refer to the four-byte Internet Protocol address (or the expanded address provided by IPv6), and the term "Web address" is intended to refer to a domain name address, along with any resource identifier and path name appropriate to identify a particular Web resource. The term "address," when used alone, may refer to either a Web address or an IP address.

In an exemplary embodiment, a browser, executing on one of the clients 102, retrieves a Web document at an address from one of the servers 104 via the internetwork 110 and displays the Web document on a viewing device, e.g., a screen. A user can retrieve and view the Web document by entering, or selecting a link to, a URL in the browser. The browser then sends an http request to the server 104 that has the Web document associated with the URL. The server 104 responds to the http request by sending the requested Web document to the client 102. The Web document is an HTTP object that includes plain text (ASCII) conforming to the HyperText Markup Language ("HTML"). Other markup languages are known and may be used on appropriately enabled browsers and servers, including the Dynamic HyperText Markup Language ("DHTML"), the Extensible Markup Language ("XML"), the Extensible Hypertext Markup Language ("XHTML"), and the Standard Generalized Markup Language ("SGML").

Each Web document usually contains hyperlinks to other Web documents. The browser displays the Web document on the screen for the user, and the hyperlinks to other Web documents are emphasized in some fashion such that the user can identify and select each hyperlink. To enhance functionality, a server 104 may execute programs associated with Web documents using programming or scripting languages, such as Perl, C, C++, C#, or Java, or a Common Gateway Interface ("CGI") script to access applications on the server. A server 104 may also use server-side scripting languages such as ColdFusion from MacroMedia or PHP. These programs and languages may perform "back-end" functions such as order processing, database management, and content searching. A Web document may also contain, or include references to, small client-side applications, or applets, that are transferred from the server 104 to the client 102 along with a Web document and are executed locally by the client 102. Java is one popular example of a programming language used for applets. The text within a Web document may further include (non-displayed) scripts that are executable by an appropriately enabled browser, using a scripting language such as JavaScript or Visual Basic Script. Browsers may further be enhanced with a variety of helper applications to interpret various media including still image formats such as JPEG and GIF, document formats such as PS and PDF, motion picture formats such as AVI and MPEG, animated media such as Flash media, and sound formats such as MP3 and MIDI. These media formats, along with a growing variety of proprietary media formats, may be used to enrich a user's interactive and audio-visual experience as each Web document is presented through the browser. The term "page" as used herein is intended to refer to the Web document described above as well as any of the above-described functional or multimedia content associated with the Web document.

In general operation, a server 104 may provide a data stream to a client 102. In an exemplary embodiment, the data stream may be a syndicated data stream such as RSS, an XML grammar for sharing data through the Web. An RSS-enabled server may include an RSS file with a title and description of items to be syndicated. As with simple HTML documents, the RSS file may be hand-coded or computer-generated. The first line of an RSS file may contain an XML declaration of the form:

```
<?xml version="1.0"?>
```

While not strictly required, this declaration may improve version compatibility. The next item in an RSS file may be a Document Type Declaration ("DTD") that identifies the file as an RSS document:

```
<!DOCTYPE rss PUBLIC "-//Netscape Communications//DTD RSS 0.91//EN"
"http://my.netscape.com/publish/ formats/rss-0.91.dtd">
```

The RSS element is the root of top-level element of an RSS file. The RSS element must specify the version attribute (in this example, version 0.91). It may also contain an encoding attribute (the default is UTF-8):

```
<rss version="0.91" encoding= "ISO_8859-1">
```

The root element is the top-level element that contains the rest of an XML document. An RSS element may contain a channel with a title (the name of the channel), description (short description of the channel), link (HTML link to the channel Web site), language (language encoding of the channel, such as en-us for U.S. English), and one or more item elements. A channel may also contain the following optional elements:

rating—an independent content rating, such as a PICS rating
copyright—copyright notice information
pubDate—date the channel was published
lastBuildDate—date the RSS was last updated
docs—additional information about the channel
managingEditor—channel's managing editor
webMaster—channel Webmaster
image—channel image
textinput—allows a user to send an HTML form text input string to a URL
skipHours—the hours that an aggregator should not collect the RSS file
skipDays—the weekdays that an aggregator should not collect the RSS file A channel may contain an image or logo. In RSS, the image element contains the image title and the URL of the image itself. The image element may also include the following optional elements: a link (a URL that the image links to), a width, a height, and a description (additional text displayed with the image). There may also be a text input element for an HTML text field. The text input element may include a title (label for a submit button), description, name, and link (to send input). The link may enable richer functionality, such as allowing a user to submit search terms, send electronic mail, or perform any other text-based function.

Once defined in this manner, a channel may contain a number of items, although some services (e.g., Netscape Netcenter) may limit the number. In general, the "item" elements provide headlines and summaries of the content to be shared. New items may be added, either manually or automatically (such as through a script), by appending them to the RSS file.

Figure 2:
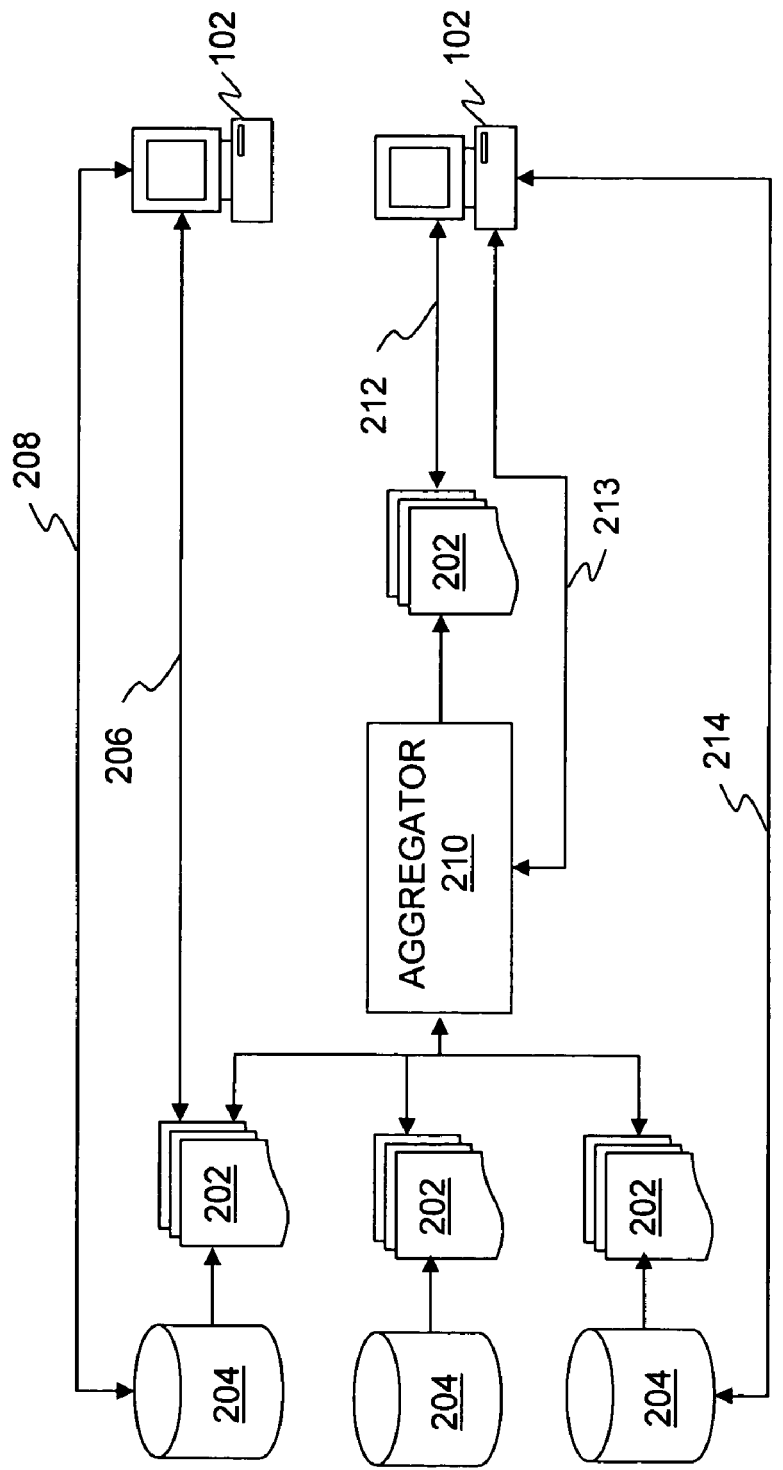
FIG. 2 shows a system for using and aggregating data feeds.

FIG. 2 depicts a system for using and aggregating data feeds or other syndicated content. In general, data feeds 202, such as RSS source files, are generated from a content source 204 and made available for use or review by clients 102 through a network.

The content source 204 may provide any electronic content including newspaper articles; Web magazine articles; academic papers; government documents such as court opinions, administrative rulings, regulation updates, or the like; opinions; editorials; product reviews; movie reviews; financial or market analysis; current events; bulletins; and the like. The content may include text, formatting, layout, graphics, audio files, image files, movie files, word processing files, spreadsheet files, presentation files, electronic documents, HTML files, executable files, scripts, multi-media, relational databases, data from relational databases and/or any other content type or combination of types suitable for syndication through a network. The content source 204 may be any commercial media provider(s) such as newspapers, news services (e.g., Reuters or Bloomberg), or individual journalists such as syndicated columnists. The content source 204 may also be from commercial entities such as corporations, non-profit corporations, charities, religious organizations, social organizations, or the like, as well as from individuals with no affiliation to any of the foregoing. The content source 204 may be edited, as with news items, or automated, as with data feeds 202 such as stock tickers, sports scores, weather conditions, and so on. While written text is commonly used in data feeds 202, it will be appreciated that any digital media may be binary encoded and included in an item of a data feed 202 such as RSS. For example, data feeds 202 may include audio, moving pictures, still pictures, executable files, application-specific files (e.g., word processing documents or spreadsheets), and the like. It should also be understood that, while a content source 204 may generally be understood as a well defined source of items for a data feed, the content source 204 may be more widely distributed or subjectively gathered by a user preparing a data feed 202. For example, an individual user interested in automotive mechanics may regularly read a number of related magazines and regularly attend trade shows. This information may be processed on an ad hoc basis by the individual and placed into a data feed 202 for review and use by others. Thus it will be understood that the data stream systems described herein may have broad commercial use, as well as non-commercial, educational, and mixed uses.

As described generally above, the data feed 202 may include, for each item of content, summary information such as a title, synopsis or abstract (or a teaser, for more marketing oriented materials), and a link to the underlying content. Thus as depicted in FIG. 2, when a client 102 accesses a data feed 202, as depicted by an arrow 206, the client 102 may then display the summary information for each item in a user interface. A client 102 may, in response to user input such as clicking on a title of an item in the user interface, retrieve the underlying item from the content source 204 as indicated by an arrow 208. In the bi-directional communication depicted by the arrow 208, the client 102 may also identify the specific data feed 202 through which the item was identified, which may be useful for tracking distribution channels, customer behavior, affiliate referral fees, and so forth. It should be appreciated that an RSS data feed 202 may be presented to a client 102 as an RSS file (in XML format) that the client 102 locally converts to HTML for viewing through a Web browser, or the data feed 202 may be converted to HTML at a Web site that responds to HTTP requests from a client 102 and responds with an HTML-formatted data feed.

A related concept is the so-called "permalink" that provides a permanent URL reference to a source document that may be provided from, for example, a dynamically generated Web site or a document repository served from a relational database behind a Web server. While there is no official standard for permalink syntax or usage, they are widely used in conjunction with data feeds. Permalinks typically consist of a string of characters which represent the date and time of posting, and some (system dependent) identifier (which includes a base URL, and often identifies the author, subscriber, or department which initially authored the item). If an item is changed, renamed, or moved, its permalink remains unaltered. If an item is deleted altogether, its permalink cannot be reused. Permalinks are exploited in a number of applications including link tracing and link track back in Weblogs and references to specific Weblog entries in RSS or Atom syndication streams. Permalinks are supported in most modern weblogging and content syndication software systems, including Movable Type, LiveJournal, and Blogger.

RSS provides a standard format for the delivery of content through data feeds. This makes it relatively straightforward for a content provider to distribute content broadly and for an affiliate to receive and process content from multiple sources. It will be appreciated that other RSS-compliant and/or non-RSS-compliant feeds may be syndicated as that term is used herein and as is described in greater detail below. As noted above, the actual content may not be distributed directly, only the headlines, which means that users will ultimately access the content source 204 if they're interested in a story. It is also possible to distribute the item of content directly through RSS, though this approach may compromise some of the advantages of network efficiency (items are not copied and distributed in their entirety) and referral tracking. Traffic to a Web site that hosts a content source 204 can increase in response to distribution of data feeds 202.

Although not depicted, a single content source 204 may also have multiple data feeds 202. These may be organized topically or according to target clients 102. Thus, the same content may have data feeds 202 for electronic mailing lists, PDAs, cell phones, and set-top boxes. For example, a content provider may decide to offer headlines in a PDA-friendly format, or it may create a weekly email newsletter describing what's new on a Web site.

Data feeds 202 in a standard format provide for significant flexibility in how content is organized and distributed. An aggregator 210, for example, may be provided that periodically updates data from a plurality of data feeds 202. In general, an aggregator 210 may make many data feeds 202 available as a single source. As a significant advantage, this intermediate point in the content distribution chain may also be used to customize feeds, and presentation thereof, as well as to filter items within feeds and provide any other administrative services to assist with syndication, distribution, and review of content.

As will be described in greater detail below, the aggregator 210 may filter, prioritize, or otherwise process the aggregated data feeds. A single processed data feed 202 may then be provided to a client 102 as depicted by an arrow 212. The client 102 may request periodic updates from the data feed 202 created by the aggregator 210 as also indicated by an arrow 212. As indicated by an arrow 213, the client 102 may also configure the aggregator 210 such as by adding data streams 202, removing data streams 202, searching for new data streams 202, explicitly filtering or prioritizing items from the data streams 202, or designating personal preferences or profile data that the aggregator 210 may apply to generate the aggregated data feed 202. When an item of interest is presented in the user interface of the client 102, a user may select a link to the item, causing the client 102 to retrieve the item from the associated content source 204 as indicated by an arrow 214. The aggregator 210 may present the data feed 202 as a static web page that is updated only upon an explicit request from the client 102, or the aggregator 210 may push updates to a client 102 using either HTTP or related Web browser technologies, or by updates through some other channel, such as e-mail updates. It will also be appreciated that, while the aggregator 210 is illustrated as separate from the client 102, the aggregator 210 may be realized as a primarily client-side technology, where software executing on the client 102 assumes responsibility for directly accessing a number of data feeds 202 and aggregating/filtering results from those feeds 202.

It will be appreciated that a user search for feeds will be improved by the availability of well organized databases. While a number of Weblogs provide local search functionality, and a number of aggregator services provide lists of available data feeds, there remains a need for a consumer-level searchable database of feed content. As such, one aspect of the system described herein is a database of data feeds that is searchable by contents as well as metadata such as title and description. In a server used with the systems described herein, the entire universe of known data feeds may be hashed or otherwise organized into searchable form in real time or near real time. The hash index may include each word or other symbol and any data necessary to locate it in a stream and in a post.

The advent of commonly available data feeds 202, such as RSS feeds, along with tools such as aggregators 210, enables new modes of communication. In one common use, a user may, through a client 102, post aggregated feeds 202 to a Weblog. The information posted on a Weblog may include an aggregated feed 202, one or more data feeds 202 that are sources for the aggregated feed 202, and any personal, political, technical, or editorial comments that are significant to the author. As such, all participants in an RSS network may become authors or sources of content, as well as consumers.

Figure 3:
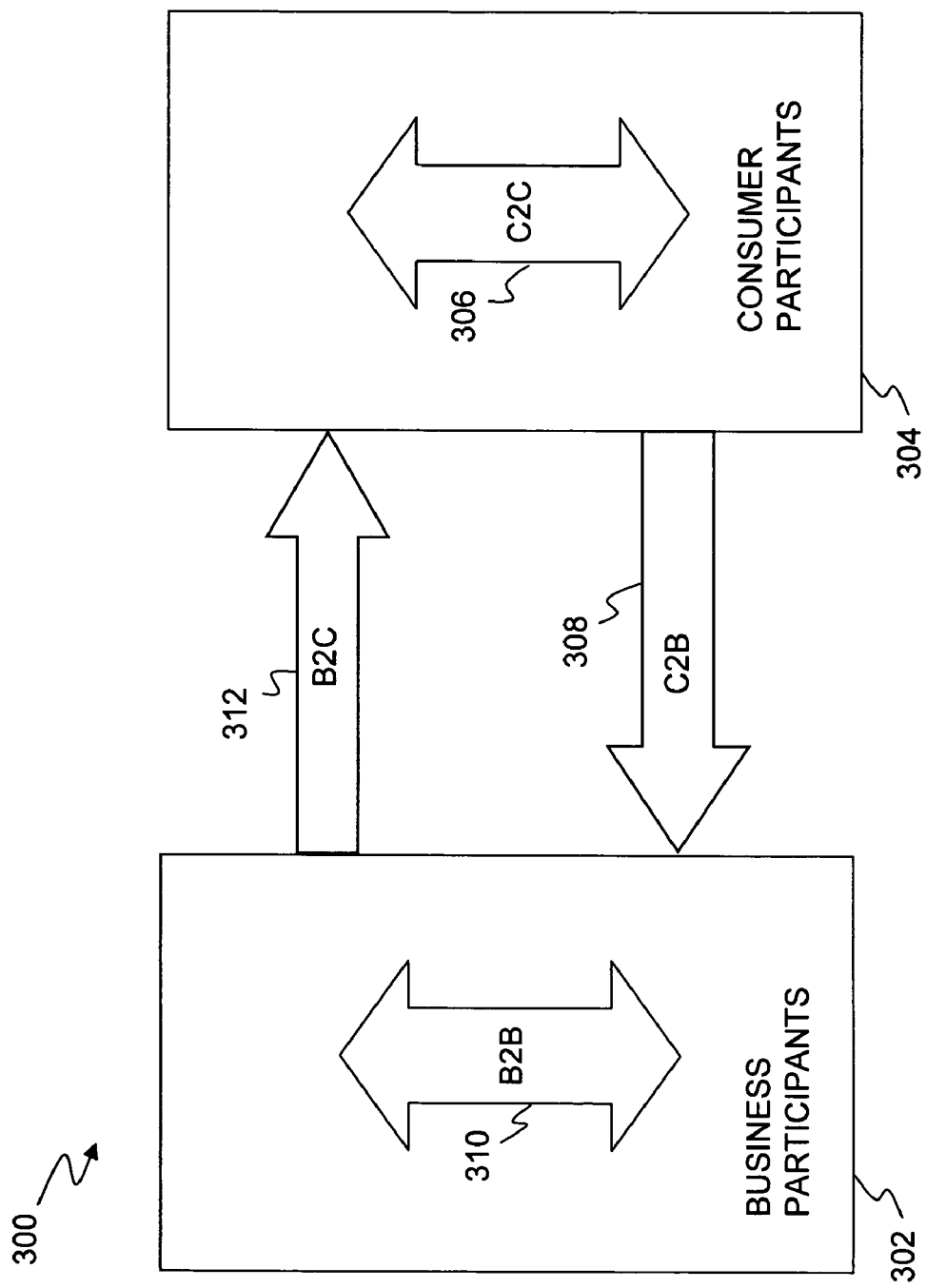
FIG. 3 depicts markets for syndicated content.

FIG. 3 depicts certain aspects of the markets for data feeds. This generally depicts characteristics that can be present in a number of different markets in which the systems described herein may be usefully deployed. Market 300 for data feeds 302 such as RSS may be understood as including four main models for information exchange among business participants in the commercial space 302 and individuals in the consumer space 304. As large, established companies such as Yahoo, Google, and Microsoft adopt and integrate RSS technologies, these markets should grow significantly.

At present, the consumer-to-consumer market model 306 consists primarily of millions of individual bloggers, mostly communicating with each other. This includes non-commercial Weblogs where individuals aggregate data feeds 302 from a variety of sources and include editorial commentary or other information. In general, a source in this space is an individual presenting aggregated feeds 302 in a Web site with some common theme or themes of interest to the author, such as history, sports, science, technology, politics, literature, art, music, and so forth. However, there are no strict requirements that any one or more themes be followed, and the Weblog may simply reflect an ad hoc selection of topics that the author finds interesting. Weblogs in this space gain popularity according to the content provided, with readership (and associated RSS subscriptions or registrations) rising or falling according to general interest.

The consumer-to-business model or segment 308 brings together consumers who are interested in a particular topic, typically a topic with a corresponding commercial market, such as automobiles, mortgages, financial services, home repair, hobbies, and the like. A topic may be still more refined, such as antique automobiles, or antique American automobiles; however, the corresponding participation of commercial participants may depend on the scope of the market. Thus, a large number of financial service providers could be expected to subscribe to an RSS data feed for general consumers of financial services; however, a smaller number of commercial subscribers might be expected for derivative currency hedge instruments among Pacific Rim country currencies. In general, consumer-to-business uses may provide consumers with concerns, interests, and preferences in a particular market with a forum that will be followed by corresponding commercial interests. In addition, by participating in this RSS network, businesses may also address consumer interests in a more direct and personal way, as distinguished from the business-to-consumer segment 312 discussed below. At the same time, it will be appreciated that the distinction between these segments 308, 312 need not be an absolute one, and a synthesis of these two communication channels may result in a greater dialogue between commercial and individual actors, to their collective and mutual benefit. Thus, for example, with a suitably configured aggregated feed 302 and associated Web presentation, an automobile manufacturer could design a new minivan or SUV in cooperation with the automobile-buying public in a manner that addresses previously unknown purchasing preferences of consumers. Additionally, since the community of participants is likely to be highly focused, this segment 308 may offer significant opportunities for revenue from targeted advertising.

The business-to-business segment 310 does not appear to be commonly used, although in the methods and systems described herein syndication may substitute for electronic mail and other forms of corporate and business-to-business communication, such as time management, inventory, supply chain, manufacturing, and customer relations information flow.

The business-to-consumer segment 312 includes an extension of traditional media companies that can add data feed capabilities to their online presence. This includes news companies in print media, radio, television media, and Internet media, including, by way of example and not limitation, the New York Times, the Washington Post, the Wall Street Journal, Forbes, time, Business Week, CSPAN, ESPN, the Weather Channel, CNBC, CNET, Bloomberg, Reuters, and so on. This may also include non-news related media that nonetheless periodically update content, such as movie studios, network television, cable television, and so on. In addition, other companies that serve consumers may also usefully employ data feed systems, including companies ranging from catalogue companies such as Land's End to consumer electronics retailers such as Best Buy. In this context, a syndication platform such as enhanced RSS offers a reliable distribution channel for advertising new products and special offers to presumably interested consumers. These and other applications may be realized using the data feed technology described herein.

All such entity-to-entity communications described above may be improved through enhanced syndication systems as generally described herein. It will be appreciated that one obstacle to expanded use across all of these markets is the absence in the primary technology, RSS, of enterprise-class features such as security, authentication, conditional access data repositories, and rich metadata, to name a few. In one aspect, the systems described herein bring many of these features to RSS-like systems to provide secure, scalable syndication systems.

It should be clear that, while the term "aggregator" is used to label aspects of the systems disclosed herein, those systems include significant useful and advantageous functionality that is not present in any aggregator in the prior art, and as such the term should be interpreted broadly to optionally include all of the functions and techniques described below, rather than narrowly in the sense that it is currently used in the art. Although broader in meaning, the aggregator and interface described below may operate, for example, from one of the servers 104 described above with reference to FIG. 1 and may cooperate with other participants and content sources in the manner depicted for the aggregator 210 described in FIG. 2.

It will be appreciated that the components described herein correspond generally to various areas of functionality for a data feed system. However, in various embodiments, other components may be added, or certain components may be removed or combined with other components. For example, the aggregator described herein may cooperate with an n-tier architecture for a more general purpose Web server or with a relational database or other back end systems not specifically depicted herein to store and access data. Similarly, the systems described herein may include FTP servers, e-mail servers, PSTN interfaces, and other physical connections and protocols for various other functions that may be usefully combined with the aggregator to enhance functionality. Any number of such combinations and variations may be employed consistent with the systems described herein and are intended to fall within the scope of the present disclosure.

It will also be appreciated that a wide range of software and hardware platforms may be used to deploy the systems described herein. Generally, the system components may be realized in hardware, software, or some combination of these. The components may be realized in one or more microprocessors, microcontrollers, embedded microcontrollers, programmable digital signal processors or other programmable devices, along with internal and/or external memory such as read-only memory, programmable read-only memory, electronically erasable programmable read-only memory, random access memory, dynamic random access memory, double data rate random access memory, Rambus direct random access memory, flash memory, or any other volatile or non-volatile memory for storing program instructions, program data, and program output or other intermediate or final results. The components may also, or instead, include one or more application specific integrated circuits (ASICs), dedicated semiconductor devices, programmable gate arrays, programmable array logic devices, or any other device that may be configured to process electronic signals.

Any combination of the above circuits and components, whether packaged discretely, as a chip, as a chip set, or as a die, may be suitably adapted to use with the systems described herein. It will further be appreciated that the above components may be realized as computer executable code created using a structured programming language such as C, an object oriented programming language such as C++, or any other high-level or low-level programming language that may be compiled or interpreted to run on one of the above devices, as well as heterogeneous combinations of processors, processor architectures, or combinations of different hardware and software.

Figure 4:
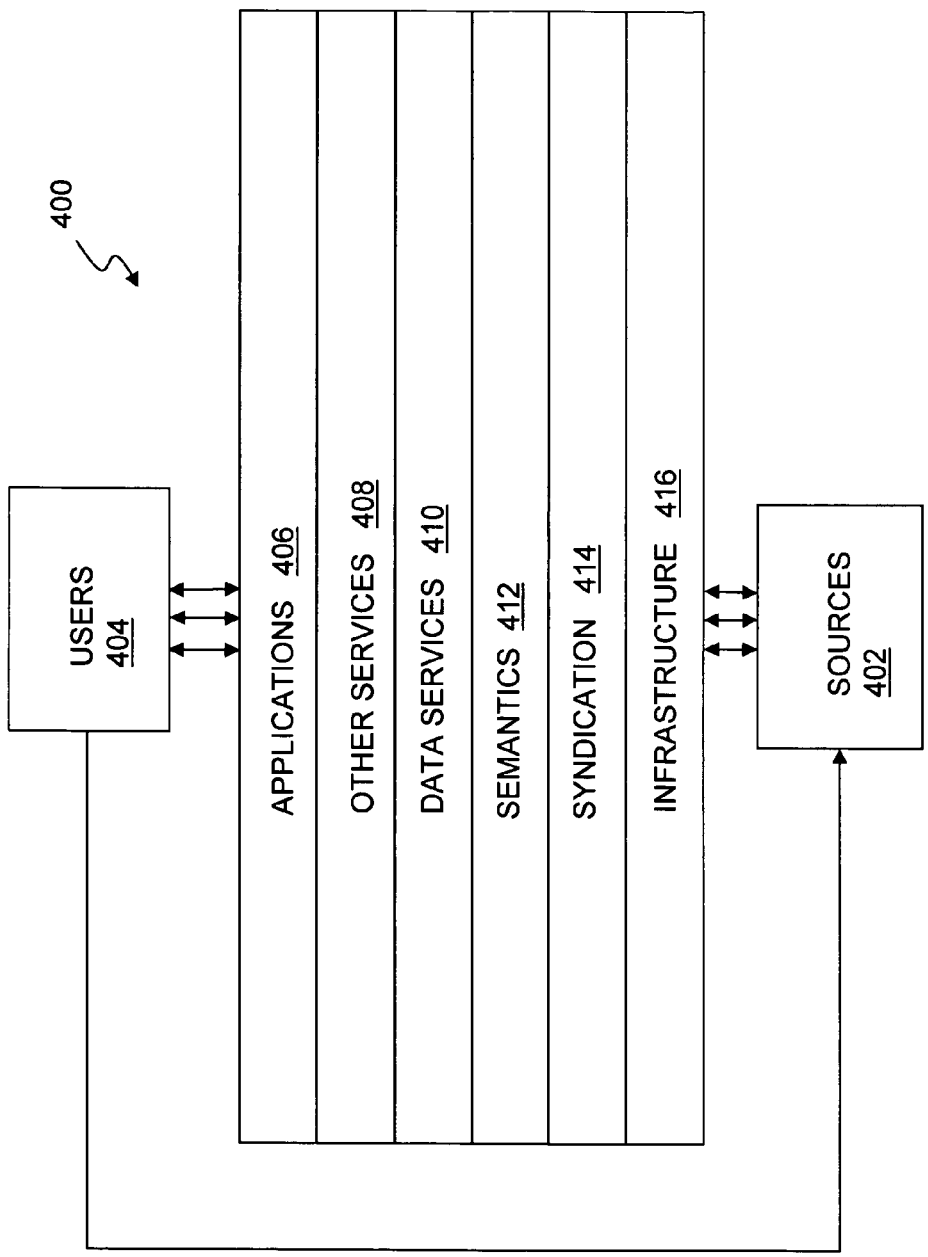
FIG. 4 depicts a conceptual framework for syndicated communications.

FIG. 4 depicts a conceptual framework for syndicated communications. In a syndication system 400, a plurality of sources 402, which may be for example any of the content sources 204 described above, are published to a plurality of users 404, which may be users of any of the clients 102 described above. Users 404 may include individuals, consumers, business entities, government entities, workgroups, and other categories of users 404. Access to the sources 402 by the users 404 may be through layers of devices, services, and systems (which may be analogous to or actually embodied in a protocol stack) in which various layers are responsible for different general areas of processing, and data is passed between layers according to a defined protocol, or set of rules, as depicted generally in FIG. 4. However, it will be appreciated that each layer of FIG. 4 may instead be provided as one or more non-layered services. This may include, for example, deployment as services in a Services Oriented Architecture or other Web-based or similar environment where individual services may be located and called from remote locations. In various embodiments, groups of the functions discussed below may be deployed at various locations throughout the syndication network. For example, database functions such as search, filter, and cluster may be performed at a server that archives syndicated content in response to user requests. In another embodiment, search, filter, and cluster may be programmatically incorporated into a spider for execution against results during spidering. In another embodiment, search, filter, and cluster may be incorporated into a syndication network edge device such as a pool or network attached storage sourcing syndicated content. More generally, each function or operation identified below, and combinations thereof, may be deployed for execution at a central server, deployed for execution at a client device, deployed for execution on syndication-enabled hardware (such as routers, switches, attached storage, and the like), deployed for execution within a process, deployed for distributed and/or coordinated execution across numerous heterogeneous or homogeneous technology platforms, and so forth. This may also, or instead, include deployment in a fixed architecture where a specific collection of services or functions, such as atomic functions, is deployed either locally or in a distributed manner and accessible through a syntax such as an instruction set. The functions within the conceptual framework may also be deployed within a web application framework such as Ruby on Rails or any other open source or proprietary application framework.

Thus in general numerous architectures and variations are possible for deploying the functions and operations described herein, and all such arrangements are intended to fall within the scope of this disclosure. In one aspect, the methods and systems disclosed herein may be understood as the functions and combinations thereof independent of how they are deployed. In another aspect, the methods and systems disclosed herein may be understood as deployment-specific or technology-specific implementations of these features into specific products or services. All such variations are intended to fall within the scope of this disclosure.

At the same time, it should be understood that within the protocol stack as depicted in FIG. 4, the number, arrangement, and functions of the layers may be varied in a number of ways within a syndication system 400; in particular, depending on the characteristics of the sources, the needs of the users 404 and the features desired for particular applications, a number of improved configurations for syndication systems 404 may be established, representing favorable combinations and sub-combinations of layers depicted in FIG. 4. The layers may provide services such as services related to applications 406, other services 408 (including relating to processing), services related to data 410, services related to semantics of content 412, syndication services 414, and services related to infrastructure 416. More generally, all of the services and functions described below, either individually or in combinations, as well as other services not specifically mentioned, may be incorporated into an enhanced syndication system as described herein. It should be understood that any of the services depicted in the layers of FIG. 4 may be embodied in hardware, software, firmware, or a combination thereof; for example, a service may be embodied in software as a web service, according to a services oriented architecture. Alternatively, without limitation, a service may be a client-side or server-side application or take any of the forms described herein and in the documents incorporated by reference herein. In one embodiment, one or more layers may be embodied in a dedicated semiconductor device, such as an ASIC, that is configured to enable syndication.

Services related to applications 406 may be embodied, for example, in a client-side application (including commercially available applications such as a word processor, spreadsheet, presentation software, database system, task management system, supply chain management system, inventory management system, human resources management system, user interface system, operating system, graphics system, computer game, electronic mail system, calendar system, media player, and the like), a remote application or service, an application layer of an enhanced syndication services protocol stack, a web service, a service oriented architecture service, a Java applet, or a combination of these. Applications 406 may include, for example, a user interface, social networking, vertical market applications, media viewers, transaction processing, alerts, event-action pairs, analysis, and so forth. Applications 406 may also accommodate vertical market uses of other aspects of the system 400 by integrating various aspects of, for example, security, interfaces, databases, syndication, and the like. Examples of vertical markets include financial services, health care, electronic commerce, communications, advertising, sales, marketing, supply chain management, retail, accounting, professional services, and so forth. In one aspect, the applications 406 may include social networking tools to support functions such as sharing and pooling of syndicated content, content filters, content sources, content commentary, and the like, as well as formation of groups, affiliations, and the like. Social networking tools may support dynamic creation of communities and moderation of dialogues within communities, while providing individual participants with any desired level of anonymity. Social networking tools may also, or instead, evaluate popularity of feeds or items in a syndication network or permit user annotation, evaluation, or categorization. A user interface from the application may also complement other services layers. For example, an application may provide a user interface that interprets semantic content to determine one or more display characteristics for associated items of syndicated content.

Other services 408 may include any other services not specifically identified herein that may be usefully employed within an enhanced syndication system. For example, content from the sources 402 may be formatted for display through a formatting service that interprets various types of data and determines an arrangement and format suitable for display. This may also include services that are specifically identified, which may be modified, enhanced, or adapted to different uses through the other services 408. Other services 408 may support one or more value added services. For example, a security service may provide for secure communications among users or from users to sources. An identity service may provide verification of user or source identities, such as by reference to a trusted third party. An authentication service may receive user credentials and control access to various sources 402 or other services 408 within the system. A financial transaction service may execute financial transactions among users 404 or between users 404 and sources 402. Any service amenable to computer implementation may be deployed as one or more other services 408, either alone or in combination with services from other elements of the system 400.

Data services 410 may be embodied, for example, in a client-side application, a remote application or service, an application layer of an enhanced syndication services protocol stack, as application services deployed, for example, in the services oriented architecture described below, or a combination of these. Data services 410 may include, for example, search, query, view, extract, or any other database functions. Data services 410 may also, or instead, include data quality functions such as data cleansing, deduplication, and the like. Data services 410 may also, or instead, include transformation functions for transforming data between data repositories or among presentation formats. Thus, for example, data may be transformed from entries in a relational database, or items within an OPML outline, into a presentation format such as MS Word, MS Excel, or MS PowerPoint. Similarly, data may be transformed from a source such as an OPML outline into a structured database. Data services 410 may also, or instead, include syndication-specific functions such as searching of data feeds, or items within data feeds, or filtering items for relevance from within selected feeds, or clustering groups of searches and/or filters for republication as an aggregated and/or filtered content source 402. In one aspect, a data service 410 as described herein provides a repository of historical data feeds, which may be combined with other services for user-configurable publication of aggregated, filtered, and/or annotated feeds. More generally, data services 410 may include any functions associated with data including storing, manipulating, retrieving, transforming, verifying, authenticating, formatting, reformatting, tagging, linking, hyperlinking, reporting, viewing, and so forth. A search engine deployed within the data services 410 may permit searching of data feeds or, with a content database as described herein, searching or filtering of content within data feeds from sources 402. Data services 410 may be adapted for use with databases such as commercially available databases from Oracle, Microsoft, IBM, and/or open source databases such as MySQL AB or PostgreSQL.

In one aspect, data services 410 may include services for searching and displaying collections of OPML or other XML-based documents. This may include a collection of user interface tools for finding, building, viewing, exploring, and traversing a knowledge structure inherent or embedded in a collection of interrelated or cross-linked documents. Such a system has particular utility, for example, in creating a structured knowledge directory of OPML structures derived from an exploration of relationships among individual outlined OPML documents and the nodes thereof (such as end nodes that do not link to further content). In one embodiment, the navigation and building of knowledge structures may advantageously be initiated from any point within a knowledge structure, such as an arbitrarily selected OPML document within a tree. A user interface including the tools described generally above may allow a user to restrict a search to specific content types, such as RSS, podcasts (which may be recognized, e.g., by presence of RSS with an MP3 or WAV attachment) or other OPML links within the corpus of OPML files searched. The interface may be supported by a searchable database of OPML content, which may in turn be fed by one or more OPML spiders that seek to continually update content either generally or within a specific domain (i.e., an enterprise, a top-level domain name, a computer, or any other domain that can be defined for operation of a spider. The OPML generated by an OPML search engine may also be searchable, permitting, e.g., recovery of lost links to OPML content.

It will be appreciated that by storing an entire knowledge structure (or entire portions thereof), the tree structure may be navigated in either direction. That is, a tree may be navigated downward in a hierarchy (which is possible with conventional outlines) as well as upward in a hierarchy (which is not supported directly by OPML). Upward navigation becomes possible with reference to a stored version of the knowledge structure, and the navigation system may include techniques for resolving upward references (e.g. where two different OPML documents refer to the same object) using explicit user selections, pre-programmed preferences, or other selection criteria, as well as combinations thereof.

Data services 410 may include access to a database management system (DBMS). In one aspect, the DBMS may provide management of syndicated content. In another aspect, the DBMS may support a virtual database of distributed data. The DBMS may allow a user, such as a human or an automatic computer program, to perform operations on a data feed, references to the data feed, metadata associated with the data feed, and the like. Thus in one aspect, a DBMS is provided for syndicated content. Operations on the data managed by the DBMS may be expressed in accordance with a query language, such as SQL, XQuery, or any other database query language. In some embodiments, the query language may be employed to describe operations on a data feed, on an aggregate of data feeds, or on a distributed set of data feeds. It should be appreciated that the data feeds may be structured according to RSS, OPML, or any other syndicated data format. In another aspect, content such as OPML content may describe a relationship among distributed data, and the data services 410 may provide a virtual DBMS interface to the distributed data. Thus, there is disclosed herein an OPML-based database wherein data relationships are encoded in OPML and data are stored as content distributed among resources referenced by the OPML.

The data services 410 may include database transactions. Each database transaction may include an atomic set of reads and/or writes to the database. The transaction mechanism for the database transactions may support concurrent and/or conditional access to the data in the database. Conditional access may support privacy, security, data integrity, and the like within the database. The transaction mechanism may allow a plurality of users to concurrently read, write, create, delete, perform a query, or perform any other operation supported by the DMBS against an RSS feed or OPML file, either of which may be supported by the data in the database or support a database infrastructure. In one aspect, the transaction mechanism may avoid or resolve conflicting operations and maintain the consistency of the database. The transaction mechanism may be adapted to support availability, scalability, mobility, serializability, and/or convergence of a DBMS. The transaction mechanism may also, or instead, support version control or revision control. The DBMS may additionally or alternatively provide methods and systems for providing access control, record locking, conflict resolution, avoidance of list updates, avoidance of system delusion, avoidance of scaleup pitfall, and the like.

The data services 410 may provide an interface to a DBMS that functions as a content source by publishing or transmitting a data feed to a client. The DBMS may additionally or alternatively perform as a client by accessing or receiving a data feed from a content source. The DBMS may perform as an aggregator of feeds. The DBMS may provide a syndication service. The DBMS may perform as an element in a service-oriented architecture. The DBMS may accept and/or provide data that are formatted according to XML, OPML, HTML, RSS, or any other markup language.

In one aspect, the data services 410 may partition content into instructions and data. For example, an expression (as described more generally below) may describe or define an interrelationship of various data referenced through one or more OPML files. The expression, which may itself be an OPML file, may be stored in a separate location from data, which may be, for example, RSS feeds available at end nodes of an OPML structure. The expression may also, or instead, be expressed within a URL along with a call to a resource, or stored in a different format. In another embodiment, the data may itself be separated into OPML descriptions of relationships and end node data. In one aspect, improved security or redundancy may be realized through separation of an OPML-based relationship description, which provides meaning or coherence to data, from the underlying data which, in the absence of the OPML, becomes unstructured data.

Semantics 412, or semantic processing, may include any functions or services associated with the meaning of content from the sources 402 and may be embodied, for example, in a client-side application, a remote application or service, an application layer of an enhanced syndication services protocol stack, as application services deployed, for example, in the services oriented architecture described below, or a combination of these. Semantics 412 may include, for example, interrelating content into a knowledge structure using, for example, OPML, adding metadata or enriching current metadata, interpreting or translating content, and so forth. Semantics 412 may also include parsing content, either linguistically for substantive or grammatical analysis, or programmatically for generation of executable events. Semantics 412 may include labeling data feeds and items within feeds, either automatically or manually. This may also include interpretation of labels or other metadata, and automated metadata enrichment. Semantics 412 may also provide a semantic hierarchy for categorizing content according to user-specified constraints or against a fixed dictionary or knowledge structure. Generally, any function relating to the categorization, interpretation, or labeling of content may be performed within a semantic layer, which may be used, for example, by users 404 to interpret content or by sources 402 to self-identify content. Categorization may be based on one or more factors, such as popularity, explicit user categorization, interpretation or analysis of textual, graphical, or other content, relationship to other items (such as through an outline or other hierarchical description), content type (e.g., file type), content metadata (e.g., author, source, distribution channel, time of publication, etc.) and so forth. Currently available tools for semantic processing include OPML, dictionaries, thesauruses, and metadata tagging. Current tools also include an array of linguistic analysis tools which may be deployed as a semantic service or used by a semantic service. These and other tools may be employed to evaluate semantic content of an item, including the body and metadata thereof, and to add or modify semantic information accordingly.

It will be understood that, while OPML is one specific outlining grammar, any similar grammar, whether XML-based, ASCII-based, or the like, may be employed, provided it offers a manner for explicitly identifying hierarchies and/or relationships among items within a document and/or among documents. Where the grammar is XML-based, it is referred to herein as an outlining markup language.

Semantics 412 may be deployed, for example, as a semantic service associated with a syndication platform or service. The semantic service may be, for example, a web service, a service in a services oriented architecture, a layer of a protocol stack, a client-side or server-side application, or any of the other technologies described herein, as well as various combinations of these. The semantic service may offer a variety of forms of automated, semi-automated, or manual semantic analysis of items of syndicated content, including feeds or channels that provide such items. The semantic service may operate in one or more ways with syndicated content. In one aspect, the semantic service may operate on metadata within the syndicated content, as generally noted above. The semantic service may also, or instead, store metadata independent from the syndicated content, such as in a database, which may be publicly accessible or privately used by a value-added semantic service provider or the like. The semantic service may also or instead specify relationships among items of syndicated content using an outlining service such as OPML. In general, an outlining service, outlining markup language, outlining syntax, or the like, provides a structured grammar for specifying relationships such as hierarchical relationships among items of content. The relationship may, for example, be a tree or other hierarchical structure that may be self-defined by a number of discrete relationships among individual items within the tree. Any number of such outlines may be provided in an outline-based semantic service.

By way of an example of use of a semantic service, a plurality of items of syndicated content, such as news items relating to a corporate entity, may be aggregated for presentation as a data feed. Other content, such as stored data items, may be associated with the data feed using an outline markup language so that an outline provided by the semantic service includes current events relating to a corporate entity, along with timely data from a suitable data source such as stock quotes, bond prices, or any other financial instrument data (e.g., privately held securities, stock options, futures contracts), and also publicly available data such as SEC filings including quarterly reports, annual reports, or other event reports. All of these data sources may be collected for a company using an outline that structures the aggregated data and provides pointers to a current source of data where the data might change (such as stock quotes or SEC filings). Thus an outline may provide a fixed, structured, and current view of the corporate entity where data from different sources changes with widely varying frequencies. Of course other content, such as message boards, discussion groups, and the like may be incorporated into the outline, along with relatively stable content such as a web site URL for the entity.

Syndication 414 may include any functions or services associated with a publish-subscribe environment and may be embodied, for example, in a client-side application, a remote application or service, an application layer of an enhanced syndication services protocol stack, as application services deployed, for example, in the services oriented architecture described below, or a combination of these. Syndication 412 may include syndication specific functions such as publication, subscription, aggregation, republication, and, more generally, management of syndication information (e.g., source, date, author, and the like). One commonly employed syndication system is RSS, although it will be appreciated from the remaining disclosure that a wide array of enhanced syndication services may provided in cooperation with, or separate from, an RSS infrastructure.

Infrastructure 416 may include any low level functions associated with enhanced syndication services and may be embodied, for example, in a client-side application, a remote application or service, an application layer of an enhanced syndication services protocol stack, as application services deployed, for example, in the services oriented architecture described below, or a combination of these. Infrastructure 416 may support, for example, security, authentication, traffic management, logging, pinging, communications, reporting, time and date services, and the like.

In one embodiment, the infrastructure 416 may include a communications interface adapted for wireless delivery of RSS content. RSS content is typically developed for viewing by a conventional, full-sized computer screen; however, users increasingly view web content, including RSS feeds, using wireless devices, such as cellular phones, Personal Digital Assistants ("PDAs"), wireless electronic mail devices such as Blackberrys, and the like. In many cases content that is suitable for a normal computer screen is not appropriate for a small screen; for example, the amount of text that can be read on the screen is reduced. Accordingly, embodiments of the invention include formatting RSS feeds for wireless devices. In particular, embodiments of the invention include methods and systems for providing content to a user, including taking a feed of RSS content, determining a user interface format for a wireless device, and reformatting the RSS content for the user interface for the wireless device. In embodiments the content may be dynamically reformatted based on the type of wireless device.

In embodiments, tags from an RSS feed can be used to feed a template, such as an XML-enabled template, that further modifies the RSS feed based on the nature of a wireless device. For example, the abstract of an RSS feed can be delivered in a shortened format, such as identifying and delivering the first sentence of the abstract. An RSS feed can also be broken up into sub-segments, and a user can be provided with a link within the feed for requesting additional sub-segments, or additional portions of the feed, thus permitting a user to control content delivery where, for example, the user has a bandwidth-constrained or display-constrained device. In embodiments the link may be interactive and may be activated or manipulated by a user with a control such as a button, thumbpad, touchscreen, dial button, or stylus.

In embodiments an RSS feed may further comprise inserting a phone number into the feed, wherein interacting with the phone number on a cellular phone or other telecommunications-capable device initiates a telephone call. The telephone call could be to a content source, so as to allow a user to hear a voice rendition of the content of the RSS feed, to hear related content, such as programming related to the RSS feed, to initiate a transaction, such as related to the content of the RSS feed, to request a particular type of additional information, to allow the user to subscribe to the feed, or the like.

In embodiments the RSS feed may include a time-related component, such as a schedule for the delivery of additional content. In embodiments the time-related component may be fed to a calendar, task list, or related facility, thus setting an appointment related to the time-related component in a user's electronic calendar, such as on a handheld device or on a conventional personal computer or laptop computer.

In embodiments an RSS feed may be provided with a separate layer of security that is associated with a security facility of a wireless device. For example, an RSS feed may be encrypted so that it may only be read by a specific type of wireless device, a specific wireless device, or on a specific wireless device only after entry of a password that is issued to a known user of that wireless device. In embodiments security may be associated with a location facility of the wireless device (such as GPS, cellular triangulation, or the like), so as to allow a user to access an RSS feed only if the user is physically located in a particular place. For example, a user attending a live concert or other event might be permitted to view an RSS feed about the concert, but other users might be excluded from that content, creating a secure new media channel for event attendees.

In embodiments a user interface for a wireless or handheld device may be customized to include menus that specifically relate to RSS content. For example, an interface may be provided with a separate RSS menu icon, drop down selection, or the like for allowing a user to place such a device in an RSS mode. Within an RSS mode, initiated by an RSS menu option, a user may be provided with options to take actions related to RSS, such as subscribing to feeds, selecting feeds from a set of feeds, prioritizing feeds, selecting feeds as favorites, or the like. In embodiments, an RSS mode may include a menu item for each of (or a subset of) the components of the RSS schema. For example, a menu icon, drop down item, or the like may allow a user to select and view the title of an RSS feed, the abstract, text, the authors, or other content. In embodiments the user interface of a wireless or handheld device may have an RSS search icon, menu, or screen that returns RSS results in response to entry of a keyword. In embodiments results may be returned that include commercial and non-commercial result sets, which may be distinguished on the screen, such as by screen location, by an icon that identifies them as such, or by another indicator of the distinction, such as color, font, underlining, italics, boldface type, highlighting, or the like.

Thus, in embodiments an RSS-customized user interface for a wireless handheld device is provided.

In another aspect, the infrastructure 416 may include improved pinging systems. The only current form of network service in an RSS environment is a primitive system of "pings", such as those provided by weblogs.com, that permit users to track changes and updates to content. When a producer updates its RSS output file, a message is sent to a central file server. When consumers want to know if there are updated RSS outputs from particular sources they go to the central file and see if there is a recent message from the producer of choice, rather than retrieving the RSS source directly. When new content is available, the consumer may send an electronic request directly to the producer's output file and read the contents into the consumers local files, archive, or repository. The infrastructure 416 for an enhanced syndication system may provide improved pinging systems. For example, a central server may be secure. In such a system, each request for a ping may carry an encryption-based key for the requestor. Responses to that requester, which may be verified, for example with reference to a trusted third party, or using some other technique, may be time bound with constraints on start times, stop times, frequency, quotas, or the like. In another embodiment, the requestor may simply use a unique identification number. Pings may be subscription based, so that a for-fee pinger may be used more frequently than a free pinger. Thus there is disclosed herein a secure pinger for use in an RSS system. Also disclosed herein is a managed pinger, which may limit ping responses according to subscription levels, frequency, or any other suitable criteria.

The infrastructure 416 may more generally provide traffic management services including but not limited to real time monitoring of message latency, traffic and congestion, and packet quality across a network of end-to-end RSS exchanges and relationships. This may include real time monitoring of special traffic problems such as denial of service attacks or overload of network capabilities. Another service may be Quality-of-Service management that provides a publisher with the ability to manage time of sending of signaling messages for pingers, time of availability of the signaled-about messages, and unique identifiers which apply to the signaling message and the signaled-about message or messages. This may also include quality of service attributes for the signaled-about message or messages and criteria for selecting end user computers that are to be treated to particular levels of end-to-end quality of service. This may be, for example, a commercial service in which users pay for higher levels of QoS.

It will be generally appreciated that the arrangement of layers and interfaces may vary; however, in one embodiment syndication 414 may communicate directly with sources 402 while the applications 406 may communicate directly with users 404. Thus, in one aspect, the systems described herein enable enhanced syndication systems by providing a consistent framework for consumption and republication of content by users 404. In general, existing technologies such as RSS provide adequate syndication services, but additional elements of a syndication system 400, such as social networking and semantic content management, have been provided only incrementally and only on an ad hoc basis from specific service providers. The functions and services described above may be realized through, for example, the services oriented architecture described below with reference to FIG. 5 and/or any of the markup languages described below with reference to FIG. 6.

In one example a model of an end-to-end content syndication system for, e.g., RSS, OPML, or other content, may include the following elements: convert, structure, store, spider, pool, search, filter, cluster, route, and run. Conversion may transform data (bi-directionally) between application-specific or database-specific formats and the syndication or outlining format. Structure may be derived from the content, such as a knowledge structure inherent in interrelated OPML outlines, or metadata contained in RSS tags. Storage may occur locally on a user device or at a remote repository. Spiders may be employed to search repositories and local data on user devices, to the extent that it is made publicly available or actively published. Pools of data may be formed at central repositories or archives. Searches may be conducted across one or more pools of data. Filters may be employed to select specific data feeds, items within a data feed, or elements of an OPML tree structure. Specific items or OPML tree branches may be clustered based upon explicit search criteria, inferences from metadata or content, or community rankings or commentary. Routing may permit combinations among content from various content sources using, e.g., web services or superservices. Such combinations may be run to generate corresponding displays of results. Other similar or different combinations of elements from the broad categories above may be devised according to various value chains or other conceptual models of syndication services.

More generally, well-defined interfaces between a collection of discrete modules for an established value chain may permit independent development, improvement, adaptation, and/or customization of modules by end users or commercial entities. This may include configurations of features within a module (which might be usefully shared with others, for example), as well as functional changes to underlying software.

For example, an author may wish to use any one or more of a number of environments to create content for syndication. By providing a module with a standardized interface to RSS posting, converters may be created for that module to convert between application formats and an RSS-ready format. This may free contributors to create content in any desired format and, with suitable converters, readily transform the content into RSS-ready material. Thus disparate applications such as Microsoft Word, Excel, and Outlook may be used to generate content, with the author leveraging off features of those applications (such as spell checking, grammar checking, calculation capabilities, scheduling capabilities, and so on). The content may then be converted into RSS material and published to an RSS feed. As a significant advantage, users may work in an environment in which they are comfortable and simply obtain needed converters to supply content to the RSS network. As a result, contributors may be able to more efficiently produce source material of higher quality. Tagging tools may also be incorporated into this module (or some author module) to provide any degree of automation and standardization desired by an author for categorization of content.

As another example, appropriate characterization of RSS material remains a constantly growing problem. However, if tagging occurs at a known and predictable point in the RSS chain, e.g., within a specific module, then any number of useful applications may be constructed within, or in communication with, that module to assist with tagging. For example, all untagged RSS posts may be extracted from feeds and pooled at a commonly accessible location where one or more people may resolve tagging issues. Or the module may automatically resolve tagging recommendations contributed by readers of the item. Different rules may be constructed for different streams of data, according to editorial demands or community preferences. In short, maintaining a separate tagging module, or fixing the tagging function at a particular module within the chain, permits a wide array of tagging functions which may be coordinated with other aspects of the RSS chain.

In another aspect, a well-defined organization of modules permits improved synchronization or coordination of different elements of the modules in the RSS chain. Thus for example centralized aggregators may be provided to improve usability or to improve the tagging of content with metadata, where a combination of lack of standards and constantly evolving topics has frustrated attempts to normalize tagging vocabulary. By explicitly separating tagging from content, visibility of tagging behavior may be improved and yield better tag selection by content authors. Similarly, search techniques (mapping and exploration) may be fully separated from indexing (pre-processing) to permit independent improvements in each.

A well-established "backplane" or other communications system for cooperating RSS modules (or other data feeds) may enable a number of business processes or enterprise applications, particularly if coupled with identity/security/role management, which may be incorporated into the backplane, or various modules connected thereto, to control access to data feeds.

For example, a document management system may be provided using an enhanced RSS system. Large companies, particularly document intensive companies such as professional services firms, including accounting firms, law firms, consulting firms, and financial services firms, employ sophisticated document management systems that provide unique identifiers and metadata for each new document created by employees. Each new document may also, for example, be added to an RSS feed. This may occur at any identifiable point during the document's life, such as when first stored, when mailed, when printed, or at any other time. By viewing the RSS feed with, for example, topical filters, an individual may filter the stream of new documents for items of interest. Thus, for example, a partner at a law firm may remain continuously updated on all external correspondence relating to SEC Regulation FD, compliance with Sarbanes Oxley, or any other matter of interest. Alternatively, a partner may wish to see all documents relating to a certain client. Similarly, a manager at a brokerage house may wish to monitor all trades of more than a certain number of shares for a certain stock. Or an accountant may wish to see all internal memoranda relating to revisions to depreciation allowances in the federal tax code. An enhanced RSS system may provide any number of different perspectives on newly created content within an organization.

Other enterprise-wide applications may be created. For example, a hospital may place all prescriptions written by physicians at the hospital into an RSS feed. This data may be viewed and analyzed to obtain a chronological view of treatment.

In one aspect, functions within the conceptual framework may include a group of atomic functions which may be accessed with a corresponding syntax. Arrangements of such calls into higher-level, more complex operations, may also be expressed in a file such as an OPML file, an XML file, or any other suitable grammar. Effectively, these groups of instructions may form programmatic expressions which may be stored for publication, re-use, and combination with other programmatic expressions. Data for these programmatic expressions may be separately stored in another physical location, in a separate partition at a location of the instructions, or together with the instructions. In one aspect, OPML may provide a grammar for expression of functional relationships, and RSS may provide a grammar for data. Thus the same complex operation may be re-executed against different data sets or against data in a syndicated feed that periodically updates. Thus, in one aspect, an architecture is provided for microprocessor-styled programming across distributed data and instructions.

Figure 5:
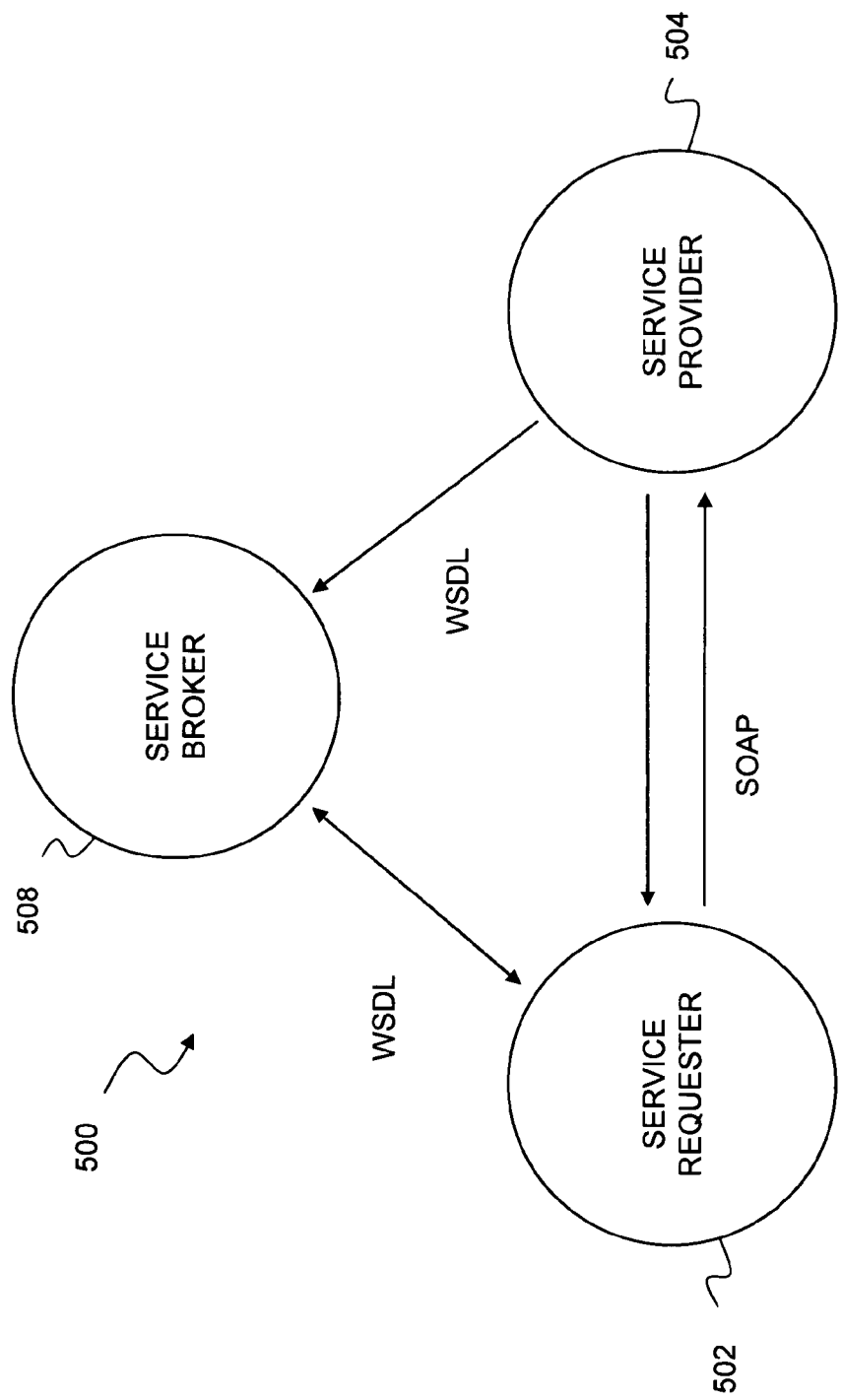
FIG. 5 depicts a system for delivering services in a syndication system.

FIG. 5 depicts a system for delivering services in a syndication system. As depicted, one technology for delivering services within the conceptual framework above is a service oriented architecture. A service oriented architecture ("SOA") 500 may include a service requester 502, a service provider 504, and a service broker 508.

In general, the service requester 502, which may be any of the clients 102 described above, discovers services and receives service descriptions through an exchange with the service broker 508 using a suitable syntax such as the Web Services Description Language ("WSDL"). The service provider 504 publishes service descriptions to the service broker 508, also using a syntax such as WSDL. The service requester 502 uses a service through communications with the service provider 504, using a transport protocol such as Simple Object Access Protocol ("SOAP"). An SOA 500 may include any number of requesters 502, brokers 508, and providers 504. Additionally, a number of protocols and standards may be employed to orchestrate the deployment of services in an SOA 500. In a web services embodiment, the Web service protocol stack is employed to define, locate, implement, and interact with Web services. In general, this includes four main areas: service transport, XML messaging, service description, and service discovery. Service transport transports messages among network applications using protocols such as HyperText Transport Protocol ("HTTP"), File Transfer Protocol ("FTP"), Simple Mail Transfer Protocol ("SMTP"), and more recently the Blocks Extensible Exchange Protocol ("BEEP"). XML messaging encodes messages in a common XML format using, for example, XML-RPC, SOAP, and REST. The service description is used to describe the public interface for services, typically using WSDL as noted above. Service discovery may use WSDL, along with Universal Description, Discovery, and Integration ("UDDI"), which provides a platform independent, XML-based registry for public Internet listings.

An SOA 500 architecture may be used, for example, in an enhanced syndication system to relate metadata in an item of content to services that are available from the registry. Thus, for example, a publicly available registry may provide, among other things, a number of viewers for graphical images. An RSS item may refer to an image source, such as an MRI image in a medical record from a hospital, and may specify a viewer for the source image that is available through the registry. In operation, a client with appropriate permission to view the image (also as managed, e.g., through the metadata for the enhanced syndication system), may retrieve the appropriate viewer service from the registry and apply the viewer to view the source image. In this example, viewers may be freely provided or may be licensed and made available through the registry on a fee per use basis or some other licensing terms. Similarly, the image source may be made available in various resolutions, each available under a different fee structure. In other embodiments, textual sources may be available in various forms ranging from a title and biographical data to an abstract to the full text of the source. Thus the SOA platform may be used to resell content from an RSS archive, using viewer or access privilege services made available through the registry. Other aspects such as identity and affiliation, as well as verification of these, may be made available as services in the SOA 500.

Figure 6:
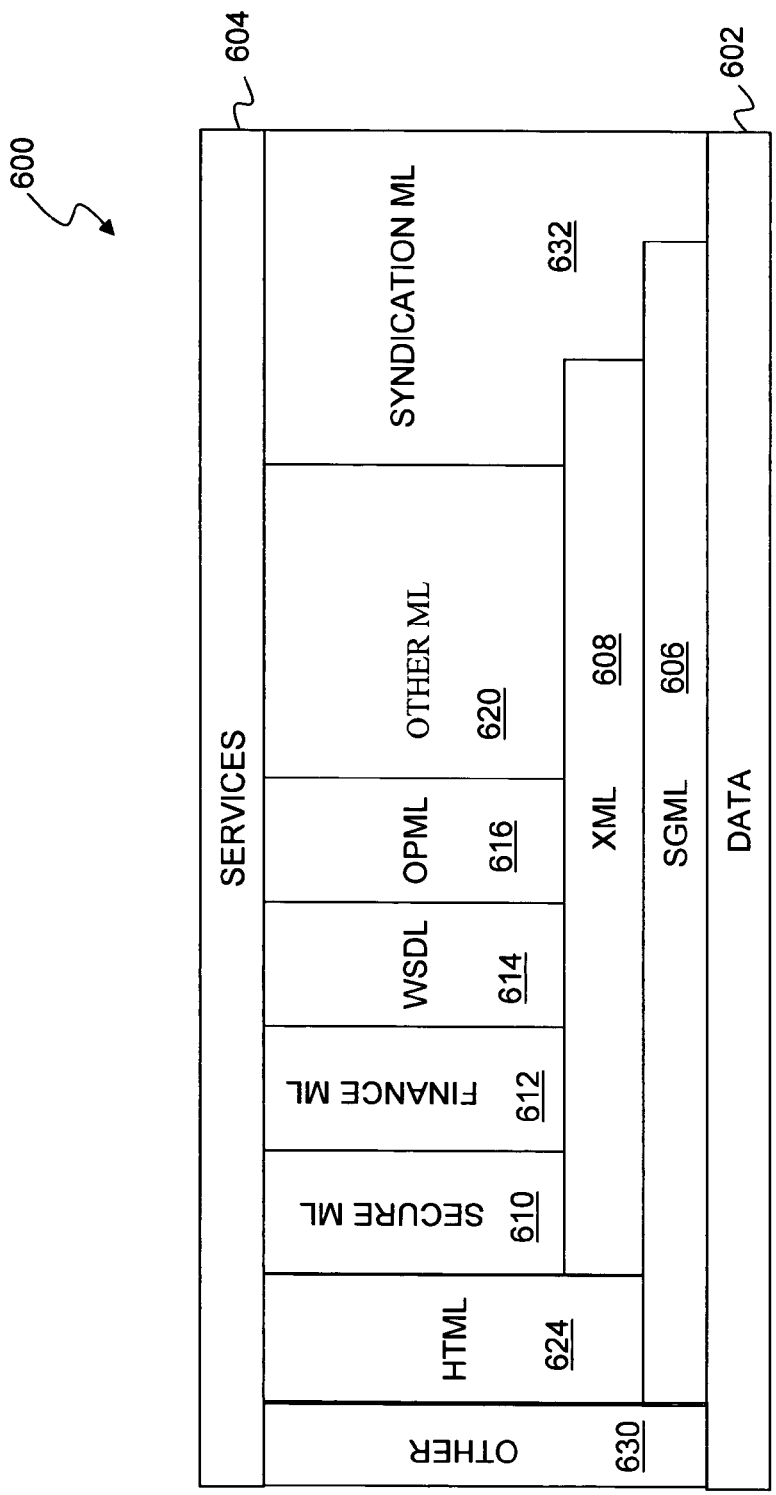
FIG. 6 shows an XML environment for syndication systems.

FIG. 6 shows an XML environment for syndication systems. As represented in FIG. 6, an XML environment 600 includes data 602, which may be any of the content sources or other data sources described above that interacts with services 604, which may execute on a client 102, a server 104, or any other entity within a network.

Services 604, which may be, for example, any of the services described above with reference to FIG. 4, may employ a variety of standards, protocols, and programming languages to interact meaningfully with the data 602. This includes, for example, the use of programming tools that permit program logic to be deployed in, e.g., Java, Windows, Perl, PHP, C/C++, and so on. This also includes parsing, processing, and database access using, e.g., data binding (mapping XML components into native formats of various programming languages), Document Object Model ("DOM", a programming interface for manipulation of XML/HTML as program objects), Simple API for XML ("SAX", another API for XML documents), XSL (a stylesheet expression language), XSL Transformations ("XSLT", a language for transforming XML documents into other XML documents), XML Path Language ("XPATH", a language for referring to parts of XML documents), XSL Formatting Objects ("XSL-FO", an XML vocabulary for formatting semantics), and a variety of tools for queries and other access to commercial databases. Further, presentation may be provided using, e.g., XHTML, CSS/XSL-FO, SMIL, WSUI, and a host of other presentation tools. Services 604 may also employ various other XML-oriented tools for messaging, metadata, and web services, including SOAP, XML-RPC, RDF, UDDI, WSDL, and the like. Other specifications, such as the Voice eXtensible Markup Language (VoiceXML), Security Services Markup Language (S2ML), and OASIS Security Assertion Markup Language (SAML), provide special purpose grammars for specific functions. In general, these tools in various combinations permit a relatively arbitrary deployment of functions as services on top of content, structured using XML grammars.

The services 604 may interact with data 602 through one or more established grammars, such as a secure markup language 610, a finance markup language 612, WSDL 614, the Outline Programming Markup Language ("OPML") 616, or other markup languages 620 based upon XML 608, which is a species of the Standard Generalized Markup Language ("SGML") 606. The interaction may be also, or instead, through non-XML grammars such as HTML 624 (which is a species of SGML) or other formats 630. More generally, a wide array of XML schemas have been devised for industry-specific and application-specific environments. For example, XML.org lists the following vertical industries with registered XML schemas, including the number of registered schemas in parentheses, all of which may be usefully combined with the systems described herein, and are hereby incorporated by reference in their entirety: Accounting (14), Advertising (6), Aerospace (20), Agriculture (3), Arts/Entertainment (24), Astronomy (14), Automotive (14), Banking (10), Biology (9), Business Reporting (2), Business Services (3), Catalogs (9), Chemistry (4), Computer (9), Construction (8), Consulting (20), Customer Relation (8), Customs (2), Databases (11), E-Commerce (60), EDI (18), ERP (4), Economics (2), Education (51), Energy/Utilities (35), Environmental (1), Financial Service (53), Food Services (3), Geography (5), Healthcare (25), Human Resources (23), Industrial Control (5), Insurance (6), Internet/Web (35), Legal (10), Literature (14), Manufacturing (8), Marketing/PR (1), Math/Data, Mining (10), Multimedia (26), News (12), Other Industry (12), Professional Service (6), Public Service (5), Publishing/Print (28), Real Estate (16), Religion, Retail (6), Robotics/AI (5), Science (64), Security (4), Social Sciences (4), Software (129), Supply Chain (23), telecommunications (26), translation (7), transportation (10), travel (4), Waste Management, Weather (6), Wholesale, and XML Technologies (238).

Syndication services, described in more detail below, may operate in an XML environment through a syndication markup language 632, which may support syndication-specific functions through a corresponding data structure. One example of a currently used syndication markup language 632 is RSS. However, it will be appreciated that a syndication markup language ("SML") as described herein may include any structure suitable for syndication, including RSS, RSS with extensions (RSS+), RSS without certain elements (RSS−), RSS with variations to elements (RSS'), or various combinations of these (e.g., RSS'−, RSS'+). Furthermore, an SML 632 may incorporate features from other markup languages, such as a financial markup language 612 and/or a secure markup language 610, or may be used in cooperation with these other markup languages 620. More generally, various combinations of XML schemas may be employed to provide syndication with enhanced services as described herein in an XML environment. It will be noted from the position of SML 632 in the XML environment that SML 632 may be XML-based, SGML-based, or employ some other grammar for services 604 related to syndication. All such variations to the syndication markup language 632 as may be usefully employed with the systems described herein are intended to fall within the scope of this disclosure and may be used in a syndication system as that term is used herein.

According to the foregoing, there is disclosed herein an enhanced syndication system. In one aspect, the enhanced syndication system permits semantic manipulation of syndicated content. In another aspect, the enhanced syndication system offers a social networking interface which permits various user interactions without a need to directly access underlying syndication technologies and the details thereof. In another aspect, a wide variety of additional services may be deployed in combination with syndicated content to enable new uses of syndicated content. In another aspect, persistence may be provided to transient syndicated content by the provision of a database or archive of data feeds, and particularly the content of data feeds, which may be searched, filtered, or otherwise investigated and manipulated in a syndication network. Such a use of a syndication system with a persistent archive of data feeds and items therein is now described in greater detail.

The syndication markup language 632, or the syndication markup language 632 in combination with other supporting markup languages and other grammars including but not limited to RSS, OPML, XML and/or any other definition, grammar, syntax, or format, either fixed or extensible, all as described in more detail below, may support syndication-related communications and functions. Syndication communications may generally occur through an internetwork between a subscriber and a publisher, with various searching, filtering, sorting, archiving, modifying, and/or outlining of information as described herein.

Two widely known message definitions for syndicated communications are RSS 2.0 (RSS) and the Atom Syndication Format Draft Version 9 (Atom, as submitted to the IETF on Jun. 7, 2005 in the form of an Internet-Draft). A syndication message definition, as used herein, will be understood to include these definitions as well as variations, modifications, extensions, simplifications, and the like as described generally herein. Thus, a syndication message definition will be understood to include the various XML specifications and other grammars described herein and may support corresponding functions and capabilities that may or may not include the conventional publish-subscribe operations of syndication. A syndication definition may be described in terms of XML or any other suitable standardized or proprietary format. XML, for example, is a widely accepted standard of the Internet community that may conveniently offer a human-readable and machine-readable format. Alternatively, the syndication definition may be described according to another syntax and/or formal grammar.

For purposes of establishing a general vocabulary, and not by way of limitation, components of syndicated communications are now described in greater detail.

A message instance, or message, may conform to a message definition, which may be an abstract, typed definition. The abstract, typed definition may be expressed, for example, in terms of an XML schema, which may without limitation comprise XML's built-in Document Type Definition (DTD), XML Schema, RELAX NG, and so forth. In some cases, information may lend itself to representation as a set of message instances, which may be atomic, and may be ordered and/or may naturally occur as a series. It should be appreciated that the information may change over time and that any change in the information may naturally be associated with a change in a particular message instance and/or a change in the set of message instances. A data feed or data stream may include a set of messages. In an RSS environment, a message instance may be referred to as an entry. In an OPML environment, the message instance may be referred to as a list. More generally, a message may include any elements of the syndication message definition noted above. Thus, it will be appreciated that the terms "list," "outline," "message," "item," and the like may be used interchangeably in the description of enhanced syndication systems herein. All such meanings are intended to fall within the scope of this disclosure unless a more specific meaning is expressly indicated or clear from the context. A channel definition may provide metadata associated with a data feed, and a subscription request may include a URI or other metadata identifying a data feed and/or data feed location. The location may without limitation comprise a network address, indication of a network protocol, path, virtual path, filename, and any other suitable identifying information.

A syndication message definition may include any or all of the elements of the following standards and drafts, all of which are hereby incorporated in their entirety by reference: RSS 2.0; Atom Syndication Format as presented in the IETF Internet-Draft Version 9 of the Atom Syndication Format; OPML 1.0; XML Signature Syntax (as published in the W3C Recommendation of 12 Feb. 2002); the XML Encryption Syntax (as published in the W3C Recommendation of 10 Dec. 2002); and the Common Markup for Micropayment per-fee-links (as published in the W3C Working Draft of 25 Aug. 1999). In summary, these elements, which are described in detail in the above documents, may include the following: channel, title, link, description, language, copyright, managing editor (managingEditor), Web master (webmaster), publication date (pubDate), last build date (lastBuildDate), category, generator, documentation URL (docs), cloud, time to live (ttl), image, rating, text input (textInput), skip hours (skipHours), skip days (skipDays), item, author, comments, enclosure, globally unique identifier (guid), source, name, URI, email, feed, entry, content, contributor, generator, icon, id, logo, published, rights, source, subtitle, updated, opml, head, date created (dateCreated), date modified (dateModified), owner name (ownerName), owner e-mail (ownerEmail), expansion state (expansionState), vertical scroll state (vertScrollState), window top (windowTop), window left (windowLeft), window bottom (windowBottom), window right (windowRight), head, body, outline, signature (Signature), signature value (SignatureValue), signed information (Signedinfo), canonicalization method (CanonicalizationMethod), signature method (SignatureMethod), reference (Reference), transforms (Transforms), digest method (DigestMethod), digest value (DigestValue), key information (KeyInfo), key value (KeyValue), DSA key value (DSAKeyvalue), RSA key value (RSAKeyValue), retrieval method (RetrievalMethod), X509 data (X509Data), PGP Data (PGPData), SPKI Data (SPKIData), management data (MgmtData), object (Object), manifest (Manifest), signature properties (SignatureProperties), encrypted type (EncryptedType), encryption method (EncryptionMethod), cipher data (CipherData), cipher reference (CipherReference), encrypted data (EncryptedData), encrypted key (EncryptedKey), reference list (ReferenceList), encryption properties (EncryptionProperties), price, text link (textlink), image link (imagelink), request URL (request URL), payment system (paymentsystem), buyer identification (buyerid), base URL (baseurl), long description (longdesc), merchant name (merchantname), duration, expiration, target, base language (hreflang), type, access key (accesskey), character set (charset), external metadata (ExtData), and external data parameter (ExtDataParm).

A syndication definition may also include elements pertaining to medical devices, crawlers, digital rights management, change logs, route traces, permanent links (also known as permalinks), time, video, devices, social networking, vertical markets, downstream processing, and other operations associated with Internet-based syndication. The additional elements may, without limitation, comprise the following: clinical note (ClinicalNote), biochemistry result (BiochemistryResult), DICOM compliant MRI image (DCMRI), keywords (Keywords), license (License), change log (ChangeLog), route trace (RouteTrace), permalink (Permalink), time (Time), shopping cart (ShoppingCart), video (Video), device (Device), friend (Friend), market (Market), downstream processing directive (DPDirective), set of associated files (FileSet), revision history (RevisionHistory), revision (Revision), branch (Branch), merge (Merge), trunk (Trunk), and symbolic revision (SymbolicRevision). Generally, in embodiments, the names of the elements may be case insensitive.

For example, the contents of the clinical note element may without limitation comprise a note written by a clinician, such as a referral letter from a primary care physician to a specialist. The contents of the biochemistry result element may without limitation comprise indicia of total cholesterol, LDL cholesterol, HDL cholesterol, and/or triglycerides. The contents of the DICOM compliant MRI image element may without limitation comprise an image file in the DICOM format. The content of the keyword element may without limitation comprise a word and/or phrase associated with the content contained in the message, wherein the word and/or phrase may be processed by a Web crawler. The content of the license element may without limitation comprise a URL that may refer to a Web page containing a description of a license under which the message is available. The content of the change log element may without limitation comprise a change log. The content of the route trace element may without limitation comprise a list of the computers through which the message has passed, such as a list of "received:" headers analogous to those commonly appended to an e-mail message as it travels from sender to receiver through one or more SMTP servers. The content of the permalink element may without limitation comprise a permalink, such as an unchanging URL. The content of the time element may without limitation comprise a time, which may be represented according to RFC 868. The content of the shopping cart element may without limitation comprise a representation of a shopping cart, such as XML data that may comprise elements representative of quantity, item, item description, weight, and unit price. The content of the video element may without limitation comprise a MPEG-4 encoded video file. The content of the device element may without limitation comprise a name of a computing facility. The content of the friend element may without limitation comprise a name of a friend associated with an author of an entry. The content of the market element may without limitation comprise a name of a market. The content of the downstream processing directive element may without limitation comprise a textual string representative of a processing step, such as and without limitation "Archive This," that ought to be carried out by a recipient of a message.

Thus, in general a syndication definition as that term is used herein describes a message format that enables Internet-syndication operations, as well as other complementary or separate operations. A message, as that term is used herein, may be associated with a feature of RSS, may be associated with a feature of Atom, may be associated with a feature of OPML, may be associated with a micropayment, may be associated with electronic commerce, may be associated with a representation of medical information, may be associated with the representation of public information, may be associated with the representation of private information, may be associated with the representation of protected information, may be associated with a tag for a crawler, may be associated with versioning and/or a change log, may be associated with a digital signature, may be associated with basic authentication, may be associated with digest authentication, may associated with encryption, may be associated with a license term, may be associated with a route trace, may be associated with a permalink, may be associated with an enclosure or file attachment, may be associated with an indication of time or a timestamp, may be associated with e-commerce, may be associated with searching, may be associated with filtering, may be associated with clustering, may be associated with a database, may be associated with security, may be associated with video, may be associated with a device, may be associated with a user interface, may be associated with a rule, may be associated with non-syndication technologies, may be associated with social networking, may be associated with a vertical market, may be associated with downstream processing, may be associated with semantic processing, and/or may be associated with a source.

A message as described herein may include, consist of, or be evaluated by one or more rules or expressions (referred to collectively in the following discussion as expressions) that provide descriptions of how a message should be processed. In this context, the message may contain data in addition to expressions or may refer to an external source for data. The expression may be asserted in a variety of syntaxes and may be executable and/or interpretable by a machine. For example, an expression may have a form such as that associated with the Lisp programming language. Although an expression may commonly be represented as what may be understood as a "Lisp-like expression" or "Lisp list"—for example, (a (b c))—this particular representation is not necessary. An expression may defined recursively and may include flow control, branching, conditional statements, loops, and any other aspects of structured, object oriented, aspect oriented, or other programming languages. For example and without limitation, it should be appreciated that information encoded as SGML or any species thereof (such as and without limitation, XML, HTML, OPML, RSS, and so forth) may easily be represented as a Lisp-like expression and vice versa. Likewise, data atoms, such as and without limitation a text string, a URL, a URI, a filename, and/or a pathname may naturally be represented as a Lisp-like expression and vice versa. Again, by way of illustration and not limitation, any representation of encoded information that can be reduced to a Lisp-like expression may be an expression as that term is used herein.

An expression may, without limitation, express the following: a data atom, a data structure, an algorithm, a style sheet, a specification, an entry, a list, an outline, a channel definition, a channel, an Internet feed, a message, metadata, a URI, a URL, a subscription, a subscription request, a network address, an indication of a network protocol, a path, a virtual path, a filename, a syntax, a syntax defining an S-expression, a set, a relation, a function, a graph, a tree, a counting algorithm, a probabilistic algorithm, a randomized algorithm, a geometric distribution, a binomial distribution, a heap, a heapsort algorithm, a priority queue, a quicksort algorithm, a counting sort algorithm, a radix sort algorithm, a bucket sort algorithm, a median, an order statistic, a selection algorithm, a stack, a queue, a linked list, a pointer, an object, a rooted tree, a hash table, a direct-address table, a hash function, an open addressing algorithm, a binary search tree, a binary search tree insertion algorithm, a binary search tree deletion algorithm, a randomly built binary search tree, a red-black tree, a red-black tree rotation algorithm, a red-black tree insertion algorithm, a red-black tree deletion algorithm, a dynamic order statistic, an interval tree, a dynamic programming algorithm, a matrix, a matrix-chain multiplication algorithm, a longest common subsequence, a polygon, a polygon triangulation, an optimal polygon triangulation, an optional polygon triangulation algorithm, a greedy algorithm, a Huffman code, a Huffman coding algorithm, an amortized analysis algorithm, an aggregate method algorithm, an accounting method algorithm, a potential method algorithm, a dynamic table, a b-tree, a b-tree algorithm (such as and without limitation search, create, split, insert, nonfull, delete), a binomial heap, a binomial tree, a binomial heap algorithm (such as and without limitation create, minimum, link, union, insert, extract minimum, decrease key, delete), a Fibonacci heap, a mergeable heap, a mergeable heap algorithm (such as and without limitation make heap, insert, minimum, extract minimum, and union), a disjoint set, a disjoint set algorithm, a cyclic graph, an acyclic graph, a directed graph, an undirected graph, a sparse graph, a breadth-first search algorithm, a depth-first search algorithm, a topological sort algorithm, a minimum spanning tree, a Kruskal algorithm, a Prim algorithm, a single-source shortest path, Dijkstra's algorithm, a Bellman-Ford algorithm, an all-pairs shortest path, a matrix, a matrix multiplication algorithm, the Floyd-Warshall algorithm, Johnson's algorithm, a flow network, the Ford-Fulkerson method, a maximum bipartite matching algorithm, a preflow-push algorithm, a lift-to-front algorithm, a sorting network, an arithmetic circuit, an algorithm for a parallel computer, a matrix operation, a polynomial, a fast Fourier transform, a number-theoretic algorithm, a string matching algorithm, a computational geometry algorithm, an algorithm in complexity class P, an algorithm in complexity class NP, and/or an approximation algorithm.

In one aspect, a message processor as described herein may include a hardware and/or software platform for evaluating messages according to any of the expressions described above. The message processor may reside, for example, on the server computer or client computer as described above. The processing may without limitation include the steps of read, evaluate, execute, interpret, apply, store, and/or print.

The machine for processing an expression may comprise software and/or hardware. The machine may be designed to process a particular representation of an expression, such as and without limitation SGML or any species thereof. Alternatively, the machine may be a metacircular evaluator capable of processing any arbitrary representation of an S-expression as specified in a representation of an expression.

Generally, a message may include or be an expression. In other embodiments, the expression evaluation process may itself be syndicated. In such an embodiment, interpretations (i.e., evaluations) of a message may vary according to a particular evaluation expression, even where the underlying message remains constant, such as by filtering, concatenating, supplementing, sorting, or otherwise processing elements of the message or a plurality of messages. Different evaluation expressions may be made available as syndicated content using the syndication techniques described generally herein.

The message may specify presentation (e.g., display) parameters, or include expressions or other elements characterizing a conversion into one or more presentation formats.

In embodiments, the message may include an OPML file with an outline of content, such as and without limitation a table of contents; an index; a subject and associated talking points, wherein the talking points may or may not be bulleted; an image; a flowchart; a spreadsheet; a chart; a diagram; a figure; or any combination thereof. A conversion facility, which may include any of the clients or servers described above, may receive the message and convert it to a specified presentation format, which may include any proprietary or open format suitable for presentation. This may include without limitation a Microsoft PowerPoint file, a Microsoft Word file, a PDF file, an HTML file, a rich text file, or any other file comprising both a representation of content and a representation of a presentation of the content. The representation of content may comprise a sequence of text, an image, a movie clip, an audio clip, or any other embodiment of content. The representation of the presentation of the content may include characteristics such as a font, a font size, a style, an emphasis, a de-emphasis, a page-relative position, a screen-relative position, an abstract position, an orientation, a scale, a font color, a background color, a foreground color, an indication of opacity, a skin, a style, a look and feel, or any other embodiment of presentation, as well as combinations of any or all of the foregoing. In a corresponding method, a message may be received and processed, and a corresponding output file may be created, that represents a presentation format of the received message. In various aspects, the message may include an OPML file with references to external data. During processing, this data may be located and additionally processed as necessary or desired for incorporation into the output file.

In one embodiment, the system may include an OPML to PowerPoint converter that traverses one or more OPML outlines and converts the OPML outline into a Microsoft PowerPoint presentation having a structure representative of the structure embodied in the outline. This may include, for example, one or more introductory slides with title, author, creation date, and other information. This may also include one or more slides summarizing the contents of the entire PowerPoint document based upon the top level contents of the outline in the OPML document. Sub-categories may be similarly previewed in the PowerPoint document with slides that list all elements of an outline at one hierarchical level, followed by a number of slides addressing each element in greater detail. Additionally, items such as graphics, charts, tables, audio clips, word documents, and the like that are contained on leaf nodes of the OPML outline may be rendered within the PowerPoint slides to capture some or all of the multi-media content represented within the OPML outline. Similarly, the system may convert a PowerPoint presentation into an OPML outline and may either employ the explicitly outlined structure of the PowerPoint presentation or infer structure from the arrangement or titles of slides within the PowerPoint document.

Figure 7:
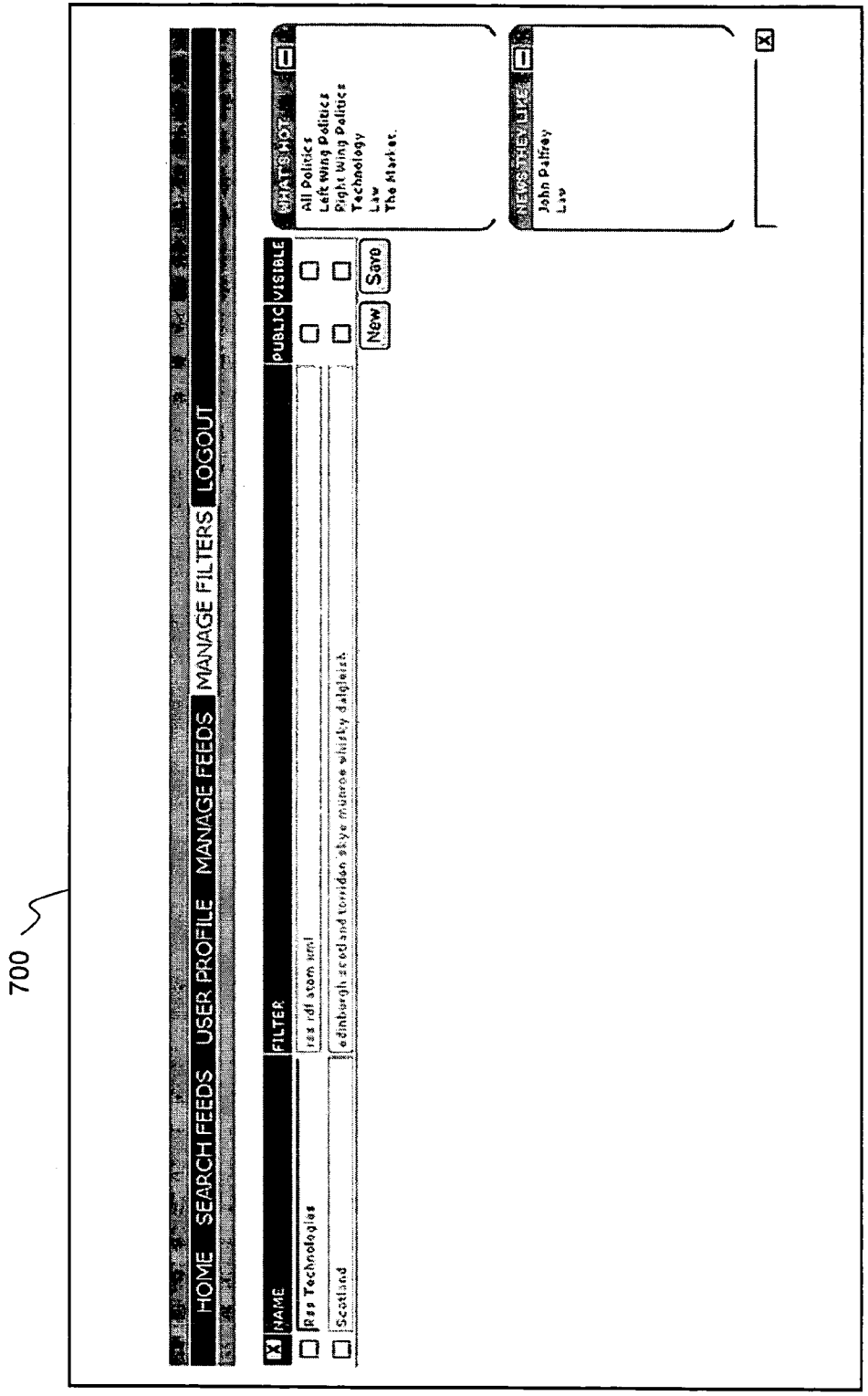
FIG. 7 shows a user interface for a syndication system.

FIG. 7 shows a user interface 700 for data feed management. More particularly, FIG. 7 depicts a manage filters page in which a user can create, edit, and share filters. The page may include navigation buttons and a "What's Hot" and a "News They Like" workspace. In addition, the page may provide a list of available filters. New filters may be created, and rules for each filter may be defined using, for example, Boolean or other operators on defined fields for data feeds or on full text of items within data fields. In order to promote community activity, each filter may be made public for others to use, and the rules and other structure of each filter may also be optionally shared for others to inspect. As a significant advantage over existing systems, these filters may be applied in real time to RSS data feeds or other data feeds to narrow the universe of items that is displayed to a user.

In one aspect, the systems described herein may be used to scan historical feed data and locate relevant data feeds. For example, filters may be applied to historical feed data to identify feeds of interest to a user. For example, by searching for words such as "optical" and "surgery" in a universe of medical feeds, a user may locate feeds relevant to optical laser surgery regardless of how those feeds are labeled or characterized by other users or content providers. In another complementary application, numerous filters may be tested against known relevant feeds, with a filter selected according to the results. This process may be iterative, where a user may design a filter, test it against relevant feeds, apply to other feeds to locate new relevant feeds, and repeat. Thus, while real-time or near real time filtering is one aspect of the systems described herein, the filtering technology may be used with historical data to improve the yield of relevant material for virtually any topic of interest.

Another advantage of filtering historical data is the ability to capture transient discussions and topics that are not currently of interest. Thus, a user interested in the 1996 U.S. Presidential campaign may find little relevant material on current data feeds but may find a high amount of relevant data in the time period immediately preceding the subsequent 2000 campaign. Similarly, an arbitrary topic such as Egyptian history may have been widely discussed at some time in the past, while receiving very little attention today. The application of filters to historical feeds may provide search functionality similar to structured searching of static Web content. Thus there is disclosed herein a time or chronology oriented search tool for searching the contents of one or more sequential data feeds.

In another aspect, the filters may be applied to a wide array of feeds, such as news sources, to build a real-time magazine dedicated to a particular topic. The results may be further parsed into categories by source. For example, for diabetes related filters, the results may be parsed into groups such as medical and research journals, patient commentaries, medical practitioner Weblogs, and so forth. The resulting aggregated data feed may also be combined with a readers' forum, editor's overview, highlights of current developments, and so forth, each of which may be an additional data feed for use, for example, in a Web-based, real-time, magazine or a new aggregated data feed.

In general, the filter may apply any known rules for discriminating text or other media to identified data feeds. For example, rules may be provided for determining the presence or absence of any word or groups of words. Wild card characters and word stems may also be used in filters. In addition, if-then rules or other logical collections of rules may be used. Proximity may be used in filters, where the number of words between two related words is factored into the filtering process. Weighting may be applied so that certain words, groups of words, or filter rules are applied with different weight toward the ultimate determination of whether to filter a particular item. External references from an item, e.g., links to other external content (either the existence of links, or the domain or other aspects thereof) may be used to filter incoming items of a data feed. External links to a data feed or data item may also be used, so as to determine relevance by looking at the number of users who have linked to an item. This process may be expanded to measure the relevance of each link by examining the number of additional links produced by the linking entity. In other words, if someone links to a reference and that user has no other links, this may be less relevant than someone who links to the reference and has one hundred other links. This type of linking analysis system is provided, for example, by Technorati.

Filters may apply semantic analysis to determine or approximate the tone, content, or other aspects of an item by analyzing words and word patterns therein. Filters may also examine the source of an item, such as whether it is from a .com top level domain or a .edu top level domain. The significance of a source designation as either increasing or decreasing the likelihood of passing through the filter may, of course, depend on the type of filter. Additionally, synonyms for search terms or criteria may be automatically generated and applied alongside user specified filter criteria.

Metadata may be used to measure relevance. Data feeds and data items may be tagged with either subject matter codes or descriptive words and phrases to indicate content. Tags may be provided by an external trusted authority, such as an editorial board, or provided by an author of each item or provider of each data feed. These and any other rules capable of expression through a user interface may be applied to items or posts in data feeds to locate content of interest to a particular user.

As noted above, a user may also share data feeds, aggregated data feeds, and/or filters with others. Thus, in general, there is provided herein a real-time data mining method for use with data feeds such as RSS feeds. Through the intelligent filtering enabled by this data feed management system, automatically updating information montages tailored to specific topics or users may be created that include any number of different perspectives from one to one hundred to one thousand or more. These real-time montages may be adapted to any number of distinct customer segments of any size, as well as to business vertical market applications.

In another aspect, filters may provide a gating technology for subsequent action. For example, when a number of items are identified meeting a particular filter criterion, specific, automated actions may be taken in response. For example, filter results, or some predetermined number of filter results, may trigger a responsive action such as displaying an alert on a user's monitor, posting the results on a Weblog, e-mailing the results to others, tagging the results with certain metadata, or signaling for user intervention to review the results and status. Thus, for example, when a filter produces four results, an e-mail containing the results may be transmitted to a user with embedded links to the source material.

Figure 8:
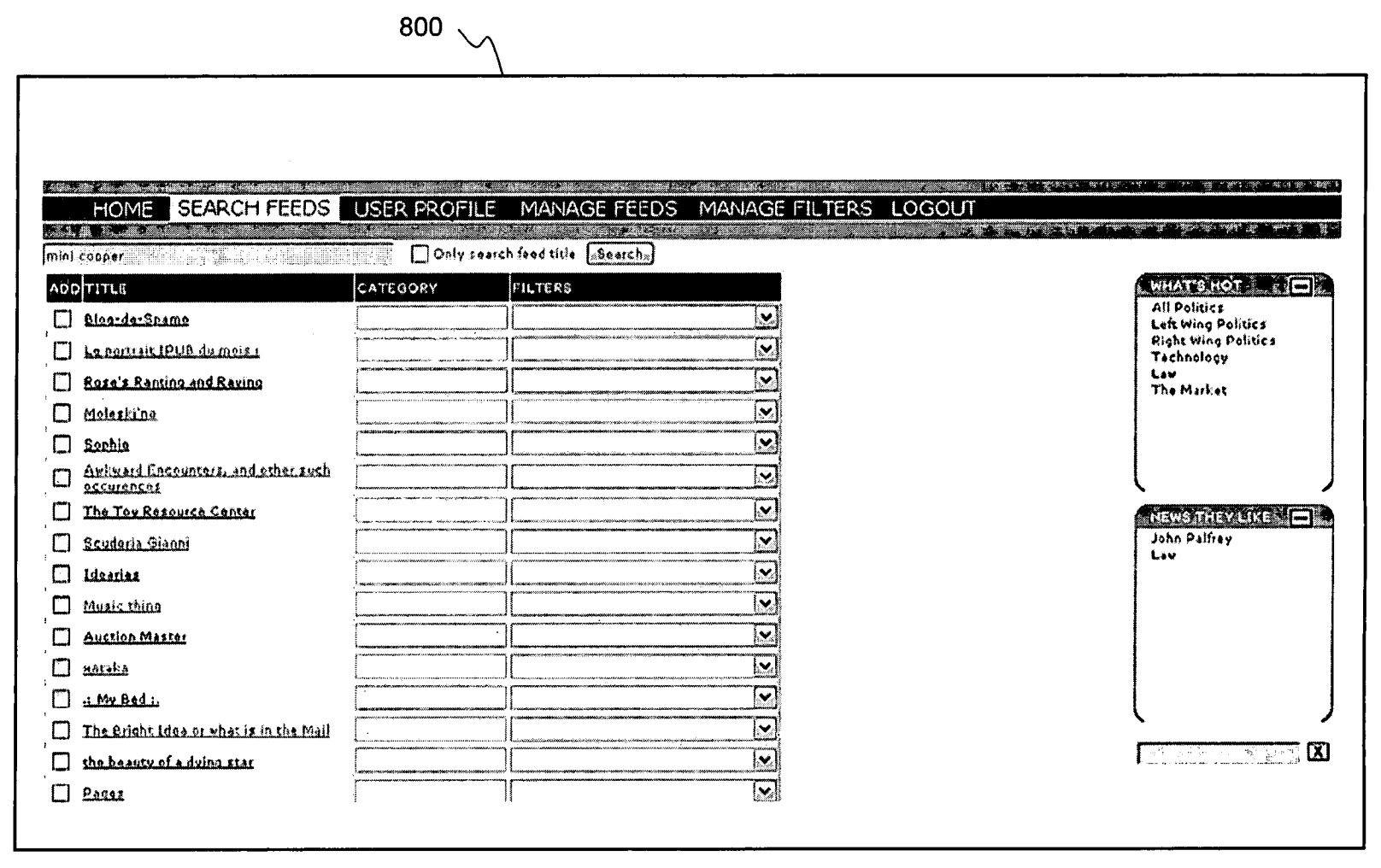

FIG. 8 shows a user interface 800 for data feed management. More particularly, FIG. 8 depicts a search feeds page in which a user can search for additional data feeds to monitor. The page may include navigation buttons and a "What's Hot" and a "News They Like" workspace. In addition, the page may include a text input field for user input of one or more search terms. There may also be one or more checkboxes or other controls for additional search parameters. For example, a user may select whether to search titles only, other information in the description of the feed, or individual items or postings in the feed. The search itself may also be stored, so that new searches for the same subject matter optionally will not include feeds that a user has already reviewed and rejected. Alternatively, the search may be persistent, so that the request search continues to execute against a database of feeds and posts as new feeds and new posts are added. Thus a user may leave the search and return to the search at a later time to review changes in results. The results for a search may be presented in the user interface along with a number of user controls for appropriately placing the feed within the user's feed environment. For example, a user may provide a new, user-assigned category to a feed or select from one or more of the user's pre-existing categories. The user may also specify one or more filters, either pre-built or custom-built by the user, to apply to items in the data feed once it is added. After a feed has been added, the user may review items passing through the assigned filter, if any, in the home page discussed above.

It will be appreciated that search results will be improved by the availability of well organized databases. While a number of Weblogs provide local search functionality, and a number of aggregator services provide lists of available data feeds, there does not presently exist a consumer-level searchable database of feed contents, at least nothing equivalent to what Google or AltaVista provide for the Web. As such, one aspect of the system described herein is a database of data feeds that is searchable by contents as well as metadata such as title and description. In a server used with the systems described herein, the entire universe of known data feeds may be hashed or otherwise organized into searchable form in real time or near real time. The hash index may include each word or other symbol and any data necessary to locate it in a stream and in a post.

One useful parameter that may be included for searching is age. That is, the age of a feed, the age of posts within a feed, and any other frequency data may be integrated into the database for use in structured user searches (and the filters discussed in reference to FIG. 7).

As a further advantage, data may be retrieved from other aggregators and data feeds on a well-defined schedule. In addition to providing a very current view of data streams, this approach prevents certain inconsistencies that occur with currently used aggregators. For example, even for aggregator sites that push notification of updates to subscribers, there may be inconsistencies between source data and data feed data if the source data is modified. While it is possible to renew notification when source material is updated, this is not universally implemented in aggregators or Weblog software commonly employed by end users. Thus an aggregator may extract data from another aggregator that has not been updated. At the same time, an aggregator or data source may prevent repeated access from the same location (e.g., IP address). By accessing all of this data on a regular schedule (that is acceptable to the respective data sources and aggregators) and storing the results locally, the server described herein may maintain a current and accurate view of data feeds. Additionally, feeds may be automatically added by searching and monitoring in real time, in a manner analogous to Web bots used by search engines for static content.

In another aspect, a method of selling data feed services is disclosed herein. In this method, RSS data which is actually static content in files may be serialized for distribution according to some time base or time standard such as one item every sixty seconds or every five minutes. In addition, data may be filtered to select one item of highest priority at each transmission interval. In another configuration, one update of all items may be pushed to subscribers every hour or on some other schedule in an effective batch mode. Optionally, a protocol may be established between the server and clients that provides real time notification of new items. A revenue model may be constructed around the serialized data in which users pay increasing subscription rates for increasing timeliness, with premium subscribers receiving nearly instantaneous updates. Thus in one aspect, a data feed system is modified to provide time-based data feeds to end users. This may be particularly useful for time sensitive information such as sports scores or stock prices. In another embodiment, the end-user feed may adhere to an RSS or other data feed standard but nonetheless use a tightly controlled feed schedule that is known to both the source and recipient of the data to create a virtual time based data feed.

Figure 9:
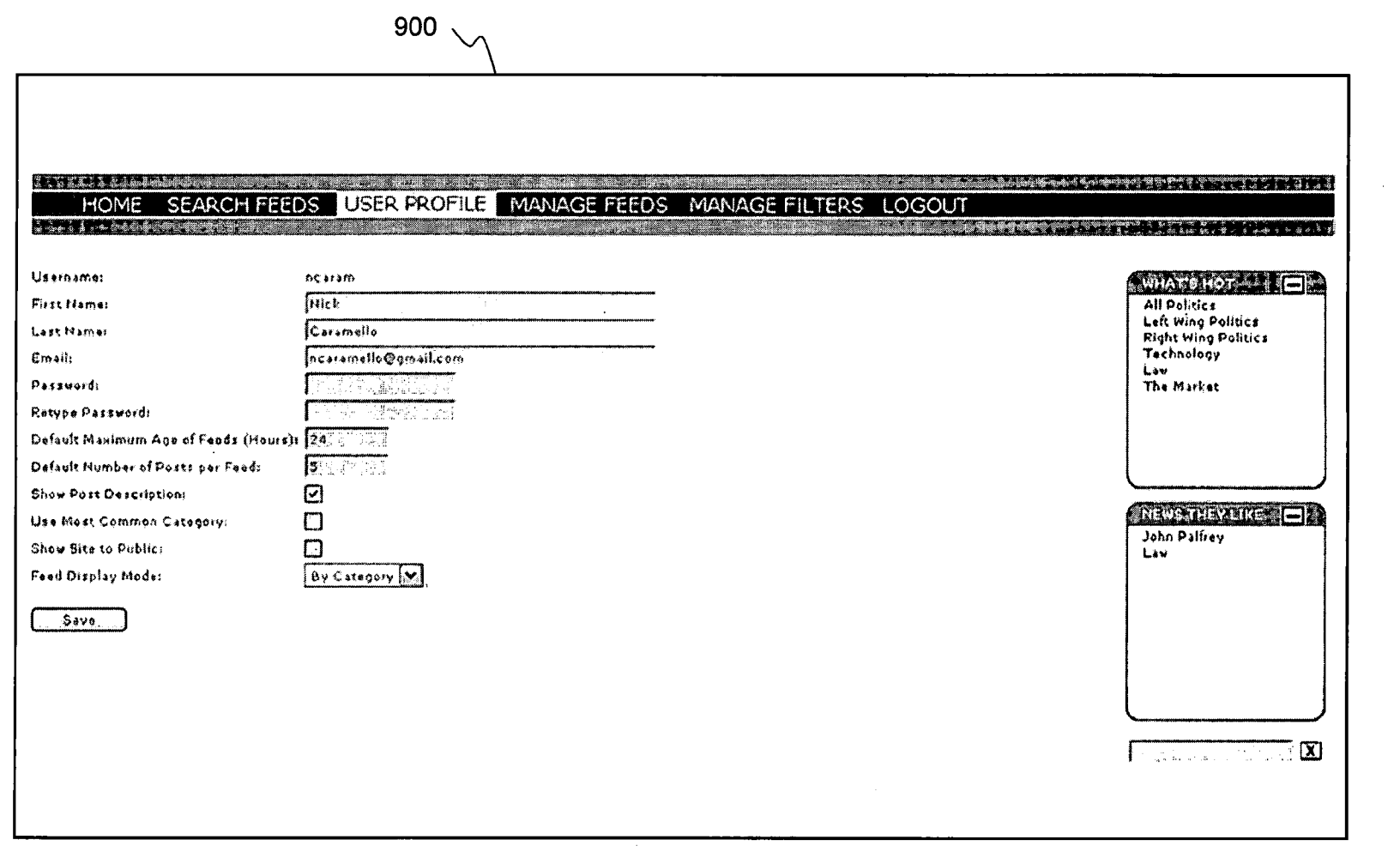

FIG. 9 shows a user interface 900 for data feed management. More particularly, FIG. 9 depicts a user profile page in which a user can search for additional data feeds to monitor. The page may include navigation buttons and a "What's Hot" and a "News They Like" workspaces. In addition, the page may include text entry boxes, check boxes, and other controls, along with a save button for saving profile data. Text entry items may include, for example, a first name, last name, e-mail address, password (and retype password), and a default maximum age of feeds (e.g., in hours) and a default minimum and/or maximum number of posts per feed for controlling a user display thereof, such as in the home page. Checkboxes may provide for selection of certain features. For example, a user may choose to have post descriptions displayed, a user may make his home page or features thereof public, a user may choose to use common categories provided by the system, and a user may choose among one or more pre-defined or user configured display modes for feeds.

Additional profile information, such as user interests, preferences, and biographical data may also be optionally provided. This data and other user profile data may be used to target advertising associated with data feed sites or content. Thus a data feed management system is described herein in which ads are delivered that are of value to customers. In addition to self-signaling through profile data, the system may apply customer-filtering, behavioral analysis, or any other analytic tools, as applied to the user's feed selection and displayed posts, to select appropriate advertisements for that user. The revenues from advertisements may be shared in a number of ways and may include shares of revenue to, for example, the operator of the data feed management system, an intermediary that places an ad that results in a sale, and/or individual or institutional content providers who contributed to the relevant data feed audience.

In another aspect of the systems described herein, feeds, posts, and/or filters may be clustered and shared in a number of ways as described above. Particular configurations may be branded and sold as a value-added service. Thus, for example, Warren Buffet's data feed selection and filtering may be of great interest to investors, bankers, and financiers. These selections may be sold to users who wish to see data feeds in the same manner as Warren Buffet. Similarly, someone may be interested in the writings and readings of Martha Stewart, Bill Clinton, Bill O'Reilly, Bill Gates, or Bill Belichick. Any of these individuals may brand and resell their selection of data feeds and design and use of filters. Similarly, commercial, political, or other institutional entities may present an official RSS feed identity. This may be provided for free for promotional purposes, such as promotion of a political party in a campaign or promotion of a seasonal sale event by a retailer. Similarly, topical selections may be promoted by trade groups or individuals. For example, a biotech or patent filter may be promoted by a patent law firm. In these applications, the service sold or promoted may include either the filters and selections themselves, which an end user may then modify or use as desired, or an aggregated feed of results from the filters and selections without identification of the underlying criteria. Access to such an aggregated feed may be controlled through password based protection to a resulting Weblog or using the identity-based RSS technology described above.

In one embodiment, a user may, either for a fee as described above, or for free, such as among a group of friends or interest-based community of bloggers, share not just search results but rules for finding those search results. In another application of this technology, a buddy list or other community may share aggregator configurations and other data. In another application of this, a recommendation engine may identify popular and successful search and filtering criteria that match a particular use profile.

In one aspect, there is described herein a systematic approach to managing data feeds in an integrated, and possibly Web-based, user interface. In a first step, the user may process feeds, including for example searching for, analyzing and selecting feeds. In a second step, a user may process posts within a feed, such as by filtering the posts as described above. In a third step, the aggregated and filtered results may be displayed to the user. This systematic approach also readily accommodates subsequent processing of the resulting items, such as by branding the technique for locating those items or by permitting sharing of the technique, both of which are described above. Additional processing steps may also include, for example, aggregating results into an aggregated feed or any of the other processing steps identified in the foregoing detailed description.

A number of enhanced syndication systems providing security are now described in greater detail. While a number of examples of RSS are provided as embodiments of a secure syndication system, it will be appreciated that RDF, Atom, or any other syndication language, or OPML or other structured grammar, including more generally the S-definition set out above, may be advantageously employed within a secure syndication framework as set forth herein.

Security may impact a number of features of a syndication system. For example, a data stream system may use identity assignment and/or encryption and/or identity authentication and/or decryption by public and private encryption keys for RSS items and similar structured data sets and data streams. The system may include notification of delivery as well as interpretation of delivery success, failure, notification of possible compromise of the end-to-end security system, non-repudiation, and so on. The identity assignment and encryption as well as the authentication and decryption as well as the notification and interpretation may occur at any or multiple points in the electronic communication process, some of which are illustrated and described below. A secure RSS system may be advantageously employed in a number of areas including, but not limited to, general business, health care, and financial services. Encryption may be employed in a number of ways within an RSS system, including encryption and/or authentication of the primary message, notification to a sender or third party of receipt of messages, interpretation of delivery method, and processing of an RSS item during delivery.

In item-level encryption of the primary message, an item from an RSS source or similar source may be assigned an identifier (which may be secure, such as a digital signature) and/or encrypted with a key (such as a private key in a Public Key Infrastructure (PKI)) and transmitted to a recipient, who may use a corresponding public key associated with a particular source to authenticate or decrypt the communication. A public key may be sent to the recipient simultaneously or in advance by a third party or collected by the recipient from a third-party source such as a public network location provided by the source or a trusted third party. In other embodiments, an intended recipient may provide a public key to a sender, so that the sender (which may be a content source, aggregator, or other RSS participant) may encrypt data in a manner that may only be decrypted by the intended recipient. In this type of exchange, the intended recipient's public key may similarly be published to a public web location, e-mailed directly from the recipient, or provided by a trusted third party.

In tag-level encryption of fields of data delimited within a message, similar encryption techniques may be employed. By using tag-level encryption, security may be controlled for specific elements of a message and may vary from field to field within a single message. Tag-level encryption may be usefully employed, for example, within a medical records context. In a medical environment (and in numerous other environments), it may be appropriate to treat different components of, e.g., a medical record, in different ways. Thus, while a medical record of an event may include information from numerous sources, it may be useful to compose the medical record from various atomic data types, each having unique security and other characteristics associated with its source. Thus, the medical record may include treatment objects, device objects, radiology objects, people objects, billing objects, insurance objects, diagnosis objects, and so forth. Each object may carry its own encryption keys and/or security features so that the entire medical record may be composed and distributed without regard to security for individual elements.

In a notification system, a secondary or meta return message may be triggered by receipt, authentication, and/or decryption of the primary message by a recipient and sent by the recipient to the message originator, or to a third party, to provide reliable notification of receipt.

In interpretation of delivery information, a sender or trusted intermediary may monitor the return message(s) and compare these with a list of expected return messages (based for example on the list of previously or recently sent messages). This comparison information may be interpreted to provide information as to whether a communication was successful and, in the case of communication to more than one recipient, to determine how many and what percentage of communications were successful. The receipt of return messages that do not match the list of expected messages may be used to determine that fraudulent messages are being sent to recipients, perhaps using a duplicate of an authentic private key, and that the security service may have been compromised.

In another aspect, a series of encryption keys may be used by the source and various aggregators or other intermediaries in order to track distribution of items through an RSS network. This tracking may either use notification and interpretation as described herein or may simply reside in the finally distributed item, which will require a specific order of keys to properly decrypt some or all of the item. If this system is being used primarily for tracking, rather than security, encryption and decryption information may be embedded directly into the RSS item, either in one of the current fields or in a new field for carrying distribution channel information (e.g., <DISTRIBUTION> . . . </DISTRIBUTION>.

In another aspect, the message may be processed at any point during distribution. For example, the communication process may include many stages of processing from the initial generation of a message through its ultimate receipt. Any two or more stages may be engaged in identity assignment and/or encryption as well as the authentication and/or decryption as well as notification and/or interpretation. These stages may include but are not limited to message generation software such as word-processors or blog software, message conversion software for producing an RSS version of a message and putting it into a file open to the Internet, relay by a messaging service such as one that might host message generation and RSS conversion software for many producers, relay by a proxy server or other caching server, relay by a notification server whose major function is notifying potential recipients to "pull" a message from a source, and services for message receiving and aggregating and filtering multiple messages, message display to recipients, and message forwarding to further recipients.

In another aspect, a message may include one or more digital signatures, which may be authenticated with reference to, for example, the message contents, or a hash or other digest thereof, in combination with a public key for the purported author. Conversely, a recipient of a digitally signed item may verify authenticity with reference to the message contents, or a hash or other digest version thereof, in combination with a private key of the recipient.

FIG. 11 shows a data pool environment. The environment 1000 may include a number of users 1002 in a user community 1004, a network 1006 such as the internetwork described above, a number of pools 1010 of data, and a pool management infrastructure 1012.

In general, the pools 1010 may be physically deployed on any data storage resource accessible through the network 1006. This may include, for example, a database, web server, FTP file, peer-to-peer file sharing resource, secure database, RSS channel, or any other technology platform and system(s) suitable for receiving, storing, and transmitting data. It will be understood that, in various embodiments, each pool may be a logically and/or physically separate storage location, permitting either distributed management of common data (e.g., for purposes of security, redundancy, or the like) or centralization of distributed data (e.g., for more efficient processing).

While a pool may be realized as, for example, a conventional RSS channel that receives and publishes items, other pools may collect and present data in more complex ways. For example, the pool management infrastructure 1012 may include a pool server or other system that either physically or logically sits between the user community 1004 and the pools 1010 and broker's interactions. The infrastructure 1012 may control access to the pools through a security system that includes, for example, any of the security features or systems described herein. In one embodiment, the infrastructure 1012 may include a firewall, router, switch, or similar device that physically resides between the pools 1010 and the user community 1004. The pools 1010 may also, or instead, be partially or completely encrypted. The infrastructure 1012 may also provide attention management by tracking user interactions with various pools and/or data within pools. In one aspect, the infrastructure 1012 may provide anonymity either to users 1002 accessing the pools 1010, or to the pools 1010 or sources of data therein. In another aspect, the infrastructure 1012 may provide formatting functions. As with anonymity, formatting may operate in either direction, i.e., by formatting user requests in a manner suitable for presentation to the pools (or that creates a logical appearance of pools to differently structured underlying data sources) or by formatting any responsive output from a pool. In one aspect, the infrastructure may provide a dynamic content system that provides different views of pools according to a user type, user identity, or the like. In another aspect, the infrastructure 1012 may provide search capabilities including structured searching and/or spidering for content within the pools 1010. It will be understood that, while depicted as a single, centralized server, the pool management infrastructure 1012 may include any number of servers and/or other network devices or systems that cooperate and/or operate autonomously to create a data pool environment for users 1002 in a community 1004.

The community 1004 may include any user or group of users 1002 that access data in pools 1012 either by providing data to the pools, extracting data from the pools, or both. This may include social groups, professional groups, commercial entities, and so forth.

Using a pool management infrastructure 1012, sources of data may be treated as populations and managed as an integrated but evolving ecology or topology, so that new forms of data can be added to the ecology continually, so that sets of data in particular forms can be added to and/or modified, and so that uses of data and combinations of data can be continually invented and implemented within the ecology without reworking the existing structure and applications.

In one example, the pool management infrastructure 1012 may enable secure management of a pool system and any associated data, data formats and pool enclosures. The infrastructure may, for example, provide an administrative dashboard that includes an administrative interface to a secure access control system, an administrative interface to a Common Vulnerabilities and Exposures system, and an administrative interface to the update notification, availability, and spider system (provided by vendor). The infrastructure 1012 may also, or instead, include an administrative interface for configuring the data converter and router systems to put data into pools, controls for a spider to control extraction, and search/filter/cluster and routing to pools and web services. It may also include interfaces for directing web services to take input directly from particular pools, to take input from the spider and other routing machines, and to output service results to particular pools and services in particular formats.

The pool data storage format may be XML, RSS, OPML, Atom, RDF or any other data format. Pool content may be managed using a file directory system maintained by an operating system such as Linux, Unix, Microsoft Windows. Pool content, including enclosures to pool items, may be provided by a client-side central data store for XML, RSS, and related formats included in the Microsoft Vista operating system for personal computers.

Sources of data for pools may include any source(s) of digital data. For example, in a medical context, sources may include machines such as x-ray, MRE, PET, CT, and other medical imaging devices, as well as blood diagnostic, inventory management, ordering, scheduling, billing, human output-fed programs such as notes on medical record diagnostic forms, and/or process-fed outputs such as the result of a cross-functional medical second opinion process. In an enterprise, suitable sources may include document management systems, electronic mail systems, instant messaging systems, billing systems, accounting systems, human resources systems, computer/network traffic management systems, and so forth.

These sources may also or instead output data to the data pools in a common format such as XML, RSS, OPML, Atom, RDF, or any other common format. Data sources may also send their customary outputs through a format converter that outputs a common format and a data pool router that directs the output to an appropriate data pool or pools.

In one aspect, data pools may be viewed as folders open to inspection or, more formally, reading and writing by a spider or other search mechanism. A spider may, for example, use remote web service calls to poll each pool (or a pool interface provided by the pool management infrastructure) to determine if a given pool is accessible or if it has had any changes to its contents, and to read and write pool content. A spider may be deployed to monitor and manage a total topology of pools and any data contained therein.

Spiders may collect information from pools and enable the shared management of information across pools by allowing diverse information to be retrieved, assembled, and analyzed in order to, for example, create a virtual medical record by combining data elements that are held in different pools of diagnostic test results, physician notes, and the results of processes. Pools also may be accessed for quality control, for example to review x-ray's and diagnostic findings for a random sample of patients, in order to ascertain the quality of diagnosis.

Pools may employ a variety of security measures to achieve conditional access, privacy, security, and the like. Access to pools can be controlled for individuals e.g., according to identity or role), spiders, web services, and so forth. Access control may be implemented, for example, using third party products such as Cisco Secure Access Server or Microsoft Products such as Windows Active Directory or the Windows Server Network Access Protection (NAP) policy enforcement platform built into the Microsoft Windows Vista and Windows Server operating systems. More generally, LDAP, Active Directory, or other services/protocols may be employed for management of passwords, identities, roles, and the like.

CVE, or Common Vulnerabilities and Exposures, analysis and remediation is a process through which network assets are analyzed to determine vulnerability to hacking, data theft, unauthorized access and the like. The US government, in cooperation with The MITRE Corporation ("MITRE") and computer software and hardware vendors, monitors and inventories vulnerabilities and exposures. A number of companies provide software, hardware, and consulting services to identify and address these risks on a network such as an enterprise or corporate network. In an enterprise pool management system, CVE may be applied to data pools and any supporting infrastructure. Pools using conditional access and security systems such as those that assure compliance with HIPPA health data protection standards may be assessed using CVE techniques. In addition to identifying common vulnerabilities and threats, a security system may accommodate automated or semi-automated interventions to secure data pools and infrastructure. In one embodiment, CVE-enabled security for pools may be provided with suitable adaptations to commercially available products and services, such as the NetClarity Auditor Enterprise system.

In general syndicated data, outlined data, or, more generally, any structured or unstructured data may be stored in "pools", which provides a useful conceptual model for interaction with syndicated content and other data, as well as a specific term to refer to data sources and/or repositories that interact with the systems described herein. Aspects of the present invention relate to pooling syndicated information. Pools may contain information relating to information that was found in data streams. A pool may represent, for example, information from one or more data streams at particular times or from particular sources. For example, a financial market may produce a stream of data relating to trades made during a trading session, and a pool of data extracted from the stream may be created for subsequent use. As another example, medical information may be produced by a medical device, and the medical device information may be pushed into a data stream. The medical information from the data stream may be extracted from the stream and placed in a pool. As another example, all information related to a particular topic, person, entity, or the like may be acquired from a range of different data streams and placed into a corresponding pool.

Pools of data can be merged with other pools of data to form larger pools (e.g. to combine things of like file type, semantic meaning, subject matter, etc.). In embodiments, pools may be drained, and in doing so new data streams may be created. An example would be streaming a series of offers to sell goods (or services, securities, etc.) at a given price, out of a pool of such offers. In embodiments, the data stream may be buffered until relevant decision points are achieved.

In embodiments, a filter may be associated with a pool of data. A pool of data may be created from unfiltered data (e.g. an unfiltered data stream), and then over time the pool can be run through filters to produce a cleaner/more relevant pool of data. The filter could be a semantic filter, a collaborative filter, a logical filter, or a human filter (such as a community that validates the presence of content in the pool). E.g., a pool could contain "good movies" that are monitored by a community.

In embodiments, pools may be linked to other pools, so that one pool spills into the other (e.g., a pool of data that takes input from another pool upon occurrence of an event, such as availability of a resource for processing, for example, when a resource becomes available to process an incoming message requesting help from a software help desk and is handed into a pool of similar requests for handling by someone who is responsible for that type of request). Pools of data can evaporate (that is, data items can be made to expire from the pool), either based on age or based on the right conditions (e.g., if a price of a security drops low enough, then limit orders may be triggered; if time passes, an option can expire, etc.). Pools may be filled by different sources (a main source, as well as secondary sources or streams that augment the main source streams).

An aspect of the systems described herein relates to the filtering of contents such as syndicated feeds and the like. Syndication content filters may be used in connection with hardware, software, firmware, in a chip set or in another configuration. In embodiments, a user may publish or subscribe to a syndication feed on his desktop system or mobile communication facility (e.g. PDA, cellular phone and the like), and the syndication feed may be filtered through a syndication filter. In embodiments, the syndication filter is a mechanism adapted to define the syndication feed. For example, a device may be set to collect certain feeds through a hardware enabled syndication filter.

Figure 11A:
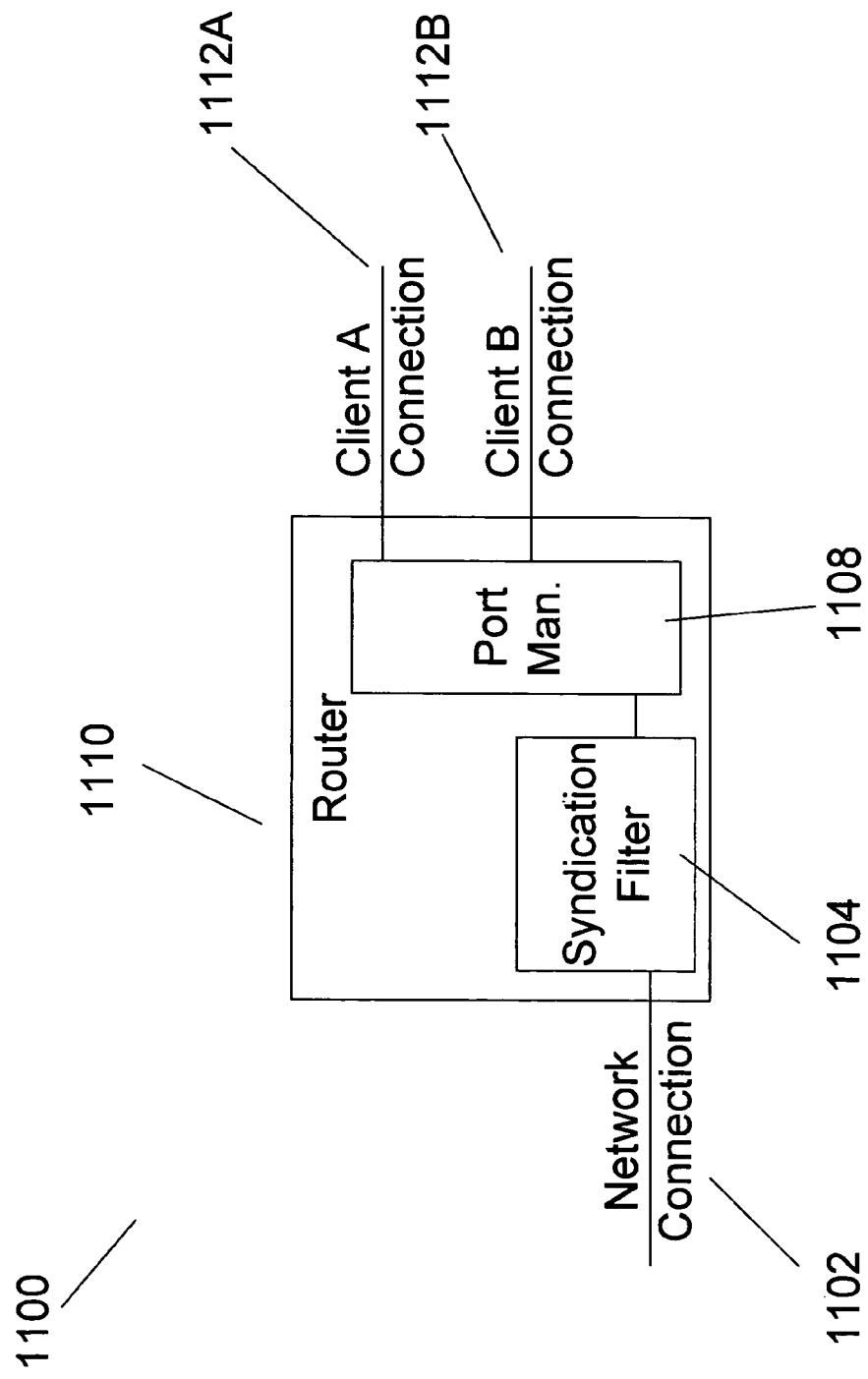
FIGS. 11A and 11B show embodiments of filters for syndicated content.

FIG. 11A illustrates a filter 1104 implemented in a hardware application 1100. The filter 1104 may be, for example, a syndication filter that operates on syndicated content such as data feeds. A router 1110 may be adapted to receive network information through a network connection 1102. The network connection 1102 may provide data received from a network, either directly or indirectly, to the filter 1104. The filter 1104 may be implemented through software, hardware, firmware, or other configurations, or some combination of these. The filter 1104 may be adapted to analyze network information received or transmitted through the network connection 1102 and perform filtering, direction, routing, or other manipulation of the data. For example, the syndication filter may analyze the data from the network connection and determine that certain data are related to a data feed that is not permitted (e.g. it may be a feed known for containing a virus, spyware, malware, or other undesirable content), and the non-permitted data may be extracted, removed, deleted, erased, logged, directed to a file, or otherwise manipulated. Information that is received on the network connection 1102 that is not determined as data requiring filtering may be passed to a port management facility 1108 in the router 1110. The port management facility 1108 may pass information to client A 1112A or client B 1112B based on an IP address or any other source or destination address, or other information.

Figure 11B:
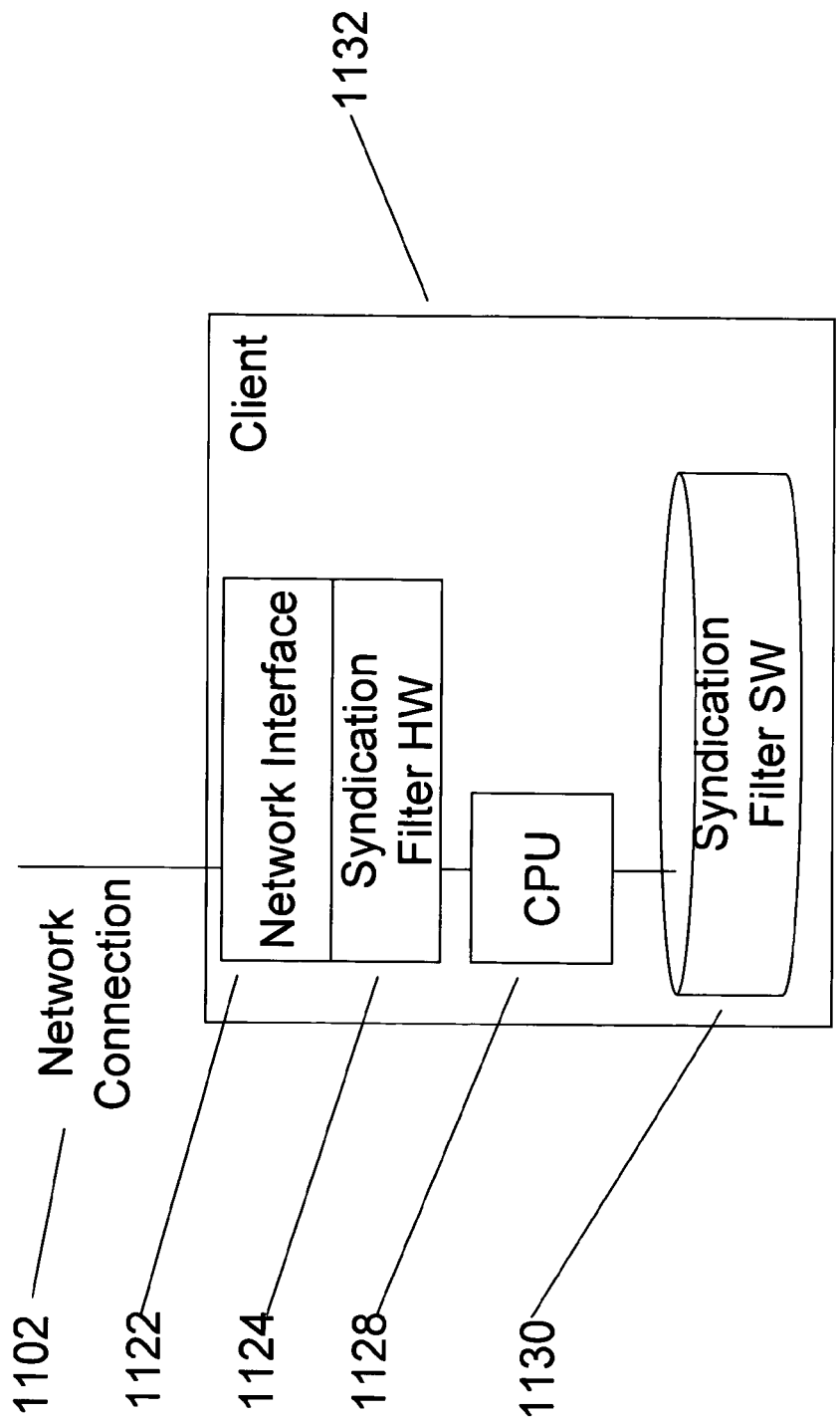

FIG. 11B illustrates a client facility 1132 with a hardware syndication filter 1124 and a software syndication filter 1130. The client facility 1132 may receive network information through a network connection 1102. The network information or data may be received by an network card 1122 (e.g. an Ethernet card, a Network Interface Card, or other communications interface) or the like. The network card 1122 may be associated with a syndication filter hardware facility 1124. The syndication hardware facility 1124 may perform functions similar to those described in connection with the filter 1104 of FIG. 11A, for example. The syndication filter hardware facility 1124 may perform filtering functions autonomously or in connection with another facility (e.g. software syndication filter facility 1130). The hardware syndication filter 1124 may operate in connection with dedicated hardware, software, and/or firmware. In embodiments, the hardware syndication filter 1124 is adapted to filter content in syndication feeds and the like. For example, the client device 1132 may be set to receive a syndication feed, and the feed may be received on the network connection 1102. The feed may include a virus, malware, spyware, or other undesired content, and the syndication filter hardware 1124 may strip or otherwise manipulate the undesired content from the syndication feed. The remaining portions of the syndication feed may be passed to other client hardware such as a central processing unit ("CPU") 1128. In embodiments, associated feed data such as enclosures, attachments, and the like may also be processed by the hardware syndication filter 1124.

The client 1132 may also or instead include a software based syndication filter 1130. The software syndication filter 1130 may execute as a background process associated with network traffic or be integrated into an operating system or an application executing on the CPU 1128, and it may run from volatile or non-volatile memory (not shown) associated with the client 1132. The software syndication filter 1130 may provide, for example, the functions of the hardware syndication filter 1124 or syndication filter 1104 described above. The CPU 1128 may call a software syndication filter routine from the data repository in the process of monitoring a syndication feed. For example, in the process of receiving a syndication feed, the CPU may call the routine to monitor, analyze, manipulate, or otherwise interact with the feed.

Figure 12:
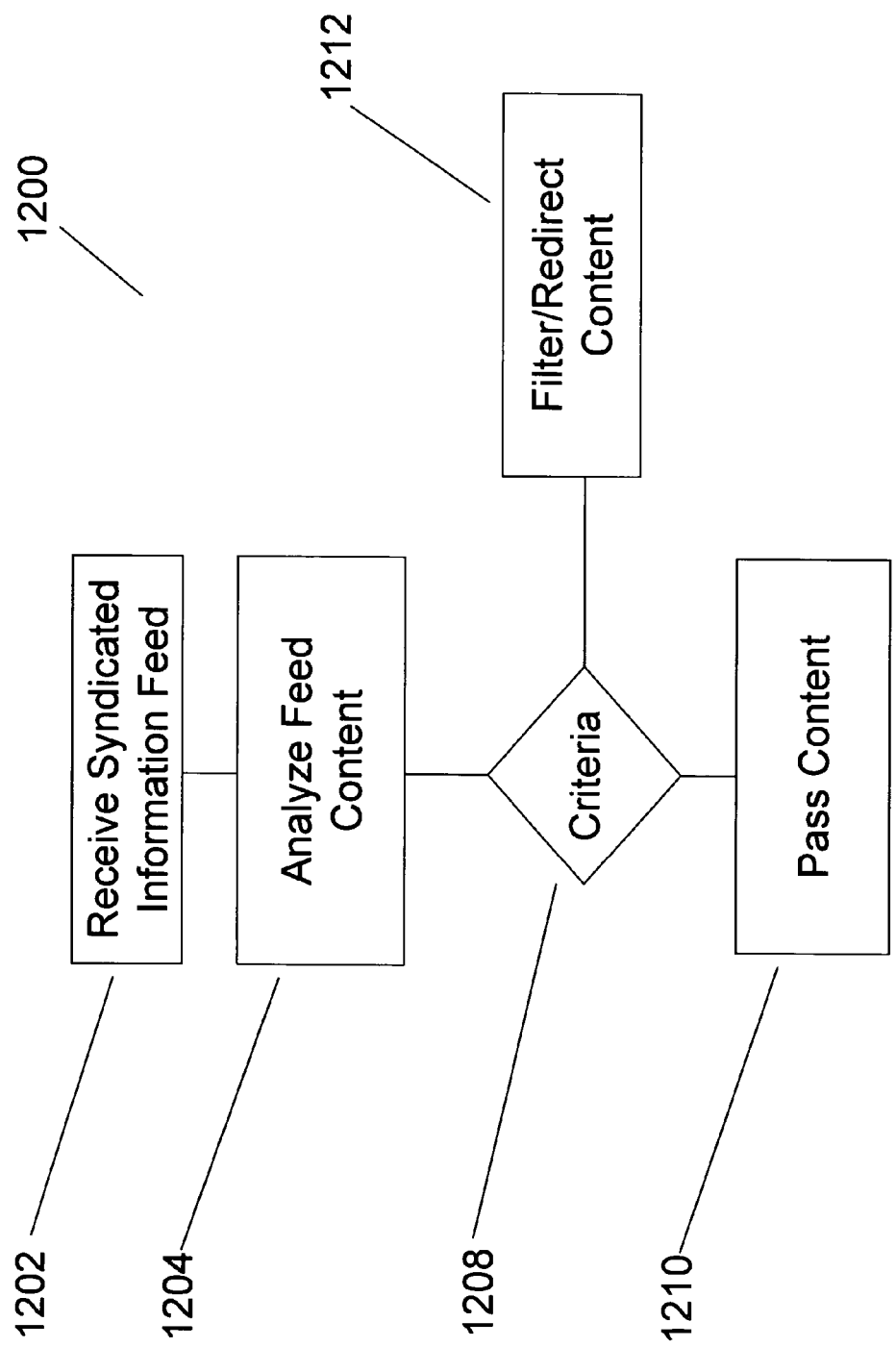
FIG. 12 shows a method for filtering syndicated content.

FIG. 12 illustrates a method for filtering syndicated data 1200. The method may involve receiving a syndicated information feed 1202, analyzing the feed 1204, and applying criteria 1208 to the feed to determine a filtering action. The analysis may be accomplished through a hardware, software, firmware, or other solution (e.g. as described in connection with FIGS. 11A, 11B and 12). The analysis may be rule-based, look-up based, heuristic, algorithmic, semantic, or may employ any other suitable techniques for analyzing content. The criteria 1208 may also be applied through a hardware solution, a software solution, a firmware solution, or any other technique, or any combination of these. The criteria applied to the analysis may be algorithm-based, table-based, or it may use other criteria for determining whether the content should be filtered. For example, a table of known viruses may be used in a process of matching information extracted from the feed to determine if the feed, or portions thereof, includes known viruses, virus parameters, or indications of a virus. The filter may apply rules or the like based upon, e.g., content, source, destination, semantic content, user criteria, and so forth. Following the application of a criterion 1208, the content may be filtered (e.g. deleted) and/or redirected (e.g. placed in a folder adapted to hold filtered content for later review, deletion, and/or manipulation) 1212, or the content may be passed on for further processing, such as formatting and presentation to a user through a client.

Filters may operate on various data types within syndicated messages. Syndicated data feeds (e.g. RSS or syndicated OPML) may contain device configuration settings, images, video, data, broadcast rating information, and the like. Syndicated feeds may be available in or contain many different formats (e.g. tables, databases, documents, multimedia, web content formats, metadata, electronic mail, and so forth), and they may contain information from a variety of sources such as electronic mail, online content, or web content. A feed may contain various types of information for signal type filters such as radio and TV broadcast content/rating, security information, and the like. The feed, or messages within a feed, may include data for suitably enabled devices to change a mode of operation, using different modes to suit different content, client devices, and so forth. In an organization, users on different IP addresses may desire different information content from the same source; a hardware device may have a syndication filter incorporated to automatically filter and/or sort the syndicated data to the proper IP address(es). Syndication applications may be capable of automatically performing an analysis on received feeds to filter IP/URL addresses, viruses, attached files in email, weblog feeds, email/instant messages, web content, phone calls, TV channels, or various analog and digital signals. A filter may apply different rules to different types of enclosures or attachments. Thus, for example, a filter may apply a first set of rules to MP3 attachments, a second set of rules to OPML attachments, a third set of rules to metadata, and a fourth set of rules to textual content within a message.

In general, a filter may operate to pass certain information and/or block certain information. In a data feed environment, filters may employ a variety of techniques to filter a feed. The filter may operate on various aspects of the feed. This may include, for example, textual content, metadata, attachments, external references (either from an item or to an item), and so forth. A filter may employ rules, algorithms, look-up tables, keywords, Boolean expressions, heuristics, and the like. A filter may operate on specific fields within an item, such as source, name, date, title, and so forth. Numerous devices may incorporate syndication filtering as described generally above. A number of non-limiting examples are provided below. Some of these examples show a device that implements filtering of syndicated content. Other examples show conventional filters that send or receive filter-related data in a syndicated format. Various combinations and modifications of the examples and these general principles will be apparent to one of ordinary skill in the art and are intended to fall within the scope of this disclosure.

Filtering may be embedded into a network router. Network routers may have syndication filter capability incorporated into the network router firmware or may have a syndication-capable chip or chip set incorporated into at least one of the network router processors or circuit boards. The syndication-capable network router may be able to recognize that a received file is a syndication data feed and may make routing decisions based on the syndication data feed contents. The syndication-capable network router may be able to route data to IP addresses on a network based on the syndication data or information contained in the header and body of a network packet or by information in the syndication feed. The syndication feeds may originate from IP addresses within the router network or may be received from outside the router network, such as from the internet. For example, if a number of users received financial data from a common syndication source but the different users were interested in different parts of the financial data, the syndication-capable router may route portions of the syndicated data according to user criteria. Thus, for example, the router may handle data from a syndicated source of mortgage data by routing trading data for secondary mortgage markets to one user (e.g., a bond fund manager), current mortgage rates to a second user (e.g., a consumer), and mortgage qualification data to a third user (e.g., a retail bank).

The syndication-capable network router may be able to route syndication data feeds for at least one of personal data, financial data, medical data, enterprise data, or business data. The syndication-capable router may be capable of routing syndication data feeds to a particular IP address on the network based on the syndication data contained in the feed. In an embodiment, the syndication-capable network router may be able to filter spam, adware, or email by comparing an originating IP or URL to known spam, adware, or email addresses or to look for key words within the incoming packets. The syndication-capable network router may be able to filter, block, route, or permit at least one of online information sources such as news, newspapers, web magazines, academic papers, government court opinions, administrative rulings, regulation updates, opinions, editorials, product reviews, movie reviews, financial or market analyses, discussions of current events, internet media, and advertisements by IP address, URL, syndication content, or packet heading. The syndication-capable network router may be able to filter, block, route, or permit at least one of internet based web pages, weblogs, websites, and web popups by IP address, URL, syndication content, or packet heading.

The syndication-capable network router may be adapted to filter, block, route, or permit at least one of network packet traffic, IP address, MAC address, and VoIP network packets based on originating source, destination address, or syndication content of the packet. The syndication-capable network router may be adapted to filter, block, route, or permit packets based on at least one of a syndication digital signature, syndication password or key, and syndication identity certificate of the packets.

Filtering may be embedded into a firewall. A software or hardware firewall may incorporate syndication filtering. The firewall may be adapted to recognize syndicated content and further adapted to filter, block, or permit the syndicated content according to filter parameters. Filter parameters may be configured through an administrative interface to the firewall, such as a web-based user interface. The syndication-capable firewall may be adapted to filter, block, or permit at least one of personal data, financial data, medical data, enterprise data, or business data based on the syndication application, syndication incoming port, syndication incoming IP, syndication IP address, or syndication content. The syndication-capable firewall may be adapted to filter or block at least one of spam, adware, or email addresses based on a syndication source IP address, a syndication source URL, or content. The syndication-capable firewall may be adapted to filter or block at least one of internet based news, newspapers, web magazines, academic papers, government court opinions, administrative rulings, regulation updates, opinions, editorials, product reviews, movie reviews, financial or market analyses, discussions of current events, internet media, and advertisements by syndication IP address, syndication URL, syndication application, syndication port, syndication content, or syndication heading. The syndication-capable firewall may be adapted to filter or block at least one of internet based web pages, weblogs, websites, and web popups by syndication IP address, syndication URL, syndication application, syndication port, syndication content, or syndication heading. The syndication-capable firewall may be adapted to filter or block network packet traffic or IP addresses based on originating or destination syndication address.

Filtering may be embedded in a virus protection application. The virus protection application may incorporate syndication filtering capabilities. The syndication-capable virus protection application may inspect attachments or enclosures to syndicated content or may analyze the syndicated content itself for malicious instructions or the like. The syndication-capable virus protection application may be adapted to identify, filter, and/or block viral syndication content and/or attachments in one or more of personal data, financial data, medical data, enterprise data, or business data, electronic mail, internet based online news, newspapers, web magazines, academic papers, government court opinions, administrative rulings, regulation updates, opinions, editorials, product reviews, movie reviews, financial or market analyses, discussions of current events, internet media, advertisements, web pages, weblogs, and websites based on known syndication virus content.

A filter may be deployed as a syndication attachment or enclosure filter. This filter may be adapted to locate other syndicated content or sources of content. RSS data feeds, for example, may contain content or attachments that contain additional syndication data. A syndication attachment file filter may scan messages from a syndicated data feed for attachments that may contain other syndication data in which a user has interest. For example, a medical data feed may have information that a user is interested in but may also contain an attachment with additional medical information. The syndication attachment file filter may be able to determine if the attachment contains information that may be of interest to the user and either keep or omit the attachment from the received data feed. The filter may filter syndication attachments using at least one of personal data, financial data, medical data, enterprise data, or business data based on syndication content. The filter may filter attachments to other media types. For example, the filter may scan electronic mail for syndication attachments and apply various filtering rules to any such attachments. As another example, the filter may scan the content of a word processing document for references to syndication sources and/or messages.

A filter may operate locally or remotely. For example, a client device may filter a weblog, or collection of weblogs, or aggregator output to remove items that are not of interest. In another aspect, a remote weblog reader may filter content and transmit the filter output to a client device. A weblog filter may filter feeds according to at least one of personal data, financial data, medical data, enterprise data, or business data based on user defined syndication content. The weblog filter may filter feeds according to source using, such as, for example, filters based on internet based online news, newspapers, web magazines, academic papers, government court opinions, administrative rulings, regulation updates, opinions, editorials, product reviews, movie reviews, financial or market analyses, discussions of current events, internet media, and advertisements.

Websites may broadcast syndication data files that may contain a brief description of the content of the website. A syndication web content filter may be able to read the syndication data file content to block access to a certain site based on any user defined feature. For example, a parent wanting to block a certain type of websites from a child may be able to define the type of site to block. The parent may define key words, phrases, ratings, and so forth to look for in the syndication data file. The filter may block web sites according to one or more of personal data, financial data, medical data, enterprise data, or business data based on the user-defined syndication web site rating. The syndication web content filter may be adapted to block web sites containing at least one of internet based online news, newspapers, web magazines, academic papers, government court opinions, administrative rulings, regulation updates, opinions, editorials, product reviews, movie reviews, financial or market analyses, discussions of current events, internet media, and advertisements based on the user defined syndication web site rating. The syndication web content filter may be able to block at least one of web pages, weblogs, websites, and web browser content based on the user defined syndication web site rating.

An instant messaging ("IM") application may incorporate a filter. The syndication-capable instant message application may be adapted to filter syndication data feeds that may be received from another instant message application either within an instant message or within an attachment or file shared through an instant messaging system.

An anti-phishing program may incorporate a filter. Internet phishing generally takes the form of a request for user information for the purposes of identity theft, credit card information, or monetary payments. These requests may be sent to a user by email, instant message, or from the web and may incorporate a syndication data feed. A syndication phishing filter may be able to block syndication phishing requests based on the syndication content and definition by the user.

A search engine may incorporate a filter. An Internet search engine may contain a filter adapted to identify sites that provide syndication data feeds responsive to a user's definition. For example, a user may be able to define a search for medical information on heart valves to get only a listing of syndication data feed sites with this information. The filter may employ any of the parameters or filtering techniques described above.

A security appliance may incorporate a filter. Security appliances operate as reverse proxy devices positioned between any type of client and a server to act as an additional layer of security for communications. A security appliance may perform checks for viruses, spam, phishing, or other undesired files sent to a server. The server may be any kind of server such as an application server, email server, or web server. A syndication-capable security appliance may be adapted to analyze syndication data feeds to determine the syndication data feed content and make decisions to block or pass the syndicated content onto the server. The filter may employ any of the parameters or filtering techniques described above. The syndication-capable security appliance may be adapted to filter at least one of unwanted syndication network packet traffic, syndication IP addresses, and syndication MAC addresses from entering a server. The syndication-capable security appliance may be adapted to filter at least one of unwanted syndication digital signatures, syndication passwords or keys, and syndication identity certificates from entering a server.

Database applications (e.g. Oracle) may incorporate syndication filter capabilities. Syndication data files may have the same structure as XML, using tags to indicate the beginning and end of information sections of the information or data. XML and syndication are becoming increasingly popular for holding data because of their small size and data types they may contain. A syndication-capable database application may be adapted to search and filter data from syndication data sources in addition to the same abilities for tables and databases. The syndication-capable database application may be adapted to filter at least one of personal data, financial data, medical data, enterprise data, or business data from syndication sources based on user or application requirements.

Filters may be integrated into an enterprise application. Enterprise applications may be adapted to search and filter data from across corporate or local area networks, as well as wide area networks including the Internet. Enterprise data may be obtained from other applications and/or databases deployed within the enterprise, and the enterprise application may apply suitable connections and converters to read the data and/or convert the data to a common format. A syndication-capable enterprise application may also be adapted to access data in syndication data files and syndication data feeds at local and/or remote locations. The syndication-capable enterprise application may be adapted to use a search engine to locate syndication data feeds on the internet that may have desired data based on a user's definition. The syndication-capable enterprise application may be adapted to filter syndication data feeds or syndication data files based upon one or more of personal data, financial data, medical data, enterprise data, business data. More generally, the syndication-capable enterprise application may employ any of the filtering parameters and techniques described above.

A filter may provide semantic processing to process data according to semantic content or meaning. The filter may be applied to data in tables, databases, and syndication metadata, and it may permit searching or handling of syndicated content based upon user-provided semantic parameters. The semantic filter may employ any of the filtering parameters or techniques described above.

A filter may provide encryption processing to permit filtering of encrypted data. The filter may employ user-provided keys to decrypt syndicated content for further filtering and other processing. The filter may also, or instead, provide encryption processing to permit filtering of data according to encryption characteristics such as encryption type, availability of public keys, and so forth. The encryption filter may employ any of the filtering parameters or techniques described above.

A filter may provide caller ID filtering. The filter may identify and extract caller information from a cellular phone, wired telephone, wireless telephone, VoIP telephone, or other telephonic device. Information may, for example, be published to a data feed or forwarded for other processing. In another aspect, the filter may identify and extract telephone numbers and other contact information from a data feed. The caller ID filter may employ any of the filtering parameters or techniques described above.

A filter may provide content filtering. A channel blocking system may be provided for a device to manage access to broadcast (e.g., radio or television) or other transmissions. The transmission may be accompanied by content ratings or other semantic data that may be employed by the channel blocking system to restrict availability at a receiving device according to user preferences. In one aspect, the ratings may be provided as a syndicated feed. In another aspect, the transmissions may be processed to derive a feed of characteristic information which may, in turn, be applied by the channel blocking system to dynamically restrict access according to current content and any user-provided constraints. The filter may be applied to one or more of a radio broadcast, a television broadcast, a satellite broadcast, a satellite radio broadcast, a cable television channel, or the like. The filter may employ analysis including content analysis and analysis of digital signatures, passwords, keys, or identity certificates, and the like.

A filter may be associated with an analog-to-digital converter (ADC), a digital-to-analog converter (DAC), or a media coder/decoder (CODEC), referred to generally as digital processors. In one embodiment, characterizations of output such as sampling rate, compression ratios, frequency spectra, and the like may be provided to a feed for transmission and processing along with the digital content. In another aspect, a data feed may be provided to guide downstream processing of the digital (or analog) signal. A filter may be applied to sort, select, block, or otherwise process associated media according to the data feed.

Similarly, any digital filter, including audio filters, digital filters, digital subscriber line filters, line filters, surface acoustic wave filters, and the like, may be adapted to receive syndicated data that provide operating parameters for the filter, or it may be adapted to publish a feed of operational data. In an embodiment, the syndication signal processing platform may be adapted to process at least one of an audio signal, electronic signal, analog signal, digital signal, and video signal using a syndication signal processing platform which uses a provided set of parameters from a syndication data file or syndication data feed.

Described below are various embodiments of the present invention, including certain embodiments relating particularly to RSS semiconductor implementations. It should be appreciated, however, that the present invention is not limited to any particular embodiment of the invention, and that the various embodiments discussed explicitly herein are primarily discussed for the purpose of illustration. Where an RSS semiconductor embodiment is described below, it should be understood to include any syndication functions, whether a part of RSS, ATOM, RDF, any syndication markup language 532, and/or some other standard or non-standard syndication system. Furthermore, the RSS semiconductor embodiments described below should also, or instead, be understood to include outlining functions provided by OPML 616 or by any other suitable outlining format.

In general, a semiconductor device or group of semiconductor devices as disclosed herein may embody any processing, including discrete groups of functions, services, and the like, as well as user-programmable libraries of such functions and services, associated with the enhanced syndication systems described above. In addition, various enhanced syndication functions may be implemented in semiconductor devices as While numerous examples of specific semiconductor devices and specific operations are provided below, this should not be understood to limit the generality of this disclosure.

Semiconductors may be constructed with transistors, AND gates, OR gates, NOR gates, flip flops, or other logical gates, and may be designed as a single chip or a chip set. Said chip or chip set may be hard coded with instructions or firmware in order to collect, process, and move data in varied types of network, consumer, auto, computer entertainment, commercial, medical, security, aircraft, and banking devices. From these devices, information may be gathered and stored, or transmitted to other devices for display, storage, or other processing of the information. The information may be stored as text, audio, still or moving images in a computer, a server, a hard disk, a CD, a DVD, a Flash memory or may be communicated to a web-capable device. The semiconductor may be a microprocessor or microcontroller capable of directing communication to other devices or it may be a smaller application specific integrated circuit (ASIC) controller that may connect to a microprocessor or microcontroller in order to communicate information.

Also described below are a number of Syndication-enabled devices. While one embodiment of the inventions disclosed herein may use RSS, it will be appreciated that other standardized formats may be used, whether syndication formats such as RDF, Atom, and the like, or outlining formats such as OPML. Thus, it should be understood that the term RSS is used throughout this application as a convenient shorthand for a wide range of possible standardized XML grammars or other formats, and does not in any way limit the scope of the inventions disclosed herein to RSS embodiments unless otherwise explicitly indicated or clear from the context. More generally, in the following discussion the term syndication generally, and references to RSS specifically, should be understood to include, for example, RDF, RSS v 0.90, 0.91, 0.9x, 1.0, and 2.0, variously attributable to Netscape, UserLand Software, and other individuals and organizations, as well as Atom from the AtomEnabled Alliance, and any other similar formats, as well as non-conventional syndication formats that can be adapted for syndication, such as OPML, as well as attachments or enclosures which may have any native format. Still more generally, while RSS technology is described, and RSS terminology is used extensively throughout, it will be appreciated that the various concepts discussed herein may be usefully employed in a variety other contexts. For example, various privacy and identity techniques described herein may be usefully combined with HTML Web content, rather than RSS-based XML data. Similarly, some of the branding and advertising techniques described herein may be usefully combined with list servers, bulletin boards, or other Internet news sources. Thus, it will be understood that the embodiments described herein are provided by way of example only, and are not intended to limit the scope of the inventive concepts disclosed herein.

Figure 13:
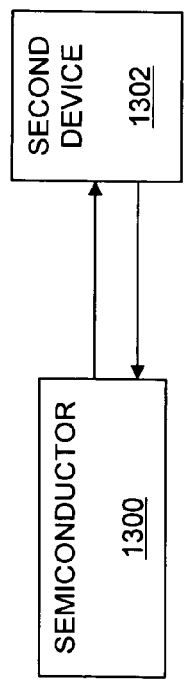
FIG. 13 depicts a syndication-enabled semiconductor interfacing with a second device.

Referring to FIG. 13, an embodiment of a semiconductor device 1300 is shown. Discrete logic may be the basic building block of integrated circuits of which the semiconductor device 1300 is comprised. The integrated circuits may comprise semiconductor AND and OR gates, which may assembled to solve and/or directed at solving expressions of Boolean logic. Thus, the semiconductor gates may be referred to as Boolean gates.

A Boolean gate may have two inputs; the AND gate passes a logical 1 if both inputs are a logical value of 1, whereas the Boolean OR gate passes a logical 1 if only one of the inputs is a logical value of 1. These gates may be combined and cascaded to create a logical function that may be used in semiconductor devices. Moreover, these operation of these gates may be associated with, triggered by, coordinated in reference to, and/or driven by a periodic clock signal, an asynchronous interrupt signal, or any other signal.

Microcode, sometimes called firmware, may be the lowest level of semiconductor programming code. Microcode may be programmed directly into the semiconductor, or else hard coded in order to control a function of the semiconductor. The microcode may not be edited after it is hard coded. On some RISC computers, the microcode is not used by the microprocessor but may act directly on the computer controllers. On some mainframe computers, the microcode may be modifiable; in this case, the microcode may be contained on an EEPROM where it may be reprogrammed.

An application specific integrated circuit (ASIC) is a semiconductor device dedicated to a specific function. ASICs may have over 100 million gates in its design and modern ASICs often include entire 32-bit processors and other large, complex building-blocks. A large scale ASIC may be called system-on-a chip (SoC).

A programmable logic device (PLD) is a semiconductor device that is programmable to execute logic commands. The PLD may be a chip or chip set containing an array of logical AND and OR gates. A PLD may be hard coded in a manufacturing facility by "blowing" the fuses to program the AND and OR gates in order to perform a certain function and so that the PLD may be mass-produced. The PLD function may be designed and coded in a software language and then converted into hardcode commands for the manufacturing process. PLDs are typically small in scale and may be used for such simple processing needs as address decoding within a computer or a network device. PLDs may be grouped together to form larger Complex Program Logic Devices (CPLC) and Field Programmable Gate Arrays (FPGA). These more complex logical devices may be used to perform larger scale processes such as processing data streams.

A programmable array logic (PAL) device is a semiconductor device that provides a fixed array of programmable cells, such as a fixed set of OR gates and programmable AND planes. The PAL device may allow the reuse of functional outputs.

A reduced instruction set computing (RISC) microprocessor is a semiconductor device comprising a processor that contains a limited number of hard coded functions or instructions in relation to other microprocessors (e.g. a personal computer). The RISC processor may contain a small simple instruction set to permit increased speed of the processor. Because of the reduced instruction set of the RISC processor, the RISC processor may contain fewer transistors than a standard microprocessor and therefore may be less expensive to design and produce. The reduced processor instruction set is typically compensated for by more extensive software to expand instructions available to higher-level processes.

A complex instruction set computing (CISC) processor is a semiconductor device comprising a processor that employs a relatively larger instruction set, and may accommodate operational codes (or instructions) and/or operands of varying length. A typical CISC processor produced by Intel or Motorola may have at least one hundred instructions in the instruction set. The instruction set may be called by software applications to perform various functions on data, voice, or audio.

A field programmable gate array (FPGA) is a semiconductor device that uses gate array technology to provide functions. A gate array may include a predetermined number of logical gates positioned on a silicon wafer, and then connected with metal interconnections to create a program function. The advantage of a FPGA is that it may be programmed for a particular purpose after the manufacture of the wafer; which permits high-volume manufacturing without loss of functional generality. The processing speeds of FPGA processors may be slower than dedicated devices such as a PLD.

A microprocessor, which may include a CISC processor or RISC processor, may be a semiconductor device that includes logic for executing instructions, along with caches or other on-chip memory to store instructions, results, and the like. Microprocessors are often characterized by the type of instruction set, instruction size, and clock speed. For example, a microprocessor may be characterized as a 32 bit RISC microprocessor running at 500 MHz.

A microcontroller may be ASIC containing enough components to be considered a controller; the controller may consist of inputs, outputs, and memory. The microcontroller may be a programmable microcontroller or a dedicated microcontroller. An embedded microcontroller may be referred to as an embedded microcontroller where the microcontroller is incorporated into a larger-scale semiconductor device. In general, microcontrollers may include adequate memory and input/outputs for standalone operation, whereas a microprocessor would typically require external RAM and other chipsets for incorporation into a computing device.

A programmable digital signal processor (DSP) is, in general, a semiconductor device optimized for processing of digital signals. DSPs may be employed in digital audio, video, and communications systems (e.g., for compression, decompression, or the like), as well as digital-to-analog or analog-to-digital conversion systems.

The semiconductor device 1300 may include any of the devices described above, and may be packaged as a chip, chipset, system-on-a-chip or the like. A chip set may be embodied on a single piece of semiconductor wafer; on multiple pieces of semiconductor wafer in a single package; or on multiple pieces of semiconductor wafer contained in more than one package, each of which may provide one or more electrical contact points or pins that provide electrical coupling to leads on a circuit board that may be designed to accept and associate together each of the packages in the chip set via electrical circuits.

The semiconductor device 1300 may be adapted to receive a data feed, and transmit the collected information to a computer, a server, a hard disk, a CD, a DVD, a Flash memory or a web-capable device. The semiconductor device 1300 may also, or instead, be adapted to process syndicated content, such as by aggregating a plurality of feeds, filtering or otherwise processing feed content, encrypting or decrypting syndicated content, formatting syndicated content for display, or more generally providing any of the services or functions associated with the conceptual syndication framework described above with reference to, e.g., FIG. 4. The semiconductor device 1300 may also, or instead be adapted to publish a data feed in a suitable syndication format, which may be a data feed processed as generally described above. The semiconductor device 1300 may be a web-capable device adapted to interact with the Web by receiving and transmitting information using, e.g., HTTP or other web-based protocols. The information received and transmitted by the semiconductor device 1300 may be RSS, OPML, or any other outlining, syndication, or data streaming formats or technologies described herein, whether based upon XML or upon some other syntax or protocol, all of which are periodically referred to herein as RSS for purposes of convenience only, and not by way of limitation.

The semiconductor device 1300 may be incorporated into a device, such as and without limitation any of the devices described below, and may provide syndication or enhanced syndication services to, from, or through the device. For example, the semiconductor device 1300, as a chip component, chip, or chipset, may be incorporated into a washing machine to provide syndication services. The syndication-enabled washing machine may transmit a data feed 202 related to, for example, the amount of water used by a washing machine during a period of time. The semiconductor device 1300 may collect the data from a metering valve in the washing machine and accumulate the data for processing or periodic publication, or publish the data in real time. A user, such as and without limitation a user of the washing machine; a vendor or manufacturer of the washing machine; and/or a state or federal water usage organization, may receive the data feed 202. The device may also incorporate a wireless communication device so that the data feed 202 can be transmitted wirelessly using, for example, a wireless standard such as 802.11x, 802.16, WiFi, WiMax, IrDA, or any other suitable communication specification.

The semiconductor device 1300 may also be able to receive instructions from a second device 1302, which may be a second semiconductor, a user interface, a smartcard (such as and without limitation a SIM card), or any other device. The second device 1302 may be able to change the output of the semiconductor device 1300 by instructing the semiconductor device 1300 to collect or aggregate different data, transmit data at different intervals, transmit data at different times, or make other changes in the collection or dissemination of data.

In some embodiments, the semiconductor device 1300 may be deployed in a non-programmable fashion. In some embodiments, the semiconductor device 1300 may operate, in whole or in part, under the direction of the second device 1302. This direction may be provided via a signal from the second device 1302 to the semiconductor device 1300. The signal may affect a parameter of the instructions that the semiconductor device 1300 processes and/or may be an instruction that the semiconductor device 1300 processes. The second device 1302 may subscribe to, process, or publish a data feed 202.

The semiconductor device 1300 and the second device 1302 may be operatively coupled, with an input of the semiconductor device 1300 connected to an output of the second device 1302 and/or an output of the semiconductor device 1300 connected to an input of the second device 1302. In this way, the second device 1302 may alter behavior in response to changing conditions, input from a user, and/or the data feed 202. For example, the washing machine semiconductor may be able to measure both water and electric usage. The second device 1302 may receive a data feed 202 from an external source that contains an instruction, or causes the second device 1302 to generate an instruction, to measure water usage. The second device 1302 may then output an instruction to collect the water usage data from the washing machine. At a later time, the second device 1302 may receive a different instruction to measure electric usage. The second device 1302 may then output to the semiconductor device 1300 a request to collect electric usage of the washing machine. In the same manner, the semiconductor device 1300 may also be able to collect more than one type of data and the second device 1302 may collect, aggregate, and transmit all of the available data as well as data types and then transmit the information as the data feed 202.

Syndication-capable semiconductor devices may be employed in a variety of environments including networking, consumer products, auto components, computer entertainment, commercial products, medical devices, security devices, aircraft components, and banking devices. The semiconductor device 1300 may be deployed in other devices or systems, and may operate in various environments to acquire data for publication as a data feed. The data feed may be published, for example, over any suitable network. The data and information may be used by: the user of the device, organizations that monitor device usage, enterprises that may monitor critical functions of their manufactured devices, government agencies, users searching for device data on a network, or by other groups or organizations interested in the device's broadcast information.

Figure 14:
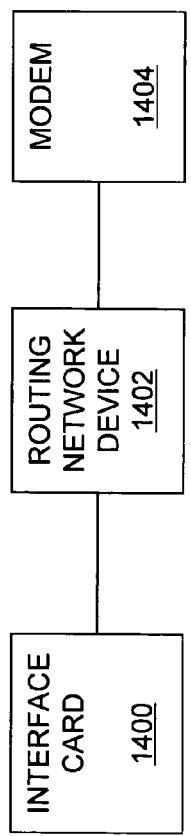
FIG. 14 depicts Syndication-enabled network devices.

Referring to FIG. 14, individual network devices such as an interface card 1400, an routing network device 1402, and a modem 1404 may incorporate a semiconductor device such as the semiconductor device 1300 described above with reference to FIG. 3. The network 100 may be any data or communications network that exchanges data between computer devices (such as the clients 102, the servers 104, and the devices of which the LAN 112 is comprised). In embodiments of the network 100, any number of instances of the network devices 1400, 1402, 1404 may be present. One or more of these devices may contain a syndication-capable semiconductor device as described above.

One of the network devices 1402 may include a routing device such as a hub, a switch, a router, and/or a repeater. Syndication capabilities may be deployed within the network device 1402, embodied as, for example one of the semiconductor devices 1300 described above or as software executing on a general purpose computer.

Each network device 1400, 1402, 1404 may contain a network interface card ("NIC"). Syndication capabilities may be deployed within such a NIC to support syndication functions which may be user-configurable and/or transparent to a user. The syndication capabilities may be embodied on a semiconductor device 1300. The NIC may publish one or more data feeds including, e.g., tags, data, and/or metadata indicating a NIC model number, a medium access controller ("MAC") address, an IP address, a connection speed, a connection type, a type of connected computer, and/or a connection protocol type. In embodiments, the data feed may be published to the Internet. Users may subscribe to the data feed to obtain status and traffic information from the NIC. This may provide useful information for, e.g., manufacturers of NIC cards, consumers interested in purchasing NIC cards, or network administrators interested in metering traffic on a network. For example, the user may obtain data reflecting actual data rates on a particular card versus other NIC cards. The transmission of this information may also allow a manufacturer of the NIC to aggregate data on a wide range of NICs; this accumulated data may allow the manufacturer to make design decisions based on the actual performance of the NIC. The manufacturer may also issue bulletins to registered users regarding any changes or best practices on certain NICs, or may also add the information to a knowledge database accessible via the Internet.

Another example may be the NIC's RSS transmission to a local network: the user may be adapted to publish certain information, possibly user defined, to a particular computer device on the local network. This RSS transmission may allow the user to view the efficiency of the network, which may enable the user to make configuration revisions in order to change the NIC performance.

Syndication capability may be incorporated into the router 1402 as a semiconductor device 1300 or as software executing on a general purpose processor or computer. The router 1402 may transmit and/or receive data and information such as a device name, number of IP packets transmitted over time, or capacity loading by, for example, subscribing to data feeds from other syndication-capable network devices. The router 1402 may aggregate and filter these feeds, and publish an aggregated feed of this data. Users connected to the network 100 may subscribe to the router 1402 data feed, and may filter or otherwise process the information therein. This information may enable purchasing decisions, network administration decisions, network infrastructure decisions, and so forth.

In another example, manufacturers may archive syndicated data feeds relating to and/or associated with the router 1402. These data feeds may contain information associated with the performance, identification, or other characteristic of the router 1402. The aggregate of data feeds 202 may then be transmitted as a new data feed, stored in a database, transmitted as an electronic mail message, published as a document, or otherwise archived or distributed in any suitable summary or other format. This information may be directed at providing information that may be employed to improve a behavior of the router 1402 and/or of the network 100. In one embodiment, this provision of information may be directed at seeding, enhancing, appending, amending, updating, or otherwise improving a manufacturer's knowledge base, which may itself be accessed as a Web site, as a data feed, or the like.

In another example, enterprises that maintain one or more of the routers 1402 associated with a large network 100 (such as the Internet) may analyze the performance of one or more of the routers 1402 that are responsible for routing the data packets for many different network branches of the larger network 100. The enterprise may, for example, determine from the one or more data feeds provided by the one or more routers 1402 whether a particular router 1402 is operating within specified parameters (such as and without limitation network performance parameters), which may relate to or be indicative of whether one or more of the routers 1402 needs maintenance, a configuration change, a replacement, or some other modification. This method of gathering one or more data feeds 202 from one or more routers 1402 may provide a syndication-based, proactive maintenance method for the enterprise.

In another example, a user may configure a router 1402 to provide certain information to a computer device (such as and without limitation a desktop computer, laptop computer, server, handheld computer, the client 102, the server 104, another router 1402, and the like) on the LAN 112 where the user may be able to review the data. This information may allow the user to make configuration revisions to the this router 1402 or network 100 to improve the data flow over the LAN 112.

A modem 1404 may provide syndication functionality using, for example, a semiconductor device 1300 as described above or a general purpose microprocessor executing software. The modem 1404 may be, for example, a telephone modem, a cable modem, a DSL modem, a VoIP modem, a satellite modem, or the like. The modem may be an external device operatively coupled to a computer device (such as and without limitation a desktop computer, a laptop computer, a server, a handheld computer, the client 102, the server 104, another router 1402, and the like). Alternatively, the modem may be internal to the computer device. The modem may be a wireless modem capable of connecting to computer devices using a wireless communication protocol such as 802.11a, 802.11b, 802.11g, IrDA, ZigBee, Bluetooth, and the like.

The modem 1404 may publish or subscribe to model-related information over the network 100. For example, the modem 1404 may publish a data feed 202 comprising indications of the modem model number, peak data rates, average data rates, connection quality, peak connection times, off peak connection times, up time, or any other information that may be of interest. This data feed 202 may be filtered, stored, or otherwise processed by other users, manufacturers, and enterprises. For example, a user may be interested in purchasing the modem 1404 for connecting a home computer to the network 100. The user may have reviewed all the standard sources of information such as websites, magazines, and recommendations of store sales personnel. The user may supplement this information by subscribing to a modem 1404 data feed, or to an aggregated data feed from a number of modems, in order to determine actual performance characteristics such as data rates. In this manner, an individual user may be able to make an informed decision on a modem based on actual performance data. As another example, a manufacturer may gather actual operation data on modems 1404 that the manufacturer has previously sold. The manufacturer may be able to aggregate individual data feeds 202 provided by the modems 1404. In one embodiment, the modems 1404 may, by default, publish a data feed 202 so that the manufacturer can archive and analyze field performance. The manufacturer may use the data feed 202 or the aggregated data feeds 202 to make improvements to modem designs, publish service bulletins to registered users (e.g. as the feed 202 or as an email), or provide service information on a company knowledgebase Web site.

As another example, an Internet service provider or enterprise resource administrator may monitor a plurality of the modems 1404 in the network 100. The modems 1404 may be dispersed geographically and/or across disparate parts of the network 100. The modems 1404 may publish operational data, and the published data may be archived, or aggregated and republished from, a certain network location. A view of the data may be provided, such as through an interface, according to a criterion, such as a modem type or a unique modem identifier. This data may enable decisions concerning readiness of both a set of instances of the modem 1404 (such as a modem bank) and a certain modem in particular. The determination may be directed at whether the modem 1404 (or an instance thereof) may require service or replacing.

A device or object that is described hereinafter as "Syndication-capable" or "Syndication-enabled," or as an "RSS device", "syndication device", "RSS object," or to which "RSS" or "syndication" is applied as an adjective (for example as in the noun phrase "RSS ATM device") may be a device or object that incorporate an RSS or syndication capability. This capability may be implemented using, for example, any of the semiconductor devices 1300 described above. The object may be able to publish and/or subscribe to data feeds about itself or other objects over the network 100. This data and/or information may be described in detail hereinafter with reference to the object. The data and/or information may be provided as the data feed 202. In general syndication rubric, a data feed is "published", however, the term "broadcast" may also be applied as a term descriptive of making data available to a range of possible viewers or readers. While syndication such as RSS typically employs a pull-based distribution platform, in embodiments, transmission to a wide audience may utilize data delivery systems and/or methods known in the art such as broadcast, multicast, unicast, push, pull, or any other data delivery system or method. The use of the word "broadcast" or "publish" as a verb may be interpreted as distribution using any of these techniques.

Figure 15:
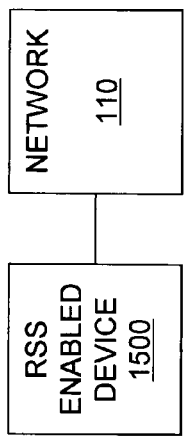
FIG. 15 a syndication-enabled device connected to a network.

Referring to FIG. 15, the network 100 may comprise a syndication-enabled device 1500, which may comprise the client 102, the server 104, or any other device. Any or all of the devices or objects described hereinafter that incorporate an RSS capability may be the syndication-enabled device 1500.

A digital subscriber line access multiplexer (DSLAM) is a device for separating or joining the voice low frequencies and data high frequencies on a digital subscriber line (DSL). The DSLAM may manage voice and data transmissions between customer locations and service providers over standard copper wires. The DSLAM may be placed in a location to handle a plurality of DSL user lines (e.g. office buildings, apartment buildings, communities) for communication back to the service provider. The DSLAM may be an RSS communication device by incorporating a syndication-capable chip or chip set into at least one of the DSLAM processors or the syndication-capable chip or chip set may be incorporated on at least one of the circuit boards of the DSLAM. The syndication-capable DSLAM may be capable of broadcasting operational data that may be collected, aggregated, or filtered by the service provider. The syndication-capable DSLAM devices may use a processor or microprocessor as described herein or in patent applications and patents referenced herein.

For example, the service provider may have a plurality of DSLAM RSS devices over a wide area in support of the service provider DSL customers. The DSLAM RSS devices may be capable of broadcasting operational data such as model name, model number, load capacity, load, number of connections, or other data needed by the service provider. The service provider may be able to aggregate or filter the broadcast data to allow for an overall picture of the efficiency of the DSLAM RSS devices, or may be able to filter the data to one DSLAM RSS device. This capability may allow the service provider to maintain a continuous picture of the operational status of the DSLAM RSS devices and the service provider may be able to use the broadcast information to take proactive action on the DSLAM RSS devices before a customer becomes aware of a connection issue.

Many consumer products used everyday may contain ASICs, microprocessors, microcontrollers, or other semiconductor devices replacing designs that once used mechanical buttons, relays, and timers. Such consumer products may include one or more of a cellular phone, a cordless phone, a telephone, a pager, a digital answer machine, a thermostat, a dishwasher, a dryer, a refrigerator, a freezer, a washing machine, an oven, a stove, a range, a trash compactor, a microwave, an energy meter, a vacuum cleaner, a treadmill, a CB radio, a clock, a toaster, a toaster oven, a coffee machine, an espresso machine, an air conditioner, a humidifier, a dehumidifier, a heater, a furnace, a gas fireplace, and an electric fireplace. Many of these devices have user interfaces that may have touch screens, buttons, dials, keypads, and so forth for the input of settings for processors that may control temperatures, time settings, cook times, atmospheric conditions, and so forth.

These consumer products may be syndication-capable devices with syndication-capable semiconductor devices incorporated therein. The syndication-capable consumer product may be adapted to publish data related to power used, water used, gas used, accumulated use time, number of cycles over a period, or other useful data. The broadcast data may be subscribed to, aggregated, stored, filtered, or otherwise processed by interested users such as manufacturers, enterprises, public utilities, government agencies, or other interested users. Syndication-capable devices may be better understood by examples of consumer products that may use RSS.

Communication devices may be syndication-capable with a syndication-capable semiconductor device incorporated into the communication device processor or the syndication-capable semiconductor processor may be incorporated into at least one of the communication device circuit boards. An RSS communication device may be at least one of a cellular phone, a cordless phone, a telephone, a pager, and a digital answer machine. These RSS communication devices may be adapted to publish data and information on device name, device model, connection times, duration of the connection, network used, call location, or other communication device information. This data may be published to a network where a plurality of users or enterprises may be able to subscribe to the data feed and collect, filter, or otherwise process the data and information.

A syndication-capable cellular phone may be adapted to publish information and data on cellular phone battery life, average distance to a cell tower, number of calls outside of calling area, calls within the plan area, and calls outside of the plan area. This published information and data may be gathered, filtered, and aggregated by users and enterprises using syndication applications. The syndication-capable cellular phone may use a processor or microprocessor as described herein or in patent applications and patents referenced herein.

For example, the user may be interested in battery life of a particular phone model or of the average signal strength in a particular area. An enterprise may be interested in collecting data on call type, call location, and call duration to help develop new calling plans based on the actual phone usage. The enterprise may also be able to determine what phone models are working well on the system by the number of dropped calls associated to a phone model and then may be able to take action with those particular cellular phones.

A syndication-capable home telephone, both wired and cordless, may publish information and data on a phone manufacturer name, a model number, a frequency used, or other phone capabilities. This published information may be used by individual users, manufacturers, and enterprises to determine the phones in use and any data that may be available. The data and information may be published to a network or may be broadcast to a user's local LAN, either to a computing device or to a server.

For example, a user may be able to use the data and information broadcast to a LAN to monitor phone usage in advance of receiving a phone company bill at the end of the month. The user may be able to aggregate the information by number called to track the calls made by children of the household. The same user may be able to aggregate and filter phone type data that may have been broadcast to the web. The user may have a syndication application where phone information may be collected from many different data feeds or from a large data feed that may contain many data sources. By collecting, aggregating, and filtering the data, a user may be able to collect data and information about the type of phones in use and additional usage data that may aid in the decision to purchase a particular type of phone or a particular phone model.

In another example, a commercial entity such as a phone company may subscribe to, store, filter, or otherwise process phone data and information from many individual data feeds or may collect data and information through the application of a filter to one or more large data sources. The enterprise may be able to subscribe to, store, filter, or otherwise process data and information on phone types in use, frequencies in use, or other helpful information that may be able to supplement the standard phone call information containing call destination and duration data that is presently collected.

As another example, a phone manufacturer may subscribe to, store, filter, or otherwise process data and information on telephones that it has manufactured from at least one data source, which may include, for example, feeds published from active telephones. The manufacturer may be able to collect information on the phone battery life, functions accessed by a user, area that the phone is in use, or other useful information. The manufacturer may be able to use the subscribed to, aggregated, stored, filtered, or otherwise processed data to make changes to the telephone design, the telephone menus, or the telephone functions. The manufacturer may publish its own information back to users to help users improve the function of the phone. The manufacturer may also post collected information onto a knowledge base website for users to gain valuable information on their phone.

The manufacturer may determine phone model usage in different regions of the country; and this information may allow the manufacturer to refine advertising plans for regions in which market penetration is low.

A syndication-capable pager may be adapted to publish a syndicated feed of data such as the pager name, pager model, paging activity such as a number of pages received or average text length, or other useful information. The feed may be accessed by individual users, manufacturers, and enterprises through a subscription process, and may be employed for example to analyze how the pagers are being used. The syndication-capable pager may be adapted to publish the RSS data and information wirelessly to a network that may have access to cellular phone technologies or through satellite networks. The syndication-capable pagers may employ a syndication semiconductor device 1300 as described generally above.

For example, the syndication-capable pager data and information may be available as a data feed that may be subscribed to, aggregated, stored, filtered, or otherwise processed. Individual users may access the feed or a stored version of feed data to make purchasing decisions on the type of pager to buy and the service to use. Manufacturers may use the data and information to make design changes in the pager or may be able to make pager information available to users through an RSS data feed or on a knowledge base website. Enterprises, such as pager companies, may be able to use the RSS data feeds to determine how users are accessing the pager system, the number of messages received, or the amount of text per message. The enterprise may then be able to use this information to make improvements to the paging system, increase pager area coverage, increase text message length, or make other revisions to the pager system.

A syndication-capable digital answering machine may publish data and information on the syndication-capable digital answering machine such as a name, model number, average number of messages stored, caller ID information or other call logging, average length of a message, percentage of memory used, or other useful information. The syndication-capable digital answering machine feed may be accessed by individual users and manufacturers to understand the way the answering machine, or groups of answering machines, are used. The syndication-capable digital answering machine may be adapted to publish the RSS data and information over the phone line to a network (e.g. LAN, WAN, Internet). The syndication-capable digital answering machine may employ a syndication semiconductor device 1300 such as any of the devices described above.

For example, the syndication-capable digital answer machine data and information may be available as a data feed that may be subscribed to, aggregated, stored, filtered, or otherwise processed. Individual users may access this collected data and information to make purchasing decisions related to answering machines. Manufacturers may use the data and information to make design changes in the syndication-capable digital answering machine or may be able to make syndication-capable answering machine information available to users through an RSS data feed or on a knowledge base website. The manufacturer may determine to make changes to the syndication-capable answering machine based on aggregate data from syndication-capable answering machine data feeds, such as increasing memory to allow more message space.

Household devices may be syndication-capable with a syndication-capable semiconductor device 1300 incorporated into the household device. Household devices capable of RSS communication may include a dishwasher, a clothes dryer, a refrigerator, a food freezer, a washing machine, an oven, a stove, a range, a trash compactor, a microwave, a toaster, a toaster oven, a coffee machine, and an espresso machine. These household devices may be adapted to publish an RSS data feed to a local network (e.g. LAN) or a larger network (e.g. WAN or Internet) that may relate at least to the kitchen household device name, a model number, power consumed (e.g. electric, gas, or oil), cycles completed, average cycles per time period, water usage, household device functions used, and temperature settings.

These household devices may be adapted to publish to a network by a wired or wireless connection to a local computer device on a LAN; may be adapted to publish to the Internet as an individual RSS data file; or may publish to an aggregation site where information on other household devices is collected and aggregated. An individual user may be able to view data that is broadcast to a LAN to track the energy consumed by the household devices. Enterprises may be able to view data aggregated from many different household devices to determine regional uses of the household devices and may allow the enterprises to make changes to the design of household devices based on the information aggregated.

For example, kitchen household devices such as a dishwasher, a refrigerator, a food freezer, an oven, a stove, a range, a trash compactor, a microwave, a toaster, a toaster oven, a coffee machine, and an espresso machine may be adapted to publish data and information on power consumed, water used, or cycles performed. An individual user may be able to view the RSS data feed on a local LAN and this information may allow the individual users to view the amount of power or water usage that a particular kitchen household device consumes. The individual user may be able to use this information to change the way the kitchen household device is used to reduce the consumed water or electricity, therefore using the kitchen household device more efficiently.

A user may subscribe to, filter, and/or aggregate data feeds for kitchen household devices on the Internet. The individual user may be interested in purchasing a new kitchen household device and may be able to view the available data from kitchen household devices. The individual user may then be able to compare the data gathered from the Internet and the data from the user's own kitchen household devices that may have been gathered on the local LAN. In this manner, the user may be able to make an informed decision on the next kitchen device to purchase.

As another example, a kitchen household device manufacturer may be able to subscribe to, filter, and aggregate kitchen household device data feeds from individual RSS data files, aggregated files, or from RSS data files that are transmitted to the manufacturer. The manufacturer may then be able to measure the amount of power use, water used, number of cycles for the device's lifetime, average number of cycles per time period, functions used, or other data that in a feed. The manufacturer may be able to use this information to make design changes to improve power usage, reduce water consumed, or add/remove available kitchen household device functions. Based on the filtered and/or aggregated data feeds the manufacturer may provide an RSS feed with information on best operation modes or other useful information to an individual user. The manufacturer may also provide data from the filtered and/or aggregated data feeds on a manufacturer knowledge base website for users to view.

Another example may be enterprises such as power companies, water companies, and/or the various government overseeing organizations to gather, filter, and aggregate RSS broadcast data on the kitchen household devices. These enterprises may be able to view the amount of electricity, oil, gas, or water consumed by these devices, but may also be able to gather, filter, and aggregate data on the time of day the electricity, oil, gas, and water were consumed. The enterprises may be able to determine the make and model of devices in use and may be able to determine the efficiency of the various makes and models. Using this efficiency information, the enterprises may be able to provide an RSS broadcast with information on the more efficient kitchen household devices to use and therefore allow an individual user to make informed purchase decisions when looking for a new kitchen household device.

Other household devices such as a clothes dryer, a washing machine, or a trash compactor may provide the same types of RSS broadcast data as the kitchen household devices discussed above. These household devices may be able to provide RSS broadcast similar to the kitchen household devices discussed above.

Other household devices may be involved in the control of household heating and cooling such as a thermostat, an air conditioner, a humidifier, a dehumidifier, a heater, a furnace, a gas fireplace, and an electric fireplace. These heating and cooling devices may be syndication-capable and may be adapted to publish an RSS feed on a wired or wireless network. The RSS broadcast may be to a local LAN for an individual user's use or may be broadcast to a larger WAN or the Internet to be used by others. These heating and cooling devices may be adapted to publish data and information at least on electricity used, oil used, gas used, room temperatures, and humidity levels. The syndication-capable household heating and cooling devices may use a processor or microprocessor as described herein or in patent applications and patents referenced herein.

For example, the heating and cooling devices may publish an RSS file to a local LAN computer device allowing the individual user to gather, filter, and aggregate data and information on the heating and cooling devices in a home. This information may allow the individual user to make decisions on the best heating and cooling conditions for a room or an entire house. From the RSS data files broadcast to the local LAN, the individual user may be able to determine the temperature and humidity combination that yields the best energy efficiency or may be able to determine when a heating and cooling device's efficiency has declined. In this manner, the individual user may be able to better understand and control the energy usage within a home.

Another example may be a manufacturer using the Internet to subscribe to, filter, and otherwise process data feeds from individual RSS sites, aggregate RSS sites, or from a manufacturer aggregated RSS site. The manufacturer may be able to use the RSS file to determine the performance of the heating and cooling device, the way individual users are using the heating and cooling device, the number of cycles until the efficiency of the heating and cooling device declines, or other useful information. The manufacture may be able to then publish an RSS data file with information on when to service a heating and cooling device to maintain the peak efficiency of the device. The manufacturer may also provide this information on a knowledge base website for users to view. The manufacturer may also use the RSS data to make design changes to improve the performance of the heating and cooling device.

Another example may be enterprises such as power companies that use RSS feeds. The enterprises may be interested in the way that users are controlling the environment of rooms and buildings with heating and cooling devices. The enterprises may be able to determine the average temperature settings of building environments, the amount of humidity in the air, and the temperatures in the building. The enterprise may be able to subscribe to device feeds to determine if users are controlling environments to the best efficiency. The enterprises may publish an RSS feed, or provide email mailings or postal mailings to educate users to the best methods of maintaining the environments of their buildings.

An energy meter may be a syndication-capable device adapted to publish an RSS feed to a local LAN or to a larger WAN or the Internet. An energy meter may be the electronic device that measures the incoming energy to a house but may also be an individual energy meter that may measure the energy of individual rooms or devices. The syndication-capable energy meter may be adapted to publish RSS data on energy consumption on a wired or wireless network connection. The published RSS data may be useful to individual users and enterprises in determining where energy is being consumed within a home. The syndication-capable energy meter may deploy syndication capability using any of the semiconductor devices 1300 described above.

For example, an individual user, with or without the help of an enterprise such as an energy provider may perform an energy survey of a home. The user may want to know the devices within the home that are consuming the most energy to determine if the device needs to be replaced with a more efficient model. The user and/or enterprise may place a number of individual energy meters within the home connected to household devices. Over a period of time, the individual energy meters may provide an aggregated RSS data feed on the power consumption of the individual household devices. At the end of the period, the RSS feed may be used to determine which room and devices are consuming the most energy in the home. This information may be provided to the individual's LAN or may have been published to an enterprise network for the creation of a report to provide the user.

Other miscellaneous household devices may publish an RSS data feed to either a local LAN or to a larger WAN or the Internet. These devices may include, for example, a vacuum cleaner, a treadmill, a CB radio, and a clock. The miscellaneous household devices may publish RSS data including a model name, model type, power consumed, mode of operation, cycles used, or other information. The syndication-capable miscellaneous household devices may include a syndication semiconductor device 1300 such as any of the devices described above.

For example, a treadmill may be setup in a home and used by an individual user. The treadmill may be capable of publishing an RSS feed that may contain the model name, model type, cycles, distance traveled, calories burned, heart rates, or other available information. The RSS feed may publish to the user's local LAN where a computer device may be able to use the feed to provide the user with a health report or performance charts in relation to the user's age.

Disclosed herein are syndication-capable vehicle devices. Semiconductors such as the semiconductor devices 1300 described above are widely used in the automotive industry such as within cars, trucks, SUVs, and motorcycles. Semiconductors may control or monitor a plurality of systems in a vehicle such as electronic fuel injection, a vehicle monitoring system, an automotive local interconnect network (LIN), an airbag, an antilock brake system, an electromechanical breaking system (break by wire), an electronic power steering system, a tire pressure monitoring system, a driver information system, a Mobile GT system, a GPS system, a vehicle stereo, a dashboard monitoring system, and a controller area network (CAN). Any of these devices may include syndication capability using, for example, an RSS chip or chip set on the device or associated with another device or circuit board within the vehicle. The syndication chip may be adapted to publish a feed to a network on the vehicle (e.g. automotive local interconnected network (LIN) or controller area network (CAN)), or through a wireless interface to a network such as a cellular phone network, satellite network, a WiMax network, a WiFi network, or any other wireless networking system. The location of the RSS data feed may be user definable or may be preprogrammed to a certain network location.

Once the RSS data feed has been published to at least one of the networks, the data may be used by the vehicle locally (LIN, CAN) or may be accessed by a larger network such as a WAN or the Internet. If the RSS data feed is published to a local network, the vehicle may be able to use the data to display information to the driver or make the data available to another device in the vehicle. The RSS data feed may be published to the Internet through the vehicle communication means as discussed above. The RSS data feed to the Internet may allow the vehicle data and information to be accessed by a vehicle owner, a manufacturer, a regulatory authority, or an enterprise. The RSS data and information may be used to track the vehicle operating telemetry, positioning, system functions, alarm indications, or other system/function by an enterprise or manufacturer.

For example, the enterprise or manufacturer may offer a service for a fee to monitor a vehicle for preventive maintenance, roadside assistance, directions, user personalized music selection, or other services. The RRS data feed may be published to an enterprise Internet site where the data from a plurality of vehicles may be republished to allow the monitoring of a fleet of vehicles or detailed monitoring of a single vehicle.

Another example may be a small repair facility (e.g. small independent repair shops or gas stations), which may employ an RSS data feed when a person brings a vehicle in for maintenance or repair. The repair facility may access an RSS source within the vehicle by accessing the Internet to subscribe to the feed for particular vehicle to be serviced. The repair facility may also be able to access the RSS data feed from the vehicle network (e.g. LIN or CAN). The RSS data feed from the Internet or the vehicle network may provide the repair facility any devices or components that may be operating out of range to speed the repair process.

Another example may be the vehicle manufacturer using an analysis of syndicated feeds to determine the status of a fleet of vehicles that are in operation. The manufacturer may be interested in the operation of a new component in a vehicle such as a new type of electronic fuel injection system. The electronic fuel ejection may be adapted to publish an RSS data feed that provides the specific operation parameters of the electronic fuel injection. Based on the received data, the manufacturer may be able to make design changes to the electronic fuel injection and/or may be able to provide the dealer service departments with upgrades to the electronic fuel injection. The upgrades may then be installed as part of a standard preventive maintenance program or provided on a fee basis to the vehicle owners. Using this method, the dealer service departments may be able to make seamless upgrades to a vehicle device or component to improve performance without the user being aware the upgrade is being made.

Many vehicle operational control devices that may provide vital control of a vehicle may contain semiconductors that may be syndication-capable. Vehicle devices consisting of at least one of an electronic fuel injection, an electronic ignition, an electronic gauge, and a vehicle monitoring system may all contain at least one semiconductor to control the device's function. As discussed above, these devices may be adapted to publish an RSS data feed to the vehicle network or to the Internet, providing operational data that may be related to the standard operational minimum and maximum ranges for the vehicle device. The RSS broadcast operational data feed may also be received and used by other devices or components within the vehicle.

For example, the electronic ignition, using semiconductor firmware, may have adjusted the electronic timing of the vehicle to improve the performance of the vehicle or to compensate for another component (e.g. an underperforming spark plug). The new settings may be broadcast over the vehicle network as an RSS data feed and the electronic fuel injection may receive the new timing data and make a change in the amount or timing of the fuel injected into the cylinder. At the same time, both the electronic ignition and the electronic fuel injection may publish the RSS data feed parameter changes to the Internet where the manufacturer or an enterprise may be able to make note of the change and compare this parameter change with a plurality of other parameter changes to determine if the parameter change should be incorporated into new designs. As part of the RSS data feed, the electronic ignition may be adapted to publish the reason for the parameter adjustment (e.g. the underperforming spark plug).

Vehicle safety devices may use semiconductors to monitor and activate the safety systems, provide an action, or provide information to the driver. These vehicle safety devices may consist of at least one of an electromechanical breaking (break by wire), an electronic power steering, a tire pressure monitoring system, an antilock brake system, and an airbag system. These vehicle safety devices may be syndication-capable to allow the broadcast of important operational status. The RSS data feed may be broadcast to the vehicle network and/or the Internet. By broadcasting the RSS data feed to the vehicle network, other components may be able to receive the operational status of the safety systems and may make adjustments based on the operational status or may display a message to the driver.

For example, the tire pressure monitoring system may detect that one of the tires may be below standard operational pressure. The tire pressure monitoring system may publish an RSS data feed to the vehicle network and the vehicle display system may receive the broadcast message and display a warning to the driver. In addition, the tire pressure monitoring system may publish the pressure information to the Internet where an enterprise providing a vehicle oversight service may gather the RSS broadcast from an Internet site. The enterprise may then broadcast an RSS tire pressure message that may be received by the driver as a text message on a PDA, cellular phone, or smart phone. The enterprise may also broadcast an RSS data feed that the driver may gather using an RSS syndication application or the enterprise may provide an email to the driver.

A vehicle information device may contain at least one semiconductor device that may monitor various vehicle parameters and display them for the driver. These semiconductor devices within the vehicle information device may be syndication-capable and therefore may be adapted to publish the information that they monitor. The vehicle information device may be at least one of a driver information system, a dashboard monitoring system, a Mobile GTTM system, and a GPS system. The vehicle information devices may receive RSS broadcast from other vehicle devices and then the vehicle information devices may display information as needed to the driver. Some of the vehicle information devices may be interactive, such as the Mobile GTTM system and the GPS system, where information is provided to the driver and the driver may provide information back to the device, while other vehicle information devices are not interactive but for display only.

For example, the Mobile GTTM system may be a combination of hardware and software that provides Internet access to a vehicle. A plurality of services may be provided through the Mobile GTTM system such as mapping, email access, Internet access, point of interest locations, and other interactive and non-interactive services. The semiconductor based Mobile GTTM system may be syndication-capable by incorporating the RSS chip or chip set into the Mobile GTTM system. The Mobile GTTM system may also be capable of receiving an RSS data feed broadcast from other vehicle devices for display and broadcast to the Internet.

For example, the driver information system and the dashboard monitoring system may be syndication-capable devices that may be able to also receive RSS broadcast from other vehicle devices. These two devices may receive RSS broadcast from at least one of a fuel system, an electronic system, a coolant system, an electronic fuel injection system, an electronic ignition system, and a lighting system. The driver information system and the dashboard monitoring system may be able to receive data from the various other vehicle devices and may combine them into an overall condition of the vehicle. The driver information system and the dashboard monitoring system may RSS publish the overall condition to the vehicle network or to the Internet at a set period of time or only when a vehicle parameter or a combination of parameters is out of range of a specification.

A vehicle audio system may be a syndication-capable device that may be adapted to publish and receive RSS data feeds. With the advent of satellite radio for vehicles, a vehicle audio system may be adapted to publish to a satellite radio provider a user specific play list. A user may be able to select between playing one of the standard audio channels provided by the satellite radio provider or the user may be able to select from a user-defined selection. The vehicle audio system may be capable of creating a user play list based on a user music selection or as the user listens to music selections, the music may be added to the play list. The vehicle audio system may be adapted to publish the user's play list to the satellite radio provider in order to have the user's play list played instead of a standard channel.

Vehicles may also contain a vehicle network to provide communication between the various devices of the vehicle. At least two types of vehicle networks may be used in vehicles, a controller area network (CAN) and an automotive local interconnect network (LIN). The CAN may be a bus-based network that may publish information between devices using unique device identifiers; a device may always be listening for a broadcast message with the correct identifier. Each device on the CAN may contain at least one semiconductor, microprocessor, and/or microcontroller; each of the devices may act as a master for the broadcast of a device message. The LIN may be a less expensive alternative to the CAN that may use a single wire to connect all of the devices on the network. Typically, the LIN may have only one master device to many slave devices of the vehicle, and the master device may contain at least one semiconductor, microprocessor, and/or microcontroller. Both the CAN and LIN may be syndication-capable devices by incorporating a syndication-capable chip or chip set into the CAN and LIN device chip or chip sets or the syndication-capable chip or chip set may be incorporated onto at least one of the CAN and LIN device circuit boards. The syndication-capable vehicle network may use a processor or microprocessor as described herein or in patent applications and patents referenced herein.

The syndication-capable vehicle networks may be capable of broadcasting an RSS data feed that may contain data or information on the vehicle network operational statistics, vehicle operational statistics, type of messages broadcast, average bandwidth used, or other network or vehicle data. The vehicle network may publish the RSS data feed to a WAN or the Internet through a cellular phone network, satellite network, MobileGT™ system, WiFi, WiMax, or other network. The RSS data feed may also be broadcast to a vehicle device that is capable of aggregating and storing the data and information for later retrieval from a wired connection that may be connected to a LAN or WAN. The RSS data or information may be broadcast to the LAN, WAN, or Internet to an individual, aggregated, or enterprise particular site. The CAN and LIN RSS broadcast data may be gathered, filtered, and aggregated from the LAN, WAN, or Internet for analysis.

For example, a vehicle manufacturer or enterprise may be interested in the data or information the CAN or LIN may publish to verify vehicle and network operability. The manufacturer may be interested in the messages or the type of messages that are broadcast between the devices to determine if the vehicle devices are operating properly. The manufacturer may be adapted to publish data to a user and/or a dealer service center when a message between devices indicates that a device may be failing or has failed. The manufacturer broadcast may be an RSS data feed, email, or postal mail to the user or dealer service center.

Another example is an enterprise that may provide a fee service for vehicle over site providing vehicle data or information to a user or another enterprise. The vehicle data may be in the form of tracking one vehicle or an entire fleet of vehicles and providing a report on the vehicle operational parameters. The report may be in the form of an RSS broadcast, email, or postal mail to the user or other enterprise.

Almost every type of computer device uses semiconductors, microprocessors, and microcontrollers that control the function of the computer device or provides control or communication to another computer device. For example, a computer microprocessor may interact with many different processors or controllers on the same circuit board or may communicate with at processors or controllers on least one of an expansion board, a serial port, a USB port, a parallel port, a wired connection, and a wireless connection. The computer devices may be at least one of a computer, a laptop, a tablet computer, a storage device, a computer monitor, a video interface card, an audio interface card, a USB port, a serial port, a wireless mouse, a wireless keyboard, an uninterruptible power supply (UPS), a printer, a scanner, a fax, an image/document center, a joy stick, a PDA, a handheld computer, a smart phone, a Treo, a Blackberry, and a bicycle computer.

The computer devices may be a syndication-capable device by incorporating a syndication-capable chip or chip set into at least one of the computer device semiconductors, microprocessors, or microcontrollers or the syndication-capable chip or chip set may be incorporated into at least one of the circuit boards of the computer device. The syndication-capable computer devices may be adapted to publish an RSS data feed that may contain data or information on the computer device. The RSS compatible computer device may publish data or information to at least an internal computer device, to an external computer device, to a LAN, to a WAN, and to the Internet. The computer device may be adapted to publish over a wired or wireless network and may use another computer device to publish the RSS data feed or may be capable of broadcasting the RSS data feed on its own. The syndication-capable computer device may use a processor or microprocessor as described herein or in patent applications and patents referenced herein.

Computer devices such as a computer, a laptop computer, a tablet computer, and a storage device may be adapted to publish an RSS data feed directly to LAN, WAN, or the Internet using either a wired or a wireless connection of the computer device. These computer devices may be adapted to publish an RSS data feed of at least the processor name, processor frequency, processor type, process model, computer memory capability, and connected devices. The syndicated data feed may be gathered, filtered, and aggregated by a user, a manufacturer, or an enterprise for monitoring the computer system.

For example, the computer device may publish the RSS data feed to a local network computer device (e.g. server) where the user may be able to gather, filter, and aggregate the data to track the performance of the user's computer system. The RSS data feed may also be broadcast to a WAN or to the Internet where the user may be able to gather, filter, and aggregate the same information. The RSS data feed that may be broadcast to the Internet may also be provided to other users. The user may be able to determine if a computer device is operating out of a set range or is not operating to peak performance allowing the user to make changes to a configuration setting or change the environment of the computer device (e.g. a location with less heat).

Another example may be the computer device broadcasting the RSS data feed to the Internet for the purposes of other entities such as users, manufacturers, or enterprises gathering, filtering, and aggregating the data. These entities may be able to use the data for at least purchasing research, determining the number and type of processors in use, and determining the type of other computer devices associated with the broadcasting computer device. For example, manufacturers and enterprises may use the RSS broadcast data and information for determining where and what type of processors are in use by region to allow the manufacturer or enterprise to best support the computer devices. This information may then be broadcast to support personnel in the regions to build support strategies for the computer devices.

Computer accessory devices may be syndication-capable devices that may be adapted to publish an RSS data feed using their own communication facility or may publish through another computer device (e.g. a computer). The computer accessory device may be at least one of a computer monitor, a video interface card, an audio interface card, a wireless mouse, a wireless keyboard, a joystick, a USB port, and a serial port. These devices may provide an interface for user communication to the computer devices discussed above. These devices may be capable of broadcasting an RSS data feed that may consist of at least monitor frequency, monitor size, video card chip set used, audio chip set used, communication frequencies, wireless or wired mouse, and wired or wireless keyboard.

For example, the computer accessory device may publish the RSS data feed to a local network computer device (e.g. server) where the user may be able to gather, filter, and aggregate the data to track the performance of the user's computer accessory devices. The RSS data feed may also be broadcast to a WAN or the Internet where the user may be able to gather, filter, and aggregate the same information. The user may be able to use this information to determine the overall configuration of the computer system and all of the computer accessory devices. The user may be able to determine information about computer accessory devices that may not be readily available to the user otherwise. For example, a user may have two individual computers on a LAN with wireless keyboards that may be interfering with each other. The user may be able to determine from the RSS data feed what frequencies or channels are being used by the wireless keyboards and make an appropriate configuration change to the keyboard frequency or channel.

Another example may be manufacturers and enterprises gathering, filtering, and aggregating RSS data broadcast from computer accessory devices; the RSS data feed may be broadcast to either individual Internet sites or may be broadcast to an aggregating Internet site. The manufacturers and enterprises may use the syndicated data feed to understand the type of computer accessory devices that may be used with various computer devices; this information may help define what type of systems are in use. This information may help the manufacturers and enterprises to make marketing decisions on the type of computer accessory devices to design, market, and advertise. The RSS data feeds may allow the computer accessory device data and information to be filtered into national and regional information.

An external peripheral computer device may be any device that may have a wired or wireless connection to a computer device and may provide an additional capability to the computer device. The external peripheral computer device may be at least one of an uninterruptible power supply (UPS), a printer, a scanner, a fax, and an image/document center. The external peripheral computer devices may contain at least one semiconductor, microprocessor, or microcontroller for controlling the function and communication of the external peripheral computer device. These devices may be syndication-capable devices by having a syndication-capable chip or chip set incorporated into at least one of the semiconductor, microprocessor, and microcontroller or may have the syndication-capable chip or chip set incorporated onto at least one of the circuit boards. The external peripheral computer devices may be adapted to publish the RSS data feed or may publish the RSS data feed through another computer device.

The external peripheral computer devices may be adapted to publish an RSS data feed to a LAN, WAN, or Internet location and provide information of at least a model name, a model number, total cycles performed, total pages processed, voltage supplied, number of UPS events, connection rate, printed pages per ink cartridge, number of faxes received, and number of faxes transmitted. This information may be used by individual users, manufacturers, and enterprises for tracking the use and performance of the external peripheral computer devices.

For example, an individual user may have the RSS data feed broadcast to a local LAN computer device (e.g. a computer or a server) to gather, filter, and aggregate the data and information from the various external peripheral computer devices. The individual user may be able to track the number of pages printed on a printer and compare this number to the rated duty rating of the printer. The individual user may be able to track the number of pages that are printed on an ink cartridge (e.g. black or color) versus the printer quality setting to determine the best setting that provides acceptable ink usage and readable printed pages. The individual user may also have this same RSS data and information broadcast to an internet site where the same gathering, filtering, and aggregation of external peripheral computer devices are possible.

The external peripheral computer device may publish the RSS data and information to an individual site or to an aggregation site where data and information is gathered, filtered, and aggregated for certain types of external peripheral computer devices. For example, a manufacturer may be able to gather, filter, and aggregate data and information of a certain printer model and information such as number of pages printed, pages per ink cartridge, and configuration settings to determine if the printer model is performing to specifications. The manufacturer may be able to use this information to make design changes to the printer model to possibly improve the duty rating or number of pages printed per ink cartridge. The manufacturer may also be able to provide best use practices to users based on this information by broadcasting an RSS data feed, email, or postal mail. The information may also be placed on a manufacturer knowledge base website.

Another example may be an enterprise that may sell ink cartridges for printers of many different printer models. The enterprise may be able to gather, filter, and aggregate the printer ink cartridge information from an Internet site. The information may be broken down by printer model and ink cartridge type with information on the average number of pages that are being printed with a cartridge. The enterprise may then be able to make informed decisions on the number of ink cartridges to produce and market to wholesale or retail stores. The RSS data feed may be filtered to a region or sub-region to allow the enterprise to support ink cartridges that may have a higher population in certain regions or sub-regions.

Syndication capabilities may be incorporated into a portable computer device. The portable computer device may be at least one of a PDA, a handheld computer, a smart phone, a Treo, GPS device, and a Blackberry. A portable computer device may be adapted to publish an RSS data feed by wired or wireless connection to a LAN, WAN, or Internet. Using the data feed, one of the portable computing devices may publish RSS data relating to the device such as a model name, a model number, processor type, installed applications, memory size, message size, communication rates, and number of messages. The syndicated data feed may be used by individual users, manufacturers, and enterprises for assessing the type of systems in use and the manner that they are used.

For example, individual users may use the syndicated data feed to gather information on the portable computer device wireless connection rates by location. The user may pay a minute fee for data exchange on the portable computer device when it is communicating using a wireless connection and a slower connection rate may mean a longer connection time. The user may be able to use the RSS broadcast data and information to determine the locations that provide the best connection rates and access these connections more often.

As another example, a manufacturer may gather data from syndicated feeds of portable computer devices that are in use. The manufacturer may analyze the content of the feeds to determine if support for a certain portable computer device should be continued or be discontinued.

Another example may be an enterprise that uses syndicated data to determine the models currently in use. Based on the number and type of portable computer devices in use, based on the syndicated data feed, the enterprise may be able to plan for new or improved applications for the available devices.

There may be unique applications for computer devices, for example a bicycle computer may provide information such as distance traveled, present speed, calories burned, or average speed. The bicycle computer may contain a GPS and may incorporate location data such as a present location, altitude, or heading into a syndication feed. The bicycle computer may be a syndication-capable device by having a syndication-capable chip or chip set incorporated into at least one of the semiconductor, microprocessor, or microcontroller of the bicycle computer. The syndication-capable chip or chip set may also be incorporated into at least one of the bicycle computer circuit boards. The bicycle computer may be adapted to publish an RSS data feed with a wireless or wired connection to a LAN, WAN, or Internet site. An individual user may subscribe to the resulting syndicated data feed to collect data on the latest bike route or gather training information. The syndicated data feed may provide information about the calories burned over a distance or instantaneously at points during the route. The user may analyze published data for more than one route for comparison of statistics for each bike route and may make changes in the route for a better training routine. The user may also obtain latitude and longitude points taken during the route and plot the route on a mapping application.

Many home entertainment devices may contain semiconductors, microprocessors, or microcontrollers to control audio, video, games, home theaters, recording systems, and lighting systems. Many of these entertainment devices may be interconnected by a wired or wireless connection so that a first entertainment device may enhance the capabilities of a second entertainment device. For example, a home theater system may be connected to a game console to provide a theater atmosphere to the playing of the game. Home entertainment devices may be at least one of a CD player, a DVD player, an MP3 player, an iPod, an MPEG player, a computer game, a handheld computer game, an Xbox, a PlayStation, a Gamecube, a remote control, a digital camera, a film camera, a camcorder, a home entertainment gateway, a home theater, a noise cancel headphone, a stereo, a radio, a VSH player, a VCR, a cassette player, an amplifier, a set-top box, a VCD player, a video disk player, a TV monitor, a digital video recorder, a TIVO system, and a lighting system.

A syndication-capable semiconductor device may be incorporated into the home entertainment device to form a syndication-capable home entertainment device. The syndication-capable home entertainment device may be adapted to publish an RSS data feed that contains information related to the home entertainment device. The RSS compatible home entertainment device may publish data or information to at least an external computer device, to a LAN, to a WAN, and to the Internet. The home entertainment device may be adapted to publish over a wired or wireless network and may use a computer device to publish the RSS data feed or may be capable of publishing syndicated data on its own.

Portable home entertainment devices such as portable CD players, portable DVD players, MP3 players, iPod, and MPEG players may be adapted to publish RSS data and information that may be available on the portable home entertainment device such as model name, model type, entertainment medium, or entertainment played (e.g. music or movie). The portable home entertainment device may publish an RSS data feed to network or Internet location for other users or enterprises to gather, filter, and aggregate.

For example, a syndication-capable portable home entertainment device may publish wirelessly through a cellular phone network the title, artist, and album that is being played to a network site. The device may subscribe to songs published to syndicated feeds, and store songs for a period of time, therefore creating a personal hit list of songs played. For example, a user may be able to create a top-fifty pop songs list by filtering feeds of songs that have been played for the week. The user could then publish this list to other users.

Another example may be the entertainment industry that may be able to track songs played on portable entertainment devices, the number of times a song is played after purchase may be a predictor of further sales of the same song or album, therefore allowing the entertainment industry to predict the number of new albums to publish. The entertainment industry may also be able to track the playing of illegally copied songs if the portable entertainment device RSS data feed included legal/illegal copy information. The information if a song is an illegal copy may be broadcast to an entertainment industry site only; the entertainment industry may be adapted to publish a warning message to the user by RSS feed, electronic mail, or postal mail.

Computer games and computer game playing devices such as a console computer game, a handheld computer game, an Xbox, a PlayStation, and a Gamecube may be a syndication-capable devices that may publish data and information on at least a device name, device model, connected interfaces, game being played, game score, and number of players of the game. The computer game and computer game playing devices may be adapted to publish an RSS data feed by wired or wireless connection to a LAN, WAN, or Internet site. The syndicated data feed may be accessed by individual users or enterprises for tracking game play.

For example, the computer game or computer game playing device may publish an RSS data feed that may include the type of computer game playing device, the game played, and the score of a game in progress or just completed. Individual users may subscribe to RSS feeds to obtain information on computer games played and high scores; this information may be aggregated and published, for example, as a top fifty computer game score list for a particular game. An individual user may be able to create a web magazine with a plurality of computer game scores or other users to be able to view the computer game scores; in this manner, a user may be able to create a centralized scoring site for casual users or for computer game tournament scores.

Another example may be the computer game industry's ability to track the number of games that are being played of a certain game or of a computer game category. The computer game playing device may publish an RSS data that may be subscribed to by a game industry entity. The content may be analyzed to predict the games that may be popular in the future and may be a guide of new games to be developed. The game industry may be able to provide an RSS data feed with the aggregated computer game data for individual users to view.

Numerous other devices may employ a syndication-capable semiconductor device or software to provide subscription, publication, filtering, and other syndication services. For example, a digital camera, film camera, or camcorder may publish syndicated data concerning usage, camera capabilities, current images. In one aspect, images may be continuously published to a feed for capture, e.g., at an image repository. A number of home entertainment devices may employ a syndication-capable semiconductor device, such as a stereo, television, home theater system, home entertainment gateway, a home theater, a noise cancellation headphones, a radio, a VHS player, a VCR player, a cassette player, a stereo amplifier, a set-top box, a VCD player, a video disk player, a TV monitor, a digital video recorder, a TIVO, and a remote control. The home entertainment devices may be adapted to publish RSS data related to the device or usage thereof, or to subscribe to one or more syndicated feeds, such as a channel guide, content rating feed, or the like, which may be filtered at the device according to user preferences.

A home lighting system may contain a syndication-capable semiconductor device adapted to publish and subscribe to syndicated feeds. The home lighting system may be able to communicate using wired or wireless communications and may provide an RSS feed of status to other in home computer devices, entertainment devices, a LAN, a WAN, or the Internet. The home lighting system may publish an RSS data feed that may include lights on, light intensity, light color, light time control, or energy used. In another aspect, the home lighting system may receive control information by subscribing to a control feed. Thus a user may control a home lighting system by publishing lighting control information to a suitable feed.

Other devices may similarly be provided with syndication capability, such as an electronic filter, an analog to digital converter, a digital to analog converter, an audio mixer, digital signal processor, a video processor, an analog multiplier, an electronic power supply, a cell tower, a repeater, a TV, a V chip, a transmitter, a receiver, a transceiver, an amplifier, a TAG reader, a card reader, a motion control, a robotic device, and a gas pump. Syndication capability may be integrated into electronic filters such as an EMI filter, an ESD filter, a SAW filter, and a DSL filter. For example, the RSS EMI and ESD filters may be adapted to publish an RSS data file with the operational parameters of the filters for subscription and analysis.

An electronic power supply may be an RSS device by incorporating a syndication-capable chip or chip set into at least one of the electronic power supply chips or chip sets. The syndication-capable chip or chip set may also be incorporated into at least one of electronic power supply circuit boards. The RSS electronic power supply may be adapted to publish RSS data or information that may contain at least one of a model name, model number, input power, output power, and operating temperature. The RSS electronic power supply may be adapted to publish the RSS data and information using a wired or wireless connection either on its own or through another device. The RSS electronic power supply may provide a manufacturer or user data or information on the operational status of the RSS electronic power supply.

For example, the RSS electronic power supply may publish RSS data or information to a manufacturer network site; the RSS data or information may contain operational data related to the input and output power and the operating temperature. The manufacturer may be able to collect, filter, and aggregate information from like type RSS electronic power supplies to monitor the performance of different models of RSS electronic power supplies. The manufacturer may make design changes to the RSS electronic power supply to improve performance or the manufacturer may be able to provide an RSS broadcast with a service bulletin for users of a particular model of RSS electronic power supply.

In another example, an individual user may be able to use the RSS data or information that may be published to a network site to gather, filter, and aggregate information to make a purchasing decision on an RSS electronic power supply. The user may be able to determine from the syndicated data or information if the RSS electronic power supply meets the needs of the user and therefore the user may make an informed purchase.

Cell tower devices may be syndication-capable by the incorporation of syndication-capable chips or chip sets into at least one of the cell tower device chips or chip sets. The syndication-capable chip or chip sets may also be incorporated into at least one of the cell tower device circuit boards. Cell tower devices may be responsible for connecting and maintaining calls with cellular phones and communicating with the cell network for tracking cellular phones as they move within a cell. The RSS cell tower device may publish RSS data and information to individual cellular phones as part of the information sent during a phone call or just at the beginning of a phone call, such as the number, name, and location of the incoming phone call. The RSS cell tower device may also syndicated data to the cell network to report cellular phone and cell tower statistics such as the number of calls maintained, the average number of calls over a time period, the average phone load, operation temperatures, and average number of dropped calls.

For example, a RSS cell tower device may publish RSS data and information with every new call connected to a cellular phone. The cellular phone may also be an RSS device that receives the RSS data or information and may use the RSS data or information for determining if a call should be blocked based on the call number, name, or location. The cellular phone may be adapted to publish RSS data or information to the RSS cell tower device indicating the blocking of the call. The blocked call RSS broadcast may also include a message that the RSS cell tower device may be adapted to publish to the calling cellular phone.

TV devices may be syndication-capable with the incorporation of syndication-capable chips or chip sets in at least one chip or chip set of the TV device. The syndication-capable chip or chip set may also be incorporated on at least one TV device circuit board. RSS TV devices may be a TV, a TV V chip, or a remote control. The RSS TV devices may be adapted to publish RSS data or information such as channel capability, channel being watched, international configuration, connection types, channels being blocked, and reason for blocked channels. The RSS TV device may be adapted to publish the RSS data or information with a wired or wireless connection or may use another device to publish the RSS data or information.

For example, an RSS TV may be adapted to publish information on channels that are watched and which channels are blocked. An enterprise or organization (e.g. TV broadcasters or TV watch groups) may be able to gather, filter, and aggregate the RSS TV data and information to make determinations of the shows that are watched or blocked. TV broadcasters may use this information to aid in making decisions for production of future shows and the TV watch groups may use the information to further a campaign for or against a particular type of show.

Broadcasting devices may be syndication-capable devices by incorporating a syndication-capable chip or chip set onto at least one of the broadcasting devices chips or chip sets. The syndication-capable chip or chip set may also be incorporated onto at least one of the broadcasting device's circuit boards. RSS broadcasting devices may include at least one of a transmitter, a receiver, a transceiver, an amplifier, and a repeater. The RSS broadcasting devices may publish RSS data or information such as model name, model type, data received, data transmitted, average data rate, and average load. The RSS broadcasting devices may be adapted to publish RSS data or information using a wired or wireless connection or may publish RSS data or information through another device.

For example, an RSS receiver, RSS transmitter, or RSS transceiver may be adapted to publish RSS data or information to a manufacturer on the operational parameters of the device. The manufacturer may be able to gather, filter, and aggregate the RSS data or information that may be broadcast to a manufacturer's aggregation network site. The manufacturer may be able to monitor the operation parameters for a certain model RSS receiver, RSS transmitter, or RSS transceiver. The manufacturer may be able to use the information to make design changes or the manufacturer may use the information to broadcast its own RSS data feed to users of the RSS broadcast devices with maintenance or performance enhancing information.

A tag reader may be a syndication-capable device by incorporating a syndication-capable chip or chip set onto at least one of the tag reader chips or chip sets. The syndication-capable chip or chip set may also be incorporated onto at least one of the tag reader circuit boards. The RSS tag reader may publish RSS data or information such as model name, model type, data received, data transmitted, average data rate, and average load. The RSS tag reader may be adapted to publish RSS data or information using either a wireless or wired connection or may connect using another device.

For example, an RSS tag reader may be used to track tagged inventory as it moves through a facility. The RSS tag reader may be adapted to publish RSS data or information on the tracked inventory and may publish the RSS data or information to a LAN, WAN, or Internet site; the Internet site may be a secure site. The RSS tag reader may publish information such as the inventory ID, number of items, and location in the facility. This information may be gathered, filtered, and aggregated by the manufacturer from the network to maintain control of the movement of the inventory. The RSS tag reader may also be able to receive RSS data or information that may contain information on any special handling of a piece of inventory. The information may include a stop order, a hold order, or a priority order for the piece of inventory.

A robotic device may be a syndication-capable device by incorporating a syndication-capable chip or chip set onto at least one of the robotic device chips or chip sets. The syndication-capable chip or chip set may also be incorporated onto at least one of the robotic device circuit boards. RSS robotic devices may include a processor, microprocessor, microcontroller, controller device, or computer device. The RSS robotic device may publish RSS data or information such as model name, model type, degrees of motion, robot load, environmental conditions, faults, traverse rates, and over travel information. The RSS robotic device may be adapted to publish RSS data or information using a wired or wireless connection or may publish RSS data or information through another device.

An RSS robotic controller may publish RSS data or information on the environment in which the RSS robotic controller is operating. The RSS robot controller may be operating in a harsh environment (e.g. heat, cold, fumes) and the RSS robotic controller may publish an RSS data file with the environmental information along with information on vital robot statistics. This information may be gathered, filtered, and aggregated by a manufacturing facility to track the RSS robotic controller for signs of breakdown from the environmental conditions. The manufacturing facility may be able to track the syndicated data and information over time to predict a failure time and schedule maintenance time.

A gas pump may be a syndication-capable device by incorporating a syndication-capable chip or chip set onto at least one of the gas pump chips or chip sets. The syndication-capable chip or chip set may also be incorporated onto at least one of the gas pump circuit boards. The RSS gas pump may include a processor, microprocessor, microcontroller, controller device, or computer device. The RSS gas pump may publish RSS data or information such as model name, model type, type of gas pumped, amount of gas pumped, and pay method (e.g. credit or cash) information. The RSS gas pump may be adapted to publish RSS data or information using a wired or wireless connection or may publish RSS data or information through another device.

For example, an RSS gas pump may be adapted to publish RSS data with a station identifier, type of gas pumped, amount of gas pumped, and pay method information to an enterprise network site; the network site may be a secure site. An enterprise may be able to gather, filter, and aggregate RSS broadcast gas pump data from a particular region to track sales. The RSS broadcast data may allow the enterprise to better understand the gas consumption in a region and the data may be updated in a timely fashion that may allow the enterprise to make better gas buying decisions than if it had waited for an end of month report from the individual gas stations.

Medical devices may be syndication-capable devices by incorporating a syndication-capable chip or chip set onto at least one of the medical device chips or chip sets. The syndication-capable chip or chip set may also be incorporated onto at least one of the medical device circuit boards. The RSS medical device may include a personal electrocardiogram (ECG) monitor, a home defibrillator, a CAT scan, a MRI scan, a PET scan, a heart monitor, a BP monitor, and an x ray. The RSS medical device may publish RSS data or information such as model name, model type, type of procedure, number of procedure, heart rate, blood pressure, technician name, or doctor name. The RSS medical device may be adapted to publish RSS data or information using a wired or wireless connection or may publish RSS data or information through another device.

For example, an RSS MRI machine may be adapted to publish RSS information to a hospital network site where the scan information may be reviewed off site from the hospital. The RSS data and information may include the RSS MRI machine scan files that may allow a remote technician or doctor to view the RSS MRI machine scan files from a location other than the hospital. Different technicians and doctors at different locations may be able to view the RSS MRI machine scan files from the network site at the same time; this may allow for collaboration of technicians and doctors from remote locations using the same RSS MRI scan files.

Many security devices may contain ASIC processors, microcontrollers, and microprocessors for systems such as recognition systems, detection systems, access control, and digital rights management. These security devices may consist of, but are not limited to, fingerprint recognition, facial identification system, security systems, motion detectors, fire detectors, gas detectors, access control devices, and digital rights management (DRM).

The security devices may be syndication-capable devices by incorporating syndication-capable chips or chip sets into the security device chip or chip sets or the syndication-capable chips or chip sets may be incorporated into the security device circuit board. The syndication-capable security device may be adapted to publish RSS data or information to a LAN, WAN, or Internet by wired or wireless communication or by communication through another device. The syndication-capable security devices may use a processor or microprocessor as described herein or in patent applications and patents referenced herein.

An RSS security recognition system may be capable of broadcasting RSS data or information to a LAN, WAN, or internet site; the internet site may be a secure site. The RSS security recognition system may be a fingerprint recognition system or a facial recognition system. These systems may be able to scan or image the finger or face to create a capture file and match the capture file with a file on record. The syndicated data or information may consist of at least one of the device name, device type, file type identifier, transmission address (e.g. email, HTTP, IP), and image file.

For example, an RSS fingerprint recognition system may scan a person's fingerprint into an image file; the image file may be processed on the RSS fingerprint recognition system or the image file may be broadcast as an RSS data file to a network location for additional processing. The RSS broadcast may be to a secure network site where the fingerprint matching is processed. The results of the fingerprint matching process may be returned to the RSS fingerprint recognition system with an RSS broadcast that may contain information of the matching person such as name and location. The RSS fingerprint recognition system may be a portable device that may be adapted to publish the RSS data or information wirelessly to the network location.

An RSS security system may be capable of broadcasting RSS data or information to a LAN, WAN, or Internet site; the Internet site may be a secure site. The RSS security system may consist of at least one of a security system, a motion detector, a fire detector, a gas detector, and an access control device. The RSS security systems may be adapted to publish RSS data or information to remote locations for the secure areas to be monitored, or secure data in the form of alerts may be reported to the remote location.

For example, a security enterprise may have many installed security systems in a region. The security systems may be RSS security systems that may be adapted to publish RSS data or information to a remote network location; the remote network site may be a secure site. The RSS security system may monitor an area or a facility for motion, fire, smoke, gas, or unauthorized entry. If a security device of the RSS security system generates an alert, the RSS security system may publish RSS data or information to a network site that is monitored by the security enterprise. The RSS data or information may consist of property location, property ID, security device with alert, alert time, location of alert, and an image file from the security device. The security system may also be able to receive an RSS broadcast from the security enterprise; the enterprise may be able to change configuration of the system, turn security devices off, turn security devices on, or reset security devices.

An RSS digital rights management (DRM) device may be any device that may be capable of playing, copying, and/or forwarding entertainment content. Devices such as cellular phones, MP3 players, CD players, or DVD players may contain RSS DRM devices. The RSS DRM device may prevent the copying or forwarding of entertainment content and may publish RSS data or information to the device for display to the user and/or may publish RSS data or information to the entertainment content owner. The RSS broadcast data or information may contain at least one of the entertainment content name, copy request information, forward request information, credit information, and device communication address.

In an embodiment, the user may attempt to copy or forward the entertainment content and the RSS DRM device may publish RSS data or information to the entertainment content owner. The syndicated data or information may be a request for copying or forwarding the entertainment content for a fee. The entertainment content owner may respond to the RSS DRM device with a syndicated data or information granting the copy or forward of the entertainment content for a fee and indicating the user's account or credit account has been charged for the copy or forward.

The aircraft industry may use many types of semiconductors in both aircraft and aircraft ground control. Aircraft RSS devices may include air traffic control and aircraft avionic control devices. These devices may be adapted to publish RSS data and information on aircraft location on the ground and in the air. The RSS avionics may be adapted to publish RSS data on the functioning of various controls of the aircraft. The syndicated data and information may be broadcast to a LAN, WAN, or Internet site; the Internet site may be a secure site. The aircraft RSS devices may be adapted to publish by wired or wireless connection; the wireless connection may be by WiFi, cell network, or satellite network.

For example, an aircraft may contain an RSS recording device (e.g. black box) that may record all of the vital control information on the aircraft during flight. The RSS recording device may be adapted to publish RSS data that is recorded by the RSS recording device. In an embodiment, the RSS recording device may be adapted to publish the RSS data to a satellite or to ground stations. The RSS data may be sent to an Internet site where the RSS data may be monitored; the Internet site may be secure. The RSS recording device data may be adapted to publish to the Internet site for an entire flight, therefore providing a complete history of the flight. In an embodiment, the RSS recording device may be adapted to publish an alert as a separate RSS file; the alert may be for any device that is out of specification. The RSS alert data file may indicate that the broadcast RSS file or information for the broadcasting aircraft should be reviewed and the aircraft contacted.

In banking, automatic teller machines (ATM) may be an RSS ATM device that may be capable of broadcasting RSS data and information. The RSS ATM data may be broadcast to the hosting bank and may be broadcast to just the hosting bank network. The RSS ATM device may connect to the hosting bank network using a wired connection. The RSS ATM device may publish information that may contain device location, device ID, money remaining, and money dispersed. The syndicated data or information may be monitored at a bank location. In an embodiment, the RSS ATM may be adapted to publish an RSS data or information to alert when the RSS ATM is low on money and request additional money.

FIG. 16 depicts a syndication-enabled telecommunications device 1600. The device 1600 may consist of a telecommunications device 1602 coupled with a processor 1604, which may comprise the semiconductor device 1300, that is adapted to manipulate RSS data. The processor 1604 may be multifunctional and manipulate other types and sources of data. The telecommunications device 1602 may be a cellular phone, a cordless phone, a telephone, a pager, a handheld computer, a smartphone, a wireless electronic mail device, a Treo, a Blackberry, a walkie-talkie, a CB radio and/or a VoIP device. Referring to FIG. 17, the device may also include a display 1702. The processor 1604 may display all or a portion of the RSS feed on the display 1702. The processor 1604 may also manipulate or process the RSS feed and display the manipulated or processed RSS feed on the display 1702. In an embodiment, if the RSS feed contains sport's scores, the processor 1604 may display only scores for certain teams in a certain league. This selective display of information may be in connection with pre-defined user preferences.

As depicted in FIG. 18, the device 1600 may receive an RSS feed 1802, which may be a feed 202. The processor 1604 may display the RSS feed 1802 on the display 1604. The processor 1604 may also convert the RSS feed 1802 into an audio signal 1804 outputted through the telecommunications device. In an embodiment, the RSS feed 1802 may contain sport's score information and the processor may convert a score to an announcement, such as, "The game is now tied at 3-3." As depicted in FIG. 19, the device 1600 may transmit an RSS feed 1902, which may be a feed 202. The received 1802 and transmitted 1902 RSS feeds may be RSS 0.9, RSS 0.91, RSS 0.92, RSS 0.93, RSS 0.94, RSS 1.0, RSS 2.0 or any other standard.

As depicted in FIG. 20, the device 1600 may receive an RSS feed 1802 and the processor 1604 may be configured to extract telephone numbers or other relevant contact information and other information from the RSS feed 1802. The telecommunications device 1602 may place an outbound call 2002 based on the extracted telephone numbers. The telecommunications device 1602 may also send an email, store a reminder, or send a text message based on the extracted contact information. The processor 1604 may display the extracted telephone numbers and/or other contact information on the display 1702. The processor 1604 may also place the extracted telephone numbers and/or other contact information in an address book 2004. It may be the case that the address book 2004 can be accessed from other devices. The contact information may include one or more of each category of name, address, phone number, email address and type of contact.

Referring to FIG. 21, the processor 1604 may be configured to generate an alert 2102 in response to the content of an RSS feed 202. The alert 2102 may be a visual alert, such as an alert outputted on the display 1604 of the device. The alert 2102 may be an audio alert, such as a beep or synthesized voice. The alert 2102 may be a tactile alert, such as a vibration. The alert 2102 may also appeal to the senses of taste or smell. The alert 2102 may relate to some pre-defined content parameter. The alert 2102 may be a weather-related alert. The alert 2102 may signal a change in the price of a stock, security or asset. The alert 2102 may also be related to the current terrorist threat level. In an embodiment, a cellular telephone may be configured to receive an RSS feed 1802 containing stock price information. In response to a stock price falling a specified percentage during a specified time period, the device may vibrate and state, "Sell alert."

Figure 22:
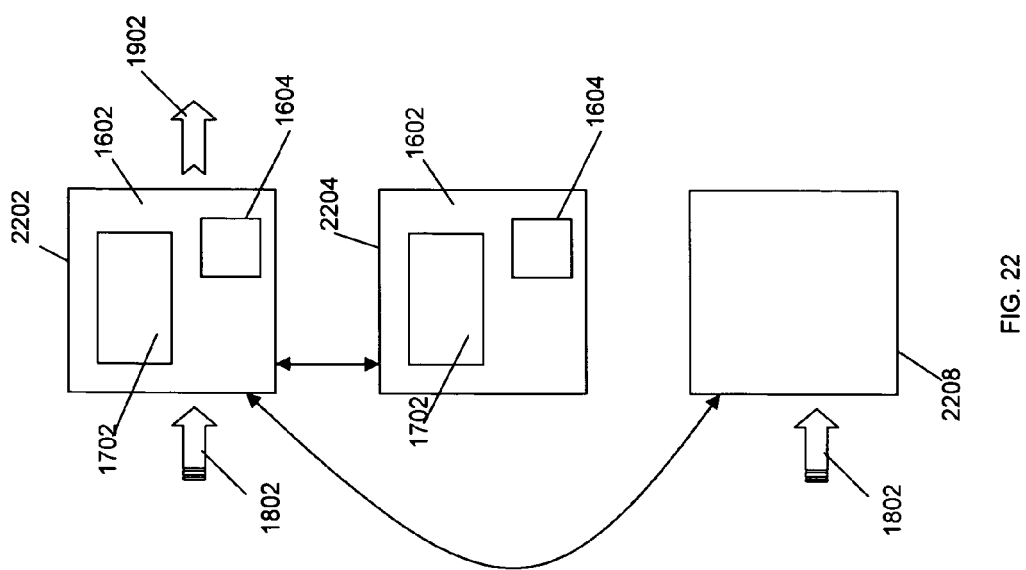
FIG. 22 depicts a syndication-enabled telecommunications device communicating with one or more other devices.

As depicted in FIG. 22, the device may communicate with one or more other devices. The communication may be in response to data contained in at least one RSS feed 1802. For example, a telecommunications device 2202, which may be Syndication-enabled, may communicate with another telecommunications device 2204 or another device 2208, either or both of which may or may not be Syndication-enabled. The other device 2208 may be a display, a personal digital assistant, a computer, a printer, a fax machine, an image center, a document center and/or a second telecommunications device. The device 2202 may communicate with one or more of the other devices 2204 and 2208 in response to data contained in the received RSS feed 1802. The device 2202 may also communicate with one or more of the other devices 2204 and 2208 for other reasons. The communications may be accomplished using one or more methods of wireless communications, Bluetooth communications, and cellular communications. The communications may be accomplished using one or more of CDMA, GMS, GPRS, EV-DO, 1X EV, 1XEV-DO, MC 3X, 1XRTT, 3G1X, 802.11a, 802.11b, 802.11g, 802.16 and cdmaOne. The communications may also be accomplished using wires.

In an embodiment, a banker may be working on an automotive deal and be required to make presentations away from her office. She may configure her cellular telephone to receive an RSS feed 1802 containing real-time stock price information. She may have user preferences defined such that any changes in automotive-related stock prices are transmitted via Bluetooth to her personal digital assistant. Her personal digital assistant may be unable to receive an RSS feed 1802 directly, but instead receives the stock price information from the cellular telephone. The stock price information may be added to a spreadsheet maintained on the personal digital assistant. The banker may use her personal digital assistant for presentations and the like. As a result, the data contained in her presentations will be updated in real-time.

Figure 23:
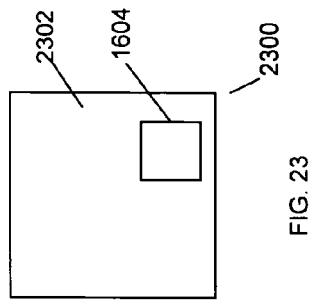
FIG. 23 depicts a syndication-enabled home appliance.
Figure 24:
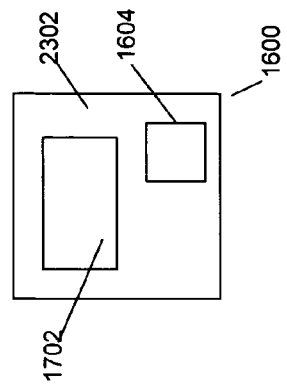
FIG. 24 depicts a syndication-enabled home appliance with a display.

FIG. 23 depicts a syndication-enabled home appliance 2300. The device 2300 may consist of a home appliance 2302 coupled with a processor 1604 adapted to manipulate RSS data. The processor 1604 may be multifunctional and manipulate other types and sources of data. The home appliance 2302 may be a microwave, an oven, a stove, a range, a refrigerator, a toaster, a toaster oven, a trash compactor, a freezer, an ice maker, a blender, a vacuum, a clock, a food processor, a coffee machine, an espresso machine, a kettle, a grill, a dishwasher, an iron, a press, a steamer, a washing machine, a dryer, an air conditioner, a heater, a furnace, a gas fireplace, an electric fireplace, a humidifier and/or a de-humidifier. Referring to FIG. 24, the device may also include a display 1702. The processor 1604 may display all or a portion of the RSS feed on the display 1702. The processor 1604 may also manipulate or process the RSS feed 1802 and display the manipulated or processed RSS feed on the display 1702. In an embodiment, if the RSS feed contains recipes, the processor 1604 may display only recipes using certain ingredients or recipes for food likely to be served in the current season. This selective display of information may be in connection with pre-defined user preferences.

Figure 25:
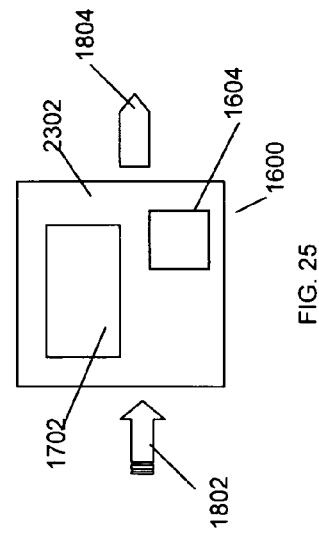
FIG. 25 depicts a syndication-enabled home appliance receiving an RSS feed.

As depicted in FIG. 25, the device 1600 may receive an RSS feed 1802. The processor 1604 may display the RSS feed on the display 1604. The processor 1604 may also convert the RSS feed 1802 into an audio signal 1804 outputted through the appliance. In an embodiment, the RSS feed 1802 may contain a recipe and the processor may convert the recipe to audio and read the recipe aloud so as to enable someone to prepare the food in accordance with the recipe. As depicted in FIG. 26, the device 1600 may transmit an RSS feed 1902. The received 1802 and transmitted 1902 RSS feeds may be RSS 0.9, RSS 0.91, RSS 0.92, RSS 0.93, RSS 0.94, RSS 1.0, RSS 2.0 or any other standard.

Referring to FIG. 27, the processor 1604 may be configured to generate an alert 2102 in response to the content of an RSS feed. The alert 2102 may be a visual alert, such as an alert outputted on the display 1604 of the device 1600. The alert 2102 may be an audio alert, such as a beep or synthesized voice. The alert 2102 may be a tactile alert, such as a vibration. The alert 2102 may also appeal to the senses of taste or smell. The alert 2102 may relate to some pre-defined content parameter. The alert 2102 may be a weather-related alert. The alert 2102 may signal a change in the price of a stock, security or asset. The alert 2102 may relate to the price or availability of a certain household good. The alert 2102 may signal a sale in connection with a certain household good. The alert 2102 may signal the availability of a new household good. The alert 2102 may also be related to the current terrorist threat level.

In embodiments, the home appliance 1602 may be a dryer. The RSS feed may contain data concerning the availability and pricing of new products. The alert 2102 may signal the availability of a new scent of dryer sheet that is currently on sale. The alert 2102 may be displayed on the display 1702 of the dryer and be accompanied by an audible tone. In another embodiment, the home appliance 1602 may be a coffee maker. Again, the RSS feed may contain data concerning the availability and pricing of new products. The alert 2102 may signal the availability of a new flavor of coffee at the local supermarket. The alert 2102 may be displayed on the display 1702 of the coffee maker.

As depicted in FIG. 28, a home appliance 2802, which may be an RSS home appliance 2300, may communicate with one or more other devices. The communication may be in response to data contained in at least one feed 202. For example, the home appliance 2802 may communicate with another home appliance 2804 or another device 2808. The other device 2808 may be a display, a personal digital assistant, a computer, a printer, a fax machine, an image center, a document center and/or a second home appliance. The device 2802 may communicate with one or more of the other devices 2804 and 2808 in response to data contained in the received RSS feed 1802. The device 2802 may also communicate with one or more of the other devices 2804 and 2808 for other reasons. The other devices may be Syndication-enabled devices or they may not be able to manipulate a feed 202. The communications may be accomplished using one or more methods and/or systems of wireless communications, Bluetooth communications, and cellular communications. The communications may be accomplished using one or more of CDMA, GMS, GPRS, EV-DO, 1X EV, 1XEV-DO, MC 3X, 1XRTT, 3G1X, 802.11a, 802.11b, 802.11g, 802.16 and cdmaOne. The communications may also be accomplished using wires.

In an embodiment, a refrigerator, which may be the home appliance 2802, may be equipped with a display 1702, such as an LCD monitor, and a processor 1604 capable of manipulating an RSS feed. The refrigerator may receive RSS feeds 1802 and display certain content from the RSS feeds on the display 1702. The processor 1604 may process the RSS feeds to determine which feeds are more suitable for other appliances in the home. The RSS feeds may then be sent to the other appliances via wires or through a wireless network. In this fashion, only one device 1600 in the home has to be capable of manipulating a feed 202 and connecting to a source 402 of feeds 202.

As depicted in FIG. 29, the home appliance 2302 may perform a-function based on the data contained in the RSS feed 1802. The home appliance 2302 may also perform a function based on the data contained in the RSS feed 1802 and pre-defined user preferences. As depicted in FIG. 30, the home appliance 2302 may stop performing a function based on the data contained in the RSS feed 1802. The home appliance 2302 may also stop performing a function based on the data contained in the RSS feed 1802 and pre-defined user preferences. As depicted in FIG. 31, the home appliance 2302 may adjust at least one setting in response to an RSS feed 1802 and, in certain cases, pre-defined user preferences. The setting may be temperature and/or cooking time. In an embodiment, the home appliance 2302 may be an oven. The oven may power on and warm to a certain temperature based on data contained in an RSS feed 1802. The data contained in the RSS feed 1802 may comprise a recipe, relate to weather conditions, or relate to traffic conditions. In another embodiment, the home appliance 2302 may be a coffee maker. The coffee maker may begin brewing coffee or delay brewing coffee in response to data contained in the RSS feed 1802. The coffee maker may also select the type of coffee to brew based on data contained in the RSS feed 1802. The data contained in the RSS feed 1802 may comprise a recipe, relate to weather conditions, or relate to traffic conditions.

FIG. 32 depicts a syndication-enabled entertainment device 3200. The device 3200 may consist of an entertainment device 3202 coupled with a processor 1604 adapted to manipulate RSS data. The processor 1604 may be multifunctional and manipulate other types and sources of data. The entertainment device 3202 may be a television, a stereo, a radio, a DVD player, a CD player, an MP3 player, iPod, a VHS player, a VCR, a cassette player, a record player, a turntable, an amplifier, a set-top box, a media center, a media player, a VCD player, a video disc player, a projector, a camera, a camcorder, a monitor, a display, an MPEG player, a digital video recorder, a TIVO, a home theater system, a robot, a video game console, an XBOX, a PlayStation, a GameCube, a remote control, a control console and/or a lighting system. Referring to FIG. 33, the device 1600 may also include a display 1702. The processor 1604 may display all or a portion of the RSS feed 1802 on the display 1702. The processor 1604 may also manipulate or process the RSS feed 1802 and display the manipulated or processed RSS feed on the display 1702. The device 1600 may also selectively display information in connection with pre-defined user preferences. In an embodiment, if the RSS feed 1802 contains television listings, the processor 1604 may display only listings for the channels to which the user subscribes. The entertainment device 3202 may play media. The entertainment device 3202 may display information. The entertainment device 3202 may communicate information.

Figure 35:
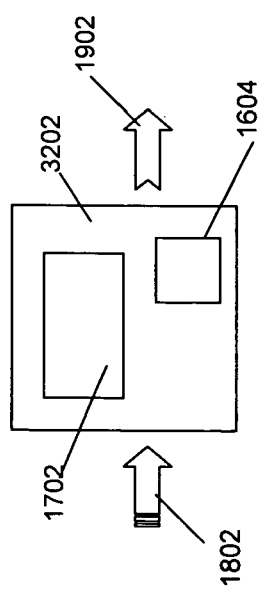
FIG. 35 depicts a syndication-enabled entertainment device transmitting an RSS feed.

As depicted in FIG. 34, the device 1600 may receive an RSS feed 1802. The processor 1604 may display the RSS feed 1802 on the display 1604. The processor 1604 may also convert the RSS feed 1802 into an audio signal 1804 outputted through the device. In an embodiment, the RSS feed 1802 may contain television listing information and the processor may convert the listing to audio and read the them aloud so as to not clutter the display with text. As depicted in FIG. 35, the device may transmit an RSS feed 1902. The received 1802 and transmitted 1902 RSS feeds may be RSS 0.9, RSS 0.91, RSS 0.92, RSS 0.93, RSS 0.94, RSS 1.0, RSS 2.0 or any other standard.

Figure 36:
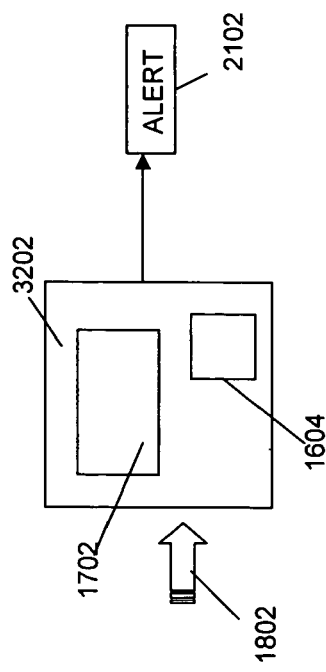
FIG. 36 depicts a syndication-enabled entertainment device generating an alert.

Referring to FIG. 36, the processor 1604 may be configured to generate an alert 2102 in response to the content of an RSS feed 1802. The alert 2102 may be a visual alert, such as an alert outputted on the display 1604 of the device. The alert 2102 may be an audio alert, such as a beep or synthesized voice. The alert 2102 may be a tactile alert, such as a vibration. The alert 2102 may also appeal to the senses of taste or smell. The alert 2102 may relate to some pre-defined content parameter. The alert 2102 may be a weather-related alert. The alert 2102 may signal a change in the price of a stock, security or asset. The alert 2102 may also be related to the current terrorist threat level. The alert 2102 may signal the availability of a new song from a certain artist. The alert 2102 may signal the availability of a new movie starring a certain actor or directed by a certain director. The alert 2102 may signal a change in time for the airing of a television program. The alert 2102 may signal breaking news.

Figure 37:
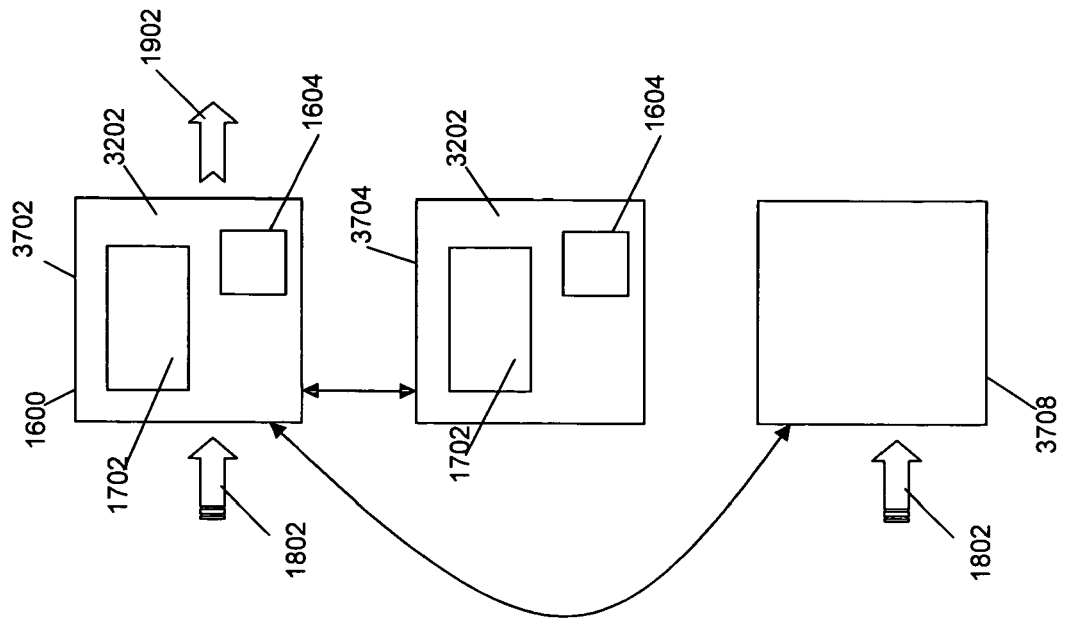
FIG. 37 depicts a syndication-enabled entertainment device communicating with one or more other devices.

As depicted in FIG. 37, the device 1600 may communicate with one or more other devices. The communication may be in response to data contained in at least one RSS feed. For example, an entertainment device 3202 may communicate with another entertainment device 1704 or another device 1708. The other device 1708 may be a display, a personal digital assistant, a computer, a printer, a fax machine, an image center, a document center and/or a second entertainment device. The device 3202 may communicate with one or more of the other devices 1704 and 1708 in response to data contained in the received RSS feed 1802. The device 3202 may also communicate with one or more of the other devices 1704 and 1708 for other reasons. The other devices may be Syndication-enabled devices or they may not be able to manipulate a feed 202. The communications may be accomplished using one or more methods of wireless communications, Bluetooth communications, and cellular communications. The communications may be accomplished using one or more of CDMA, GMS, GPRS, EV-DO, 1X EV, 1XEV-DO, MC 3X, 1XRTT, 3G1X, 802.11a, 802.11b, 802.11g, 802.16 and cdmaOne. The communications may also be accomplished using wires.

Figure 38:
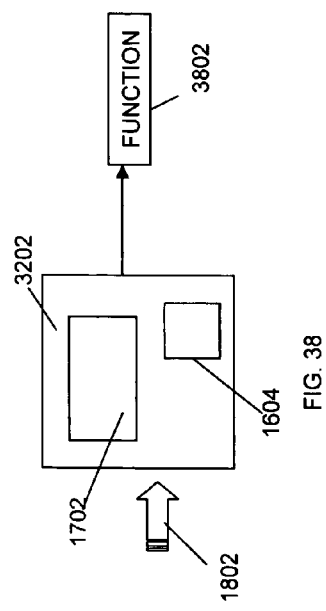
FIG. 38 depicts a syndication-enabled entertainment device performing a function based on the data contained in the RSS feed.
Figure 39:
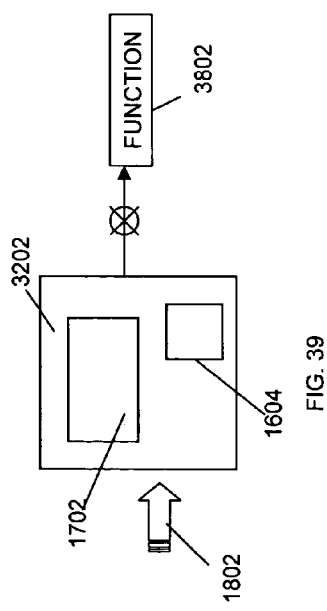
FIG. 39 depicts a syndication-enabled entertainment device ceasing performance of a function based on the data contained in the RSS feed.
Figure 40:
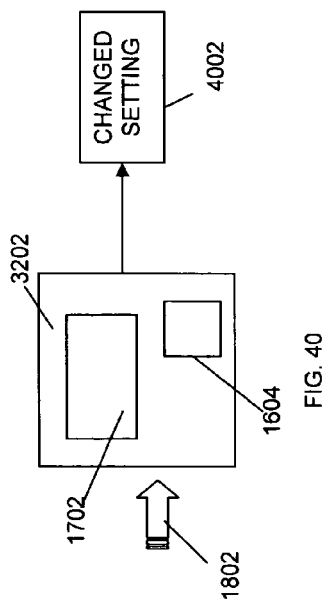
FIG. 40 depicts a syndication-enabled entertainment device adjusting at least one setting in response to an RSS feed.

As depicted in FIG. 38, the entertainment device 3202 may perform a function based on the data contained in the RSS feed 1802. The entertainment device 3202 may also perform a function based on the data contained in the RSS feed 1802 and pre-defined user preferences. As depicted in FIG. 39, the entertainment device 3202 may stop performing a function based on the data contained in the RSS feed 1802. The entertainment device 3202 may also stop performing a function based on the data contained in the RSS feed 1802 and pre-defined user preferences. As depicted in FIG. 40, the entertainment device 3202 may adjust at least one setting in response to an RSS feed 1802 and, in certain cases, pre-defined user preferences. The setting may be one or more of channel, volume, station and track. The device may become programmed as a result of the RSS feed 1802. The RSS feed 1802 may program the device.

For example, the entertainment device 3202 may be a television that turns to a certain channel in response to data contained in the RSS feed 1802. The entertainment device 3202 may be a display that displays breaking news in response to data contained in the RSS feed 1802. The display may be located in an elevator, a waiting area or a shopping cart. The display may be located in a vehicle, such as part of the dashboard or in the back seat, and the vehicle may be a taxi. The display may be mounted on a vehicle and the vehicle may be a taxi. The display may be part of a billboard or other form of advertisement. In another embodiment, the entertainment device 3202 may be a radio or stereo that plays breaking news in response to data contained in the RSS feed 1802. The entertainment device 3202 may be a radio or stereo that plays certain music in response to data contained in the RSS feed 1802. The music may be new music mentioned in the RSS feed 1802. In another embodiment, the entertainment device 3202 may be a lighting system that changes in response to data contained in the RSS feed 1802. The data may be weather related-data and the lighting system may function as a barometer. The data may relate to the current terrorist threat level and the display may function as a warning system.

Figure 41:
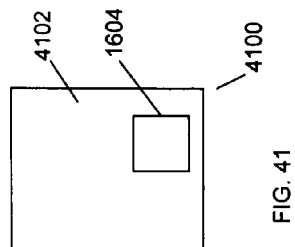
FIG. 41 depicts a syndication-enabled mobile electronic device.
Figure 42:
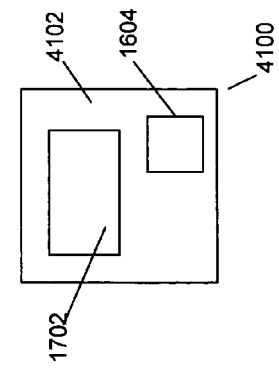
FIG. 42 depicts a syndication-enabled mobile electronic device with a display.

FIG. 41 depicts a syndication-enabled mobile electronic device 4100. The device 4100 may consist of a mobile electronic device 4102 coupled with a processor 1604 adapted to manipulate RSS data such as and without limitation the feed 202. The processor 1604 may be multifunctional and manipulate other types and sources of data. The mobile electronic device 4102 may be a television, a stereo, a radio, a DVD player, a CD player, an MP3 player, an iPod, a laptop, a camera, a camcorder, an electronic photo album, a robot, a personal digital assistant, a bicycle computer, a cellular phone, a smart phone, a car stereo, a stock ticker, a dashboard, a desktop dashboard, a palmtop computer, a remote control and/or a control console. Referring to FIG. 42, the device 4100 may also include a display 1702. The processor 1604 may display all or a portion of the RSS feed 1802 on the display 1702. The processor 1604 may also manipulate or process the RSS feed 1802 and display the manipulated or processed RSS feed on the display 1702. This selective display of information may be in connection with pre-defined user preferences. For example, if the RSS feed 1802 contains data relating to the locations of new Wi-Fi hotspots, the processor 1604 may display only hotspots in the vicinity of the device. The mobile electronic device 4102 may play media. The mobile electronic device 4102 may display information. The mobile electronic device 4102 may communicate information.

Figure 43:
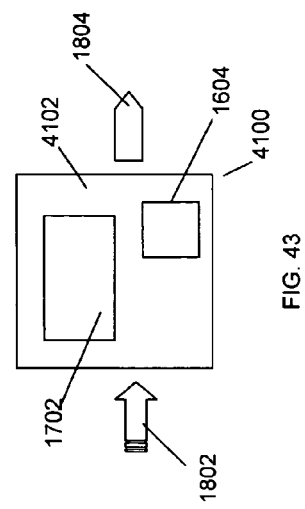
FIG. 43 depicts a syndication-enabled mobile electronic device receiving an RSS feed.
Figure 44:
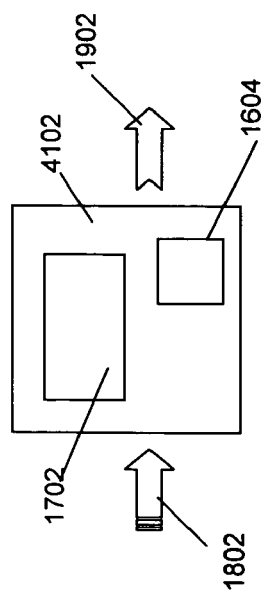
FIG. 44 depicts a syndication-enabled mobile electronic device transmitting an RSS feed.

As depicted in FIG. 43, the device 4100 may receive an RSS feed 1802. The processor 1604 may display the RSS feed on the display 1604. The processor 1604 may also convert the RSS feed into an audio signal 1804 outputted through the device. In an embodiment, the RSS feed may contain data relating to the locations of new Wi-Fi hotspots and the processor may convert the listing to audio and read them aloud. As depicted in FIG. 44, the device may transmit an RSS feed 1902. The received 1802 and transmitted 1902 RSS feeds may be RSS 0.9, RSS 0.91, RSS 0.92, RSS 0.93, RSS 0.94, RSS 1.0, RSS 2.0 or any other standard.

Figure 45:
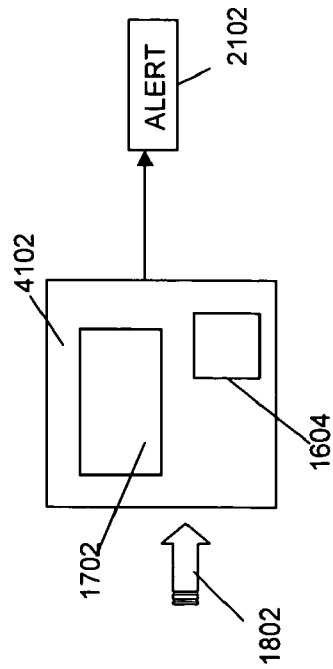
FIG. 45 depicts a syndication-enabled mobile electronic device generating an alert.

Referring to FIG. 45, the processor 1604 may be configured to generate an alert 2102 in response to the content of an RSS feed 1802. The alert 2102 may be a visual alert, such as an alert outputted on the display 1604 of the device. The alert 2102 may be an audio alert, such as a beep or synthesized voice. The alert 2102 may be a tactile alert, such as a vibration. The alert 2102 may also appeal to the senses of taste or smell. The alert 2102 may relate to some pre-defined content parameter. The alert 2102 may be a weather-related alert. The alert 2102 may signal a change in the price of a stock, security or asset. The alert 2102 may also be related to the current terrorist threat level.

Figure 46:
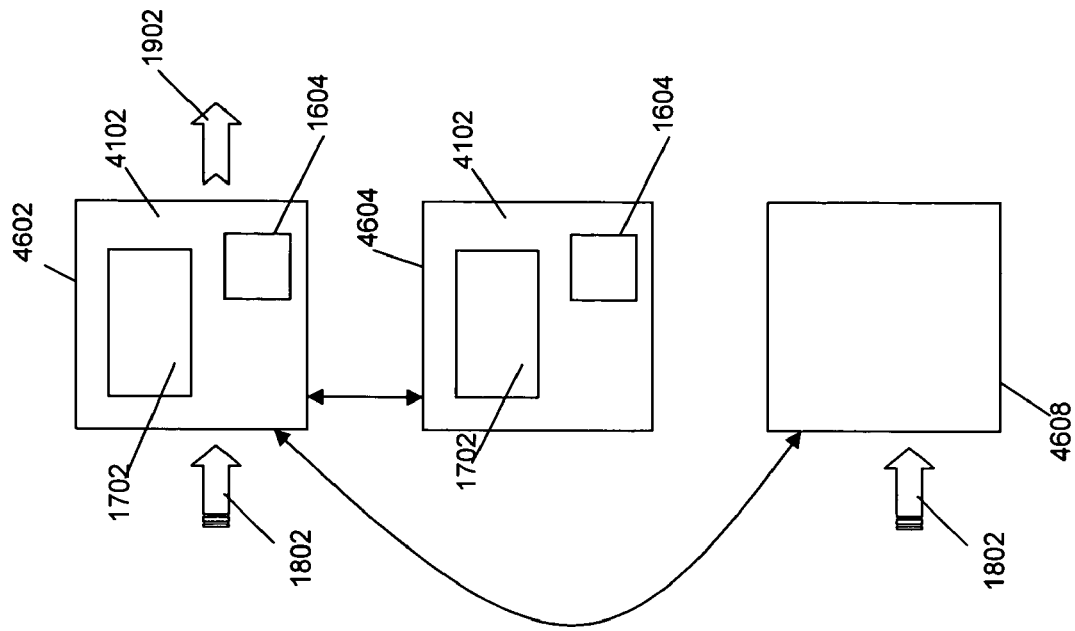
FIG. 46 depicts a syndication-enabled mobile electronic device communicating with one or more other devices.

As depicted in FIG. 46, a syndication-enabled mobile electronic device 4602 may communicate with one or more other devices. The communication may be in response to data contained in at least one RSS feed. In an embodiment, the device 4602 may communicate with another mobile electronic device 4604 or another device 4608. The other device 4608 may be a display, a personal digital assistant, a computer, a printer, a fax machine, an image center, a document center and/or a second mobile electronic device. The device 4602 may communicate with one or more of the other devices 4604 and 4608 in response to data contained in the received RSS feed 1802. The device 4602 may also communicate with one or more of the other devices 4604 and 4608 for other reasons. The other devices may be Syndication-enabled devices or they may not be able to manipulate an RSS feed 1802. The communications may be accomplished using one or more methods and/or systems of wireless communications, Bluetooth communications, and cellular communications. The communications may be accomplished using one or more of CDMA, GMS, GPRS, EV-DO, 1X EV, 1XEV-DO, MC 3X, 1XRTT, 3G1X, 802.11a, 802.11b, 802.11g, 802.16 and cdmaOne. The communications may also be accomplished using wires.

As depicted in FIG. 47, the mobile electronic device 4102 may perform a function based on the data contained in the RSS feed 1802. The mobile electronic device 4102 may also perform a function 4702 based on the data contained in the RSS feed 1802 and pre-defined user preferences. As depicted in FIG. 48, the mobile electronic device 4102 may stop performing a function based on the data contained in the RSS feed 1802. The mobile electronic device 4102 may also stop performing a function 4702 based on the data contained in the RSS feed and pre-defined user preferences. As depicted in FIG. 49, the mobile electronic device 4102 may adjust at least one setting 3402 in response to an RSS feed 1802 and, in certain cases, pre-defined user preferences. The setting 3402 may be one or more of channel, volume, station and track. The device may become programmed as a result of the RSS feed 1802. The RSS feed 1802 may program the device.

In embodiments, the mobile electronic device 4102 may be a portable television that turns to a certain channel in response to data contained in the RSS feed 1802. In another embodiment, the mobile electronic device 4102 may be a portable DVD or CD player that turns to a certain track in response to data contained in the RSS feed 1802. The mobile electronic device 4602 may be a portable MP3 player that plays a certain file in response to data contained in the RSS feed 1802. The mobile electronic device 4102 may be a display that displays breaking news in response to data contained in the RSS feed. The mobile electronic device 4102 may be a portable radio or stereo that plays breaking news in response to data contained in the RSS feed 1802. In another embodiment, the mobile electronic device 4102 may be a portable radio or stereo that plays certain music in response to data contained in the RSS feed 1802. The music may be new music mentioned in the RSS feed.

FIG. 50 depicts a syndication-enabled computing device 5000. The device 5000 may consist of a computing device 5002 coupled with a processor 1604 adapted to manipulate RSS data. The processor 1604 may be multifunctional and manipulate other types and sources of data. The computing device 5002 may be a laptop computer, a palmtop computer, a computer, a tablet computer, a printer, a computer peripheral, a fax machine, a scanner, a copier, an all-in-one solution, a storage device, a network device, a network appliance, an Internet appliance, a server, an MP3 player, an iPod, a personal digital assistant, a cellular phone and/or a smart phone. Referring to FIG. 51, the device may also include a display 1702. The processor 1604 may display all of or a portion of the RSS feed 1802 on the display 1702. The processor 1604 may also manipulate or process the RSS 1802 feed and display the manipulated or processed RSS feed on the display 1702. This selective display of information may be in connection with pre-defined user preferences. For example, if the RSS feed 1802 contains data relating to the locations of new Wi-Fi hotspots, the processor 1604 may display only hotspots in the vicinity of the device. The computing device 5002 may play media. The computing device 5002 may display information. The computing device 5002 may communicate information.

Figure 53:
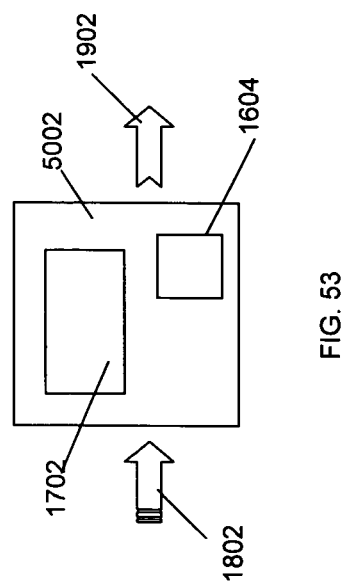
FIG. 53 depicts a syndication-enabled computing device transmitting an RSS feed.

As depicted in FIG. 52, the device 5002 may receive an RSS feed 1802. The processor 1604 may display the RSS feed 1802 on the display 1604. The processor 1604 may also convert the RSS feed 1802 into an audio signal 1804 outputted through the device. For example, the RSS feed 1802 may contain data relating to the locations of new Wi-Fi hotspots and the processor 1604 may convert the listing to audio and read them aloud. As depicted in FIG. 53, the device may transmit an RSS feed 1902. The received 1802 and transmitted 1902 RSS feeds may be RSS 0.9, RSS 0.91, RSS 0.92, RSS 0.93, RSS 0.94, RSS 1.0, RSS 2.0 or any other standard.

Figure 54:
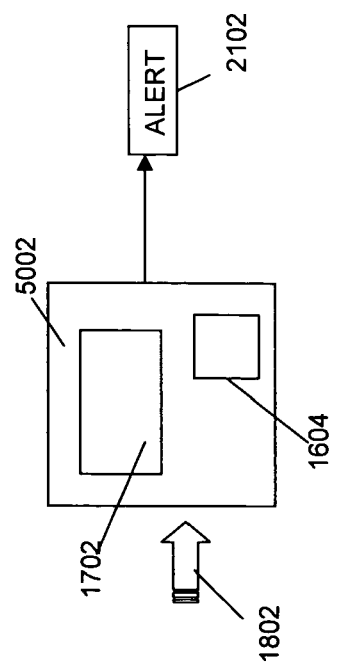
FIG. 54 depicts a syndication-enabled computing device generating an alert.

Referring to FIG. 54, the processor 1604 may be configured to generate an alert 2102 in response to the content of an RSS feed. The alert 2102 may be a visual alert, such as an alert outputted on the display 1604 of the device. The alert 2102 may be an audio alert, such as a beep or synthesized voice. The alert 2102 may be a tactile alert, such as a vibration. The alert 2102 may also appeal to the senses of taste or smell. The alert 2102 may relate to some pre-defined content parameter. The alert 2102 may be a weather-related alert. The alert 2102 may signal a change in the price of a stock, security or asset. The alert 2102 may also be related to the current terrorist threat level.

Figure 55:
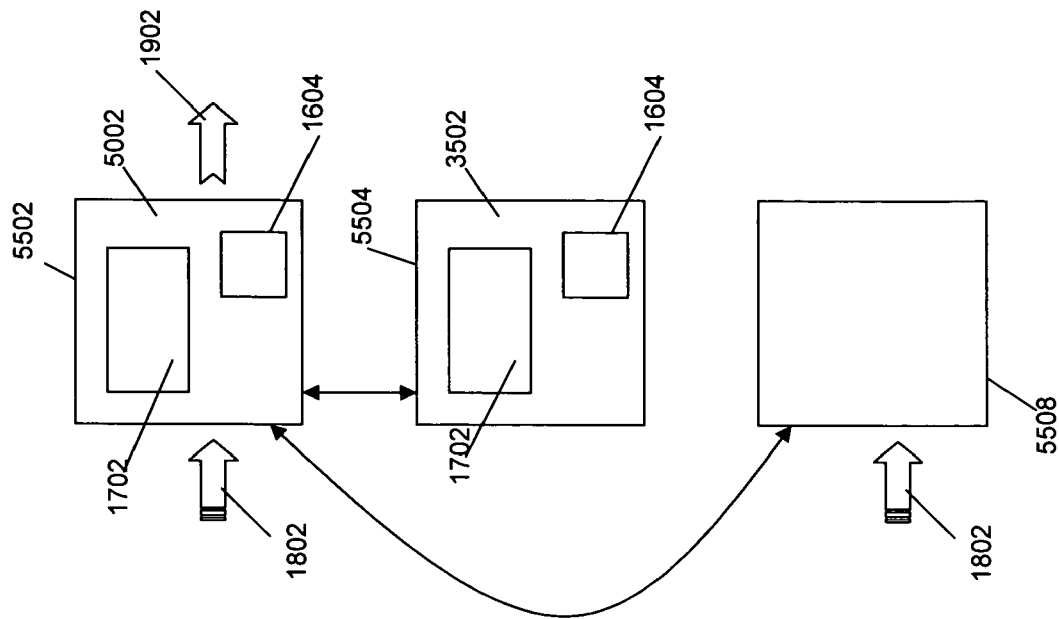
FIG. 55 depicts a syndication-enabled computing device communicating with one or more other devices.

As depicted in FIG. 55, a syndication-enabled computing device 5502 may communicate with one or more other devices. The communication may be in response to data contained in at least one RSS feed. For example, the syndication-enabled computing device 5502 may communicate with another computing device 5504 or another device 5508. The other device 5508 may be a display, a personal digital assistant, a computer, a printer, a fax machine, an image center, a document center and/or a second computing device. The device 5502 may communicate with one or more of the other devices 5504 and 5508 in response to data contained in the received RSS feed 1802. The device 5502 may also communicate with one or more of the other devices 5504 and 5508 for other reasons. The other devices may be Syndication-enabled devices or they may not be able to manipulate an RSS feed. The communications may be accomplished using one or more methods of wireless communications, Bluetooth communications, and cellular communications. The communications may be accomplished using one or more of CDMA, GMS, GPRS, EV-DO, 1X EV, 1XEV-DO, MC 3X, 1XRTT, 3G1X, 802.11a, 802.11b, 802.11g, 802.16 and cdmaOne. The communications may also be accomplished using wires.

As depicted in FIG. 56, the computing device 5002 may perform a function based on the data contained in the RSS feed 1802. The computing device 5002 may also perform a function based on the data contained in the RSS feed and pre-defined user preferences. As depicted in FIG. 57, the computing device 5002 may stop performing a function based on the data contained in the RSS feed 1802. The computing device 5002 may also stop performing a function based on the data contained in the RSS feed 1802 and pre-defined user preferences. As depicted in FIG. 58, the computing device 5002 may adjust at least one setting in response to an RSS feed 1802 and, in certain cases, pre-defined user preferences. The setting may be one or more of memory allocation, volume, backup frequency or a bandwidth-related setting. The device may become programmed as a result of the RSS feed 1802. The RSS feed 1802 may program the device.

Figure 59:
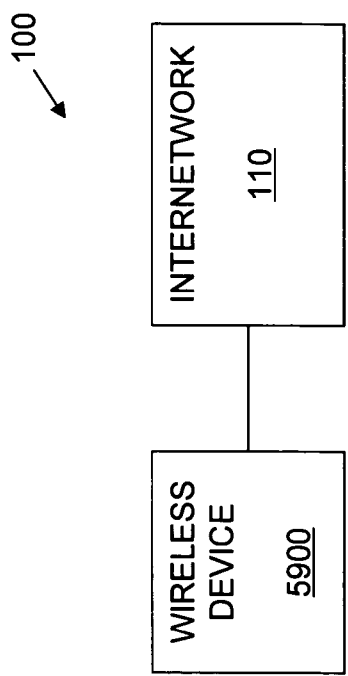
FIG. 59 depicts a syndication-enabled wireless device as part of a network.

Referring to FIG. 59, RSS content is typically developed for viewing by a conventional, full-sized computer screen; however, users increasingly view Web content, including the feeds 202, using wireless devices 5900, such as cellular phones, Personal Digital Assistants ("PDAs"), wireless electronic mail devices such as Blackberrys, and the like. In many cases content that is suitable for a normal computer screen is not appropriate for a small screen; for example, the amount of text that can be read on the screen is reduced. Accordingly, embodiments of the invention include formatting RSS feeds for wireless devices 5900. In particular, embodiments of the invention include methods and systems for providing content to a user, including taking the feed 202, determining a user interface format for a wireless device 5900, and reformatting the RSS content for the user interface for the wireless device 5900. In embodiments the content may be dynamically reformatted based on the type of wireless device 5900.

The wireless device 5900 may comprise the client 102 or the server 104 and, thus, may be a part of the network 100 and may be operatively coupled to the internetwork 110. It will be appreciated that the wireless device 5900 may provide and/or receive the data feed 202 and may function as the content source 204 and/or the aggregator 210. The wireless device 5900 may provide a service associated with the market 300. Numerous uses of the wireless device 5900 with respect to the commercial market space 302 and the consumer market space 304 will be apparent. The wireless device 5900 may function as a data source 402 and may provide one or more services associated with the syndication system 400. In some embodiments, the wireless device 5900 may provide the application 406, which may or may not relate to the service associated with the market 300. The wireless device 5900 may operate as an object within the service-oriented architecture 500. Thus, the wireless device 5900 may function as the service requester 502, the service provider 504, and/or the service broker 508. The wireless device 5900 may accept, generate, and/or process data that is embodied according to an aspect of the XML environment 600, such as and without limitation XML 608, OPML 616, HTML 624, the syndication markup language 632, and so forth. The wireless device 5900 may present a graphical user interface to a user. The graphical user interface may comprise a user interface directed at managing filters 700, a user interface directed at searching for feeds 800, and/or a user interface directed at viewing and/or modifying a user profile 900.

In embodiments, tags from a feed 202 can be used to feed a template, such as an XML-enabled template (which may be embodied as the XML 608), that further modifies the feed 202 based on the nature of a wireless device 5900. For example, the abstract of a feed 202 can be delivered in a shortened format, such as identifying and delivering the first sentence of the abstract. A feed 202 can also be broken up into sub-segments, and a user can be provided with a link within the feed for requesting additional sub-segments, or additional portions of the feed, thus permitting a user to control content delivery where, for example, the user has a bandwidth-constrained or display-constrained device. In embodiments the link may be interactive, and may be activated or manipulated by a user with a control such as a button, thumbpad, touchscreen, dial button, or stylus, of which the wireless device 5900 may be comprised.

In embodiments a feed 202 may further comprise a phone number, which may be used in a process directed at initiating a telephone call. The telephone call could be to a content source 204, such as to allow a user to hear a voice rendition of the content of the feed 202, to hear related content, such as programming related to the feed 202, to initiate a transaction, such as related to the content of the feed 202, to request a particular type of additional information, to allow the user to subscribe to the feed, or the like.

In embodiments the feed 202 may include a time-related component, such as a schedule for the delivery of additional content. In embodiments the time-related component may be fed to a calendar, task list, or related facility, thus setting an appointment related to the time-related component in a user's electronic calendar, such as on a handheld device, or on a conventional personal computer or laptop computer.

In embodiments a feed 202 may be provided with a separate layer of security that is associated with a security facility of a wireless device 5900. For example, a feed 202 may be encrypted so that it may only be read by a specific type of wireless device 5900, a specific wireless device 5900, or on a specific wireless device 5900 only after entry of a password that is issued to a known user of that wireless device 5900. In embodiments security may be associated with a location facility of the wireless device 5900 (such as GPS, cellular triangulation, or the like), such as to allow a user to access a feed 202 only if the user is physically located in a particular place. For example, a user attending a live concert or other event might be permitted to view a feed 202 about the concert, but other users might be excluded from that content, creating a secure new media channel for event attendees.

In embodiments a user interface for the wireless device 5900 device may be customized to include menus that specifically relate to RSS content, which may comprise some or all of the contents of the feed 202. For example, an interface may be provided with a separate RSS menu icon, drop down selection or the like for allowing a user to place such a device in an RSS mode. Within an RSS mode, initiated by an RSS menu option, a user may be provided with options to take actions related to RSS, such as subscribing to feeds, selecting feeds from a set of feeds, prioritizing feeds, selecting feeds as favorites, or the like. In embodiments, an RSS mode may include a menu item for each of (or a subset of) the components of the RSS schema. For example, a menu icon, drop down item, or the like may allow a user to select and view the title of a feed 202, the abstract, text, the authors, or other content. In embodiments the user interface of a wireless or handheld device may have an RSS search icon, menu or screen that returns RSS results in response to entry of a keyword. In embodiments results may be returned that include commercial and non-commercial result sets, which may be distinguished on the screen, such as by screen location, by an icon that identifies them as such, or by another indicator of the distinction, such as color, font, underlining, italics, boldface type, highlighting, or the like.

Thus, in embodiments an RSS-customized user interface for a wireless handheld device is provided.

Figure 60:
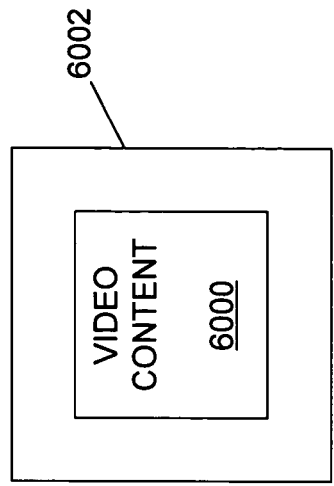
FIG. 60 depicts RSS content as video content displayed on a computer screen.

Referring to FIG. 60, in embodiments RSS content, which may comprise some or all of the contents of the feed 202, may be associated with video content 6000 on a user's computer screen 6002 (which may be a component of a personal computer, a computing-enabled television, a laptop, a handheld device, or other computer with video capability, such as enabled by a video card). Any device that comprises a component on which the video content 6000 may be displayed may be referred to as a video device. Video content 6000 may be coordinated with RSS content. For example, the RSS schema may be expanded to include a tag related to video, or video files may be attached or referenced in a feed 202, so as to link the RSS content to the video content 6000. Thus, a user may be prompted to play video 6000 by a feed 202, or the video 6000 may be launched when a user views the feed.

Figure 61:
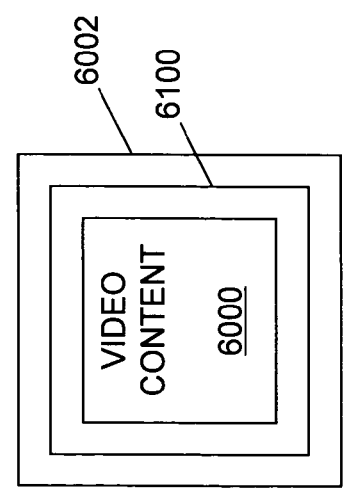
FIG. 61 depicts RSS content as video content displayed in a main window on a computer screen.

Referring to FIG. 61, in embodiments a user interface may be provided that allows a user to view video 6000 in a main video window 6100, while content for a feed 202 scrolls in a scrolling text bar below the video 6000. In embodiments RSS content may be provided in a column to the side of video 6000, either on the left or right of the main video window 6100. In embodiments the main video window 6100 may include scrolling text that is fed by a feed 202. In embodiments the main video window 6100 may include bars or menus that allow a user to select from among multiple RSS feeds that are related to the content of the video 6000.

Figure 62:
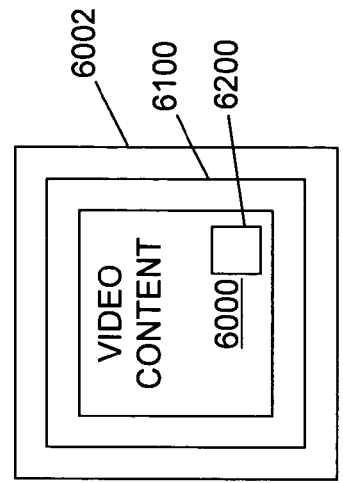
FIG. 62 depicts a search field related to video content.

Referring to FIG. 62, in embodiments a user may see multiple video sources in a user interface and select a source by clicking on a frame of the video 6000, clicking a link, or the like. The user may be prompted to select a feed 202 that is associated with the video 6000. In embodiments the user interface may include a search field 6200 that allows a user to search for content that is related to the video 6000. In embodiments the search field 6200 may be pre-populated with search terms that are related to the video 6000, such as drawn from metadata associated with the video file, drawn from speech recognition software applied to the audio component of the video feed, such as to extract keywords from the audio feed, or drawn from pattern-recognition software applied to the video 6000 itself.

Referring to FIG. 63, in embodiments a publisher application 6300 may be provided that enables the association of the feed 202 with video content 6000, such as to create linked and associated Feed-Video content 6302 for display on a video-enabled user interface, which may comprise the video window 6100. In embodiments the publisher application 6300 may include a security facility to secure content and to allow access solely to authorized users. In embodiments the publisher application 6300 may include a digital rights management application for managing rights of content holders with respect to the video content 6000, such as to allow access only to users who pay for the content. In embodiments the publisher application 6300 may include a electronic commerce component, such as to allow a user to pay for video content 6000, RSS content, or both, including to pay rights holders whose content is included with the video 6000.

Referring to FIG. 64, in embodiments an the aggregator 210 may comprise a video aggregator 6400, so that all the displays produced by the aggregator are in video format. The displays may comprise the video window 6100 and/or may be displayed on the computer screen 6002. For example, a user might open up the aggregator 210 and find newspaper headlines converted into video format and displayed on the computer screen 6002. A user interface provided by the aggregator 210 and, perhaps, displayed on the computer screen 6002 may then allow a user to execute video functions, such as pausing the video 6000, rewinding and fast-forwarding, storing the video 6000 to a disk (such as on a personal video recording device, and the like).

Referring to FIG. 65, in embodiments a remote control 6500 for a video device can include an RSS button 6502 or RSS mode, such as to control RSS content displayed on the video 6000.

Referring to FIG. 66, in embodiments an onscreen interactive menu 6600 may be displayed on the computer screen 6002 and may include an RSS capability, such as allowing a user to view a feed 202, schedule viewing of a feed 202, schedule recording of a feed 202, search for a feed 202, or the like.

Referring to FIG. 67, in embodiments a feed 202 may be provided in a video stream 6700, such as according to known video formats, such as NTSC, MPEG or other formats, such as suitable for satellite TV transmission, HDTV transmission, cable transmission, broadcast transmission, enhanced TV transmission, or the like. The stream 6700 may be provided with security features, as well as with error correction facilities in order to ensure quality of the stream.

Referring to FIG. 68, in embodiments a feed 202 may be converted into a packet-based video stream 6800, enabling secure video transmission over conventional video platforms. In embodiments the video stream 6800 may include a backchannel 6802, such as for enabling a user to interact with a feed 202, such as to select additional content, such as to select among different content in the feed 202, or otherwise to interact with the feed 202.

Figure 69:
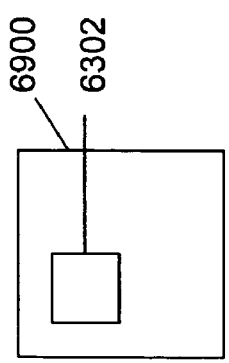
FIG. 69 depicts an enhanced video stream.

Referring to FIG. 69, in embodiments the invention may provide to the user an enhanced video stream 6900 comprising the Feed-Video content 6302. The enhanced video stream 6900, in some embodiments, may comprise or be embodied as the video stream 6700. From the perspective of the user, a presentation of the enhanced video stream 6900 may appear to be analogous to that provided by a traditional, over-the-air television broadcast. The enhanced video stream 6900 may be provided in association with features that may be analogous to those of a digital video recorder such as record, rewind, fast-forward, and other such features. Additionally or alternatively, interactive features may be provided. These interactive features may allow the user to affect the content of the enhanced video stream 6900, such as an without limitation by selecting what a character in a movie should say next; by selecting and/or interacting with an on-screen commercial; by selecting from a plurality of alternate endings for a movie; by selecting a racing car from which a NASCAR race should be displayed; by selecting a physical or virtual camera from which a sporting event should be displayed; by selecting a sequence of physical exercises to be displayed in an exercise video stream; to provide feedback to the publisher, provider, actor, director, producer, and/or sponsor of content in the video stream; and so forth. The particular Feed-Video 6302 that appears in the enhanced video feed 6900 may be manually selected by a human or may be automatically selected by a computer process. In either case, the selected video 6000 may be chosen according to a criterion that may be associated with the user of the enhanced video stream 6900; a characteristic of the user of the enhanced video stream 6900; and/or the nature or topic of the enhanced video stream 6900.

In some embodiments, the enhanced video stream 6900 may allow the user to view television-like programming (such as a video presentation of a sporting event) or concert events in real time. Many examples of television-like programming will be apparent. The presentation of the enhanced video stream 6900 may enable viewing of a live concert or sporting event without the user having to buy a ticket to or to travel to a venue at which concert or event may occur. Alternatively, the enhanced video stream 6900 may be associated with the ticket or the venue and may be enabled for viewing only if the user has purchased the ticket or has traveled to the venue.

In embodiments the enhanced video stream 6900 may also provide a forum or virtual classroom for an otherwise non-interactive classroom/collegiate experience directed at students of online colleges or Universities. The forum or virtual classroom may avail the students of the opportunity to have a live instructor available to them; by providing an access control, such as a password, that may enable only registered students to access the enhanced video stream 6900; which may comprise a live classroom video, accessible by the use of a passcode; by enabling learners who rely distinctly on visual and verbal clues, who learn by observation and engagement, and not by text learning in isolation; by offering interactive features such as a asking the instructor questions or being able to engage in meaningful dialogue; by offering a more "traditional" learning experience for a "non traditional" learner who may be disabled or ill, and unable to attend a brick and mortar school; by availing an instructor the opportunity to reach a wider audience of students by teaching via the enhanced video stream 6900, resulting in a "studentless classroom" in the traditional sense but by reaching students at a plurality of locations in real time.

In other embodiments, the invention may provide the enhanced video stream 6900 directed at capturing and storing important life events. These life events may include a sport game, a birthday party, a holiday party, a vacation, and the like. The enhanced video stream 6900 may comprise video that may be captured with a video capture device, such as and without limitation a camcorder, a phone, a "video chat" device, and the like. The enhanced video stream 6900 may be tagged, perhaps facilitating a later identification and/or organization of one or more instances of the video stream 6900. These tags with which the enhanced video stream 6900 may be tagged may be words and/or concepts that somehow reflect the content of the video stream 6900 and/or may facilitate an organization of video storage or review. A user and/or automatic computer system may identify, perhaps based upon the tag, a particular instance of the enhanced video stream 6900 within a library or archive of such streams 6900. In one embodiment, this identification may be performed using a search engine. Alternatively or additionally, the tagging may enabling the enhanced video stream 6900 to identify itself to the user and/or an automatic computer program.

Figure 70:
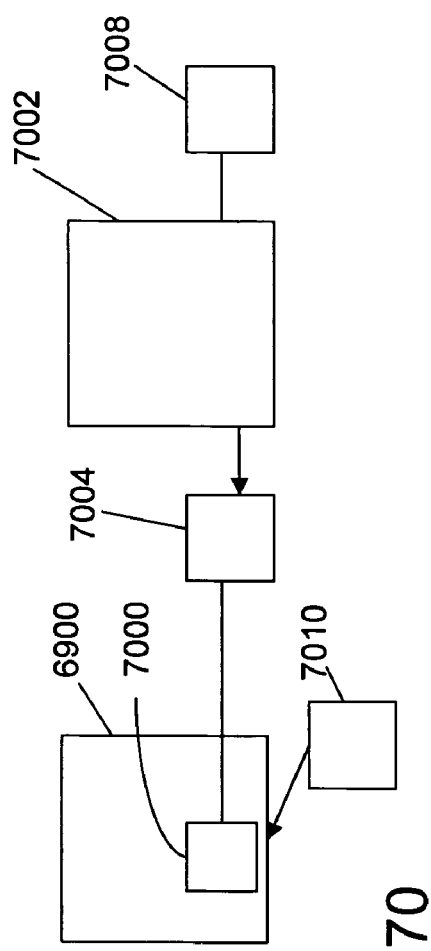
FIG. 70 depicts an embodiment of the invention providing a surveillance system.

Referring to FIG. 70, in embodiments, the invention may provide to an enhanced video stream 6900 that may comprise a surveillance video 7000, of which the video content 6000 may be comprised, directed at security and home, family, and business surveillance systems. This video 7000 may be associated with and/or captured in response to a signal 7004 generated by a sensor 7002 such as and without limitation a motion sensor, a heat sensor, a light sensor, a sound sensor, a smoke sensor, and the like. A plurality of instances of the sensor 7002 may be installed in multiple places throughout a residence or other building, and may generate the signal 7004, at least in part, by a measurement or change of an environmental condition 7008 in the residence or other building. The environmental condition 7008 may, without limitation, comprise a movement, a temperature fluctuation, a change in illumination, a sound (such as may be associated with an unauthorized entrance through glass or doorways), smoke, carbon monoxide, and the like. A video camera 7010, which may be a syndication-enabled device 1500, may capture the video 7000 in response to the signal 7004. Alternatively or additionally, the video 7000 may be captured continuously, periodically, from time to time, or not in response to the signal 7004. In any case, the video camera 7010 may generate the enhanced video stream 6900.

In one embodiment, a plurality of instances of the video camera 7010 may be placed at multiple points throughout the building so that the cameras 7010 may provide a viewing option to the user of the system. The cameras 7010 may be camouflaged, may be fixed in place, may be portable, and/or may be mounted on a robotic device able to travel to multiple points in the building. Each of the cameras 7010 may provide video an instance of the feed 202, which may comprise the enhanced video stream 6900. These instances of the feed 202 may be aggregated by the video aggregator 6400, the aggregator 210, or any other system providing one or more feeds 202 to one or more users, wherein the one or more provided feeds 202 may comprise the surveillance video 7000 and the users may without limitation comprise an owner of the building under surveillance, a fire station, an insurance company, a police station, a homeowner, and so forth.

Likewise, a robotic device comprising the video camera 7010 may provide a live enhanced video stream 6900, which may responsive personnel, such as and without limitation firefighters or law enforcement personnel, to scan a building from the outside. This scan may enable a full, moveable view of a premises with internal safety risks or criminal occurrence without compromising the safety of the responsive personnel. Alternatively or additionally, the video camera 7010 may be embedded in a safety uniform or headgear worn by the responsive personnel. In embodiments, the surveillance video 7000 provided by the video camera 7010 may be aggregated, as described hereinabove with reference to FIG. 70. In any case, the surveillance video 7000 or any replica or representation thereof may be password protected, with viewing enabled and/or reserved for particular users only.

In another embodiment, the surveillance video 7000 may be directed at of non-emergent home surveillance. In this embodiment, usage of the invention may be preventative and may provide remote users the ability to monitor an elderly relative, teenage children, or ill family member. Monitoring may include the use of fixed cameras 7010 in various points throughout the residence so that the user may gain viewable access to a household member, pet, and so forth.

Figure 71:
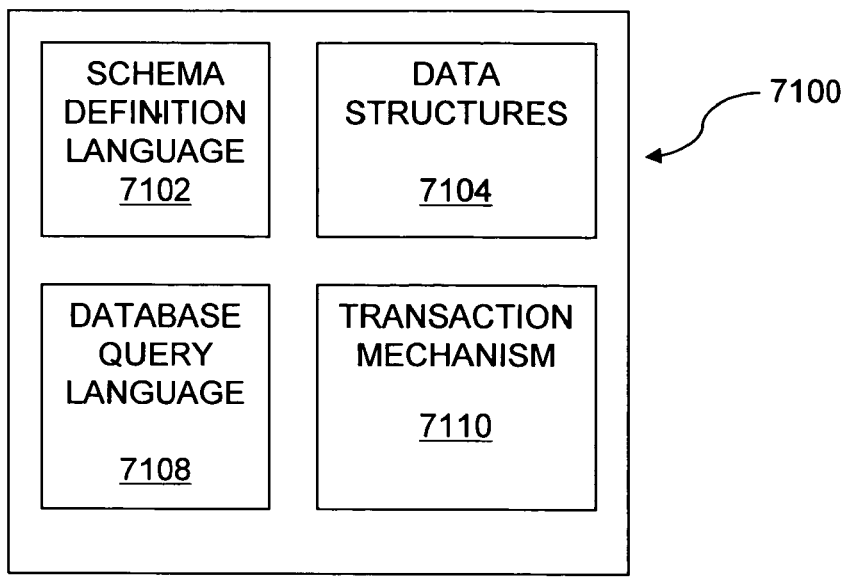
FIG. 71 shows a conceptual framework of a database management system.

FIG. 71 shows a database management system 7100 (DBMS), which may include a schema definition language 7102, data structures 7104, a database query language 7108, and a transaction mechanism 1010.7110.

The database query language 7108 allows a user, such as and without limitation a human or an automatic computer program, to interactively interrogate the database, view the contents of the database, update the contents of the database, update the logical structure or organization of the database, create logical or materialized views of the contents in the database, and so forth. The database query language 7108 may be SQL, XQuery, or any other database query language. In general, the functionality of the database query language 7108 may be employed to describe database-like operations across an OPML-based content pool—that is, a collection of distributed content that is interrelated using OPML or any similar language or syntax for defining hierarchies and relationships among documents, RSS feeds, and/or other objects.

The schema definition language 7102 may define a schema of a database hosted in the DBMS 7100. The schema definition language 7102 may without limitation be the Universal Modeling Language (UML), XML Schema, or any other language suitable for the definition of a database schema. Alternatively and commonly, the schema definition language 7102 may be implicit in the database query language 7108, such as is the case with SQL.

In a conventional data system, the data structures 7104 may be the particular logical and/or physical arrangement of the data in the database, wherein such arrangement may be particularly suited for rapid disposal onto and/or rapid retrieval from a secondary storage medium such as a platter in a hard disk drive. In an OPML 616-based content pool, the data structures 7104 may be outline-defined knowledge structures that exist independent of content, while pointing to, linking to, or otherwise identifying content within the pool, and relationships among same.

The transaction mechanism 7110 may provide for concurrent access to the data in the database. In an OPML 616-based content pool, the transaction mechanism may similarly provide for shared and/or conditional access to items of content. In one aspect, this may be deployed as a conditional access to content for purposes of privacy, security, or data integrity. In another aspect, this may be deployed as a technique for permitting individual users to both read and write to content items, or create new items, while preventing conflicts or inconsistencies. In transaction processing technologies generally, one aim of the transaction mechanism 7110 is to provide Atomicity, Consistency, Isolation, and Durability—know in the art as the "ACID properties." The ACID properties are described in ISO/IEC 10026-1:1992 Section 4, included herein by reference. For a number of reasons, many of which are well known in the art, implementing the ACID properties is not trivial. This is particularly true in systems that aim to provide high transaction throughput involving concurrent reads from and writes to the database. This is also particularly true in systems such as a distributed content pool that comprise network environments in which network connections may fail; in which data delivery may be subject to intermittent lag and/or loss due to contention for network resources; in which data transmission between remote sites may be necessarily delayed due to the a physical limit such as the speed of light; in which sites are only intermittently connected to the network environment; in which the network environment may contain partitions; and so forth.

In some applications comprising the DBMS 7100, the ACID properties may be desirable but not strictly necessary. For example, without limitation, in a contact management system, a plurality of users may contribute contact information pertaining to a plurality of people and/or businesses, which may consistent of an array of independent contact lists, or a centralized contact database. This contact information may be stored in a database and may comprise phone numbers, URLs, names, addresses, and so forth. If one of the plurality of users were to contribute a new piece of contact information, it may be acceptable for that new information to be temporarily unavailable to the other users of the contact management system. A common situation in which this occurs is the business traveler who, during a cross country flight, may take the time to enter new contact information into a copy of Microsoft Outlook running on his laptop computer. The copy of Microsoft Outlook may be part of a contact management system that comprises multiple copies of Microsoft Outlook running on multiple laptop computers, all of which are synchronized through an instance of Microsoft Exchange Server running on a server machine in a central office. Each copy of Microsoft Outlook may maintain a replica of the database. The purpose of the synchronization may be to return the database replicas to a state in which they are identical, thus making the same contact information available to all of the laptop computers. It is unreasonable to expect that the business traveler will have access to a data network during flight so that his laptop computer may be connected to the Exchange Server. It is equally unreasonable for the contact management system to force the business traveler to wait until he has access to such a data network before entering the new contact information into his laptop. Thus, his copy of Microsoft Outlook may store, in a data store local to his laptop computer, the new contact information. Later, when the laptop computer is connected to the data network, his copy of Microsoft Outlook may upload this new contact information to the Exchange Server and may download from the Exchange Server any updates or additions to the contact information that may be been entered by other users on other laptops. In this common situation, the ACID properties are clearly violated: In some embodiments, a laptop computer may be a client 102 in the network 100. Thus, an individual's contacts may be maintained as a feed 202 that is published for use within, e.g., an enterprise. The individual may post a new contact to the feed 202 locally, with updates provided as the feed 202 to clients 102 and/or servers 104 of the network 100. The same principle may be employed where multiple users can post to the same feed 202. In any case, the multitude of laptop computers, clients 102, and/or servers 104 will, at least temporarily and from time to time, have an inconsistent view of the contacts managed by the contact management system. Nevertheless, this type of contact management system may be preferable to one that attempts to enforce the ACID properties, which would at the very least require that the laptop computers be connected to a data network at the time that updates and additions are applied by the business traveler.

It should be appreciated that numerous systems of human communication and commerce rely on methods that violate the ACID properties. The system of writing checks is one. Here, the ledger balance maintained by a check writer may not always be synchronized with the account balance maintained by a bank. The system of sending electronic mail is another. Here, a sender of e-mail will often have a copy of his e-mail in his sent folder before a recipient has a copy of the e-mail in his inbox. The system of transmitting and receiving blog pings via a ping aggregator is still another. Here, a sender of a ping will often have updated information associated with the ping available in a blog before a subscriber to an aggregator's ping feed has received the ping. Many other examples should be apparent.

Figure 72:
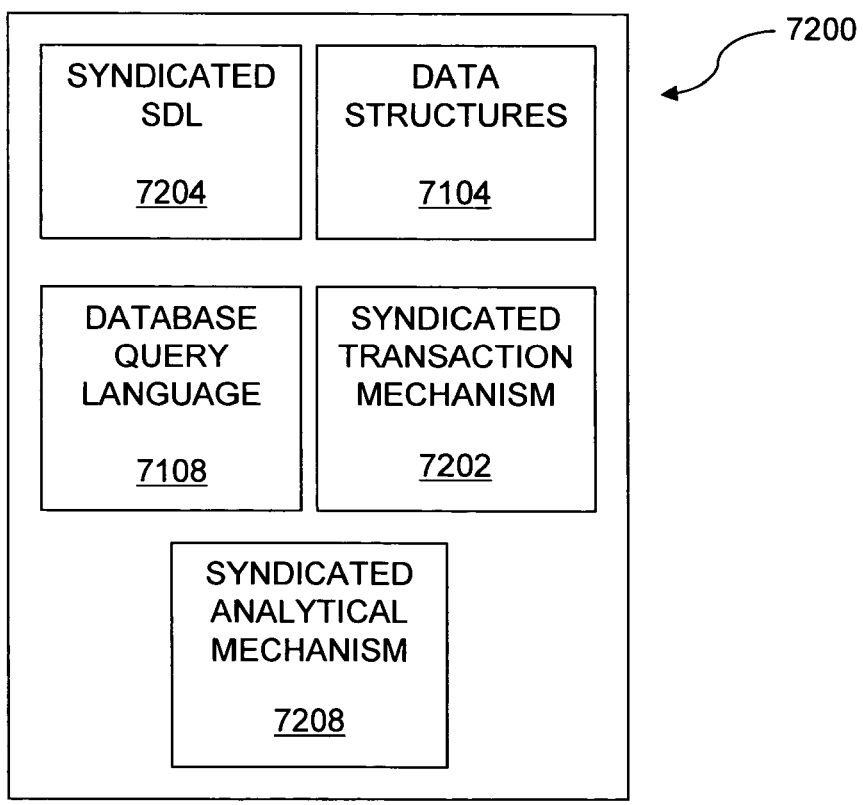
FIG. 72 shows a conceptual framework of a syndicated database management system.

Referring now to FIG. 72, a syndicated database management system 7200 (S-DBMS) may include a syndicated transaction mechanism 7202, a syndicated analytical mechanism 7208, a syndicated schema definition language 7204, the data structures 7104, and the database query language 7108. An OPML 616-based content pool may provide similar functionality with suitable adaptations. In other embodiments, a conventional database system may be configured to provide efficient access to syndicated content.

The syndicated schema definition language 7204 may define a schema of a database managed by the S-DBMS 7200. This language 7204 may enable the specification of a hierarchical data model, a network data model, a relational data model, or any other data model. The database managed by the S-DBMS 7200 may comprise the data feeds 202 and associated permalinks. The language 7204 may comprise the syndication markup language 632. The S-DBMS 7200 may support more one or more languages 7204. For example, the S-DBMS 7200 may support RSS, OPML 616, and another markup language 620. For another example, the S-DBMS

7200 may support OPML 616 in association with RSS. Among other things, the syndicated schema definition language 7204 may enable the presentation of the S-DBMS 7200 as the syndication service 414. Thus, the S-DBMS 7200 may provide the aforementioned syndication specific functions (described hereinabove with reference to FIG. 4) as they relate to the database. For example, in embodiments, the S-DBMS 7200 may act as the content source 204 and thus may publish 206 the data feed 202 to the client 102. Likewise, in embodiments, the S-DBMS 7200 may act as the client 102 and thus may access 206 or subscribe to the data feed 202 from the content source 204. Similarly, in embodiments, the S-DBMS 7200 may act as the aggregator 210 of data feeds 202 and/or may republish or replicate the data feed 202.

The syndicated transaction mechanism 7202 may provide concurrent access to the database managed by the S-DBMS 7200. This mechanism 7202 may provide the ACID properties. Additionally or alternatively, the syndicated transaction mechanism 7202 may provide the properties of availability, scalability, mobility, serializability, and convergence. These additional or alternative properties may apply to embodiments where the database is replicated. Availability may refer to the contents of the S-DBMS 7200 to be available substantially any time, anywhere. As was shown in the previous example of a contact management system, availability may require replication of the database (recall: replicas of the database needed to be maintained on the laptops and in the Exchange Server). Scalability refers to the ability of the S-DBMS 7200 to gracefully handle increasing numbers of reads and writes to and from the database. Mobility refers to the ability of a disconnected facility, such as and without limitation a laptop computer without a data network connection, to read and write to a database that is shared amongst many facilities, such as the clients 102 and the servers 104. Serializability refers to the ability to commit transactions (that is, sets of reads and writes) to the database in a serial fashion based, for example, on the original time of execution of the transactions. Convergence refers to the tendency of the replicas of the database, independently modified, to tend to converge back to being identical.

The syndicated transaction mechanism 7202 may additionally provide one or more of the functionalities known in the art as lazy-group replication, eager-group replication, lazy-master replication, eager-master replication, and two-tier replication. In general, these techniques may be adapted for maintenance of an OPML-based content pool, or a database for syndication content, or some combination of these.

Group replication refers to a replication method in which any-replica of a database may be updated. Master replication refers to a replication method in which one of the replicas of the database is designated the "primary copy" and the system managing the primary copy is designated the "master." Replication methods of this type allow updates only the primary copy. All other replicas are treated as read-only. Moreover, only the master is allowed to write to the primary copy. When any system other than the master wants to update the database, that system must issue a request to the master to do the update. Lazy replication refers to a replication method in which database updates are applied asynchronously across all replicas. Eager replication refers to a replication method in which database updates are applied all together across all replicas.

Two-tier replication may refer to a replication method in which one version of the database is designated the "master version" and all other versions of the database are designated "local versions." Updates to the database replicas that represent local versions are conducted in a lazy-group fashion. However, these updates are deemed "tentative" until they have been committed to the master version. Under certain conditions, tentative updates may be accepted or rejected as updates to the master. This method is the subject of considerable discussion hereinafter.

The syndicated transaction mechanism 7202 may additionally provide one or more additional functionalities, known collectively in the art as version control or revision control or versioning. In this case, the database may be considered a repository. Data feeds 202 may be written into and read from the database. Perhaps under the direction of the syndicated transaction mechanism 7202, the current version of the data feeds 202 may be checked out to a user who wishes to edit the data feeds 202. During a checkout process, the data feeds 202 may become locked. While locked, the user may edit a copy of the feeds 202. The user may then check the edited copy of the feeds 202 back into the database. A check-in process may simultaneously unlock the feeds 202 and commit to the database the edits of the feeds 202. The user that checked out the data feeds 202 may be said to "possess the lock" and, thus, may be the only user allowed to check-in the feeds 202. Modifications to the data feeds 202 by any user who does not possess the lock may be prohibited by the syndicated transaction mechanism 7202 while the data feeds 202 are locked. This may prevent other would-be editors from checking in potentially conflicting modifications to the data feeds 202. When the user who possesses the lock is ready to commit the changes he has made to the data feeds 202, he checks in his changes, which may create a new version or revision of the data feeds 202. This new version may replace the old version in the database. Or, it may simply supersede the old version, while the old version (or sufficient information to reconstitute the old version from the new version) may remain in the database. Alternatively, the data feeds 202 may not become locked during the checkout process. In this case it is possible for different users to apply changes to the same version of the data feeds 202. This may lead to a conflict when the changes are checked in, because it may not be obvious to the how to apply all of the different changes to the same version of the data feeds 202. In these cases, the syndicated transaction mechanism may initiate a resolution procedure, deferring the check in and perhaps informing the users of the conflicts. The syndicated transaction mechanism 7202 may maintain a change list, which may identify the changes that have been applied to the data feeds 202, perhaps in sequential order. In embodiments, this change list may be maintained in the OPML 616 format or any other format.

The syndicated transaction mechanism 7202 may additionally provide one or more additional functionalities, known collectively in the art as transaction processing or online transaction processing. These functionalities may allow a series of operations, designated as a transaction, to be applied to the database either entirely or not at all. A transaction may begin with a directive issued to the syndicated transaction mechanism 7202 to initiate a transaction. This directive may be followed by a plurality of queries or other operations to the database. At this point (that is, during the transaction), any updates applied to the database may not be visible to queries or other operations that are not part of the transaction. Finally, the transaction may end with a directive to commit the transaction to the database. The commit may succeed or fail. Upon success, the updates that were applied to the database during the transaction may become visible to queries or other operations that are not part of the transaction. Upon failure, an error code may be issued by the syndicated transaction mechanism 7202 and the updates that were applied to the database during the transaction may be discarded.

In another embodiment, version and/or revision control may be maintained at the OPML 616 level. That is, a user may, without modifying any underlying content, alter an OPML 616 structure that interrelates the content. During this editing process, the OPML 616 structure may be checked out to that user, or otherwise shielded from concurrent and inconsistent editing. In another embodiment, both the OPML 616 structure and the underlying content of all or some of an OPML 616-based content pool may be modified and manipulated by a user as an integral unit.

The syndicated transaction mechanism 7202 may also provide any other functionality or implementation of a method or algorithm associated with enabling transactions, reads, writes, updates, access control, record locking, conflict resolution, synchronization, atomicity, consistency, isolation, durability, availability, scalability, serializability, convergence, avoidance of lost updates, avoidance of system delusion, avoidance of scaleup pitfall, or any other desirable property or feature of the S-DBMS 7200 as it may be applied to managing a non-replicated database and/or a replicated database. Some desirable properties or features may be explicitly mentioned in this disclosure, while others may be apparent from this disclosure. All such functions may be deployed at the structural (e.g., OPML 616) or data (e.g., content) levels for improving access to and use of a shared, OPML 616-based content pool.

The syndicated analytical mechanism 7208 may additionally provide one or more functionalities, known collectively in the art as online analytical processing. These functionalities may include taking a snapshot of the database, organizing the snapshot of the database along dimensions, and processing analytical or other queries against the dimensional organization of the snapshot of the database. The analytical or other queries may be formed according to the syndicated schema definition language 7204 or any other suitable language. The dimensional organization of the snapshot of the database may comprise a number of hierarchical organizations of the snapshot of the database, wherein the number may have an upper bound defined only by the maximum number of possible hierarchical organizations. For example, a database comprising patient data may include ages, symptoms, and dates of symptom onset. The database may be organized hierarchically by ages, symptoms, and dates of onset. In one organization, the top level of the hierarchy may be ages, the next level may be symptoms, and the next level may be dates of onset. Many alternate organizations should be apparent. In embodiments, the hierarchical organization may be stored, presented, and/or generated in the OPML 616 format. In some embodiments, one or more of the dimensional organizations may be produced by the syndicated analytical mechanism 7208, but no processing of analytical or other queries may be provided. In other embodiments, the syndicated analytical mechanism 7208 may both produce one or more dimensional organizations and provide the processing of analytical or other queries against these organizations.

The syndicated analytical mechanism 7208 may also provide one or more functionalities aimed at receiving a dimensional organization of the database; unpacking the dimensional organization into a full or partial snapshot of the database; and updating the database according to the contents of the full or partial snapshot. In practice, the step of unpacking the organization may be unnecessary as the syndicated analytical mechanism 7208 may be capable of updating the database directly from the contents of the organization. The updating of the database by the syndicated analytical mechanism 7208 may be done in conjunction with the syndicated transaction mechanism 7202, which may provide one or more of its functionalities to the syndicated analytical mechanism 7208 during the updating. In embodiments, the receipt of the dimensional organization may be via a mechanism that reads one of the data feeds 202. Alternatively, the receipt of the dimensional organization may be via a Web page submission, a file upload, a peer-to-peer data transfer, a client-server data transfer, or any other data transfer.

Figure 73:
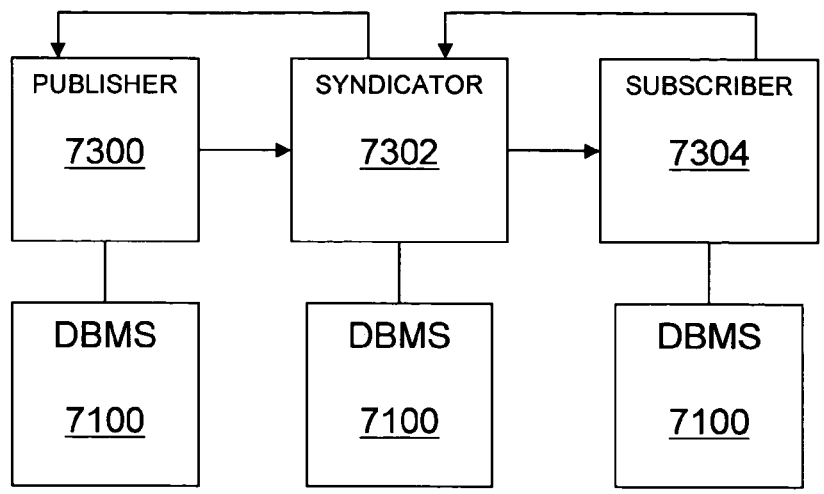
FIG. 73 shows entities of a system in which a traditional database management system is used in conjunction with a syndication system.

Referring now to FIG. 73, the syndication system 100, which may be capable of providing Internet or other network-based syndication, may include a publisher 7300, a syndicator 7302, and a subscriber 7304. The syndicator 7302 may include any suitable facility and/or facilities that may be capable of (1) receiving data associated with the data feeds 202 via a network, such as the internetwork 110 or LAN (112, 114, 116), that may be connected to the syndicator 7302; (2) providing syndicated data, which may be associated with the original data; (3) embodying an instance of the syndicated data as the data feeds 202 or as another syndication format according to the syndication markup language 632 or any other language; (4) transmitting the syndicated data as indicated by the arrow from the syndicator 7302 to the subscriber 7304; (5) receiving the subscriber's subscription request as indicated by the arrow from the subscriber 7304 to the syndicator 7302; and (6) transmitting a subscription request as indicated by the arrow from the syndicator 7302 to the publisher 7300. The publisher 7300 may further include any suitable facility and/or facilities that may be capable of receiving the syndicator's 7302 subscription request.

The syndicated data may include a real-time version of the data received by the syndicator 7302 and/or may include a time-delayed version of this data. In any case, the syndicate data may include a verbatim reproduction of the received data; a partial reproduction of the received data, which may without limitation represent a shortened, abbreviated, abridged, digested, summarized, and/or truncated version of the original data; a modified instance of the received data, such as and without limitation a translation of the original data into another language; and/or an instance of data generated by a process that may have used the original data as an input. This process may without limitation include a user behavior analyzer, a product reviewer, and/or an aggregator.

In embodiments, the publisher 7300, the syndicator 7302, and/or the subscriber 7304 may each be associated with its own instance of the DBMS 7100. For example, the syndicator 7302 may be a Web service that provides aggregation of data feeds 202. In this case the syndicator 7302 may access the data feeds 202 of the publisher 7300 and cache these data feeds 202 into its instance of the DBMS 7100. Likewise, the publisher 7300 may store its news feeds 202 in its instance of the DBMS 7100. Similarly, the subscriber 7304 may store a local copy of news feeds 202 for offline viewing or archival purposes in its instance of the DBMS 7100. Each of these instances of the DBMS 7100 is a separate installation and they are not associated with each other.

Figure 74:
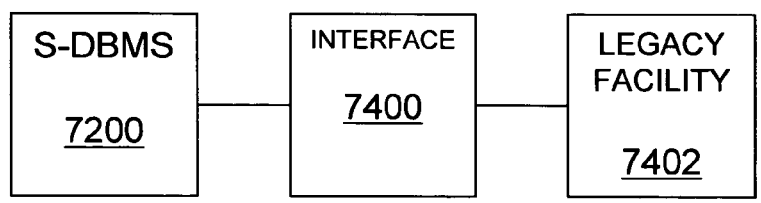
FIG. 74 shows entities of a system in which a syndicated database management system is used in a backward compatible configuration.

Referring now to FIG. 74, an embodiment of a syndication system 100 may comprise the S-DBMS 7200, an interface 7400, and a legacy facility 7402.

In embodiments, the interface 7400 may comprise an implementation of the Open Database Connectivity (ODBC) API. The legacy facility 7402 may comprise an application written to interface with the DBMS 7100 but not the S-DBMS 7200. The interface 7400, as shown, may act as middleware between the legacy facility 7402 and the S-DBMS 7200. The use of ODBC as a bridge or interface between an application and a database is well known in the art.

In other embodiments, the interface 7400 may comprise an implementation of SMTP, IMAP, POP, or any other protocol associated with e-mail. The legacy facility 7402 in this case may comprise a legacy e-mail client application written to interface with an SMTP, IMAP, POP, or other legacy e-mail server. Numerous legacy e-mail client applications, such as Thunderbird, Outlook Express, and Lotus Notes are known in the art. When the legacy facility 7402 sends an e-mail, reads an e-mail, receives an e-mail, deletes an e-mail, or performs another action associated with e-mail, a message or series of messages may be passed between the legacy e-mail client and the interface 7400. The interface 7400 may convert these messages into the database query language 7108 of the S-DBMS 7200. These converted messages may be embodied according to the syndicated schema definition language 7204 or any other syndication markup language 632, other markup language 620, or other format 630.

For example, without limitation, in the case where the legacy facility 7402 is a legacy e-mail client, the interface 7400 may convert the message or series of messages from the legacy facility 7402 and publish it in an RSS feed. The S-DBMS 7200 may subscribe to this feed and may appropriately react to changes in the feed. When the legacy facility 7402 transmits an outgoing e-mail via SMTP to the interface 7400, that outgoing e-mail may be associated with one or more intended recipients as specified in the "to:", "cc:", and/or "bcc:" lines of the e-mail. This e-mail may be received by the interface 7400 and then published by the interface in a "sent mail" RSS feed 202. The S-DBMS 7200 may have subscribed to the "sent mail" RSS feed 202 of the interface 7400 and may recognize a published update to this feed 202. In response to this update, the S-DBMS 7200 may retrieve 208 the new item in the feed 202 and may update a "received mail" RSS feed 202 associated with the one or more intended recipients of the e-mail. Another interface 7400 may be associated with a legacy facility 7402 that may be associated with the intended recipient of the e-mail. This interface 7400 may have subscribed to the "received mail" RSS feed 202 of the S-DBMS 7200. In response to the update of this feed, the interface 7400 may retrieve 208 the new item in the feed 202. This new item may comprise the outgoing e-mail that is now, from the perspective of the intended recipient, incoming e-mail. The interface 7400 may convert the e-mail into a message or series of messages that are compatible with POP, IMAP, or any other application layer Internet protocol used by the legacy facility 7402 for accessing e-mail.

Figure 75:
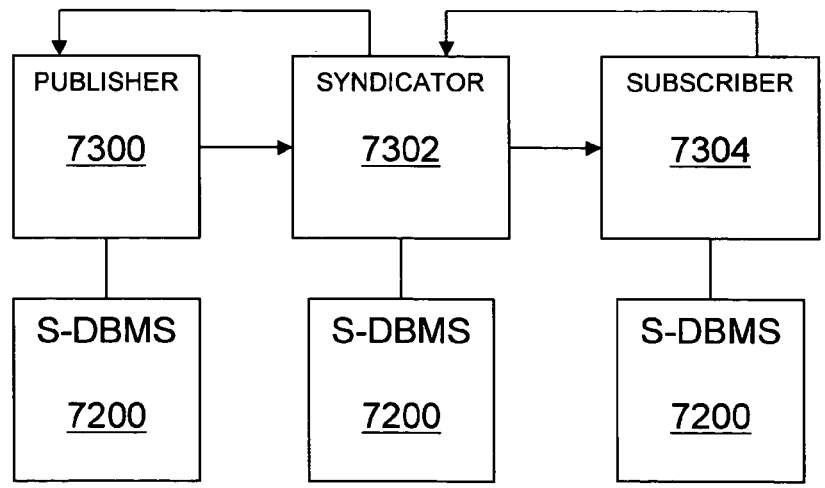
FIG. 75 depicts entities of a syndication system in which syndicated database management systems are used.

Referring now to FIG. 75, an embodiment of the syndication system 100 may comprise one or more instances of the S-DBMS 7200, a publisher 7300, a syndicator 7302, and a subscriber 7304. The publisher 7300 may comprise one of the clients 102 or one of the servers 104, and may provide data to the syndicator 7302, as indicated by the arrow from the publisher 7300 to the syndicator 7302. This data may, without limitation, be expressed according to the syndication markup language 632. The syndicator 7302 may pull, push, gather, summarize, index, search, filter, cluster, archive, compress, decompress, or otherwise access and/or process this data. The data may be embodied as one or more of the data feeds 202.

The arrow from the syndicator 7302 to the publisher 7300 may indicate the access 206 of the syndicated data feed 202. The syndicator 7302 may comprise one of the clients 102 or one of the servers 104. In some embodiments, the syndicator 7302 may function as the aggregator 210 or may provide any of the syndication services 414. The data feeds 202 may be provided to the subscriber 7304 in the format that the syndicator 7302 received them. Alternatively, the data feeds 202 may be provided to the subscriber 7304 in an alternate syndication format. For example and without limitation, the data feeds may be received by the syndicator 7302 in the RSS format and may be provided to the subscriber 7304 in the OPML 616 format.

The subscriber 7304 may be the one of the clients 102 or one of the servers 104. The subscriber 7304 may subscribe to one or more of the data feeds 202. The arrow from the subscriber 7304 to the syndicator 7302 indicates this. The subscriber 7304 may receive one or more of the data feeds 202 provided by the syndicator 7302, as indicated by the arrow from the syndicator 7302 to the subscriber 7304.

Each of the publisher 7300, the syndicator 7302, and the subscriber 7304 may be associated with an instance of the S-DBMS 7200, as shown. Each of these S-DBMS 7200 instances may manage a database that is unique. Alternatively, the database managed by the instance of the S-DBMS 7200 may in whole or in part be a replica of a database managed by another instance of the S-DBMS 7200. In any case, the databases may be associated with one or more of the other databases, such as might be the case with a replicated or distributed database. This association is of particular relevance to the present invention and may lead to the conceptual framework described hereinafter with reference to FIG. 77. Alternatively, each of these databases may not be associated with any of the other databases. In any case, the databases may contain the data feeds 202, metadata associated with the data feeds 202, and other data. In other aspects, the S-DBMS may itself be implemented as an OPML based content pool structure cooperating with publish/subscribe elements of a syndication system.

Figure 76:
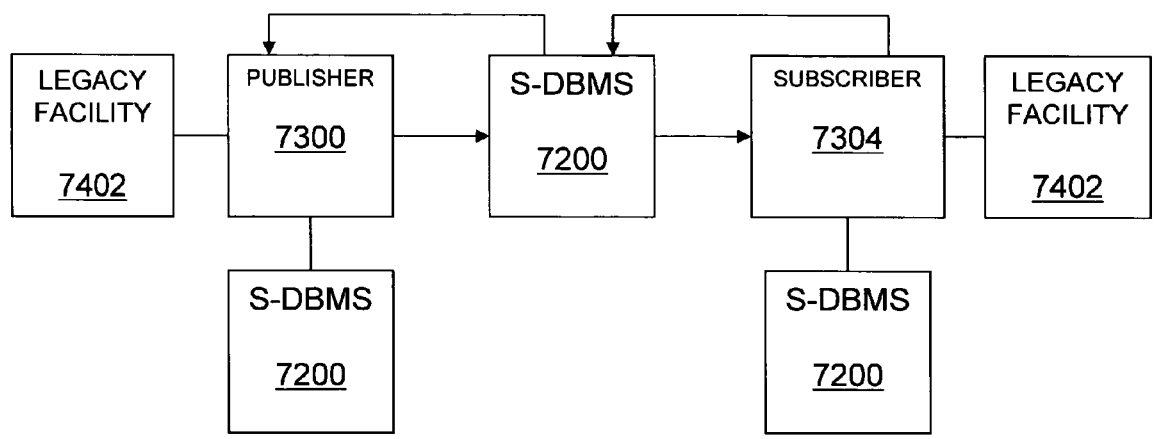
FIG. 76 shows entities of a syndication system that provides backward compatibility and in which syndicated database management systems are used.

Referring now to FIG. 76, instances of the legacy facility 7402 may be associated with the publisher 7300 and/or the subscriber 7304. In this configuration, the instances of the legacy facility 7402 may participate as part of an embodiment of the syndication system 100. The publisher 7300 and/or the subscriber 7304 may function as the interface 7400 with respect to the instances of the legacy facility 7402.

Figure 10:
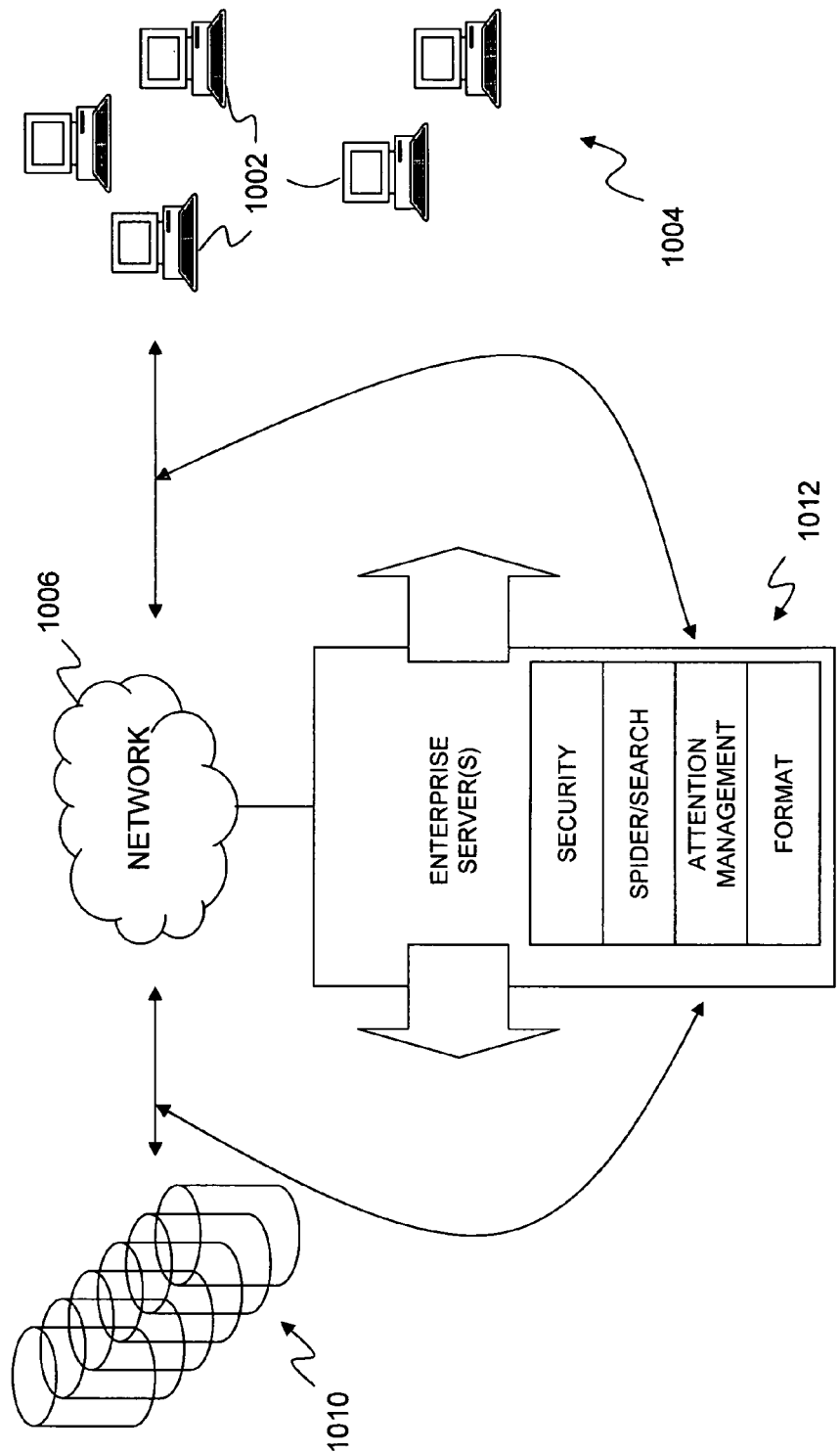
FIG. 10 shows a data pool environment.

The centrally located S-DBMS 7200 may function as the syndicator 7302 described hereinabove with references to FIG. 10 and FIG. 11. In this arrangement, data management and syndication are unified, in contrast to the current state of the art in which syndication is a service built on top of the legacy DBMS 7100.

Figure 77:
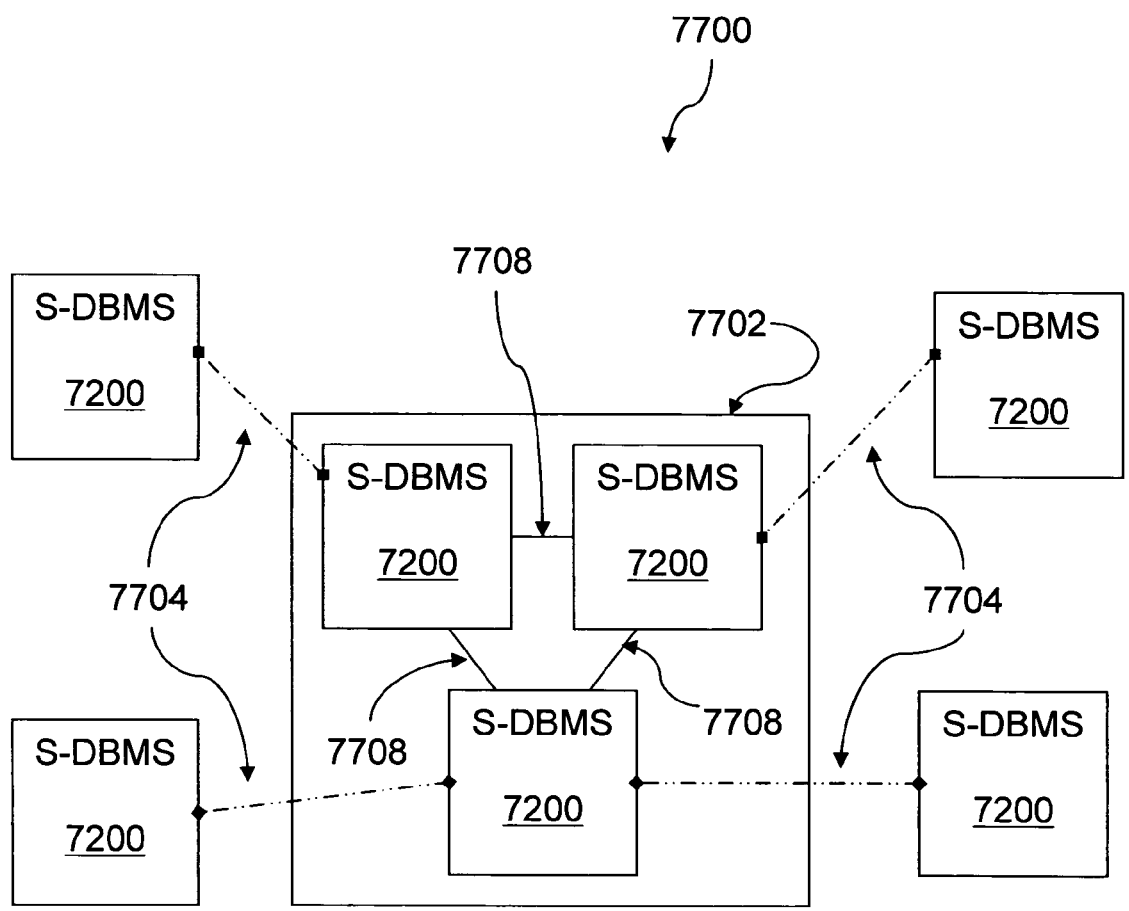
FIG. 77 shows a conceptual framework of a distributed, syndicated database management system.

Referring now to FIG. 77, the conceptual framework for a distributed, syndicated database management system 7700 (DS-DMBS) is depicted. The instances of the S-DBMS 7200 within the DS-DMBS 7700 may be operatively coupled via intermittent connections 7704 or via continuous connections 7708. In embodiments, these connections may comprise the internetwork 110, the hub or LAN server 113, the gateway 116, a USB interface, an IrDA interface, or any other facility enabling transmission the data feeds 202. The instances of the S-DMBS 7200 that are connected to each other via the continuous connections 7708 may be referred to as the "base nodes." As depicted, a base 7702 may comprise these base nodes. In embodiments, the base 7702 may comprise zero or more base nodes. The instances of the S-DBMS 7200 that are connected to the base nodes via the intermittent connections 7704 may be referred to as "mobile nodes." In embodiments, the DS-DMBS 7700 may comprise zero or more mobile nodes. In any case, each node in the DS-DMBS 7700 may provide a view of some or all of contents of the one or more databases associated with one or more of the S-DBMS 7200 nodes. This view may be provided as one or more of the data feeds 202 provided by the S-DBMS 7200 nodes described in FIGS. 74, 75, and 76. The connections 7704, 7708 allow for the syndication of content between the various nodes of the DS-DBMS 7700. The connections 7704, 7708 also allow for the transmission of control signals that may be dictated by the particular implementation of the syndicated transaction mechanism 7202.

Based upon this disclosure, it should now be clear that the aggregator 210, as described hereinbefore with reference to FIG. 2, could be implemented as the S-DBMS 7200 or as the DS-DBMS 7700. In an exemplary embodiment, the aggregator 210 could comprise one or more of the S-DBMS 7200 nodes of the DS-DBMS 7700. In this case, the content sources 204 and the clients 102 may also comprise S-DBMS 7200 nodes and may, together with S-DBMS 7200 node or nodes of the aggregator 210, constitute the DS-DBMS 7700. In this embodiment, the syndicated transaction mechanism 7202 may implement two-tier replication and the syndicated schema definition language may be RSS used in association with OPML 616.

The DS-DBMS 7700, whether a conventional database system or an OPML-based structure, may provide the logical features that connect all participants (7400, 7402, 7300, 7302, and 7304) in the syndication system 100 to a universal syndication database or "database of all syndication databases." Thus, the participants may have the illusion of accessing a single, shared database to which syndicated data may be published, from which syndicated data may be subscribed, and in which syndicated data may be modified by a plurality of participants, and so forth. As with a conventional DBMS 7100, users of the DS-DBMS 7700 may create different views of the data in the database.

In general, a collection of databases and/or database management systems, including various combinations of the databases and database management systems described above, or other combinations, is referred to herein as a global data facility. As will be appreciated from the foregoing, the global data facility may provide a user or programming interface that permits interaction with the global data facility as though the global data facility were a single database using, for example, a structured query language. The global data facility may include any number of data sources or databases, and may include any number of database management systems. Further, relational data across the global data facility may be created and manipulated using any number of techniques. In one embodiment, the relational data is maintained is maintained in one or more OPML files.

Figure 78:
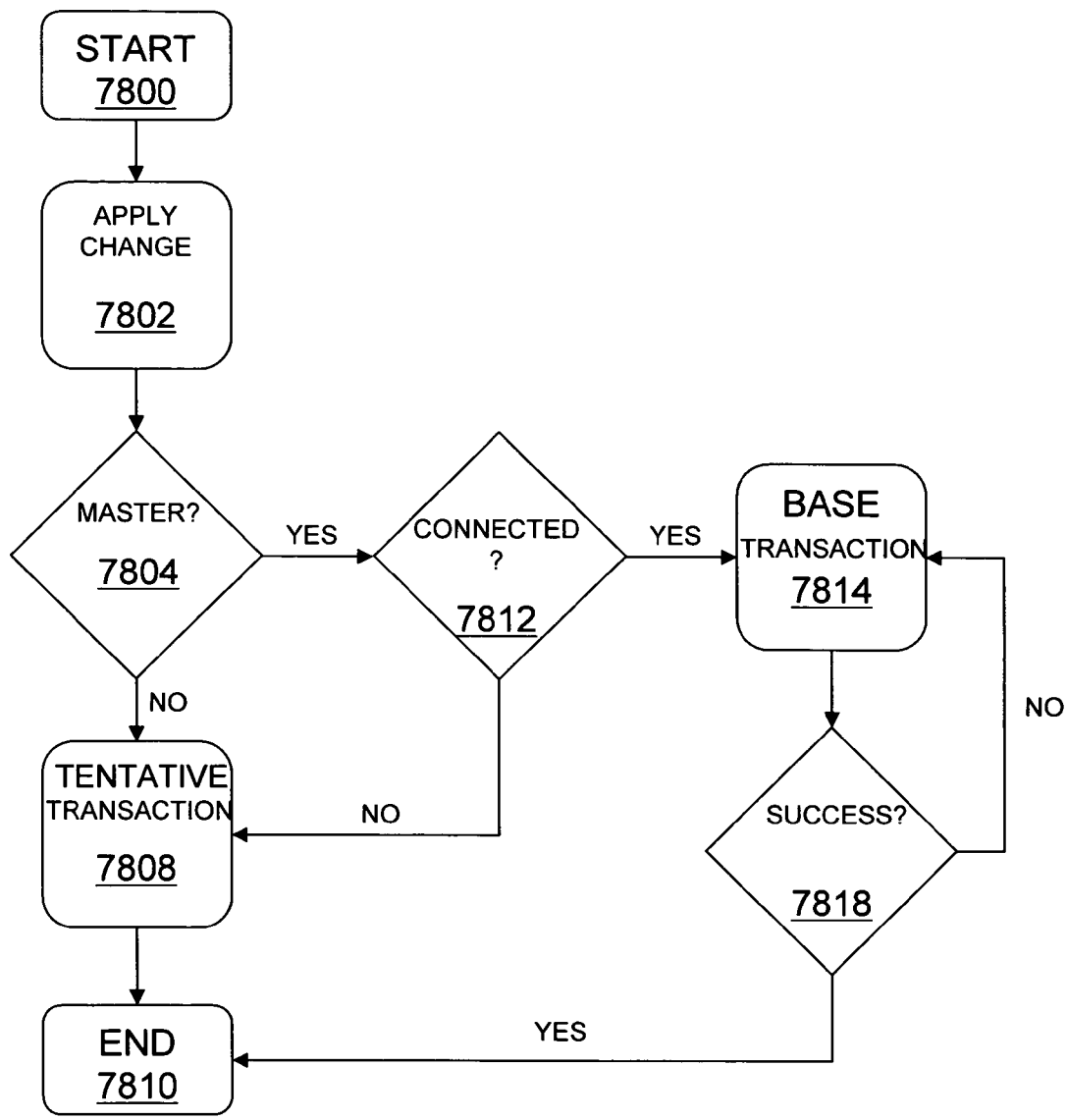
FIG. 78 is a logical flow diagram of a method directed at two-tier replication.

Referring now to FIG. 78, the logical flow of a two-tier replication process directed at applying a change to the database is shown. Beginning at the START 7800 logical block, logical flow proceeds to the APPLY CHANGE 7802 logical block, where a change is applied to the local version of the database. Then, a test is conducted at logical block 7804 to determine if the S-DBMS 7200 node that received the change is the master of the portion of the database that has been changed. If so, logical flow proceeds to the test at logical block 7812 where the S-DBMS 7200 determines if it is connected to the base nodes. If so, a base transaction is conducted at logical block 7814, followed by a test at logical block 7818 to see if the base transaction succeeded. If it succeeded, then the change has been committed to the master version of the database and the change process ends at END 7810. However, if the base transaction fails, then the base transaction is retried, as shown by a return arrow from logical block 7818 to logical block 7814. If the S-DBMS 7200 is not connected to the base, then instead of attempting a base transaction, the process flows from logical block 7812 to logical block TENTATIVE TRANSACTION 7808, where the change to the local version of the database is recorded as a tentative transaction. From there, logical flow proceeds to logical block 7810, where the process ends.

Figure 79:
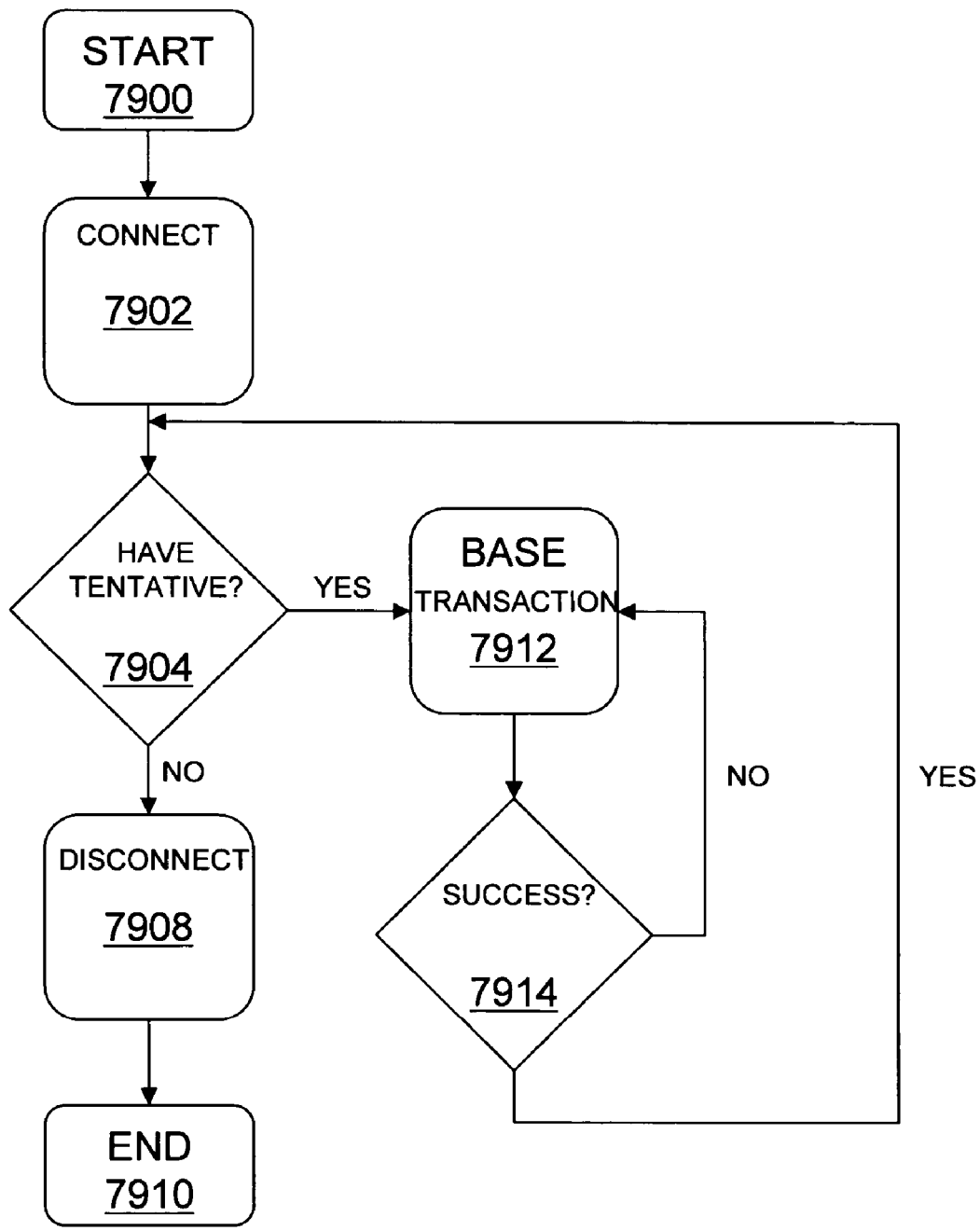
FIG. 79 is a logical flow diagram of another method directed at two-tier replication.

Referring now to FIG. 79, the logical flow of a two-tier replication process directed at applying one or more tentative transactions to the base nodes is shown. Beginning at the START 7900 logical block, logical flow proceeds to the CONNECT 7902 logical block, where the mobile node connects to one of the base nodes. Next, a test is conducted at logical block 7904 to determine if the mobile node has any tentative transactions recorded in its local database that have not been processed as a base transaction. If so, a base transaction is conducted at logical block 7912. After that, a test is conducted at logical block 7914 to determine if the base transaction succeeded. If it didn't, logical flow returns to logical block BASE TRANSACTION 7912, where the base transaction is retried. Otherwise, the base transaction succeeded and logical flow returns to the test at logical block 7904. When there are no more tentative transactions that need to be processed as base transactions, the test at logical block 7904 has a negative result and processing flow continues to logical block DISCONNECT 7908, where the mobile node disconnects from the base node. Finally, processing flow continues to logical block 7910 where the process ends.

Figure 80:
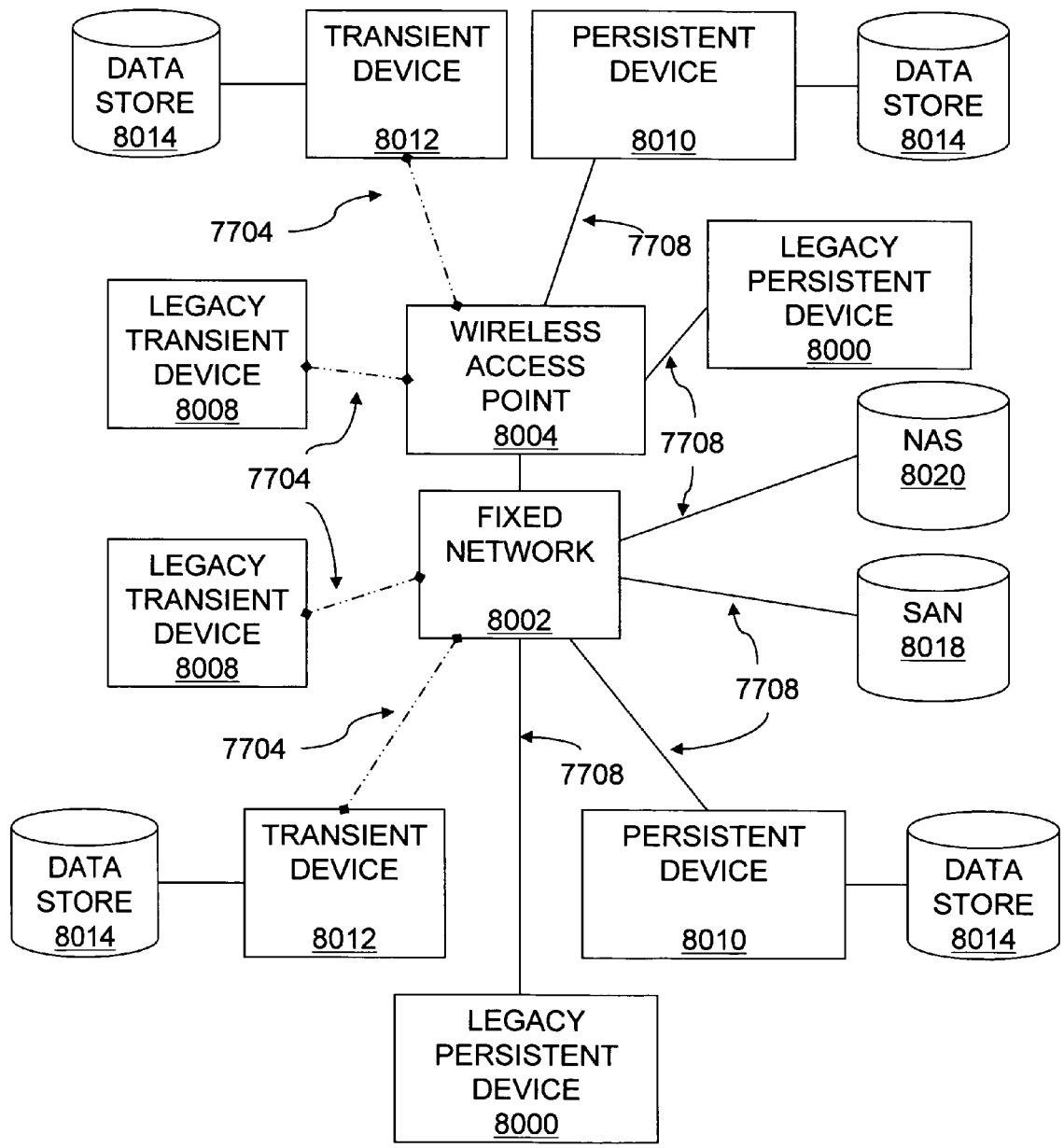
FIG. 80 depicts an implementation of a syndication system that provides backward compatibility and in which distributed and/or non-distributed syndicated database management systems may be used.

Referring now to FIG. 80, here is depicted an implementation of a syndication system that provides backward compatibility to legacy devices DS-DBMS 7700 and/or S-DBMS 7200 implementations may be used. A fixed network 8002, which may comprise the Internetwork 110, is operatively coupled to a wireless access point 8004. The wireless access point 8004 may be an 802.11 access point, a cellular phone tower, a satellite, or any other device facilitating wireless data transmission between a device and the fixed network 8002.

Transient devices 8012 and legacy transient devices 8008, which may be clients 102 and/or servers 104, may be operatively coupled to the wireless access point 8004 or the fixed network 8002. This operative coupling may be enabled by any of a variety of wireless (in the case of the wireless access point 8004) or tethered (in the case of the fixed network 8002) transmission media, including without limitation optical, aural, radio frequency, quantum, or any other wireless or tethered transmission media. The intermittent connections 7704 and/or the continuous connections 7708 may comprise this operative coupling. The transient devices 8012 may be comprised of the publisher 7300, the syndicator 7302, the subscriber 7304, and/or the S-DBMS 7200. The publisher 7300, the syndicator 7302, and the subscriber 7304 may comprise an instance of the S-DBMS 7200. The legacy transient devices 8008 may be comprised of the legacy facility 7402. The transient devices 8012 and the legacy transient devices 8008 may be associated with instances of a data store 8014, in which the database may be stored. The data store 8014 may comprise the memory and/or the mass storage devices that may be associated with the clients 102 and/or the servers 104.

Persistent devices 8010 and legacy persistent devices 8000, which may be the clients 102 and/or servers 104, may be operatively coupled to the wireless access point 8004 or the fixed network 8002. This operative coupling may be enabled by any of a variety of wireless (in the case of the wireless access point 8004) or tethered (in the case of the fixed network 8002) transmission media, including without limitation optical, aural, radio frequency, quantum, or any other wireless or tethered transmission media. The intermittent connections 7704 and/or the continuous connections 7708 may comprise this operative coupling. The persistent devices 8010 may be comprised of the publisher 7300, the syndicator 7302, the subscriber 7304, and/or the S-DBMS 7200. The legacy persistent devices 8000 may be comprised of the legacy facility 7402. The persistent devices 8010 and the legacy persistent devices 8000 may be associated with instances of the data store 8014.

A network-attached storage (NAS) 8020 may be operatively coupled to the fixed network 8002 via the persistent connection 7708. The NAS 8020 may comprise an instance of the S-DBMS 7200. More generally, the NAS 8020 may incorporate any of the syndication functionality described above, such as the services described in reference to FIG. 4, which may be deployed as database management functions within the S-DBMS 7200 or as other services. All such functionality, functions, and services, may be, for example, incorporated into the NAS 802 as one or more syndication-capable semiconductor devices 1300. In one embodiment a pool such as one of the pools 1010 described above with reference to FIG. 10 may be realized as a NAS 8020 with an integrated syndication-capable semiconductor device that provides syndication functions in association with the NAS 8020 and data stored thereon.

A storage-area network (SAN) 8018 may be operatively coupled to the fixed network 8002 via the persistent connection 7708. The SAN 8018 may comprise an instance of the S-DBMS 7200.

As shown, the legacy devices 8000, 8008 may not be directly associated with instances of the data store 8014. Instead, these devices 8000, 8008 may rely on one of the non-legacy devices 8012, 8010, which may be associated with an instance of the data store 8014, to perform as the interface 7400 in providing access to the S-DBMS 7200 that may be comprise by the data store 8014.

Any instances of the S-DBMS 7200 may be associated to form the DS-DBMS 7700. For example, in an enterprise, the DS-DBMS 7700 may be used to track working versions of documents such as e-mail, calendars, contacts, to-do items, organizational charts, presentations, Web pages, data feeds 202, outlines, spreadsheets, word processing files, diagrams, software code, access control lists, financial data, images, videos, audio files, URLs, and so forth. The DS-DBMS 7700 may make provide these documents in a data feed 202 or outline such as in the OPML 616 format.

Referring now to FIG. 81, a sample document of the OPML 616 format is shown. In this specification, numerous elements are shown, four of which are identified as opml, head, body, and outline. The opml element may be the root element of a file in the OPML 616 format. In embodiments, such as the present one, it may contain a version attribute, a head element, and a body element. The head element, in embodiments, may contain metadata. This metadata may include the optional elements shown, which are identified as title, dateCreated, DateModified, and ownerName. Other optional elements, may include ownerEmail, expansionState, vertScrollState, windowTop, windowLeft, windowBottom, and windowRight. The contents of these optional elements many be plain text. The contents of the dateCreated and dateModified optional elements may conform to the date-time format specified in RFC 822 or RFC 2822. The contents of the expansionState optional element may contain a comma-separated list of numbers, wherein the numbers may be associated with the head elements in an opml file that, when rendered, may be displayed in an expanded form. The body element may contain one or more outline elements. The outline element may contain zero or more arbitrary attributes and may contain any number of nested outline elements. While the foregoing discussion of the OPML 616 format may refer to version 1.0 of the OPML 616 format, it should be appreciated that as of this writing further developments to the OPML 616 format have been publicly anticipated. Incorporation of these and any other developments to the OPML 616 format is within the scope of the present invention.

Embodiments of the syndication system 100 that are associated with a database management system (such as the DBMS 7100, the S-DBMS 7200, or DS-DBMS 7700) may provide a materialized view of the source database managed by the database management system. The materialized view may comprise records, fields, entries, relations, hierarchies, or any other data originating from the source database. In some cases, this view may comprise the hierarchical organization of the database that may be provided by the syndicated analytical mechanism 7208. In any case, this view may be provided in the OPML 616 format. This materialized view may be stored on one of the servers 104 or one of the clients 102. The materialized view may be delivered to the client 102 as one of the data feeds 202. The materialized view may be presented to the user, such as by a via an application programming running on the client 102. Alternatively, the materialized view itself may be treated as a database and, thus, may be queried, searched, filtered, or otherwise processed. The view may be stored as a flat file, a table, a set of fields and relations, or any other database format. The view may be subject to versioning, transactions, analysis, or any other database management or data processing function. The view may be modified by the client 102 or the server 104 and then submitted back the database management system, where it may be committed to the source database. The view may contain records that are locked in the source database. This may ensure that the records in the view are consistent with the corresponding records in the source database. The view may comprise a current or historical snapshot of aspects of the source database. The view may be generated once and thenceforth be static. Alternatively, the view may by dynamic and this subject to real-time or near real-time updates from the database management system. In this case, updates to the view may be published as one of the data feeds 202, which may be received by one of the clients 102. Updates to the view may be received directly from the database management system by one of the servers 104 that is charged with maintaining the view. In some embodiments, the view may be maintained entirely within the database management system.

A query, or a sequence or set of queries, may be submitted to the database management system to create the view. Depending upon the particular query or which database management system is being utilized (7100, 7200, or 7700), the query may be processed by the transaction mechanism 7110, the syndicated transaction mechanism 7202, and/or the syndicated analytical mechanism 7208. In any case, this query may originate directly from a user of one of the clients 102. For example, a user may enter a keyword, phrase, or sequence or set of keywords or phrases into a text box in a Web browser or the user interface of any other software application running on the client 102. The entry or entries into the text box may be transmitted directly to the database management system for processing. Alternatively, the entry or entries may be received by a software application running on one of the clients 102 or on one of the servers 104. In this case, the software application may translate the entry or entries into the form of a query that may be suitable for submission to the database management system. In some embodiments, an automatic software facility may monitor inputs from the user of one of the clients 102 and may automatically formulate the query based upon these inputs.

For example and without limitation, in an e-commerce application, the automatic software facility may reside on one of the servers 104 and may observe that the user is browsing particular items in an on-line store. These items may be just a few of a plurality of items that may be stored in the database. The automatic software facility may recognize a commonality among the browsed items (for example, that they are all camping goods) or may recognize an association between the browsed items and other items (for example, that other people who also viewed the browsed items expressed interest in other particular items).

In generating the view, the database management system may process tags, or metadata, that may be associated with the entries in the database. These tags may exist within the database, in one or more of the data feeds 202, in the content source 204, or in any data storage facility within the syndication system 100. In one aspect, the tags may identify a categorization of the entries, such as topical area of interest, source/author, publication date, content rating (such as and without limitation, the Motion Picture Association of America ratings G/PG/R/etc., the Amazon.com 5-star rating, the Zagat Rating, a user consensus rating akin to the eBay user-feedback rating, and so forth), or any other categorization, a very large number of which should be apparent. In any case, the database management system may generate the view in whole or in part based upon the tags. For example and without limitation, in response to a query requesting a view related to hunting, the database management system may scan all tags in the database and/or associated with entries in the database for the word "hunting." The materialized view, in this example, may comprise some or all of the entries associated with a tag containing "hunting."

In embodiments, a plurality of views or other OPML 616 files may reside in a database or other facility capable of storing information. As is mentioned hereinbefore, one aspect of the present invention may be to provide transaction, analysis, and versioning services in association with these files.

In one of many possible applications of the syndication system 100, a number of databases containing healthcare-related information may be viewed and/or updated. Generally, for a variety of legal and organizational reasons, it is common for healthcare-related information to be widely disbursed across a number of databases. For the purposes of having a concrete example of this one application, a hypothetical scenario follows. This scenario may be referred to in the detailed descriptions of FIGS. 82, 83, and 84.

In a hypothetical scenario, one of the databases may contain hematologic lab test results associated patient identification codes. Another database may contain digitized X-ray images associated with patient identification codes. Yet another database may contain patient contact information and health insurance information associated with patient identification codes. Still yet another database may contain social security numbers associated with patient identification codes. The syndication system 100 or aspects of it may be utilized to provide a plurality of views of these databases. Some views may be directed at a lateral organization of the information. Other views may be directed at a hierarchical organization of the information.

Referring now to FIG. 82, for the purpose of illustration and not limitation, a lateral organization may be presented in a table or a flat file. Here, database entries associated with patient identification code "143943" are displayed in a lateral view 8200. Two hematologic test results are shown, perhaps corresponding to two entries in the database that contains hematologic lab test results associated with patient identification codes. A URL pointing to an X-ray image is shown, perhaps corresponding to an entry in the database that contains digitized X-ray images associated with patient identification codes. Contact information and health insurance information are shown, perhaps corresponding to one or two entries in the database that contains patient contact information and health insurance information associated with patient identification codes. A social security number (SSN) is shown, perhaps corresponding to an entry in the database that contains social security numbers associated with patient identification codes. A benefit of this view 8200 may be that it obscures whether there are one or more databases from which the information in the view is drawn. Another benefit of this view 2100 may be that it obscures whether the databases from which the information is drawn exist in one or more divisions, offices, organizations, functional areas, or other business, private, or governmental units. Still another benefit of this view 8200 may be that it obscures whether the databases from which the information is drawn are managed by DBMS 7100, S-DBMS 7200, or DS-DBMS 7700. Yet still another benefit of this view 8200 may be that it obscures the physical and/or logical organization of the information as it exists in the database(s). Other benefits of this view 2100 will be apparent.

Referring now to FIG. 83, for the purpose of illustration and not limitation, a hierarchical organization may presented in the OPML 616 format as a hierarchical view 8300 that includes the feed 202. Here, database entries are organized primarily by hematologic lab test result and secondarily by patient identification code. At the top level of the XML structure is the opml element. That is followed by the head element, which contains two elements, title and dateCreated, each of which contain plain-text metadata. Immediately following the close of the head element appears the body element, which contains nested outline elements. The top-level outline element has a title attribute ("hematologic lab test results"). Within that element are three nested outline elements, each of which has a title attribute (respectively, "LDL<100", "LDL 100 to 189", "LDL>189"). These elements may correspond to ranges of LDL cholesterol that may be stored in the database that contains hematologic lab test results associated with patient identification codes. Within the first of these three nested outlines are two nested outline elements ("Patient #43523" and "Patient #54343"). These elements may correspond to patient identification numbers, which may be stored in a number of databases. Within both of the "Patient" elements are an "X-ray images" element and a "health insurance information" element. These elements contain leaf outline elements, which do not contain further nesting. The values of the attributes of these leaves may be associated with the database that contains digitized X-ray images associated with patient identification codes and the database that contains contact information and health insurance information associated with patient identification codes. The ellipsis in the "LDL 100 to 189" and the "LDL>189" elements indicate that the contents of these elements may be analogous to the contents of the "LDL<100" element. This hierarchical view 8300 may have all of the benefits of the lateral view 8200, as described hereinabove with reference to FIG. 82. A further benefit of this view 8300 is that it may present information along dimensions that are not explicitly represented in the databases. Yet another benefit of this view 8300 is that it may present information in relation to these dimensions. Still other benefits of this view 8300 will be apparent.

Figure 84:
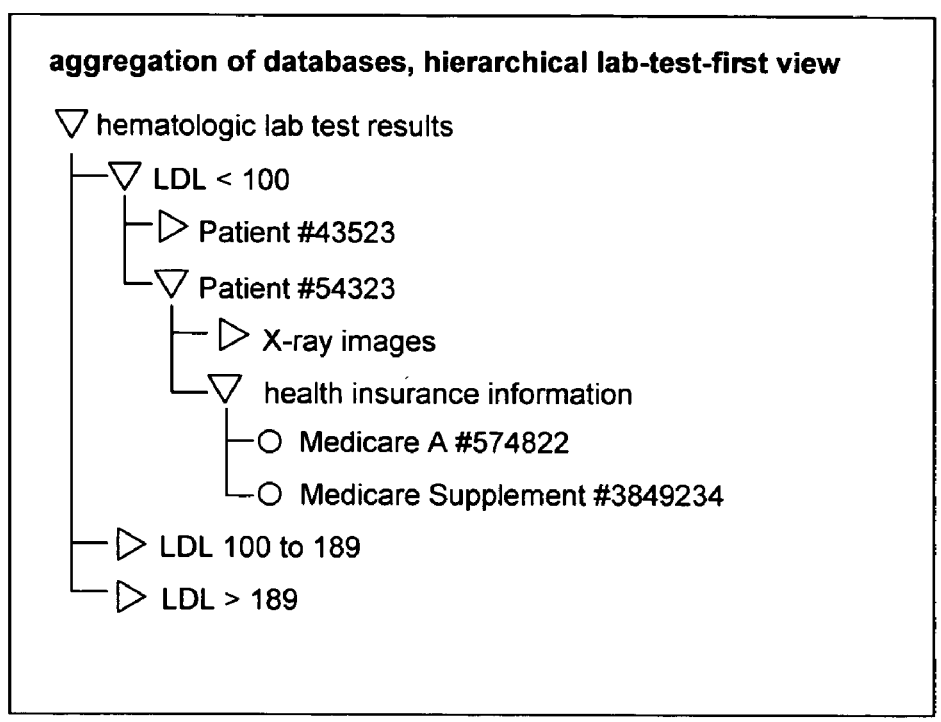
FIG. 84 depicts a visualization of the OPML file representing a hierarchical view.

Referring now to FIG. 84, for the purpose of illustration and not limitation, an interactive rendering 8400 of the hierarchical view 8300 described hereinbefore with reference to FIG. 83 is shown. In embodiments, the rendering 8400 may appear on a visual user interface associated with one of the clients 102 and may be generated by an application running on the client 102. In the rendering 8400, the title element of the head element of the hierarchical view 8300 is displayed in bold type. Below that, the hierarchy is displayed, with some elements expanded and other not. Expanded elements are indicated by a rightward-pointing triangle. Unexpanded elements are indicated by a downward-pointing triangle. Leaf elements are indicated by a circle. The structural hierarchy of the view 8300 is redundantly displayed, both by indentation and by horizontal and vertical lines. In embodiments, a user at the client 102 may interact with this rendering, such as by clicking on the triangles to toggle their orientation from rightward facing to downward facing and vice versa. As the state of different elements is changed between expanded and unexpanded, the rendering may be updated to reveal or hide appropriate parts of the view 8300. This rendering 8400 may have all of the benefits of the hierarchical view 8300, as described hereinabove with reference to FIG. 83. Another benefit of the rendering 8400 may be to allow the user to rapidly drill-down to information of interest. Still other benefits of the rendering 8400 will be apparent. It should be appreciated that the application providing the rendering 8400 may also allow the user to modify the information displayed in elements of the view 8300. These changes may be transmitted back to the database management system to be committed to the affected database or databases. When the changes are transmitted, they may be transmitted in the form of the hierarchical view 8300 and may be processed as described hereinbefore with reference to FIG. 72.

Figure 85:
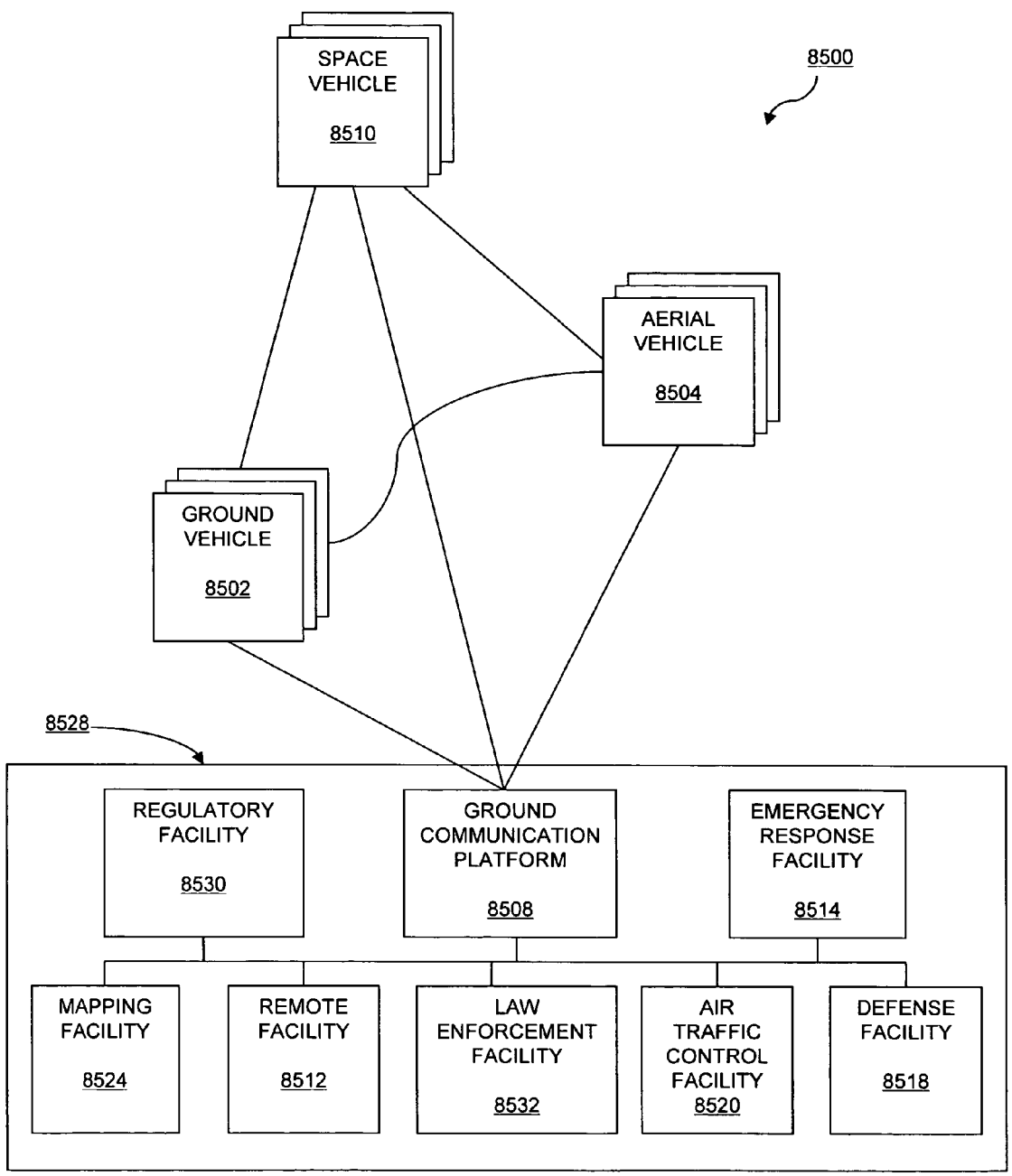
FIG. 85 depicts an embodiment of a syndication system.

Referring now to FIG. 85, a system 8500 for providing aerospace, defense, and transportation services may comprise the syndication system 100. The system 8500 may comprise a ground facility 8528; a plurality of ground vehicles 8502; a plurality of aerial vehicles 8504; and plurality of space platforms 8510. The ground facility 8528 may comprise a regulatory facility 8514; a ground communication platform 8508; an emergency response facility 8514; a mapping facility 8524; a remote facility 8512; a law enforcement facility 8518; an air traffic control facility 8520; and a defense facility 8518. Any of the platforms 8510, 8528, 8508; facilities 8530, 8514, 8524, 8512, 8532, 8520, 8518; and vehicles 8502, 8504 may comprise the clients 102 or servers 104; may comprise an instance of the gateway 116 and/or an instance of the LAN server 114; and/or may comprise the aggregator 210. Any line interconnecting any two of the various elements of this figure may indicate that the two elements are interconnected in a communicating relationship. The communicating relationship between the elements within the ground facility 8528 may, in embodiments, be wired and/or wireless. The communicating relationship between the elements of the ground facility 8528 and the other elements 8502, 8504, 8510 may be provided by the ground communication platform 8508 and may be wireless. In embodiments, the internetwork 110 and/or LAN server 114 may provide some or all of the communicating relationships. Although the depiction shows that only the ground communication platform 8508 may be in a direct communicating relationship with the elements 8502, 8504, 8510 that are not within the ground platform 8528, it should be appreciated that, in embodiments, any element of the system 8500 may be in a direct communicating relationship with any other element of the system 8500. It should also be appreciated that a communicating relationship may be established through the ground communication platform 8508 and between two other entities.

Each object in the system 8500 may publish one or more of the data feeds 202. For example and without limitation: The mapping facility may publish road maps, aeronautical charts, weather maps, and so forth. The regulatory facility 8530 may publish airspace restrictions, speed limits associated with roads, and other regulations applying to the operation of the ground vehicles 8502 and the aerial vehicles 8504. The emergency response facility 8514 may publish alerts relating to emergency situations, such as a natural disaster, terrorist act, and so forth. The law enforcement facility 8534 may publish an all-points bulletin and such. The defense facility 8518 may publish warnings, restrictions, or other defensive information. The remote facility 8512 may comprise the aggregator 210. The ground vehicle 8502 and aerial vehicle 8504 may publish position reports. The space vehicle 8510 may publish digital imagery. The ground communication platform may comprise one or more communication facilities directed at providing the wireless communications relationships between the elements that are contained in the ground facility 8528 and the other elements 8502, 8504, 8510. Without limitation, in embodiments, these wireless communications facilities may comprise WiMax, WiFi, CDMA, CDPD, 3G, satellite, microwave, free-space optical, near-field radiofrequency, far-field radiofrequency, contactless, quantum, or any other wireless communications technology or medium. Generally, in embodiments, each instance of the objects may publish one or more data feeds 202 associated with a parameter, measurement, condition, observation, prediction, situation, formal or informal communication, or any other information that is associated with each instance of the objects. Some of these types of information are described hereinafter, while others will be apparent.

Each object in the system 8500 may receive one or more of the data feeds 202. For example and without limitation: The ground vehicle 8502 may benefit from receiving timely traffic updates and road condition. The aerial vehicle 8504 may benefit from receiving regulatory updates such as temporary airspace restrictions. The law enforcement facility 8532 may likewise receive regulatory updates. The space vehicle 8510 may benefit from receiving coordinates specifying areas of interest (in space or on the Earth). The regulatory facility 8530 may benefit from receiving information from the defense facility 8518 (such as the whereabouts of the President of the United States, perhaps used in issuing the temporary airspace restrictions). The air traffic control facility 8520 may receive regulatory updates, defense activity reports, positional coordinates associated with the ground vehicle 8502, the aerial vehicle 8504, and/or the space platform 8510. The remote facility 8512 may receive any information and process it for distribution or redistribution to the other elements of the system 8500. The mapping facility 8524 may receive coordinates or other information that is incorporated into a map, such as satellite weather imagery. Generally, in embodiments, each instance of the objects may receive and/or subscribe to one or more of the data feeds 202, some of which are described herein and other of which will be apparent.

It will be appreciated that there exist many applications of the system 8500 for providing aerospace, defense, and transportation services. It will further be appreciated that any or all of the following features and aspects of the embodiment of the DBMS 7100, S-DBMS 7200, or DS-DBMS 7700 may be employed in instances of the system 8500 or any other syndication system. Various illustrative aspects of an implementation of the DBMS 7100, S-DBMS 7200, or DS-DBMS 7700 are described hereinafter. A more detailed description of a suitable DBMS 7100 is provided in, "Fundamentals of Database Systems," by Ramez Elmasri and Shamkant B. Navathe, fourth edition, published by Addison-Wesley, 2004, the entire contents of which is incorporated herein by reference.

In the context of the system 8500, and in general embodiments, the DBMS 7100, S-DBMS 7200, or DS-DBMS 7700 may comprise a software server that provides data in a format associated with syndication, such as OPML 616, or in another format such as those described hereinabove with reference to FIG. 6.

The software server may manage one or more data files that together may comprise the database. The database may be composed of records. These data files may be organized in a way that is optimized for rapid storage and retrieval to and from a physical disk such as a platter in a hard disk drive. On the platter, these data files, typically, are logically arranged as disk pages or "blocks." Various organization methods for data files are known in the art and generally fall into one of three categories: unordered, ordered, and hashed. These organization methods may be supplemented, and storage/retrieval performance may be further enhanced, with an application of an access structure known in the art as an index. In some embodiments, the index may comprise one level and may generally be implemented as a primary, a clustering index, a secondary index, a multicolumn index, a combination of indexes, a unique index, and/or a partial index, all of which are well known in the art. In other embodiments, the index may comprise multiple levels and may generally be implemented as a B-tree, a B+-tree, an R-tree, a hash, or another implementation such as may be supported by an infrastructure, such as GiST, that supports the specification of multiple and/or arbitrary index strategies. On still other embodiments, any combination of organization methods and indexes may be applied. In the system 8500 or any other syndication system, the database may contain a message in the OPML 616 format and of which the data feed 202 may be comprised.

The software server may support one or more logical connections provided in association with an authentication technique. In some embodiments, a software application that accesses the DBMS 7100, S-DBMS 7200, or DS-DBMS 7700 may be running on the client 102 while the DBMS 7100, S-DBMS 7200, or DS-DBMS 7700 itself is running on the server 104. In other embodiments, the software application may be running on the server 104 and the DBMS 7100, S-DBMS 7200, or DS-DBMS 7700 may be running on the client 102. In any case, the connection may comprise data communications (for example and without limitation, TCP/IP data communications) between the client 102 and the server 104. To establish such communications, the DBMS 7100, S-DBMS 7200, or DS-DBMS 7700 may require that the client 102 (or the software application running on the client) be authenticated and/or the client 102 may require that the DBMS 7100, S-DBMS 7200, or DS-DBMS 7700 be authenticated. Various methods of authentication are known in the art, such as password, public key, keyboard-interactive, and GSSAPI. In the system 8500, the ground vehicle 8502 may authenticate the ground communication platform 8508 prior to accepting an OPML 616 file via the data feed 202 provided by the ground communication platform 8508.

Operation of the software server may require the consumption of computing resources. These resources may include network bandwidth, central processing unit cycles, primary memory, primary memory bandwidth, secondary storage, secondary storage bandwidth, and so forth. The implementation of the software server may generally be directed toward a balance of reduced resource consumption combined with increased performance characteristics of the software server. These performance characteristics may be measured in terms of latency and/or response time. It will be appreciated that the physical implementation of the server 104 and or client 102 may be directed at boosting the performance of the DBMS 7100, S-DBMS 7200, or DS-DBMS 7700, such as by providing additional bandwidth, cycles, and/or memory. Likewise, it will be appreciated that the increased performance of the DBMS 7100, S-DBMS 7200, or DS-DBMS 7700 may lead to increased performance of an overall system that includes the DBMS 7100, S-DBMS 7200, or DS-DBMS 7700. For example, in the system 8500 or any other syndication system, the DBMS 7100, S-DBMS 7200, or DS-DBMS 7700 may in some respect reduce resource consumption by publishing summaries of the feed 202 in the form of an OPML 616 data file, thus saving bandwidth and perhaps improving the performance of the system 8500 or other syndication system.

The software server may include a method generally known as a recovery method or recovery method. The recovery method may provide for the restoration of the database to the most recent consistent state prior to a failure. The recovery method may rely on what is generally known as a log file, which may contain a sequential, historical list of operations applied to the database.

The failure may be a power failure, hardware failure, software failure, or any other systemic catastrophe that may adversely affect the operation of the DBMS 7100, S-DBMS 7200, or DS-DBMS 7700. The system failure may cause widespread damage to the database. In this case, the recovery method may provide for retrieving an archived version of the database in a state that is known to be consistent. To this retrieved database, the recovery method may redo operations to the database according to the instructions in the log file.

Alternatively, the failure may comprise a minor system failure or a logical failure, such as a failure of main memory or a portion thereof, a failure of a transaction to complete (such as due to interruption, failure of a consistency test, and so forth), a failure of primary storage, or any of a host of other possible such failures. In this case, localized inconsistency to the database could be possible. To recover from this, the recovery method may provide for undoing and/or redoing operations to the database according to entries in a log file, without consulting an archived version of the database.

In some embodiments, the DBMS 7100, S-DBMS 7200, or DS-DBMS 7700 may employ a method known in the art as in-place updating. In this method, when a block of which the database is comprised is read from disk, its physical location on the disk is noted. The contents of this block may be modified in primary storage and then written back to disk. When the block is written back to disk, it is written to the same physical location from which it was originally read. Thus, once written to disk, the old version of the block is lost. If a system failure occurs while the block is being written to disk, the data in the block may become corrupted (such as do to the block being partially overwritten) and the database, therefore, may be in an inconsistent state. To recover from this situation, a technique known in the art as write-ahead logging may be employed. The write-ahead log is created and maintained by the DBMS 7100, S-DBMS 7200, or DS-DBMS 7700 and contains undo and redo instructions, corresponding to actions applied to the database. The DBMS 7100, S-DBMS 7200, or DS-DBMS 7700 ensures that, before attempting to write a block of which the database is comprised, the undo and redo commands associated with the changes in the block are written to disk in the form of a write-ahead log. Thus, should there be a system failure during the writing of the log, the write-ahead log may become corrupted, but this is of no consequence as the database would be consistent. Should there be a failure during the writing of the database, the write-ahead log would contain all the information required to convert either an old but consistent version of the database into the most recent consistent state or to convert a current but inconsistent version of the database back into its most recent consistent state.

In the system 8500 or any other syndication system, many possible applications of the recovery method are evident. One application may involve the publication of an OPML 616 file from an instance of the aerial vehicle 8504 to the ground communication platform 8508. Subsequent to receipt of the OPML 616 file, the DBMS 7100, S-DBMS 7200, or DS-DBMS 7700 in the ground communication platform 8508 may write the OPML 616 file to the database on disk. During this write operation, a power loss may disable the DBMS 7100, S-DBMS 7200, or DS-DBMS 7700, leaving the database in an inconsistent state. When the power comes back on, the DBMS 7100, S-DBMS 7200, or DS-DBMS 7700 may retrieve an archived copy of the database, read instructions from the write-ahead log corresponding to the previously attempted write of the OPML 616 file, and apply these instructions to restore the database to a current and consistent state.

The software server may translate a query from an intermediate form into an execution plan. This translation may be performed by a component of the DBMS 7100, S-DBMS 7200, or DS-DBMS 7700 known as a query optimizer. The query optimizer may determine an efficient strategy for executing the query and may embody this strategy as the execution plan. The query optimizer may utilize techniques known in the art as pipelining, heuristics, selectivity, or cost estimates. The techniques may include rules-based techniques, cost-based techniques, semantic processing, or any other query optimization technique. In the system 8500 or any other syndication system, the query optimizer may be employed as much as every time a query associated with an OPML 616 file is submitted to the DBMS 7100, S-DBMS 7200, or DS-DBMS 7700.

The software server, from time to time, may detect an error. A vast number of sources of the error will be appreciated and may comprise a software server configuration error, a persistent or intermittent hardware error, a network error, a data communications error, a programming error such as a bug in the software server, an attempt to process a malformed query, a failed authentication attempt, and the like. When such errors are detected, the software server may write information describing or associated with the error to a log file, which may be specially designated as an log file for error logging. In one example, the software server in the system 8500 may detect when it receives a malformed query associated with retrieving or generating an OPML 616 file. Upon detection, the software server may write to the information describing the error to the log file for error logging.

The software server may monitor and collect run-time statistics associated with the performance of the software server, including statistics specifically associated with queries, query processing, and indexes. A number of these statistics are discussed in, "PostgreSQL 8.1.0 Documentation," written and published by The PostgreSQL Global Development Group, 2005, included herein by reference. These statistics may without limitation comprise a database object ID, a database name, a process ID, a user object ID, a user name, a current query, a time at which the current query began execution, a time at which the process was started, an IP address of the client 200, an IP port of the client 200, a number associated with active service processes connected to the a database, a number associated with transactions committed and/or rolled back in the database, a number associated with a count of disk blocks read, a number associated with a total count of buffer hits, a schema name, a table name, a number associated with a count of sequential scans initiated, a number associated with a count of live rows fetched by sequential scan, a number associated with a count of index scans initiated, a number associated with a count of row insertions, a number associated with a count of row updates, a number associated with a count of row deletions, an index name, a number associated with a count of index scans initiated on a particular index, a number associated with a count of index entries returned by index scans, a number associated with a count of live table rows fetched by simple index scans using that index, a number associated with a count of disk blocks read from a table, a number associated with a count of disk blocks read and buffer hits in all indexes of a table, a number associated with a count of disk blocks read and buffer hits from a table's auxiliary table, a number associated with a count of disk blocks read and buffer hits for an auxiliary table's index, a table object ID associated with an index in a database, an index object ID associated with an index in the database, a table name associated with a database, an index name associated with a database, a number associated with a count of disk blocks read in an index, a number associated with a count of buffer hits in a index, a sequence object, a sequence object ID, a schema associated with a sequence, a name associated with a sequence, a number associated with a count of disk blocks read in a sequence, a number associated with a count of buffer hits in a sequence, and the like. In the system 8500 or any other syndication system, these run-time statistics may assist a maintainer of the system 8500 (or other syndication system) in optimizing the performance of the system 8500 (or other syndication system) and/or troubleshooting aspects of the system 8500 (or other syndication system) associated with processing OPML 616.

The software server may conduct routine maintenance tasks directed at providing consistent and reliable database performance. On such task may be referred to as vacuuming, in which disk space associated with updated or deleted rows in tables in the database may be recovered; usage statistics used by the query optimizer may be updated; and so forth. In some embodiments, the task of vacuuming may be automated, such as performed according to a temporal schedule. Another such task may be referred to as reindexing, which may involve recalculating the indexes in the database to remedy an inefficient use of memory and/or disk space associated with the indexes, which may develop over time as the database is used. Yet another such task may be directed at properly maintaining log files, which may grow to contain vast and potentially unlimited quantities of information as the database is used. Given, that unlimited information storage space is never available, the log files may from time to time be rotated, a technique that is well known in the art. It will be appreciated that, in the system 8500 or any other syndication system, routine maintenance tasks performed by or in association with the software server may assist in maintaining the consistent and reliable performance of the system 8500 or other syndication system.

The software server my support any number of concurrent connections from clients 102 (or, "client connections"), wherein the connections may comprise the logical connections described hereinabove. The client connections may be directed at a single database, which may be specified in an initial request to establish the client connection. In the system 8500 or any other syndication system, any of the servers 104 may accept client connections, through which may occur the transmission of queries and results, both of which may be associated with OPML 616.

The software server may support the locking of tables, rows, elements, and/or fields in the database. Generally, locking provides one transaction (the transaction that "holds the lock") greater access to the locked entity than is granted to other transactions. In one example, locking may provide read-write access to the one transaction and no access to the other transactions. In another example, locking may provide read-write access to the one transaction and read-only access to the other transactions. When an entity becomes locked, this fact may be associated with a lock ID, which may be stored in a data structure commonly known as a lock table. Typically, when a transaction is denied access to an entity because of the lock, the transaction may wait until the lock is released by the transaction that holds the lock. In practice, it is possible that, from time to time, two or more transactions will become deadlocked as they simultaneously wait for locks held by each other. The software server, perhaps in accordance with a timeout parameter, may check to see if a deadlock exists after a transaction has been waiting for an amount of time in excess of that specified by the timeout parameter. If a deadlock is detected, the software server may cancel or roll back one or more of the transactions to resolve the deadlock condition. As an alternative to (or in addition to) locking, the software server may support a concurrency control technique that is known in the art as multiversion concurrency control (MVCC). In any case, in the system 8500, lock management or some other method of concurrency control may be used in many readily apparent circumstances associated with OPML 616.

The software server may support set of access permissions, wherein the set may be referred to as a role and the permissions may be referred to as privileges. Each role may have a name and may be associated with one or more users of the database. The privileges may relate to various permissions to access and/or modify the database. A user may or may not be authorized to delegate permissions and/or roles to another user. In just one of many evident examples, provided here for the purposes of illustration and not limitation, the software server in the system 8500 may contain a regulatory role, which comprises permissions to write to a database table containing regulations. This role may be associated with the regulatory facility 8530. Thus, the software server may allow only the regulatory facility 8530 to update the table containing regulations.

The software server may allow users to insert code into it, thus enhancing, modifying, and or limiting the functionality of the software server. Generally, this inserted code may comprise any code whatsoever. Due to the sweeping capabilities and, therefore, potential for abuse, this software server may allow only a particularly privileged user, commonly known as the superuser, to insert this code. These functions may be automatically activated or triggered according to a trigger or event defined by the user that inserted the code. Such an event may be the execution of a particular database function, the passage of a particular amount of time, an external signal, and so forth. In the system 8500, triggers may be utilized to automatically update OPML 616 files when information in the database that is associated with the OPML 616 file is modified. Many other applications of triggers in the system 8500 or any other syndication system are evident.

The software server may provide for creating, configuring, and destroying the database. The database may be a collection of schemas comprising tables, functions, and the like. The creation of the database may associate a name with the database and may comprise copying an existing database or database template. The database template may be a specially crafted database that exists to provide a well-defined, standard starting point and/or initial configuration for all new databases. The database template, generally, may comprise any database that is designated to be copied for the purposes of providing the starting point and/or initial configuration of a newly created database. It should be apparent that the creation, configuration, and destruction of the database, as well as the database template, may be essential and integral to the operation of the system 8500 or any other syndication system. In one aspect, the software server may provide for creating, configuration, and/or destroying data relationships independent from the underlying data. This may have particular applicability where, as with an OPML/RSS based architecture, the relationships are by their nature expressed independently from the data.

The software server may provide a feature, known as locale support, that allows for the representation of multiple alphabets, character sets, sorting orders, number formats, and the like. In the system 8500 or any other syndication system, the locale support may allow OPML 616 files to be represented, stored, created, modified, or otherwise processed or provided according to a language, alphabet, number format, or other local preference associated with a deployment or use of the system 8500 or other syndication system.

The software server may provide what is known in the art as backup and restore functionality. In some embodiments, the backup may involve the creation of an SQL dump, which is a set of SQL instructions that when provided to the software server will recreate the database represented by the dump as it existed at the time that the dump was originally created. In other embodiments, the backup may involve making a copy of the files that the software server stores on disk. Other backup and restore techniques exist, such as those that involve applying the write-ahead log to a backup copy of the database, the result of which may be to provide for restoring the database to a (nearly) up-to-date state, even though the backup copy of the database may be relatively old. In the system 8500 or any other syndication system, the backup functionality may be employed periodically in any or all of the instances of the software server to insure that there is an recent backup of the database should a failure or error occur that necessitates restoring the database. Backup and restore may be provided independently for data and for data relationships.

The software server may provide or be associated with regression tests. These test may allow the integrity, reliability, functionality, or any feature of the server to be tested to ensure that failures, bugs, configuration problems, or other mistakes or errors have not been introduced into the server. In the system 8500 or any other syndication system, these tests may comprise a comprehensive set of operations, perhaps expressed as SQL or XQuery, directed at supporting OPML 616 files as they may be associated with the software server.

The software server may support a number of client interfaces, which may be software facilities by which the client 102 may access the software server running on the server 104. These software facilities may take the form of a software library, which may be written in a language such as C, Java, or any other programming language. These software facilities may be directed at one particular brand of software server or may be directed at providing a singular or unified interface for clients 102 to a plurality of brands of software server. Clearly, any client 102 that accesses the software server in the system 8500 may utilize or be implemented with one or more of the client interfaces.

The database managed by the software server may be embodied as one or more data structures. A table in the database may consist of a number of rows and columns. The number and order of the columns may be fixed and each column may be associated with a name. The number and order of the rows may be variable. Values stored in the table may or may not be subjects to defaults and constraints. Many detailed aspects of the table are well known in the art. In one aspect, data structures of a relational database may be captured in an OPML structure and associated with unstructured data through external references.

In embodiments, the tables may be accessed directly or may be accessed through a view, which may be a query associated with a name that may be referred to in other queries as though it were a table. The result of the query associated with the name may be stored as an object in the database, in which case the view may be referred to as a materialized view. In any case, the table, view, and/or materialized view (any or all of which may be generally referred to herein as "the table") may contain a representation of an array of one or more dimensions.

An index used in association with the table may comprise an specialized index, known as an application domain index, that may be tailored to a custom data type, such as an OPML 616 file, that may not traditionally be found in a stock implementation the DBMS 7100, S-DBMS 7200, or DS-DBMS 7700.

A plurality of tables may be stored in an arrangement known as a cluster or tablespace, in which tables that are often accessed together share the same data blocks (which collectively may be referred to as an extent or a segment), thus potentially improving system performance by minimizing the space and/or time required to access and/or modify the clustered tables. In a special application of the cluster, the rows in the tables are stored in an order associated with the result of a hash function, potentially further improving system performance, especially in some circumstances such as tables are frequently queried to find entries that are equal to a specified value.

Some embodiments of the software server may provide support for a synonym, which may be an alias for any table, view, materialized view, sequence, trigger, function, type, synonym, and the like. Some rows may contain a value, such as and without limitation unique identification number, may need to be generated uniquely and sequentially even in the case where multiple rows are being created by different users at the same time. To support this generation, the software server may include a sequence generator that provides this functionality.

Each table may contain one or more columns referred to as system columns, which may be implicitly defined by the software server when the table is created. Alternatively or additionally, a read-only set of tables and views, collectively referred to as a data dictionary, may be created and maintained by the software server. In any case, the system columns or the data dictionary may contain fields, which may contain data sometimes referred to as database object metadata, that are used by the software server in processing queries, maintaining the consistency of the values in the table, and so forth.

The table may in some cases be modified after it is created and perhaps even after it is filled with data. These modifications may include addition of a column, removal of a column, addition of a constraint, removal of a constraint, modification of a default value, modification of a column data type, modification of the name of a column, modification of the name of the table, and so forth.

To prevent the removal of a column or table on which another table may depend, such as due to a foreign key constraint, the software system may implement a feature commonly known as dependency tracking, which may detect such a dependency and prevent the removal of such a column or table.

The software server may support a feature known as table inheritance, which allows one table to inherit all of the columns of an another table, referred to as its parent table. In practice, a table may inherit from any number of tables and queries may be applied to all rows of a table and/or all rows of a table and the tables that inherit from it.

To improve performance, the table may be partitioned, or split, into a number of smaller tables that, together, logically form one large table. This split may result in some rows existing in one of the smaller tables with other rows existing in another of the smaller tables. The software server may, in addition to tables, support other database objects, including without limitation views, functions, operators, data types, domains, triggers, rewrite rules, and any other database object. Of the numerous features, functions, and aspects of the software server that are mentioned in the preceding paragraphs describing tables and associated functions and features, a tremendous number of embodiments and uses are apparent as they relate to the use of OPML 616 in the system 8500.

The data stored by the software server in a table of the database may be manipulated. This manipulation may comprise an insert, delete, and/or update operation. It should be clear that without these operations, the software server would be of limited or no use in the system 8500 or any other syndication system.

The software server may process a query. This query may comprise a command to retrieve data from the database. In the art, the act of processing the query may be referred to as querying. In embodiments, querying may be the primary or only way of retrieving data from the database. The query may be expressed in terms of SQL, XQuery, or any other query language. Clearly, the application of the software server in the system 8500 or any other syndication system may require querying and the use of queries.

The software server may support any number of data types, with respect to the data that may be stored in the database. These types may, without limitation, be numeric, monetary, alphanumeric, binary, directed toward representing a date, directed toward representing a time, Boolean, geometric, directed toward representing a network address, a set of bits, an array, composite, complex, directed toward representing an object ID, directed toward describing the structure of a row or record, and the like. The software server may implicitly and/or explicitly convert data from one type to another during the processing a query. It is readily apparent that data types may be a fundamental and essential aspect of the software server as it applies to the system 8500 or any other syndication system.

The software server may support any number of functions and/or operators that may be applied to the data in the database and/or other parameters associated with the software server. These functions and/or operators may or may not be defined in a stock implementation of the software server, may or may not be defined by the query language, and may or may not be defined by the user of the software server. These functions and/or operators may be directed at manipulating or processing logic, a comparison, mathematics, a string, a binary string, a bit string, a format, a date, a time, geometry, a network address, a sequence, a condition, an array, an aggregate, a query, a row, a set, system information, and the like. Furthermore, the functions and/or operators may be directed at system administration. Many applications of such functions and/or operators are apparent as they relate to the system 8500 or any other syndication system.

The software server may comprise facilities that are directed at the supporting XML 608 and/or OPML 616. These facilities may comprise what are known in the art as an XML processor, an object processor, and/or an object composer. The software server may be capable of accepting incoming messages in the XPath and/or XQuery formats, delivered via HTTP/SOAP. The software server may be capable of providing messages in the XML 608, OPML 616, the Wireless Markup Language (WML, which is a species of XML 608), and/or non-XML formats 685 (for example, HTML). Many applications of these facilities are apparent as they relate to the system 8500 or any other syndication system.

Any or all of the database functions, features, and architectures, may be employed with the enhanced syndication systems described herein. In various embodiments, a database management system may reproduce aspects of the above database systems across an environment where unstructured data, including syndication data, is associated through an outline or other expression of data relationships. In other embodiments, a database management system may be employed to support various elements of an enhanced syndication system such as pools, data services, security, transactions, infrastructure, semantic processing, and so forth. All such variations are intended to fall within the scope of this disclosure.

In embodiments, systems and methods are presented that involve providing records including a first data item and a second data item, the first data item including personal data and the second data item including non-personal data. The first data item may be transmitted to a secure data pool; and the second data item may be transmitted to an unsecure data pool. The two data items may have a relationship, but they may be provided to users through different interfaces with different security policies and for different purposes. For example, a data storage routine such as this may be used in a situation where one wants to store information that can be separated into two or more parts and the two or more parts may have part specific security features or handling parameters. For example, healthcare data may be divided into personal and non-personal information. The personal information (e.g. payment information, such as credit card information) may be provided through a conditional access security facility adapted to protect the personal information. This may require a high degree of security as well as a connection with other facilities, such as a bank where the information is credit card information. The personal security facility may, for example, ensure anyone accessing the information has authority to do so and that the information is being accessed for the proper reason (e.g. a credit payment). Likewise, the non-personal information may be protected by another security facility. The non-personal security facility may have different levels of conditional access and may be generally higher or lower in its level (as compared to the personal security facility). For example, the non-personal information may relate to heath care testing, but it may not be personally identifiable. Doctors in general may be able to access the non-personal data by entering information into the security facility that identify the person as a doctor and thus permitted.

The data items stored in the separate data pools may be syndicated data items, the data items may be syndicated in the pool, or the data items may be processed to form syndicated data items at some point in the process of loading them into the pool or extracting them from the pools. Once stored in the separate pools, a collection facility, such as a crawler or spider, may search for the non-personal data and extract the non-personal data from the non-personal data pool. However, when this spider comes to the secure pool, it may need access codes or protocols to enter the pool. Without proper authentication, the crawler may not be able to take any data from the pool. Similarly, a crawler may have proper access protocols to enter the pool and once inside the pool it may require further permissions to take any of the specific data. For example, it may have the proper authority to take data specific to a particular person (e.g. because that person's physician sent the crawler). Thus, in one aspect a spider may be configured to receive security credentials and apply them at appropriate times during a spidering process. In another aspect, the spider may be adapted to stop spidering activity when confronted with a security request, and present the request (such as a request for a username and/or password) to a user that initiated the spider.

There are several ways to provide secure syndicated information. For example, a data pool containing syndicated information may itself be secured so access to the pool is made conditional. As another example, the syndicated data in the data pool may be protected through a security facility, such as wrapping the syndicated data in a secure layer that has with it a conditional access or conditional collection ability. In addition, the data streams going into and out of the pools may be secured or otherwise protected. In another aspect, depersonalizing and distributing data across a number of pools provides inherent security. Relationships among the distributed data may be retained, for example, in an OPML file or other structured format, which may itself be stored in a secure location such as another pool.

Syndicated data may be secured in pools, but it may also be secured through data streams. The data streams may be inbound data streams (e.g. storage of the data into the pool from a published source) or outbound data streams (e.g. collection feeds). The streams may be protected by encoding the data prior to transmitting the data or before allowing the data to be collected from a collection facility, such as a spider. A decoder may be associated with a pool such that encoded information transmitted into the pool is available for collection without the need for decoding after collection.

In embodiments, systems and methods are provided that involve providing a device-based facility for subscribing to syndicated information. The device-based facility may also include a local security facility that permits a user of the device to access the syndicated information. For example, the device may have a subscription facility adapted to collect personal information related to the owner of the device. So the device may be continually collecting personal information, healthcare information, or other information and to properly protect the collected information, the device may have a security facility (e.g. such as a software operated pass code system). Likewise, systems and methods may be involve providing a device-based facility for publishing syndicated information; and providing a local security facility associated with the device that permits a user of the device to publish the syndicated information. The user of the device may want to publish certain information and the device may require proper authorization from the user prior to executing the publication function.

In embodiments, systems and methods are provided that involve receiving syndicated data; displaying the syndicated data; and destroying the syndicated data after display. For example, a kiosk, credit card payment station, or other facility may be adapted to collect information (e.g. personal information) to verify a transaction or make some other use of the information. However, once the transaction is verified or the information is otherwise used, the system that collected the syndicated information may destroy the data. In certain embodiments, the destruction is certified and the certification may be sent to an authorized agent to verify the proper destruction of the data.

In embodiments, systems and methods are provided that involve providing a set of pools of data configured to be syndicated for use by one or more subscription facilities where the location of the pools is optimized on a network to facilitate rapid access by frequent subscribers. For example, a healthcare pool of data may be valuable in helping doctors diagnose certain ailments. Doctors on in California, Massachusetts, Germany and elsewhere would like access to the information that is generated and deposited into the pool. To increase the speed at which the access can be accomplished from the several geographic regions, the pool of data may be replicated and the replicates may be store in geographic regions near the access points. Then the different doctors in the different locations can instruct their collection facilities (e.g. spiders) to go to the local pool because they will get the information quicker. The spider may also go to the remotely located pools to see if there is any updated or non-replicated information that is relevant for collecting. The pools of syndicated data may also be separately populated with locally generated or collected information and the several pools may be updated and replicated periodically or through a syndication service of there own.

In embodiments, systems and methods are provided that involve providing a data facility for healthcare information, wherein the data facility provides a structure for subscribing to syndicated healthcare data, wherein a user may modify the structure through which the user accesses the syndicated health care data. For example the structure may be a security structure where the user has the ability to manipulate the structure or features of the structure (e.g. whether the password facility is turned on).

In embodiments, systems and methods are provided that involve allowing a user anonymous access to health care data. The systems and methods may involve disposing the health care data in a secure pool; generating a secure key that allows a user access to the secure pool; providing the user the key; and certifying the destruction of the record that the user has access to the key. In embodiments, the key allows time-based user access. This can be a useful way of creating an anonymous access procedure to health care or other forms of data.

In embodiments, systems and methods are provided that involve publishing of authenticated health care data. The systems and methods may involve disposing health care data into a plurality of pools, the health care data being disposed by authenticated sources; and syndicating the data, wherein the syndicated data is associated with an authentication certificate that certifies that the data has been published by an authenticated pool. For example, in drug testing, biopsy results, or other services that require lab certification, a certification from the lab may be included with the data. The certification may, for example, be disposed in a field within an OPML structure.

In embodiments, systems and methods are provided that involve anonymous publication of syndicated data. The methods and systems may involve storing data into a plurality of data storage facilities; authenticating the identity of the entity storing the data; de-identifying the data; and syndicating the data. This may provide authenticated data in a pool but when the data is extracted (e.g. through a spider or other collection facility) one may not be able to identify from where it originated or was authenticated. So the lab may not be identifiable but the data that is extracted can be considered authenticated. In embodiments, there may be a step that involves verifying the certifying lab is in good standing so people who extract data from the pool can remain confident in the authentic nature of the data.

In embodiments, systems and methods are provided that involve dynamically generating syndicated data. The methods and systems may involve receiving a request for a data feed from a requester; processing the request to provide responsive content; and publishing the responsive content as the data feed. There are many times where the sought after information is not in a syndication format and it needs to be converted (e.g. converting a power point presentation into OPML). In embodiments, the request may be processed without the requester knowing the conversion even needed to be made. The process may go on in real-time or quasi real-time. The process may also involve sending the request off to a secondary process where a secondary process, like a security check, takes place prior to converting and/or transmitting the syndicated information. A requestor may pose a security threat and the secondary process may identify the threat. In this situation, the syndicated information may not be provided. In addition, the secondary process may involve sending the request or information relating to the request to another agency for security analysis.

While the invention has been disclosed in connection with the preferred embodiments shown and described in detail, various modifications and improvements thereon will become readily apparent to those skilled in the art. Accordingly, the spirit and scope of the present invention as claimed below is not to be limited by the foregoing examples, but is to be understood in the broadest sense allowable by law.

What is claimed is:

1. A method for encrypting, authenticating, and aggregating data pools, the method comprising a computer having a computer readable medium having stored thereon instructions which, when executed by a processor of the computer, causes the processor to perform the steps of:
providing a record including a first data item and a second data item, the first data item including secure data and the second data item including unsecure data;
using tag-level encryption to encode a security level to the first data item and a security level to the second data item, wherein the levels of security are different;
authenticating the first data item and the second data item using a security function triggered by a content of the first data item and a content of the second data item;
aggregating the first data item into a secure data pool based at least in part on the security function; and
aggregating the second data item into an unsecure data pool based at least in part on the security function, wherein aggregating the first data item and aggregating the second data item includes separate routing for the first data item and for the second data item.

2. The method of claim 1, wherein the first data item includes one or more of a name, birth date, social security number, bank account and password.

3. The method of claim 1, wherein the second data item includes medical data.

4. The method of claim 1, wherein the secure data pool provides conditional access to content.

5. The method of claim 4, wherein the conditional access includes password-based access.

6. The method of claim 4, wherein the conditional access includes role-based access.

7. The method of claim 4, wherein the conditional access includes conditional read access.

8. The method of claim 4, wherein the conditional access includes conditional write access.

9. The method of claim 1, wherein the record includes one or more of a medical record, a financial record, a psychological record, and a tax record.

10. The method of claim 1, wherein the unsecure data pool is available for public use.

11. A method for storing a relationship among a plurality of authenticated data within aggregated data pools, the method comprising a computer having a computer readable medium having stored thereon instructions which, when executed by a processor of the computer, causes the processor to perform the steps of:
- providing a record including a first data item and a second data item;
- using tag-level encryption to encode a first metadata to the first data item and a second metadata to the second data item, wherein the encoding of the first metadata and the second metadata are different;
- authenticating the first metadata item for the first data item and the second metadata item for the second data item using a security function triggered by the metadata;
- aggregating the first data item in a first data pool based at least in part on the first metadata and the security function;
- aggregating the second data item in a second data pool based at least in part on the second metadata and the security function, wherein aggregating the first data item and aggregating the second data item includes a separate routing for the first data item and for the second data item; and
- expressing a relationship between the first data item and the second data item in a file external to the first data pool and the second data pool.

12. The method of claim 11, wherein the access to the first data pool is controlled by a security layer.

13. The method of claim 12, wherein the content in the first data pool includes syndicated content with message-level encryption.

14. The method of claim 12, wherein the content in the first data pool includes syndicated content with tag-level encryption.

15. The method of claim 12, wherein the content in the first data pool includes syndicated content with channel-level encryption.

16. The method of claim 12, wherein the security layer employs an Active Directory service.

17. The method of claim 1, wherein the file is encrypted.

18. The method of claim 11, wherein the file includes a password for accessing at least one of the first item and the second item.

19. The method of claim 11, wherein the first data item includes a syndicated message.

20. The method of claim 19, wherein the syndicated message includes an RSS message.

21. The method of claim 19, wherein the syndicated message includes an OPML file.

* * * * *

UNITED STATES PATENT AND TRADEMARK OFFICE
CERTIFICATE OF CORRECTION

Page 1 of 1

PATENT NO. : 8,347,088 B2
APPLICATION NO. : 11/346586
DATED : January 1, 2013
INVENTOR(S) : James F. Moore and Bela A. Labovitch It is certified that error appears in the above-identified patent and that said Letters Patent is hereby corrected as shown below:

Title Page 2, item (56):
Under U.S. PATENT DOCUMENTS, right column, line 38, insert -- 2002/0049614 A1 4/2002 Rice --;

In the CLAIMS:
Column 134, line 14, claim 17, delete "The method of claim 1" and insert -- The method of claim 11 --.

Signed and Sealed this
Ninth Day of April, 2013

Teresa Stanek Rea
*Acting Director of the United States Patent and Trademark Office*